US012655217B2

(12) United States Patent
Watkins et al.

(10) Patent No.: US 12,655,217 B2
(45) Date of Patent: \*Jun. 16, 2026

(54) ANTI-ROR1 / ANTI-CD3 BISPECIFIC BINDING MOLECULES

(71) Applicant: VelosBio Inc., Rahway, NJ (US)

(72) Inventors: Jeffry D. Watkins, Encinitas, CA (US);
Katti Jessen, San Diego, CA (US);
Mira Ko, San Diego, CA (US); **Brian
Lannutti**, San Diego, CA (US);
Thanh-Trang Vo, San Diego, CA (US);
J. Monty Watkins, La Jolla, CA (US)

(73) Assignee: VelosBio Inc., Rahway, NJ (US)

( * ) Notice: Subject to any disclaimer, the term of this
patent is extended or adjusted under 35
U.S.C. 154(b) by 1151 days.

This patent is subject to a terminal dis-
claimer.

(21) Appl. No.: 17/613,251

(22) PCT Filed: May 22, 2020

(86) PCT No.: PCT/US2020/034281
§ 371 (c)(1),
(2) Date: Nov. 22, 2021

(87) PCT Pub. No.: WO2020/237173
PCT Pub. Date: Nov. 26, 2020

(65) Prior Publication Data
US 2022/0227866 A1      Jul. 21, 2022

Related U.S. Application Data

(60) Provisional application No. 62/852,039, filed on May
23, 2019.

(51) Int. Cl.
*C07K 16/28*        (2006.01)

(52) U.S. Cl.
CPC ...... *C07K 16/2809* (2013.01); *C07K 2317/31*
(2013.01); *C07K 2317/35* (2013.01); *C07K
2317/526* (2013.01); *C07K 2317/55* (2013.01);
*C07K 2317/565* (2013.01); *C07K 2317/622*
(2013.01); *C07K 2317/624* (2013.01); *C07K
2317/64* (2013.01); *C07K 2317/73* (2013.01);
*C07K 2317/77* (2013.01); *C07K 2317/92*
(2013.01)

(58) Field of Classification Search
None
See application file for complete search history.

(56) References Cited

U.S. PATENT DOCUMENTS

| | | | |
|---|---|---|---|
| 7,635,475 B2 | 12/2009 | Kumagai | |
| 2015/0133640 A1* | 5/2015 | Blein ................. | C07K 16/2863 |
| | | | 435/69.6 |
| 2015/0232569 A1* | 8/2015 | Kipps ................. | C07K 14/435 |
| | | | 424/139.1 |
| 2016/0297881 A1 | 10/2016 | Vu | |

| | | | |
|---|---|---|---|
| 2017/0210799 A1 | 7/2017 | Anderson | |
| 2017/0210819 A1* | 7/2017 | Cheung ................. | C07K 16/32 |
| 2017/0233472 A1 | 8/2017 | Barat et al. | |
| 2018/0369406 A1 | 12/2018 | Lannutti et al. | |
| 2023/0021388 A1* | 1/2023 | Watkins ............. | A61K 47/6879 |

FOREIGN PATENT DOCUMENTS

| | | | |
|---|---|---|---|
| WO | 2014031174 A1 | 2/2014 | |
| WO | 2014163684 A1 | 10/2014 | |
| WO | WO-2015063339 A1 * | 5/2015 | ......... C07K 16/2887 |
| WO | WO-2016055592 A1 * | 4/2016 | ............. A61P 35/00 |
| WO | 2016071355 A1 | 5/2016 | |
| WO | 2016180721 A1 | 11/2016 | |
| WO | 2017125897 A1 | 7/2017 | |
| WO | 2017127499 A1 | 7/2017 | |
| WO | WO-2018140831 A2 * | 8/2018 | ............. A61P 37/04 |
| WO | 2019008379 A1 | 1/2019 | |
| WO | 2019084060 A1 | 5/2019 | |

OTHER PUBLICATIONS

Janeway, et al., Immunobiology: The Immune System in Health and
Disease, 5th edition, 2001 (Year: 2001).*
Rudikoff, et al., PNAS, 1982, 79, p. 1979-1983 (Year: 1982).*
Brinkmann, et. al., MABS, 2017, 9, 182-212 (Year: 2017).*
Brinkmann, Ulrich et al., The making of bispecific antibodies,
mAbs, 2017, 182-212, 9.
Choi, Michael Y. et al., Phase I Trial: Cirmtuzumab Inhibits ROR1
Signaling and Stemness Signatures in Patients with Chronic
Lymphocytic Leukemia, Cell Stem Cell, 2018, 951-959, 22.
Daneshmanesh, Amir Hossein et al., Orphan receptor tyrosine
kinases ROR1 and ROR2 in hematological malignancies, Leukemia
& Lymphoma, 2013, 843-850, 54(4).
Dave, Hema et al., Restricted Cell Surface Expression of Receptor
Tyrosine Kinase ROR1 in Pediatric B-Lineage Acute Lymphoblastic
Leukemia Suggests Targetability with Therapeutic Monoclonal Anti-
bodies, PLoS One, 2012, 1-12, 7(12): e52655.
Gohil, Satyen Harish et al., An ROR1 bi-specific T-cell engager
provides effective targeting and cytotoxicity against a range of solid
tumors, OncoImmunology, 2017, e1326437 (pp. 1-11), 6:7.
Qi, Junpeng et al., Potent and selective antitumor activity of a T
cell—engaging bispecific antibody targeting a membrane-proximal
epitope of ROR1, Proceedings of the National Academy of Sci-
ences, 2018, E5467-E5476, 115 (24).
Tunnacliffe, Alan et al., The majority of human CD3 epitopes are
conferred by the epsilon chain, International Immunology, 1989,
546-550, 1(5).
Zhang, Suping et al., The onco-embryonic antigen ROR1 is expressed
by a variety of human cancer, The American Journal of Pathology,
2018, 1903-1910, 181(6).
Lu, Dan et al., Acquired antagonistic activity of a bispecific diabody
directed against two different epitopes on vascular endothelial
growth factor receptor 2, Journal of Immunological Methods, 1999,
159-171, 230.

(Continued)

*Primary Examiner* — Misook Yu
*Assistant Examiner* — Samantha Lake Hopkins
(74) *Attorney, Agent, or Firm* — Tamaria Dewdney;
Andrew W. Cuister

(57)        ABSTRACT

This invention relates to bispecific binding molecules that
bind to ROR1 and CD3, and methods of using them to treat
diseases and conditions such as cancer.

8 Claims, 29 Drawing Sheets

Specification includes a Sequence Listing.

(56) References Cited

OTHER PUBLICATIONS

Barat, Bhaswati et al., Abstract 1489: Development of a humanized ROR1 x CD3bispecific DART® molecule for the treatment of solid andliquid tumors, Cancer Res, 76 (14 Supplement): 1489, 1-4, 2016.

Belikov, V.G., Pharmaceutical Chemistry, Moscow MEDpress-inform, 4th Edition, 27-29, 2007.

Chen, Xiaoying et al., Fusion Protein Linkers: Property, Design and Functionality, Adv. Drug Deliv. Rev., 65, 1357-1369, 2013.

Dyson, G. and May, P., Chemistry of Synthetic Medicinal Substances, M: World, N/A, 12-19, 1964.

Gohil, Satyen et al., Preclinical development of novel humanised ROR1 targeting chimeric antigen receptor T cells and bispecific T-cell engagers, Poster Abstracts, 389, 40, 2017.

Liu, Jia et al., Cell-Penetrating Peptide-Mediated Delivery of TALEN Proteins via Bioconjugation for Genome Engineering, PLoS ONE, 9(1): e85755, 1-7, 2014.

Zhao, Ming et al., Intracellular Cargo Delivery Using Tat Peptide and Derivatives, Med Res Rev, 24(1), 1-12, 2004.

* cited by examiner

A    B    C    D    E

A

B

A

B

A

B

C

A

B

A

B

C

A

B

A

B

C

A

B

A

B

A

B

A

B

A

B

A

B

A

B

A

B

A

B

A

B

C

A

B

C

A

B

C

A

B

C

A

B

C

A

B

C

| | Antibody | H-CDR1 | H-CDR2 | H-CDR3 | L-CDR1 | L-CDR2 | L-CDR3 | VH | VL | D-VH* | D-VL* | LC | HC | HC (LALAGA) | K-HC+ | H-HC# | H-HC^ |
|---|---|---|---|---|---|---|---|---|---|---|---|---|---|---|---|---|---|
| ROR1 | Ab1 | 60 | 61 | 62 | 63 | 64 | 65 | 72 | 73 | -- | -- | 83 | 82 | 7 | 86 | 106 | 109 |
| | Ab2 (T32A) | 97 | 61 | 62 | 63 | 64 | 65 | 74 | 73 | -- | -- | 83 | 84 | 14 | 87 | 107 | 109 |
| | Ab3 (T32E) | 98 | 61 | 62 | 63 | 64 | 65 | 75 | 73 | -- | -- | 83 | 85 | 105 | 88 | 108 | 109 |
| | Ab4 (A25P) | 60 | 61 | 62 | 99 | 64 | 65 | 72 | 100 | -- | -- | 101 | 82 | 7 | 86 | 106 | 109 |
| | Ab5 (T69R) | 60 | 61 | 62 | 63 | 102 | 65 | 72 | 103 | -- | -- | 104 | 82 | 7 | 86 | 106 | 109 |
| | Ab6 (T32A+A25P) | 97 | 61 | 62 | 99 | 64 | 65 | 74 | 100 | -- | -- | 101 | 84 | 14 | 87 | 107 | 109 |
| | Ab7 (T32A+T69R) | 97 | 61 | 62 | 63 | 102 | 65 | 74 | 103 | -- | -- | 104 | 84 | 14 | 87 | 107 | 109 |
| CD3 | Ab8 (OKT3(1)) | 47 | 48 | 49 | 50 | 51 | 52 | 66 | 67 | 76 | 77 | -- | -- | -- | -- | -- | -- |
| | Ab9 (OKT3(2)) | 47 | 53 | 49 | 50 | 51 | 52 | 68 | 69 | 78 | 79 | -- | -- | -- | -- | -- | -- |
| | Ab10 (SP34) | 54 | 55 | 56 | 57 | 58 | 59 | 70 | 71 | 80 | 81 | -- | -- | -- | -- | -- | -- |

* D-VH and D-VL: disulfide-stabilized variants
+ K-HC: "knobs" variant of heavy chain
H-HC: "holes" variant of heavy chain for configuration D
^ H-HC: "holes" variant of heavy chain for configuration C

FIG. 29

SEQUENCE LISTING

<160> NUMBER OF SEQ ID NOS: 114

<210> SEQ ID NO 1
<211> LENGTH: 701
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic polypeptide"

<400> SEQUENCE: 1

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ala Phe Thr Ala Tyr
            20                  25                  30

Asn Ile His Trp Val Arg Gln Ala Pro Gly Gln Gly Leu Glu Trp Met
        35                  40                  45

Gly Ser Phe Asp Pro Tyr Asp Gly Gly Ser Ser Tyr Asn Gln Lys Phe
    50                  55                  60

Lys Asp Arg Leu Thr Ile Ser Lys Asp Thr Ser Lys Asn Gln Val Val
65                  70                  75                  80

Leu Thr Met Thr Asn Met Asp Pro Val Asp Thr Ala Thr Tyr Tyr Cys
                85                  90                  95

Ala Arg Gly Trp Tyr Tyr Phe Asp Tyr Trp Gly His Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
        210                 215                 220

Cys Pro Pro Cys Pro Ala Pro Glu Ala Ala Gly Ala Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
    370                 375                 380
```

-continued

```
Gln Pro Glu Asn Asn Tyr Lys Thr Thr Pro Pro Val Leu Asp Ser Asp
385                 390             395                 400

Gly Ser Phe Phe Leu Tyr Ser Lys Leu Thr Val Asp Lys Ser Arg Trp
            405             410             415

Gln Gln Gly Asn Val Phe Ser Cys Ser Val Met His Glu Ala Leu His
            420             425             430

Asn His Tyr Thr Gln Lys Ser Leu Ser Leu Ser Pro Gly Lys Gly Gly
        435             440             445

Gly Gly Ser Gly Gly Gly Gly Ser Gln Val Gln Leu Val Gln Ser Gly
    450             455             460

Gly Gly Val Val Gln Pro Gly Arg Ser Leu Arg Leu Ser Cys Lys Ala
465             470             475                 480

Ser Gly Tyr Thr Phe Thr Arg Tyr Thr Met His Trp Val Arg Gln Ala
            485             490             495

Pro Gly Lys Gly Leu Glu Trp Ile Gly Tyr Ile Asn Pro Ser Arg Gly
            500             505             510

Tyr Thr Asn Tyr Asn Gln Lys Val Lys Asp Arg Phe Thr Ile Ser Arg
        515             520             525

Asp Asn Ser Lys Asn Thr Leu Tyr Leu Gln Met Asp Ser Leu Arg Ala
        530             535             540

Glu Asp Thr Ala Val Tyr Tyr Cys Ala Arg Tyr Tyr Asp Asp His Tyr
545             550             555                 560

Ser Leu Asp Tyr Trp Gly Gln Gly Thr Thr Val Thr Val Ser Ser Gly
            565             570             575

Gly Gly Gly Ser Gly Gly Gly Gly Ser Gly Gly Gly Gly Ser Gly Gly
            580             585             590

Gly Gly Ser Asp Ile Gln Met Thr Gln Ser Pro Ser Ser Leu Ser Ala
        595             600             605

Ser Val Gly Asp Arg Val Thr Ile Thr Cys Ser Ala Ser Ser Ser Val
        610             615             620

Ser Tyr Met Asn Trp Tyr Gln Gln Lys Pro Gly Lys Ala Pro Lys Arg
625             630             635                 640

Trp Ile Tyr Asp Thr Ser Lys Leu Ala Ser Gly Val Pro Ser Arg Phe
            645             650             655

Ser Gly Ser Gly Ser Gly Thr Asp Phe Thr Phe Thr Ile Ser Ser Leu
            660             665             670

Gln Pro Glu Asp Ile Ala Thr Tyr Tyr Cys Gln Gln Trp Ser Ser Asn
        675             680             685

Pro Phe Thr Phe Gly Gln Gly Thr Lys Leu Glu Ile Lys
    690             695             700
```

```
<210> SEQ ID NO 2
<211> LENGTH: 701
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Gln Val Gln Leu Gln Glu Ser Gly Pro Gly Leu Val Lys Pro Ser Gln
1               5               10              15

Thr Leu Ser Leu Thr Cys Thr Val Ser Gly Tyr Ala Phe Thr Ala Tyr
            20              25              30
```

-continued

```
Asn Ile His Trp Val Arg Gln Ala Pro Gly Gln Gly Leu Glu Trp Met
        35                  40                  45

Gly Ser Phe Asp Pro Tyr Asp Gly Gly Ser Ser Tyr Asn Gln Lys Phe
        50                  55                  60

Lys Asp Arg Leu Thr Ile Ser Lys Asp Thr Ser Lys Asn Gln Val Val
65                  70                  75                  80

Leu Thr Met Thr Asn Met Asp Pro Val Asp Thr Ala Thr Tyr Tyr Cys
                85                  90                  95

Ala Arg Gly Trp Tyr Tyr Phe Asp Tyr Trp Gly His Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
        210                 215                 220

Cys Pro Pro Cys Pro Ala Pro Glu Ala Ala Gly Ala Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys Gly Gly
        435                 440                 445
```

-continued

```
Gly Gly Ser Gly Gly Gly Gly Ser Gln Val Gln Leu Val Gln Ser Gly
    450             455                 460

Ala Glu Val Lys Lys Pro Gly Ala Ser Val Lys Val Ser Cys Lys Ala
465             470              475                 480

Ser Gly Tyr Thr Phe Thr Arg Tyr Thr Met His Trp Val Arg Gln Ala
                485             490              495

Pro Gly Gln Gly Leu Glu Trp Met Gly Tyr Ile Asn Pro Ser Arg Gly
                500             505              510

Tyr Thr Asn Tyr Asn Gln Lys Phe Lys Asp Arg Val Thr Leu Thr Thr
                515             520              525

Asp Lys Ser Ser Ser Thr Ala Tyr Met Glu Leu Ser Ser Leu Arg Ser
    530             535              540

Glu Asp Thr Ala Val Tyr Tyr Cys Ala Arg Tyr Tyr Asp Asp His Tyr
545             550              555                 560

Ser Leu Asp Tyr Trp Gly Gln Gly Thr Leu Val Thr Val Ser Ser Gly
                565             570              575

Gly Gly Gly Ser Gly Gly Gly Gly Ser Gly Gly Gly Gly Ser Gly Gly
                580             585              590

Gly Gly Ser Asp Ile Gln Met Thr Gln Ser Pro Ser Ser Leu Ser Ala
    595             600              605

Ser Val Gly Asp Arg Val Thr Ile Thr Cys Ser Ala Ser Ser Ser Val
    610             615              620

Ser Tyr Met Asn Trp Tyr Gln Gln Lys Pro Gly Lys Ala Pro Lys Arg
625             630              635                 640

Leu Ile Tyr Asp Thr Ser Lys Leu Ala Ser Gly Val Pro Ser Arg Phe
                645             650              655

Ser Gly Ser Gly Ser Gly Thr Asp Phe Thr Leu Thr Ile Ser Ser Leu
                660             665              670

Gln Pro Glu Asp Phe Ala Thr Tyr Tyr Cys Gln Gln Trp Ser Ser Asn
                675             680              685

Pro Phe Thr Phe Gly Gln Gly Thr Lys Leu Glu Ile Lys
    690             695              700

<210> SEQ ID NO 3
<211> LENGTH: 711
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ala Phe Thr Ala Tyr
                20                  25                  30

Asn Ile His Trp Val Arg Gln Ala Pro Gly Gln Gly Leu Glu Trp Met
        35                  40                  45

Gly Ser Phe Asp Pro Tyr Asp Gly Gly Ser Ser Tyr Asn Gln Lys Phe
    50                  55                  60

Lys Asp Arg Leu Thr Ile Ser Lys Asp Thr Ser Lys Asn Gln Val Val
65                  70                  75                  80

Leu Thr Met Thr Asn Met Asp Pro Val Asp Thr Ala Thr Tyr Tyr Cys
                85                  90                  95
```

-continued

```
Ala Arg Gly Trp Tyr Tyr Phe Asp Tyr Trp Gly His Gly Thr Leu Val
            100             105             110

Thr Val Ser Ser Ala Ser Thr Lys Gly Pro Ser Val Phe Pro Leu Ala
            115             120             125

Pro Ser Ser Lys Ser Thr Ser Gly Gly Thr Ala Ala Leu Gly Cys Leu
    130             135             140

Val Lys Asp Tyr Phe Pro Glu Pro Val Thr Val Ser Trp Asn Ser Gly
145             150             155             160

Ala Leu Thr Ser Gly Val His Thr Phe Pro Ala Val Leu Gln Ser Ser
            165             170             175

Gly Leu Tyr Ser Leu Ser Ser Val Val Thr Val Pro Ser Ser Ser Leu
            180             185             190

Gly Thr Gln Thr Tyr Ile Cys Asn Val Asn His Lys Pro Ser Asn Thr
            195             200             205

Lys Val Asp Lys Lys Val Glu Pro Lys Ser Cys Asp Lys Thr His Thr
    210             215             220

Cys Pro Pro Cys Pro Ala Pro Glu Ala Ala Gly Ala Pro Ser Val Phe
225             230             235             240

Leu Phe Pro Pro Lys Pro Lys Asp Thr Leu Met Ile Ser Arg Thr Pro
            245             250             255

Glu Val Thr Cys Val Val Val Asp Val Ser His Glu Asp Pro Glu Val
            260             265             270

Lys Phe Asn Trp Tyr Val Asp Gly Val Glu Val His Asn Ala Lys Thr
            275             280             285

Lys Pro Arg Glu Glu Gln Tyr Asn Ser Thr Tyr Arg Val Val Ser Val
    290             295             300

Leu Thr Val Leu His Gln Asp Trp Leu Asn Gly Lys Glu Tyr Lys Cys
305             310             315             320

Lys Val Ser Asn Lys Ala Leu Pro Ala Pro Ile Glu Lys Thr Ile Ser
            325             330             335

Lys Ala Lys Gly Gln Pro Arg Glu Pro Gln Val Tyr Thr Leu Pro Pro
            340             345             350

Ser Arg Asp Glu Leu Thr Lys Asn Gln Val Ser Leu Thr Cys Leu Val
            355             360             365

Lys Gly Phe Tyr Pro Ser Asp Ile Ala Val Glu Trp Glu Ser Asn Gly
    370             375             380

Gln Pro Glu Asn Asn Tyr Lys Thr Thr Pro Pro Val Leu Asp Ser Asp
385             390             395             400

Gly Ser Phe Phe Leu Tyr Ser Lys Leu Thr Val Asp Lys Ser Arg Trp
            405             410             415

Gln Gln Gly Asn Val Phe Ser Cys Ser Val Met His Glu Ala Leu His
            420             425             430

Asn His Tyr Thr Gln Lys Ser Leu Ser Leu Ser Pro Gly Lys Gly Gly
            435             440             445

Gly Gly Ser Gly Gly Gly Gly Ser Glu Val Gln Leu Val Glu Ser Gly
            450             455             460

Gly Gly Leu Val Gln Pro Gly Gly Ser Leu Arg Leu Ser Cys Ala Ala
465             470             475             480

Ser Gly Phe Thr Phe Asn Thr Tyr Ala Met Asn Trp Val Arg Gln Ala
            485             490             495

Pro Gly Lys Gly Leu Glu Trp Val Ala Arg Ile Arg Ser Lys Tyr Asn
            500             505             510
```

-continued

```
Asn Tyr Ala Thr Tyr Tyr Ala Asp Ser Val Lys Gly Arg Phe Thr Ile
        515                 520                 525

Ser Arg Asp Asp Ser Lys Asn Thr Leu Tyr Leu Gln Met Asn Ser Leu
    530                 535                 540

Arg Ala Glu Asp Thr Ala Val Tyr Tyr Cys Val Arg His Gly Asn Phe
545                 550                 555                 560

Gly Asn Ser Tyr Val Ser Tyr Phe Ala Tyr Trp Gly Gln Gly Thr Thr
                565                 570                 575

Val Thr Val Ser Ser Gly Gly Gly Ser Gly Gly Gly Gly Ser Gly
                580                 585                 590

Gly Gly Gly Ser Gly Gly Gly Gly Ser Glu Ile Val Val Thr Gln Ser
                595                 600                 605

Pro Ala Thr Leu Ser Val Ser Pro Gly Glu Arg Ala Thr Leu Ser Cys
        610                 615                 620

Arg Ser Ser Thr Gly Ala Val Thr Ala Ala Asn Tyr Ala Asn Trp Val
625                 630                 635                 640

Gln Glu Lys Pro Gly Gln Ala Phe Arg Gly Leu Ile Gly Gly Ala Asn
                645                 650                 655

Lys Arg Ala Pro Gly Val Pro Ala Arg Phe Ser Gly Ser Leu Ser Gly
                660                 665                 670

Asp Glu Ala Thr Leu Thr Ile Ser Ser Leu Gln Ser Glu Asp Phe Ala
        675                 680                 685

Val Tyr Tyr Cys Ala Leu Phe Tyr Ser Asn Leu Trp Val Phe Gly Gln
        690                 695                 700

Gly Thr Lys Leu Glu Ile Lys
705                 710
```

```
<210> SEQ ID NO 4
<211> LENGTH: 701
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ala Phe Thr Ala Tyr
                20                  25                  30

Asn Ile His Trp Val Arg Gln Ala Pro Gly Gln Gly Leu Glu Trp Met
        35                  40                  45

Gly Ser Phe Asp Pro Tyr Asp Gly Gly Ser Ser Tyr Asn Gln Lys Phe
        50                  55                  60

Lys Asp Arg Leu Thr Ile Ser Lys Asp Thr Ser Lys Asn Gln Val Val
65                  70                  75                  80

Leu Thr Met Thr Asn Met Asp Pro Val Asp Thr Ala Thr Tyr Tyr Cys
                85                  90                  95

Ala Arg Gly Trp Tyr Tyr Phe Asp Tyr Trp Gly His Gly Thr Leu Val
                100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
        130                 135                 140
```

-continued

```
Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
                195                 200                 205

Lys Val Asp Lys Lys Val Glu Pro Lys Ser Cys Asp Lys Thr His Thr
        210                 215                 220

Cys Pro Pro Cys Pro Ala Pro Glu Ala Ala Gly Ala Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
                275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Asp Glu Leu Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys Gly Gly
                435                 440                 445

Gly Gly Ser Gly Gly Gly Gly Ser Gln Val Gln Leu Val Gln Ser Gly
        450                 455                 460

Gly Gly Val Val Gln Pro Gly Arg Ser Leu Arg Leu Ser Cys Lys Ala
465                 470                 475                 480

Ser Gly Tyr Thr Phe Thr Arg Tyr Thr Met His Trp Val Arg Gln Ala
                485                 490                 495

Pro Gly Lys Cys Leu Glu Trp Ile Gly Tyr Ile Asn Pro Ser Arg Gly
                500                 505                 510

Tyr Thr Asn Tyr Asn Gln Lys Val Lys Asp Arg Phe Thr Ile Ser Arg
                515                 520                 525

Asp Asn Ser Lys Asn Thr Leu Tyr Leu Gln Met Asp Ser Leu Arg Ala
        530                 535                 540

Glu Asp Thr Ala Val Tyr Tyr Cys Ala Arg Tyr Tyr Asp Asp His Tyr
545                 550                 555                 560
```

-continued

```
Ser Leu Asp Tyr Trp Gly Gln Gly Thr Thr Val Thr Val Ser Ser Gly
                565             570             575

Gly Gly Gly Ser Gly Gly Gly Gly Ser Gly Gly Gly Gly Ser Gly Gly
            580             585             590

Gly Gly Ser Asp Ile Gln Met Thr Gln Ser Pro Ser Ser Leu Ser Ala
        595             600             605

Ser Val Gly Asp Arg Val Thr Ile Thr Cys Ser Ala Ser Ser Ser Val
    610             615             620

Ser Tyr Met Asn Trp Tyr Gln Gln Lys Pro Gly Lys Ala Pro Lys Arg
625             630             635             640

Trp Ile Tyr Asp Thr Ser Lys Leu Ala Ser Gly Val Pro Ser Arg Phe
            645             650             655

Ser Gly Ser Gly Ser Gly Thr Asp Phe Thr Phe Thr Ile Ser Ser Leu
            660             665             670

Gln Pro Glu Asp Ile Ala Thr Tyr Tyr Cys Gln Gln Trp Ser Ser Asn
        675             680             685

Pro Phe Thr Phe Gly Cys Gly Thr Lys Leu Glu Ile Lys
    690             695             700
```

```
<210> SEQ ID NO 5
<211> LENGTH: 701
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5
```

```
Gln Val Gln Leu Gln Glu Ser Gly Pro Gly Leu Val Lys Pro Ser Gln
1               5               10              15

Thr Leu Ser Leu Thr Cys Thr Val Ser Gly Tyr Ala Phe Thr Ala Tyr
            20              25              30

Asn Ile His Trp Val Arg Gln Ala Pro Gly Gln Gly Leu Glu Trp Met
        35              40              45

Gly Ser Phe Asp Pro Tyr Asp Gly Gly Ser Ser Tyr Asn Gln Lys Phe
    50              55              60

Lys Asp Arg Leu Thr Ile Ser Lys Asp Thr Ser Lys Asn Gln Val Val
65              70              75              80

Leu Thr Met Thr Asn Met Asp Pro Val Asp Thr Ala Thr Tyr Tyr Cys
            85              90              95

Ala Arg Gly Trp Tyr Tyr Phe Asp Tyr Trp Gly His Gly Thr Leu Val
            100             105             110

Thr Val Ser Ser Ala Ser Thr Lys Gly Pro Ser Val Phe Pro Leu Ala
            115             120             125

Pro Ser Ser Lys Ser Thr Ser Gly Gly Thr Ala Ala Leu Gly Cys Leu
        130             135             140

Val Lys Asp Tyr Phe Pro Glu Pro Val Thr Val Ser Trp Asn Ser Gly
145             150             155             160

Ala Leu Thr Ser Gly Val His Thr Phe Pro Ala Val Leu Gln Ser Ser
            165             170             175

Gly Leu Tyr Ser Leu Ser Ser Val Val Thr Val Pro Ser Ser Ser Leu
            180             185             190

Gly Thr Gln Thr Tyr Ile Cys Asn Val Asn His Lys Pro Ser Asn Thr
        195             200             205
```

-continued

```
Lys Val Asp Lys Lys Val Glu Pro Lys Ser Cys Asp Lys Thr His Thr
    210             215                 220

Cys Pro Pro Cys Pro Ala Pro Glu Ala Ala Gly Ala Pro Ser Val Phe
225             230                 235             240

Leu Phe Pro Pro Lys Pro Lys Asp Thr Leu Met Ile Ser Arg Thr Pro
            245             250                 255

Glu Val Thr Cys Val Val Val Asp Val Ser His Glu Asp Pro Glu Val
            260             265                 270

Lys Phe Asn Trp Tyr Val Asp Gly Val Glu Val His Asn Ala Lys Thr
        275             280                 285

Lys Pro Arg Glu Glu Gln Tyr Asn Ser Thr Tyr Arg Val Val Ser Val
    290             295                 300

Leu Thr Val Leu His Gln Asp Trp Leu Asn Gly Lys Glu Tyr Lys Cys
305             310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
            340             345                 350

Ser Arg Asp Glu Leu Thr Lys Asn Gln Val Ser Leu Thr Cys Leu Val
            355             360                 365

Lys Gly Phe Tyr Pro Ser Asp Ile Ala Val Glu Trp Glu Ser Asn Gly
    370             375                 380

Gln Pro Glu Asn Asn Tyr Lys Thr Thr Pro Pro Val Leu Asp Ser Asp
385             390                 395                 400

Gly Ser Phe Phe Leu Tyr Ser Lys Leu Thr Val Asp Lys Ser Arg Trp
            405             410                 415

Gln Gln Gly Asn Val Phe Ser Cys Ser Val Met His Glu Ala Leu His
            420             425                 430

Asn His Tyr Thr Gln Lys Ser Leu Ser Leu Ser Pro Gly Lys Gly Gly
        435             440                 445

Gly Gly Ser Gly Gly Gly Gly Ser Gln Val Gln Leu Val Gln Ser Gly
    450             455                 460

Ala Glu Val Lys Lys Pro Gly Ala Ser Val Lys Val Ser Cys Lys Ala
465             470                 475                 480

Ser Gly Tyr Thr Phe Thr Arg Tyr Thr Met His Trp Val Arg Gln Ala
            485             490                 495

Pro Gly Gln Cys Leu Glu Trp Met Gly Tyr Ile Asn Pro Ser Arg Gly
            500             505                 510

Tyr Thr Asn Tyr Asn Gln Lys Phe Lys Asp Arg Val Thr Leu Thr Thr
        515             520                 525

Asp Lys Ser Ser Ser Thr Ala Tyr Met Glu Leu Ser Ser Leu Arg Ser
    530             535                 540

Glu Asp Thr Ala Val Tyr Tyr Cys Ala Arg Tyr Tyr Asp Asp His Tyr
545             550                 555             560

Ser Leu Asp Tyr Trp Gly Gln Gly Thr Leu Val Thr Val Ser Ser Gly
            565             570                 575

Gly Gly Gly Ser Gly Gly Gly Gly Ser Gly Gly Gly Gly Ser Gly Gly
            580             585                 590

Gly Gly Ser Asp Ile Gln Met Thr Gln Ser Pro Ser Ser Leu Ser Ala
        595             600                 605

Ser Val Gly Asp Arg Val Thr Ile Thr Cys Ser Ala Ser Ser Ser Val
    610             615                 620
```

-continued

```
Ser Tyr Met Asn Trp Tyr Gln Gln Lys Pro Gly Lys Ala Pro Lys Arg
625             630             635             640

Leu Ile Tyr Asp Thr Ser Lys Leu Ala Ser Gly Val Pro Ser Arg Phe
            645             650             655

Ser Gly Ser Gly Ser Gly Thr Asp Phe Thr Leu Thr Ile Ser Ser Leu
            660             665             670

Gln Pro Glu Asp Phe Ala Thr Tyr Tyr Cys Gln Gln Trp Ser Ser Asn
        675             680             685

Pro Phe Thr Phe Gly Cys Gly Thr Lys Leu Glu Ile Lys
    690             695             700

<210> SEQ ID NO 6
<211> LENGTH: 711
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Gln Val Gln Leu Gln Glu Ser Gly Pro Gly Leu Val Lys Pro Ser Gln
1               5               10              15

Thr Leu Ser Leu Thr Cys Thr Val Ser Gly Tyr Ala Phe Thr Ala Tyr
            20              25              30

Asn Ile His Trp Val Arg Gln Ala Pro Gly Gln Gly Leu Glu Trp Met
        35              40              45

Gly Ser Phe Asp Pro Tyr Asp Gly Gly Ser Ser Tyr Asn Gln Lys Phe
    50              55              60

Lys Asp Arg Leu Thr Ile Ser Lys Asp Thr Ser Lys Asn Gln Val Val
65              70              75              80

Leu Thr Met Thr Asn Met Asp Pro Val Asp Thr Ala Thr Tyr Tyr Cys
            85              90              95

Ala Arg Gly Trp Tyr Tyr Phe Asp Tyr Trp Gly His Gly Thr Leu Val
            100             105             110

Thr Val Ser Ser Ala Ser Thr Lys Gly Pro Ser Val Phe Pro Leu Ala
        115             120             125

Pro Ser Ser Lys Ser Thr Ser Gly Gly Thr Ala Ala Leu Gly Cys Leu
    130             135             140

Val Lys Asp Tyr Phe Pro Glu Pro Val Thr Val Ser Trp Asn Ser Gly
145             150             155             160

Ala Leu Thr Ser Gly Val His Thr Phe Pro Ala Val Leu Gln Ser Ser
            165             170             175

Gly Leu Tyr Ser Leu Ser Ser Val Val Thr Val Pro Ser Ser Ser Leu
            180             185             190

Gly Thr Gln Thr Tyr Ile Cys Asn Val Asn His Lys Pro Ser Asn Thr
        195             200             205

Lys Val Asp Lys Lys Val Glu Pro Lys Ser Cys Asp Lys Thr His Thr
    210             215             220

Cys Pro Pro Cys Pro Ala Pro Glu Ala Ala Gly Ala Pro Ser Val Phe
225             230             235             240

Leu Phe Pro Pro Lys Pro Lys Asp Thr Leu Met Ile Ser Arg Thr Pro
            245             250             255

Glu Val Thr Cys Val Val Val Asp Val Ser His Glu Asp Pro Glu Val
            260             265             270
```

-continued

```
Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Asp Glu Leu Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys Gly Gly
                435                 440                 445

Gly Gly Ser Gly Gly Gly Gly Ser Glu Val Gln Leu Val Glu Ser Gly
    450                 455                 460

Gly Gly Leu Val Gln Pro Gly Gly Ser Leu Arg Leu Ser Cys Ala Ala
465                 470                 475                 480

Ser Gly Phe Thr Phe Asn Thr Tyr Ala Met Asn Trp Val Arg Gln Ala
                485                 490                 495

Pro Gly Lys Cys Leu Glu Trp Val Ala Arg Ile Arg Ser Lys Tyr Asn
                500                 505                 510

Asn Tyr Ala Thr Tyr Tyr Ala Asp Ser Val Lys Gly Arg Phe Thr Ile
                515                 520                 525

Ser Arg Asp Asp Ser Lys Asn Thr Leu Tyr Leu Gln Met Asn Ser Leu
    530                 535                 540

Arg Ala Glu Asp Thr Ala Val Tyr Tyr Cys Val Arg His Gly Asn Phe
545                 550                 555                 560

Gly Asn Ser Tyr Val Ser Tyr Phe Ala Tyr Trp Gly Gln Gly Thr Thr
                565                 570                 575

Val Thr Val Ser Ser Gly Gly Gly Ser Gly Gly Gly Gly Ser Gly
                580                 585                 590

Gly Gly Gly Ser Gly Gly Gly Gly Ser Glu Ile Val Val Thr Gln Ser
                595                 600                 605

Pro Ala Thr Leu Ser Val Ser Pro Gly Glu Arg Ala Thr Leu Ser Cys
    610                 615                 620

Arg Ser Ser Thr Gly Ala Val Thr Ala Ala Asn Tyr Ala Asn Trp Val
625                 630                 635                 640

Gln Glu Lys Pro Gly Gln Ala Phe Arg Gly Leu Ile Gly Gly Ala Asn
                645                 650                 655

Lys Arg Ala Pro Gly Val Pro Ala Arg Phe Ser Gly Ser Leu Ser Gly
                660                 665                 670

Asp Glu Ala Thr Leu Thr Ile Ser Ser Leu Gln Ser Glu Asp Phe Ala
                675                 680                 685
```

-continued

```
Val Tyr Tyr Cys Ala Leu Phe Tyr Ser Asn Leu Trp Val Phe Gly Cys
    690                     695                 700

Gly Thr Lys Leu Glu Ile Lys
705                 710

<210> SEQ ID NO 7
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ala Phe Thr Ala Tyr
            20                  25                  30

Asn Ile His Trp Val Arg Gln Ala Pro Gly Gln Gly Leu Glu Trp Met
        35                  40                  45

Gly Ser Phe Asp Pro Tyr Asp Gly Gly Ser Ser Tyr Asn Gln Lys Phe
    50                  55                  60

Lys Asp Arg Leu Thr Ile Ser Lys Asp Thr Ser Lys Asn Gln Val Val
65                  70                  75                  80

Leu Thr Met Thr Asn Met Asp Pro Val Asp Thr Ala Thr Tyr Tyr Cys
                85                  90                  95

Ala Arg Gly Trp Tyr Tyr Phe Asp Tyr Trp Gly His Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Ala Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320
```

```
Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Asp Glu Leu Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
        435                 440                 445
```

<210> SEQ ID NO 8
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ala Phe Thr Ala Tyr
                20                  25                  30

Asn Ile His Trp Val Arg Gln Ala Pro Gly Gln Gly Leu Glu Trp Met
        35                  40                  45

Gly Ser Phe Asp Pro Tyr Asp Gly Gly Ser Ser Tyr Asn Gln Lys Phe
    50                  55                  60

Lys Asp Arg Leu Thr Ile Ser Lys Asp Thr Ser Lys Asn Gln Val Val
65                  70                  75                  80

Leu Thr Met Thr Asn Met Asp Pro Val Asp Thr Ala Thr Tyr Tyr Cys
                85                  90                  95

Ala Arg Gly Trp Tyr Tyr Phe Asp Tyr Trp Gly His Gly Thr Leu Val
                100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
        180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220
```

-continued

```
Cys Pro Pro Cys Pro Ala Pro Glu Ala Ala Gly Ala Pro Ser Val Phe
225             230             235             240

Leu Phe Pro Pro Lys Pro Lys Asp Thr Leu Met Ile Ser Arg Thr Pro
            245             250             255

Glu Val Thr Cys Val Val Val Asp Val Ser His Glu Asp Pro Glu Val
            260             265             270

Lys Phe Asn Trp Tyr Val Asp Gly Val Glu Val His Asn Ala Lys Thr
        275             280             285

Lys Pro Arg Glu Glu Gln Tyr Asn Ser Thr Tyr Arg Val Val Ser Val
    290             295             300

Leu Thr Val Leu His Gln Asp Trp Leu Asn Gly Lys Glu Tyr Lys Cys
305             310             315             320

Lys Val Ser Asn Lys Ala Leu Pro Ala Pro Ile Glu Lys Thr Ile Ser
            325             330             335

Lys Ala Lys Gly Gln Pro Arg Glu Pro Gln Val Tyr Thr Leu Pro Pro
            340             345             350

Ser Arg Asp Glu Leu Thr Lys Asn Gln Val Ser Leu Trp Cys Leu Val
            355             360             365

Lys Gly Phe Tyr Pro Ser Asp Ile Ala Val Glu Trp Glu Ser Asn Gly
    370             375             380

Gln Pro Glu Asn Asn Tyr Lys Thr Thr Pro Pro Val Leu Asp Ser Asp
385             390             395             400

Gly Ser Phe Phe Leu Tyr Ser Lys Leu Thr Val Asp Lys Ser Arg Trp
            405             410             415

Gln Gln Gly Asn Val Phe Ser Cys Ser Val Met His Glu Ala Leu His
            420             425             430

Asn His Tyr Thr Gln Lys Ser Leu Ser Leu Ser Pro Gly Lys
            435             440             445

<210> SEQ ID NO 9
<211> LENGTH: 477
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Gln Val Gln Leu Val Gln Ser Gly Gly Gly Val Val Gln Pro Gly Arg
1               5               10              15

Ser Leu Arg Leu Ser Cys Lys Ala Ser Gly Tyr Thr Phe Thr Arg Tyr
            20              25              30

Thr Met His Trp Val Arg Gln Ala Pro Gly Lys Gly Leu Glu Trp Ile
        35              40              45

Gly Tyr Ile Asn Pro Ser Arg Gly Tyr Thr Asn Tyr Asn Gln Lys Val
    50              55              60

Lys Asp Arg Phe Thr Ile Ser Arg Asp Asn Ser Lys Asn Thr Leu Tyr
65              70              75              80

Leu Gln Met Asp Ser Leu Arg Ala Glu Asp Thr Ala Val Tyr Tyr Cys
            85              90              95

Ala Arg Tyr Tyr Asp Asp His Tyr Ser Leu Asp Tyr Trp Gly Gln Gly
            100             105             110

Thr Thr Val Thr Val Ser Ser Gly Gly Gly Gly Ser Gly Gly Gly Gly
            115             120             125
```

-continued

```
Ser Gly Gly Gly Gly Ser Gly Gly Gly Gly Ser Asp Ile Gln Met Thr
    130             135             140

Gln Ser Pro Ser Ser Leu Ser Ala Ser Val Gly Asp Arg Val Thr Ile
145             150             155             160

Thr Cys Ser Ala Ser Ser Ser Val Ser Tyr Met Asn Trp Tyr Gln Gln
            165             170             175

Lys Pro Gly Lys Ala Pro Lys Arg Trp Ile Tyr Asp Thr Ser Lys Leu
            180             185             190

Ala Ser Gly Val Pro Ser Arg Phe Ser Gly Ser Gly Ser Gly Thr Asp
            195             200             205

Phe Thr Phe Thr Ile Ser Ser Leu Gln Pro Glu Asp Ile Ala Thr Tyr
    210             215             220

Tyr Cys Gln Gln Trp Ser Ser Asn Pro Phe Thr Phe Gly Gln Gly Thr
225             230             235             240

Lys Leu Glu Ile Lys Glu Pro Lys Ser Ser Asp Lys Thr His Thr Cys
            245             250             255

Pro Pro Cys Pro Ala Pro Glu Ala Ala Gly Ala Pro Ser Val Phe Leu
            260             265             270

Phe Pro Pro Lys Pro Lys Asp Thr Leu Met Ile Ser Arg Thr Pro Glu
            275             280             285

Val Thr Cys Val Val Val Asp Val Ser His Glu Asp Pro Glu Val Lys
    290             295             300

Phe Asn Trp Tyr Val Asp Gly Val Glu Val His Asn Ala Lys Thr Lys
305             310             315             320

Pro Arg Glu Glu Gln Tyr Asn Ser Thr Tyr Arg Val Val Ser Val Leu
            325             330             335

Thr Val Leu His Gln Asp Trp Leu Asn Gly Lys Glu Tyr Lys Cys Lys
            340             345             350

Val Ser Asn Lys Ala Leu Pro Ala Pro Ile Glu Lys Thr Ile Ser Lys
            355             360             365

Ala Lys Gly Gln Pro Arg Glu Pro Gln Val Tyr Thr Leu Pro Pro Ser
    370             375             380

Arg Asp Glu Leu Thr Lys Asn Gln Val Ser Leu Ser Cys Ala Val Lys
385             390             395             400

Gly Phe Tyr Pro Ser Asp Ile Ala Val Glu Trp Glu Ser Asn Gly Gln
            405             410             415

Pro Glu Asn Asn Tyr Lys Thr Thr Pro Pro Val Leu Asp Ser Asp Gly
            420             425             430

Ser Phe Phe Leu Val Ser Lys Leu Thr Val Asp Lys Ser Arg Trp Gln
            435             440             445

Gln Gly Asn Val Phe Ser Cys Ser Val Met His Glu Ala Leu His Asn
    450             455             460

His Tyr Thr Gln Lys Ser Leu Ser Leu Ser Pro Gly Lys
465             470             475
```

```
<210> SEQ ID NO 10
<211> LENGTH: 477
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

-continued

<400> SEQUENCE: 10

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
                20                  25                  30

Thr Met His Trp Val Arg Gln Ala Pro Gly Gln Gly Leu Glu Trp Met
            35                  40                  45

Gly Tyr Ile Asn Pro Ser Arg Gly Tyr Thr Asn Tyr Asn Gln Lys Phe
        50                  55                  60

Lys Asp Arg Val Thr Leu Thr Thr Asp Lys Ser Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Gly Gly Gly Gly Ser Asp Ile Gln Met Thr
    130                 135                 140

Gln Ser Pro Ser Ser Leu Ser Ala Ser Val Gly Asp Arg Val Thr Ile
145                 150                 155                 160

Thr Cys Ser Ala Ser Ser Ser Val Ser Tyr Met Asn Trp Tyr Gln Gln
                165                 170                 175

Lys Pro Gly Lys Ala Pro Lys Arg Leu Ile Tyr Asp Thr Ser Lys Leu
            180                 185                 190

Ala Ser Gly Val Pro Ser Arg Phe Ser Gly Ser Gly Ser Gly Thr Asp
            195                 200                 205

Phe Thr Leu Thr Ile Ser Ser Leu Gln Pro Glu Asp Phe Ala Thr Tyr
        210                 215                 220

Tyr Cys Gln Gln Trp Ser Ser Asn Pro Phe Thr Phe Gly Gln Gly Thr
225                 230                 235                 240

Lys Leu Glu Ile Lys Glu Pro Lys Ser Ser Asp Lys Thr His Thr Cys
                245                 250                 255

Pro Pro Cys Pro Ala Pro Glu Ala Ala Gly Ala Pro Ser Val Phe Leu
            260                 265                 270

Phe Pro Pro Lys Pro Lys Asp Thr Leu Met Ile Ser Arg Thr Pro Glu
            275                 280                 285

Val Thr Cys Val Val Val Asp Val Ser His Glu Asp Pro Glu Val Lys
        290                 295                 300

Phe Asn Trp Tyr Val Asp Gly Val Glu Val His Asn Ala Lys Thr Lys
305                 310                 315                 320

Pro Arg Glu Glu Gln Tyr Asn Ser Thr Tyr Arg Val Val Ser Val Leu
            325                 330                 335

Thr Val Leu His Gln Asp Trp Leu Asn Gly Lys Glu Tyr Lys Cys Lys
            340                 345                 350

Val Ser Asn Lys Ala Leu Pro Ala Pro Ile Glu Lys Thr Ile Ser Lys
            355                 360                 365

Ala Lys Gly Gln Pro Arg Glu Pro Gln Val Tyr Thr Leu Pro Pro Ser
    370                 375                 380

Arg Asp Glu Leu Thr Lys Asn Gln Val Ser Leu Ser Cys Ala Val Lys
385                 390                 395                 400
```

-continued

```
Gly Phe Tyr Pro Ser Asp Ile Ala Val Glu Trp Glu Ser Asn Gly Gln
            405                 410                 415

Pro Glu Asn Asn Tyr Lys Thr Thr Pro Pro Val Leu Asp Ser Asp Gly
            420                 425                 430

Ser Phe Phe Leu Val Ser Lys Leu Thr Val Asp Lys Ser Arg Trp Gln
        435                 440                 445

Gln Gly Asn Val Phe Ser Cys Ser Val Met His Glu Ala Leu His Asn
    450                 455                 460

His Tyr Thr Gln Lys Ser Leu Ser Leu Ser Pro Gly Lys
465                 470                 475

<210> SEQ ID NO 11
<211> LENGTH: 487
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
            85                  90                  95

Tyr Cys Val Arg His Gly Asn Phe Gly Asn Ser Tyr Val Ser Tyr Phe
            100                 105                 110

Ala Tyr Trp Gly Gln Gly Thr Thr Val Thr Val Ser Ser Gly Gly Gly
        115                 120                 125

Gly Ser Gly Gly Gly Gly Ser Gly Gly Gly Gly Ser Gly Gly Gly Gly
    130                 135                 140

Ser Glu Ile Val Val Thr Gln Ser Pro Ala Thr Leu Ser Val Ser Pro
145                 150                 155                 160

Gly Glu Arg Ala Thr Leu Ser Cys Arg Ser Ser Thr Gly Ala Val Thr
            165                 170                 175

Ala Ala Asn Tyr Ala Asn Trp Val Gln Glu Lys Pro Gly Gln Ala Phe
            180                 185                 190

Arg Gly Leu Ile Gly Gly Ala Asn Lys Arg Ala Pro Gly Val Pro Ala
        195                 200                 205

Arg Phe Ser Gly Ser Leu Ser Gly Asp Glu Ala Thr Leu Thr Ile Ser
    210                 215                 220

Ser Leu Gln Ser Glu Asp Phe Ala Val Tyr Tyr Cys Ala Leu Phe Tyr
225                 230                 235                 240

Ser Asn Leu Trp Val Phe Gly Gln Gly Thr Lys Leu Glu Ile Lys Glu
            245                 250                 255

Pro Lys Ser Ser Asp Lys Thr His Thr Cys Pro Pro Cys Pro Ala Pro
            260                 265                 270
```

-continued

```
Glu Ala Ala Gly Ala Pro Ser Val Phe Leu Phe Pro Pro Lys Pro Lys
        275             280             285

Asp Thr Leu Met Ile Ser Arg Thr Pro Glu Val Thr Cys Val Val Val
    290             295             300

Asp Val Ser His Glu Asp Pro Glu Val Lys Phe Asn Trp Tyr Val Asp
305             310             315             320

Gly Val Glu Val His Asn Ala Lys Thr Lys Pro Arg Glu Glu Gln Tyr
            325             330             335

Asn Ser Thr Tyr Arg Val Val Ser Val Leu Thr Val Leu His Gln Asp
            340             345             350

Trp Leu Asn Gly Lys Glu Tyr Lys Cys Lys Val Ser Asn Lys Ala Leu
        355             360             365

Pro Ala Pro Ile Glu Lys Thr Ile Ser Lys Ala Lys Gly Gln Pro Arg
    370             375             380

Glu Pro Gln Val Tyr Thr Leu Pro Pro Ser Arg Asp Glu Leu Thr Lys
385             390             395             400

Asn Gln Val Ser Leu Ser Cys Ala Val Lys Gly Phe Tyr Pro Ser Asp
            405             410             415

Ile Ala Val Glu Trp Glu Ser Asn Gly Gln Pro Glu Asn Asn Tyr Lys
            420             425             430

Thr Thr Pro Pro Val Leu Asp Ser Asp Gly Ser Phe Phe Leu Val Ser
        435             440             445

Lys Leu Thr Val Asp Lys Ser Arg Trp Gln Gln Gly Asn Val Phe Ser
    450             455             460

Cys Ser Val Met His Glu Ala Leu His Asn His Tyr Thr Gln Lys Ser
465             470             475             480

Leu Ser Leu Ser Pro Gly Lys
            485
```

```
<210> SEQ ID NO 12
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12
```

```
Gln Val Gln Leu Gln Glu Ser Gly Pro Gly Leu Val Lys Pro Ser Gln
1               5               10              15

Thr Leu Ser Leu Thr Cys Thr Val Ser Gly Tyr Ala Phe Ala Ala Tyr
            20              25              30

Asn Ile His Trp Val Arg Gln Ala Pro Gly Gln Gly Leu Glu Trp Met
            35              40              45

Gly Ser Phe Asp Pro Tyr Asp Gly Gly Ser Ser Tyr Asn Gln Lys Phe
    50              55              60

Lys Asp Arg Leu Thr Ile Ser Lys Asp Thr Ser Lys Asn Gln Val Val
65              70              75              80

Leu Thr Met Thr Asn Met Asp Pro Val Asp Thr Ala Thr Tyr Tyr Cys
            85              90              95

Ala Arg Gly Trp Tyr Tyr Phe Asp Tyr Trp Gly His Gly Thr Leu Val
            100             105             110

Thr Val Ser Ser Ala Ser Thr Lys Gly Pro Ser Val Phe Pro Leu Ala
            115             120             125
```

-continued

```
Pro Ser Ser Lys Ser Thr Ser Gly Gly Thr Ala Ala Leu Gly Cys Leu
    130             135             140

Val Lys Asp Tyr Phe Pro Glu Pro Val Thr Val Ser Trp Asn Ser Gly
145             150             155             160

Ala Leu Thr Ser Gly Val His Thr Phe Pro Ala Val Leu Gln Ser Ser
            165             170             175

Gly Leu Tyr Ser Leu Ser Ser Val Val Thr Val Pro Ser Ser Ser Leu
            180             185             190

Gly Thr Gln Thr Tyr Ile Cys Asn Val Asn His Lys Pro Ser Asn Thr
            195             200             205

Lys Val Asp Lys Lys Val Glu Pro Lys Ser Cys Asp Lys Thr His Thr
    210             215             220

Cys Pro Pro Cys Pro Ala Pro Glu Ala Ala Gly Ala Pro Ser Val Phe
225             230             235             240

Leu Phe Pro Pro Lys Pro Lys Asp Thr Leu Met Ile Ser Arg Thr Pro
            245             250             255

Glu Val Thr Cys Val Val Val Asp Val Ser His Glu Asp Pro Glu Val
            260             265             270

Lys Phe Asn Trp Tyr Val Asp Gly Val Glu Val His Asn Ala Lys Thr
    275             280             285

Lys Pro Arg Glu Glu Gln Tyr Asn Ser Thr Tyr Arg Val Val Ser Val
    290             295             300

Leu Thr Val Leu His Gln Asp Trp Leu Asn Gly Lys Glu Tyr Lys Cys
305             310             315             320

Lys Val Ser Asn Lys Ala Leu Pro Ala Pro Ile Glu Lys Thr Ile Ser
            325             330             335

Lys Ala Lys Gly Gln Pro Arg Glu Pro Gln Val Tyr Thr Leu Pro Pro
            340             345             350

Ser Arg Asp Glu Leu Thr Lys Asn Gln Val Ser Leu Trp Cys Leu Val
            355             360             365

Lys Gly Phe Tyr Pro Ser Asp Ile Ala Val Glu Trp Glu Ser Asn Gly
    370             375             380

Gln Pro Glu Asn Asn Tyr Lys Thr Thr Pro Pro Val Leu Asp Ser Asp
385             390             395             400

Gly Ser Phe Phe Leu Tyr Ser Lys Leu Thr Val Asp Lys Ser Arg Trp
            405             410             415

Gln Gln Gly Asn Val Phe Ser Cys Ser Val Met His Glu Ala Leu His
            420             425             430

Asn His Tyr Thr Gln Lys Ser Leu Ser Leu Ser Pro Gly Lys
            435             440             445
```

```
<210> SEQ ID NO 13
<211> LENGTH: 487
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13
```

```
Glu Val Gln Leu Val Glu Ser Gly Gly Gly Leu Val Gln Pro Gly Gly
1               5               10              15

Ser Leu Arg Leu Ser Cys Ala Ala Ser Gly Phe Thr Phe Asn Thr Tyr
            20              25              30
```

-continued

Ala Met Asn Trp Val Arg Gln Ala Pro Gly Lys Cys Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Tyr Phe
            100                 105                 110

Ala Tyr Trp Gly Gln Gly Thr Thr Val Thr Val Ser Ser Gly Gly Gly
            115                 120                 125

Gly Ser Gly Gly Gly Gly Ser Gly Gly Gly Gly Ser Gly Gly Gly Gly
    130                 135                 140

Ser Glu Ile Val Val Thr Gln Ser Pro Ala Thr Leu Ser Val Ser Pro
145                 150                 155                 160

Gly Glu Arg Ala Thr Leu Ser Cys Arg Ser Ser Thr Gly Ala Val Thr
                165                 170                 175

Ala Ala Asn Tyr Ala Asn Trp Val Gln Glu Lys Pro Gly Gln Ala Phe
            180                 185                 190

Arg Gly Leu Ile Gly Gly Ala Asn Lys Arg Ala Pro Gly Val Pro Ala
            195                 200                 205

Arg Phe Ser Gly Ser Leu Ser Gly Asp Glu Ala Thr Leu Thr Ile Ser
    210                 215                 220

Ser Leu Gln Ser Glu Asp Phe Ala Val Tyr Tyr Cys Ala Leu Phe Tyr
225                 230                 235                 240

Ser Asn Leu Trp Val Phe Gly Cys Gly Thr Lys Leu Glu Ile Lys Glu
                245                 250                 255

Pro Lys Ser Ser Asp Lys Thr His Thr Cys Pro Pro Cys Pro Ala Pro
            260                 265                 270

Glu Ala Ala Gly Ala Pro Ser Val Phe Leu Phe Pro Pro Lys Pro Lys
            275                 280                 285

Asp Thr Leu Met Ile Ser Arg Thr Pro Glu Val Thr Cys Val Val Val
    290                 295                 300

Asp Val Ser His Glu Asp Pro Glu Val Lys Phe Asn Trp Tyr Val Asp
305                 310                 315                 320

Gly Val Glu Val His Asn Ala Lys Thr Lys Pro Arg Glu Glu Gln Tyr
            325                 330                 335

Asn Ser Thr Tyr Arg Val Val Ser Val Leu Thr Val Leu His Gln Asp
            340                 345                 350

Trp Leu Asn Gly Lys Glu Tyr Lys Cys Lys Val Ser Asn Lys Ala Leu
    355                 360                 365

Pro Ala Pro Ile Glu Lys Thr Ile Ser Lys Ala Lys Gly Gln Pro Arg
    370                 375                 380

Glu Pro Gln Val Tyr Thr Leu Pro Pro Ser Arg Asp Glu Leu Thr Lys
385                 390                 395                 400

Asn Gln Val Ser Leu Ser Cys Ala Val Lys Gly Phe Tyr Pro Ser Asp
                405                 410                 415

Ile Ala Val Glu Trp Glu Ser Asn Gly Gln Pro Glu Asn Asn Tyr Lys
            420                 425                 430

Thr Thr Pro Pro Val Leu Asp Ser Asp Gly Ser Phe Phe Leu Val Ser
    435                 440                 445

-continued

```
Lys Leu Thr Val Asp Lys Ser Arg Trp Gln Gln Gly Asn Val Phe Ser
    450                 455                 460

Cys Ser Val Met His Glu Ala Leu His Asn His Tyr Thr Gln Lys Ser
465                 470                 475                 480

Leu Ser Leu Ser Pro Gly Lys
                485

<210> SEQ ID NO 14
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ala Phe Ala Ala Tyr
                20                  25                  30

Asn Ile His Trp Val Arg Gln Ala Pro Gly Gln Gly Leu Glu Trp Met
            35                  40                  45

Gly Ser Phe Asp Pro Tyr Asp Gly Gly Ser Ser Tyr Asn Gln Lys Phe
    50                  55                  60

Lys Asp Arg Leu Thr Ile Ser Lys Asp Thr Ser Lys Asn Gln Val Val
65                  70                  75                  80

Leu Thr Met Thr Asn Met Asp Pro Val Asp Thr Ala Thr Tyr Tyr Cys
                85                  90                  95

Ala Arg Gly Trp Tyr Tyr Phe Asp Tyr Trp Gly His Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Ala Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
    290                 295                 300
```

```
Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
            435                 440                 445

<210> SEQ ID NO 15
<211> LENGTH: 711
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Glu Val Gln Leu Val Glu Ser Gly Gly Gly Leu Val Gln Pro Gly Gly
1                   5                   10                  15

Ser Leu Arg Leu Ser Cys Ala Ala Ser Gly Phe Thr Phe Asn Thr Tyr
                20                  25                  30

Ala Met Asn Trp Val Arg Gln Ala Pro Gly Lys Gly Leu Glu Trp Val
                35                  40                  45

Ala Arg Ile Arg Ser Lys Tyr Asn Asn Tyr Ala Thr Tyr Tyr Ala Asp
            50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Tyr Phe
                100                 105                 110

Ala Tyr Trp Gly Gln Gly Thr Thr Val Thr Val Ser Ser Gly Gly Gly
            115                 120                 125

Gly Ser Gly Gly Gly Gly Ser Gly Gly Gly Gly Ser Gly Gly Gly Gly
            130                 135                 140

Ser Glu Ile Val Val Thr Gln Ser Pro Ala Thr Leu Ser Val Ser Pro
145                 150                 155                 160

Gly Glu Arg Ala Thr Leu Ser Cys Arg Ser Ser Thr Gly Ala Val Thr
                165                 170                 175

Ala Ala Asn Tyr Ala Asn Trp Val Gln Glu Lys Pro Gly Gln Ala Phe
                180                 185                 190

Arg Gly Leu Ile Gly Gly Ala Asn Lys Arg Ala Pro Gly Val Pro Ala
            195                 200                 205
```

-continued

```
Arg Phe Ser Gly Ser Leu Ser Gly Asp Glu Ala Thr Leu Thr Ile Ser
    210             215                 220

Ser Leu Gln Ser Glu Asp Phe Ala Val Tyr Tyr Cys Ala Leu Phe Tyr
225             230                 235                 240

Ser Asn Leu Trp Val Phe Gly Gln Gly Thr Lys Leu Glu Ile Lys Gly
                245                 250                 255

Gly Gly Gly Ser Gly Gly Gly Gly Ser Gln Val Gln Leu Gln Glu Ser
                260             265                 270

Gly Pro Gly Leu Val Lys Pro Ser Gln Thr Leu Ser Leu Thr Cys Thr
        275             280                 285

Val Ser Gly Tyr Ala Phe Thr Ala Tyr Asn Ile His Trp Val Arg Gln
    290             295                 300

Ala Pro Gly Gln Gly Leu Glu Trp Met Gly Ser Phe Asp Pro Tyr Asp
305             310                 315                 320

Gly Gly Ser Ser Tyr Asn Gln Lys Phe Lys Asp Arg Leu Thr Ile Ser
                325                 330                 335

Lys Asp Thr Ser Lys Asn Gln Val Val Leu Thr Met Thr Asn Met Asp
                340             345                 350

Pro Val Asp Thr Ala Thr Tyr Tyr Cys Ala Arg Gly Trp Tyr Tyr Phe
        355                 360                 365

Asp Tyr Trp Gly His Gly Thr Leu Val Thr Val Ser Ser Ala Ser Thr
    370             375                 380

Lys Gly Pro Ser Val Phe Pro Leu Ala Pro Ser Ser Lys Ser Thr Ser
385             390                 395                 400

Gly Gly Thr Ala Ala Leu Gly Cys Leu Val Lys Asp Tyr Phe Pro Glu
                405                 410                 415

Pro Val Thr Val Ser Trp Asn Ser Gly Ala Leu Thr Ser Gly Val His
                420             425                 430

Thr Phe Pro Ala Val Leu Gln Ser Ser Gly Leu Tyr Ser Leu Ser Ser
        435             440                 445

Val Val Thr Val Pro Ser Ser Ser Leu Gly Thr Gln Thr Tyr Ile Cys
    450             455                 460

Asn Val Asn His Lys Pro Ser Asn Thr Lys Val Asp Lys Lys Val Glu
465                 470                 475                 480

Pro Lys Ser Cys Asp Lys Thr His Thr Cys Pro Pro Cys Pro Ala Pro
                485                 490                 495

Glu Ala Ala Gly Ala Pro Ser Val Phe Leu Phe Pro Pro Lys Pro Lys
                500             505                 510

Asp Thr Leu Met Ile Ser Arg Thr Pro Glu Val Thr Cys Val Val Val
        515             520                 525

Asp Val Ser His Glu Asp Pro Glu Val Lys Phe Asn Trp Tyr Val Asp
    530             535                 540

Gly Val Glu Val His Asn Ala Lys Thr Lys Pro Arg Glu Glu Gln Tyr
545             550                 555                 560

Asn Ser Thr Tyr Arg Val Val Ser Val Leu Thr Val Leu His Gln Asp
                565                 570                 575

Trp Leu Asn Gly Lys Glu Tyr Lys Cys Lys Val Ser Asn Lys Ala Leu
                580             585                 590

Pro Ala Pro Ile Glu Lys Thr Ile Ser Lys Ala Lys Gly Gln Pro Arg
        595             600                 605

Glu Pro Gln Val Tyr Thr Leu Pro Pro Ser Arg Asp Glu Leu Thr Lys
    610             615                 620
```

-continued

```
Asn Gln Val Ser Leu Ser Cys Ala Val Lys Gly Phe Tyr Pro Ser Asp
625             630                 635                 640

Ile Ala Val Glu Trp Glu Ser Asn Gly Gln Pro Glu Asn Asn Tyr Lys
                645                 650                 655

Thr Thr Pro Pro Val Leu Asp Ser Asp Gly Ser Phe Phe Leu Val Ser
                660                 665                 670

Lys Leu Thr Val Asp Lys Ser Arg Trp Gln Gln Gly Asn Val Phe Ser
            675                 680                 685

Cys Ser Val Met His Glu Ala Leu His Asn His Tyr Thr Gln Lys Ser
            690                 695                 700

Leu Ser Leu Ser Pro Gly Lys
705                 710
```

```
<210> SEQ ID NO 16
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16
```

```
Asp Ile Val Met Thr Gln Thr Pro Leu Ser Leu Pro Val Thr Pro Gly
1               5                   10                  15

Glu Pro Ala Ser Ile Ser Cys Arg Ala Ser Lys Ser Ile Ser Lys Tyr
                20                  25                  30

Leu Ala Trp Tyr Gln Gln Lys Pro Gly Gln Ala Pro Arg Leu Leu Ile
            35                  40                  45

Tyr Ser Gly Ser Thr Leu Gln Ser Gly Ile Pro Pro Arg Phe Ser Gly
            50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Gln Gln His Asp Glu Ser Pro Tyr
                85                  90                  95

Thr Phe Gly Glu Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210
```

```
<210> SEQ ID NO 17
<211> LENGTH: 469
<212> TYPE: PRT
<213> ORGANISM: Artificial Sequence
<220> FEATURE:
<221> NAME/KEY: source
```

-continued

```
<223> OTHER INFORMATION: /note="Description of Artificial Sequence:
      Synthetic polypeptide"

<400> SEQUENCE: 17

Asp Ile Val Met Thr Gln Thr Pro Leu Ser Leu Pro Val Thr Pro Gly
1               5                   10                  15

Glu Pro Ala Ser Ile Ser Cys Arg Ala Ser Lys Ser Ile Ser Lys Tyr
            20                  25                  30

Leu Ala Trp Tyr Gln Gln Lys Pro Gly Gln Ala Pro Arg Leu Leu Ile
        35                  40                  45

Tyr Ser Gly Ser Thr Leu Gln Ser Gly Ile Pro Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Gln Gln His Asp Glu Ser Pro Tyr
                85                  90                  95

Thr Phe Gly Glu Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys Gly Gly Gly Gly Ser Gly Gly Gly Gly Ser
    210                 215                 220

Gln Val Gln Leu Val Gln Ser Gly Gly Gly Val Val Gln Pro Gly Arg
225                 230                 235                 240

Ser Leu Arg Leu Ser Cys Lys Ala Ser Gly Tyr Thr Phe Thr Arg Tyr
            245                 250                 255

Thr Met His Trp Val Arg Gln Ala Pro Gly Lys Gly Leu Glu Trp Ile
            260                 265                 270

Gly Tyr Ile Asn Pro Ser Arg Gly Tyr Thr Asn Tyr Asn Gln Lys Val
            275                 280                 285

Lys Asp Arg Phe Thr Ile Ser Arg Asp Asn Ser Lys Asn Thr Leu Tyr
    290                 295                 300

Leu Gln Met Asp Ser Leu Arg Ala Glu Asp Thr Ala Val Tyr Tyr Cys
305                 310                 315                 320

Ala Arg Tyr Tyr Asp Asp His Tyr Ser Leu Asp Tyr Trp Gly Gln Gly
            325                 330                 335

Thr Thr Val Thr Val Ser Ser Gly Gly Gly Ser Gly Gly Gly Gly
            340                 345                 350

Ser Gly Gly Gly Gly Ser Gly Gly Gly Gly Ser Asp Ile Gln Met Thr
            355                 360                 365

Gln Ser Pro Ser Ser Leu Ser Ala Ser Val Gly Asp Arg Val Thr Ile
    370                 375                 380

Thr Cys Ser Ala Ser Ser Ser Val Ser Tyr Met Asn Trp Tyr Gln Gln
385                 390                 395                 400
```

```
Lys Pro Gly Lys Ala Pro Lys Arg Trp Ile Tyr Asp Thr Ser Lys Leu
                405             410             415

Ala Ser Gly Val Pro Ser Arg Phe Ser Gly Ser Gly Ser Gly Thr Asp
            420             425             430

Phe Thr Phe Thr Ile Ser Ser Leu Gln Pro Glu Asp Ile Ala Thr Tyr
        435             440             445

Tyr Cys Gln Gln Trp Ser Ser Asn Pro Phe Thr Phe Gly Gln Gly Thr
    450             455             460

Lys Leu Glu Ile Lys
465

<210> SEQ ID NO 18
<211> LENGTH: 469
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Asp Ile Val Met Thr Gln Thr Pro Leu Ser Leu Pro Val Thr Pro Gly
1               5               10              15

Glu Pro Ala Ser Ile Ser Cys Arg Ala Ser Lys Ser Ile Ser Lys Tyr
            20              25              30

Leu Ala Trp Tyr Gln Gln Lys Pro Gly Gln Ala Pro Arg Leu Leu Ile
        35              40              45

Tyr Ser Gly Ser Thr Leu Gln Ser Gly Ile Pro Pro Arg Phe Ser Gly
    50              55              60

Ser Gly Tyr Gly Thr Asp Phe Thr Leu Thr Ile Asn Asn Ile Glu Ser
65              70              75              80

Glu Asp Ala Ala Tyr Tyr Phe Cys Gln Gln His Asp Glu Ser Pro Tyr
            85              90              95

Thr Phe Gly Glu Gly Thr Lys Val Glu Ile Lys Arg Thr Val Ala Ala
            100             105             110

Pro Ser Val Phe Ile Phe Pro Pro Ser Asp Glu Gln Leu Lys Ser Gly
        115             120             125

Thr Ala Ser Val Val Cys Leu Leu Asn Asn Phe Tyr Pro Arg Glu Ala
    130             135             140

Lys Val Gln Trp Lys Val Asp Asn Ala Leu Gln Ser Gly Asn Ser Gln
145             150             155             160

Glu Ser Val Thr Glu Gln Asp Ser Lys Asp Ser Thr Tyr Ser Leu Ser
            165             170             175

Ser Thr Leu Thr Leu Ser Lys Ala Asp Tyr Glu Lys His Lys Val Tyr
            180             185             190

Ala Cys Glu Val Thr His Gln Gly Leu Ser Ser Pro Val Thr Lys Ser
            195             200             205

Phe Asn Arg Gly Glu Cys Gly Gly Gly Ser Gly Gly Gly Gly Ser
    210             215             220

Gln Val Gln Leu Val Gln Ser Gly Ala Glu Val Lys Lys Pro Gly Ala
225             230             235             240

Ser Val Lys Val Ser Cys Lys Ala Ser Gly Tyr Thr Phe Thr Arg Tyr
            245             250             255

Thr Met His Trp Val Arg Gln Ala Pro Gly Gln Gly Leu Glu Trp Met
            260             265             270
```

-continued

```
Gly Tyr Ile Asn Pro Ser Arg Gly Tyr Thr Asn Tyr Asn Gln Lys Phe
        275             280             285

Lys Asp Arg Val Thr Leu Thr Thr Asp Lys Ser Ser Ser Thr Ala Tyr
    290             295             300

Met Glu Leu Ser Ser Leu Arg Ser Glu Asp Thr Ala Val Tyr Tyr Cys
305             310             315             320

Ala Arg Tyr Tyr Asp Asp His Tyr Ser Leu Asp Tyr Trp Gly Gln Gly
            325             330             335

Thr Leu Val Thr Val Ser Ser Gly Gly Gly Ser Gly Gly Gly Gly
            340             345             350

Ser Gly Gly Gly Gly Ser Gly Gly Gly Gly Ser Asp Ile Gln Met Thr
        355             360             365

Gln Ser Pro Ser Ser Leu Ser Ala Ser Val Gly Asp Arg Val Thr Ile
    370             375             380

Thr Cys Ser Ala Ser Ser Ser Val Ser Tyr Met Asn Trp Tyr Gln Gln
385             390             395             400

Lys Pro Gly Lys Ala Pro Lys Arg Leu Ile Tyr Asp Thr Ser Lys Leu
            405             410             415

Ala Ser Gly Val Pro Ser Arg Phe Ser Gly Ser Gly Ser Gly Thr Asp
            420             425             430

Phe Thr Leu Thr Ile Ser Ser Leu Gln Pro Glu Asp Phe Ala Thr Tyr
            435             440             445

Tyr Cys Gln Gln Trp Ser Ser Asn Pro Phe Thr Phe Gly Gln Gly Thr
    450             455             460

Lys Leu Glu Ile Lys
465
```

```
<210> SEQ ID NO 19
<211> LENGTH: 479
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Asp Ile Val Met Thr Gln Thr Pro Leu Ser Leu Pro Val Thr Pro Gly
1               5               10              15

Glu Pro Ala Ser Ile Ser Cys Arg Ala Ser Lys Ser Ile Ser Lys Tyr
            20              25              30

Leu Ala Trp Tyr Gln Gln Lys Pro Gly Gln Ala Pro Arg Leu Leu Ile
        35              40              45

Tyr Ser Gly Ser Thr Leu Gln Ser Gly Ile Pro Pro Arg Phe Ser Gly
    50              55              60

Ser Gly Tyr Gly Thr Asp Phe Thr Leu Thr Ile Asn Asn Ile Glu Ser
65              70              75              80

Glu Asp Ala Ala Tyr Tyr Phe Cys Gln Gln His Asp Glu Ser Pro Tyr
            85              90              95

Thr Phe Gly Glu Gly Thr Lys Val Glu Ile Lys Arg Thr Val Ala Ala
            100             105             110

Pro Ser Val Phe Ile Phe Pro Pro Ser Asp Glu Gln Leu Lys Ser Gly
        115             120             125

Thr Ala Ser Val Val Cys Leu Leu Asn Asn Phe Tyr Pro Arg Glu Ala
    130             135             140
```

-continued

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys Gly Gly Gly Ser Gly Gly Gly Ser
        210                 215                 220

Glu Val Gln Leu Val Glu Ser Gly Gly Gly Leu Val Gln Pro Gly Gly
225                 230                 235                 240

Ser Leu Arg Leu Ser Cys Ala Ala Ser Gly Phe Thr Phe Asn Thr Tyr
                245                 250                 255

Ala Met Asn Trp Val Arg Gln Ala Pro Gly Lys Gly Leu Glu Trp Val
                260                 265                 270

Ala Arg Ile Arg Ser Lys Tyr Asn Asn Tyr Ala Thr Tyr Tyr Ala Asp
                275                 280                 285

Ser Val Lys Gly Arg Phe Thr Ile Ser Arg Asp Asp Ser Lys Asn Thr
        290                 295                 300

Leu Tyr Leu Gln Met Asn Ser Leu Arg Ala Glu Asp Thr Ala Val Tyr
305                 310                 315                 320

Tyr Cys Val Arg His Gly Asn Phe Gly Asn Ser Tyr Val Ser Tyr Phe
                325                 330                 335

Ala Tyr Trp Gly Gln Gly Thr Thr Val Thr Val Ser Ser Gly Gly Gly
                340                 345                 350

Gly Ser Gly Gly Gly Gly Ser Gly Gly Gly Gly Ser Gly Gly Gly Gly
                355                 360                 365

Ser Glu Ile Val Val Thr Gln Ser Pro Ala Thr Leu Ser Val Ser Pro
        370                 375                 380

Gly Glu Arg Ala Thr Leu Ser Cys Arg Ser Ser Thr Gly Ala Val Thr
385                 390                 395                 400

Ala Ala Asn Tyr Ala Asn Trp Val Gln Glu Lys Pro Gly Gln Ala Phe
                405                 410                 415

Arg Gly Leu Ile Gly Gly Ala Asn Lys Arg Ala Pro Gly Val Pro Ala
                420                 425                 430

Arg Phe Ser Gly Ser Leu Ser Gly Asp Glu Ala Thr Leu Thr Ile Ser
        435                 440                 445

Ser Leu Gln Ser Glu Asp Phe Ala Val Tyr Tyr Cys Ala Leu Phe Tyr
        450                 455                 460

Ser Asn Leu Trp Val Phe Gly Gln Gly Thr Lys Leu Glu Ile Lys
465                 470                 475
```

<210> SEQ ID NO 20
<211> LENGTH: 469
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 20

```
Asp Ile Val Met Thr Gln Thr Pro Leu Ser Leu Pro Val Thr Pro Gly
1               5                   10                  15
```

-continued

```
Glu Pro Ala Ser Ile Ser Cys Arg Ala Ser Lys Ser Ile Ser Lys Tyr
            20                  25                  30

Leu Ala Trp Tyr Gln Gln Lys Pro Gly Gln Ala Pro Arg Leu Leu Ile
        35                  40                  45

Tyr Ser Gly Ser Thr Leu Gln Ser Gly Ile Pro Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Gln Gln His Asp Glu Ser Pro Tyr
                85                  90                  95

Thr Phe Gly Glu Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys Gly Gly Gly Gly Ser Gly Gly Gly Gly Ser
    210                 215                 220

Gln Val Gln Leu Val Gln Ser Gly Gly Gly Val Val Gln Pro Gly Arg
225                 230                 235                 240

Ser Leu Arg Leu Ser Cys Lys Ala Ser Gly Tyr Thr Phe Thr Arg Tyr
            245                 250                 255

Thr Met His Trp Val Arg Gln Ala Pro Gly Lys Cys Leu Glu Trp Ile
            260                 265                 270

Gly Tyr Ile Asn Pro Ser Arg Gly Tyr Thr Asn Tyr Asn Gln Lys Val
    275                 280                 285

Lys Asp Arg Phe Thr Ile Ser Arg Asp Asn Ser Lys Asn Thr Leu Tyr
    290                 295                 300

Leu Gln Met Asp Ser Leu Arg Ala Glu Asp Thr Ala Val Tyr Tyr Cys
305                 310                 315                 320

Ala Arg Tyr Tyr Asp Asp His Tyr Ser Leu Asp Tyr Trp Gly Gln Gly
            325                 330                 335

Thr Thr Val Thr Val Ser Ser Gly Gly Gly Ser Gly Gly Gly Gly
            340                 345                 350

Ser Gly Gly Gly Gly Ser Gly Gly Gly Gly Ser Asp Ile Gln Met Thr
            355                 360                 365

Gln Ser Pro Ser Ser Leu Ser Ala Ser Val Gly Asp Arg Val Thr Ile
    370                 375                 380

Thr Cys Ser Ala Ser Ser Ser Val Ser Tyr Met Asn Trp Tyr Gln Gln
385                 390                 395                 400

Lys Pro Gly Lys Ala Pro Lys Arg Trp Ile Tyr Asp Thr Ser Lys Leu
            405                 410                 415

Ala Ser Gly Val Pro Ser Arg Phe Ser Gly Ser Gly Ser Gly Thr Asp
            420                 425                 430
```

```
Phe Thr Phe Thr Ile Ser Ser Leu Gln Pro Glu Asp Ile Ala Thr Tyr
        435                 440                 445

Tyr Cys Gln Gln Trp Ser Ser Asn Pro Phe Thr Phe Gly Cys Gly Thr
    450                 455                 460

Lys Leu Glu Ile Lys
465

<210> SEQ ID NO 21
<211> LENGTH: 469
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Asp Ile Val Met Thr Gln Thr Pro Leu Ser Leu Pro Val Thr Pro Gly
1               5                   10                  15

Glu Pro Ala Ser Ile Ser Cys Arg Ala Ser Lys Ser Ile Ser Lys Tyr
            20                  25                  30

Leu Ala Trp Tyr Gln Gln Lys Pro Gly Gln Ala Pro Arg Leu Leu Ile
        35                  40                  45

Tyr Ser Gly Ser Thr Leu Gln Ser Gly Ile Pro Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Gln Gln His Asp Glu Ser Pro Tyr
                85                  90                  95

Thr Phe Gly Glu Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Gly Gly Gly Gly Ser
    210                 215                 220

Gln Val Gln Leu Val Gln Ser Gly Ala Glu Val Lys Lys Pro Gly Ala
225                 230                 235                 240

Ser Val Lys Val Ser Cys Lys Ala Ser Gly Tyr Thr Phe Thr Arg Tyr
                245                 250                 255

Thr Met His Trp Val Arg Gln Ala Pro Gly Gln Cys Leu Glu Trp Met
            260                 265                 270

Gly Tyr Ile Asn Pro Ser Arg Gly Tyr Thr Asn Tyr Asn Gln Lys Phe
        275                 280                 285

Lys Asp Arg Val Thr Leu Thr Thr Asp Lys Ser Ser Ser Thr Ala Tyr
    290                 295                 300
```

```
Met Glu Leu Ser Ser Leu Arg Ser Glu Asp Thr Ala Val Tyr Tyr Cys
305             310                 315                 320

Ala Arg Tyr Tyr Asp Asp His Tyr Ser Leu Asp Tyr Trp Gly Gln Gly
                325             330             335

Thr Leu Val Thr Val Ser Ser Gly Gly Gly Gly Ser Gly Gly Gly Gly
            340             345             350

Ser Gly Gly Gly Gly Ser Gly Gly Gly Gly Ser Asp Ile Gln Met Thr
            355             360             365

Gln Ser Pro Ser Ser Leu Ser Ala Ser Val Gly Asp Arg Val Thr Ile
        370             375             380

Thr Cys Ser Ala Ser Ser Ser Val Ser Tyr Met Asn Trp Tyr Gln Gln
385             390             395                 400

Lys Pro Gly Lys Ala Pro Lys Arg Leu Ile Tyr Asp Thr Ser Lys Leu
                405             410             415

Ala Ser Gly Val Pro Ser Arg Phe Ser Gly Ser Gly Ser Gly Thr Asp
                420             425             430

Phe Thr Leu Thr Ile Ser Ser Leu Gln Pro Glu Asp Phe Ala Thr Tyr
            435             440             445

Tyr Cys Gln Gln Trp Ser Ser Asn Pro Phe Thr Phe Gly Cys Gly Thr
        450             455             460

Lys Leu Glu Ile Lys
465
```

```
<210> SEQ ID NO 22
<211> LENGTH: 479
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

Asp Ile Val Met Thr Gln Thr Pro Leu Ser Leu Pro Val Thr Pro Gly
1               5               10                  15

Glu Pro Ala Ser Ile Ser Cys Arg Ala Ser Lys Ser Ile Ser Lys Tyr
            20              25              30

Leu Ala Trp Tyr Gln Gln Lys Pro Gly Gln Ala Pro Arg Leu Leu Ile
        35              40              45

Tyr Ser Gly Ser Thr Leu Gln Ser Gly Ile Pro Pro Arg Phe Ser Gly
    50              55              60

Ser Gly Tyr Gly Thr Asp Phe Thr Leu Thr Ile Asn Asn Ile Glu Ser
65              70              75                  80

Glu Asp Ala Ala Tyr Tyr Phe Cys Gln Gln His Asp Glu Ser Pro Tyr
                85              90                  95

Thr Phe Gly Glu Gly Thr Lys Val Glu Ile Lys Arg Thr Val Ala Ala
            100             105             110

Pro Ser Val Phe Ile Phe Pro Pro Ser Asp Glu Gln Leu Lys Ser Gly
        115             120             125

Thr Ala Ser Val Val Cys Leu Leu Asn Asn Phe Tyr Pro Arg Glu Ala
        130             135             140

Lys Val Gln Trp Lys Val Asp Asn Ala Leu Gln Ser Gly Asn Ser Gln
145             150             155             160

Glu Ser Val Thr Glu Gln Asp Ser Lys Asp Ser Thr Tyr Ser Leu Ser
            165             170             175
```

-continued

```
Ser Thr Leu Thr Leu Ser Lys Ala Asp Tyr Glu Lys His Lys Val Tyr
        180             185             190

Ala Cys Glu Val Thr His Gln Gly Leu Ser Ser Pro Val Thr Lys Ser
        195             200             205

Phe Asn Arg Gly Glu Cys Gly Gly Gly Ser Gly Gly Gly Gly Ser
        210             215             220

Glu Val Gln Leu Val Glu Ser Gly Gly Gly Leu Val Gln Pro Gly Gly
225             230             235             240

Ser Leu Arg Leu Ser Cys Ala Ala Ser Gly Phe Thr Phe Asn Thr Tyr
        245             250             255

Ala Met Asn Trp Val Arg Gln Ala Pro Gly Lys Cys Leu Glu Trp Val
        260             265             270

Ala Arg Ile Arg Ser Lys Tyr Asn Asn Tyr Ala Thr Tyr Tyr Ala Asp
        275             280             285

Ser Val Lys Gly Arg Phe Thr Ile Ser Arg Asp Asp Ser Lys Asn Thr
        290             295             300

Leu Tyr Leu Gln Met Asn Ser Leu Arg Ala Glu Asp Thr Ala Val Tyr
305             310             315             320

Tyr Cys Val Arg His Gly Asn Phe Gly Asn Ser Tyr Val Ser Tyr Phe
        325             330             335

Ala Tyr Trp Gly Gln Gly Thr Thr Val Thr Val Ser Ser Gly Gly Gly
        340             345             350

Gly Ser Gly Gly Gly Gly Ser Gly Gly Gly Gly Ser Gly Gly Gly Gly
        355             360             365

Ser Glu Ile Val Val Thr Gln Ser Pro Ala Thr Leu Ser Val Ser Pro
        370             375             380

Gly Glu Arg Ala Thr Leu Ser Cys Arg Ser Ser Thr Gly Ala Val Thr
385             390             395             400

Ala Ala Asn Tyr Ala Asn Trp Val Gln Glu Lys Pro Gly Gln Ala Phe
        405             410             415

Arg Gly Leu Ile Gly Gly Ala Asn Lys Arg Ala Pro Gly Val Pro Ala
        420             425             430

Arg Phe Ser Gly Ser Leu Ser Gly Asp Glu Ala Thr Leu Thr Ile Ser
        435             440             445

Ser Leu Gln Ser Glu Asp Phe Ala Val Tyr Tyr Cys Ala Leu Phe Tyr
        450             455             460

Ser Asn Leu Trp Val Phe Gly Cys Gly Thr Lys Leu Glu Ile Lys
465             470             475
```

```
<210> SEQ ID NO 23
<211> LENGTH: 479
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23
```

```
Glu Val Gln Leu Val Glu Ser Gly Gly Gly Leu Val Gln Pro Gly Gly
1               5               10              15

Ser Leu Arg Leu Ser Cys Ala Ala Ser Gly Phe Thr Phe Asn Thr Tyr
        20              25              30

Ala Met Asn Trp Val Arg Gln Ala Pro Gly Lys Gly Leu Glu Trp Val
        35              40              45
```

```
Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Tyr Phe
            100                 105                 110

Ala Tyr Trp Gly Gln Gly Thr Thr Val Thr Val Ser Ser Gly Gly Gly
            115                 120                 125

Gly Ser Gly Gly Gly Gly Ser Gly Gly Gly Gly Ser Gly Gly Gly Gly
    130                 135                 140

Ser Glu Ile Val Val Thr Gln Ser Pro Ala Thr Leu Ser Val Ser Pro
145                 150                 155                 160

Gly Glu Arg Ala Thr Leu Ser Cys Arg Ser Ser Thr Gly Ala Val Thr
                165                 170                 175

Ala Ala Asn Tyr Ala Asn Trp Val Gln Glu Lys Pro Gly Gln Ala Phe
            180                 185                 190

Arg Gly Leu Ile Gly Gly Ala Asn Lys Arg Ala Pro Gly Val Pro Ala
            195                 200                 205

Arg Phe Ser Gly Ser Leu Ser Gly Asp Glu Ala Thr Leu Thr Ile Ser
    210                 215                 220

Ser Leu Gln Ser Glu Asp Phe Ala Val Tyr Tyr Cys Ala Leu Phe Tyr
225                 230                 235                 240

Ser Asn Leu Trp Val Phe Gly Gln Gly Thr Lys Leu Glu Ile Lys Gly
                245                 250                 255

Gly Gly Gly Ser Gly Gly Gly Gly Ser Asp Ile Val Met Thr Gln Thr
            260                 265                 270

Pro Leu Ser Leu Pro Val Thr Pro Gly Glu Pro Ala Ser Ile Ser Cys
            275                 280                 285

Arg Ala Ser Lys Ser Ile Ser Lys Tyr Leu Ala Trp Tyr Gln Gln Lys
    290                 295                 300

Pro Gly Gln Ala Pro Arg Leu Leu Ile Tyr Ser Gly Ser Thr Leu Gln
305                 310                 315                 320

Ser Gly Ile Pro Pro Arg Phe Ser Gly Ser Gly Tyr Gly Thr Asp Phe
                325                 330                 335

Thr Leu Thr Ile Asn Asn Ile Glu Ser Glu Asp Ala Ala Tyr Tyr Phe
            340                 345                 350

Cys Gln Gln His Asp Glu Ser Pro Tyr Thr Phe Gly Glu Gly Thr Lys
            355                 360                 365

Val Glu Ile Lys Arg Thr Val Ala Ala Pro Ser Val Phe Ile Phe Pro
    370                 375                 380

Pro Ser Asp Glu Gln Leu Lys Ser Gly Thr Ala Ser Val Val Cys Leu
385                 390                 395                 400

Leu Asn Asn Phe Tyr Pro Arg Glu Ala Lys Val Gln Trp Lys Val Asp
                405                 410                 415

Asn Ala Leu Gln Ser Gly Asn Ser Gln Glu Ser Val Thr Glu Gln Asp
            420                 425                 430

Ser Lys Asp Ser Thr Tyr Ser Leu Ser Ser Thr Leu Thr Leu Ser Lys
            435                 440                 445

Ala Asp Tyr Glu Lys His Lys Val Tyr Ala Cys Glu Val Thr His Gln
    450                 455                 460
```

-continued

```
Gly Leu Ser Ser Pro Val Thr Lys Ser Phe Asn Arg Gly Glu Cys
465                 470                 475

<210> SEQ ID NO 24
<211> LENGTH: 2103
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 24
caggttcagc tgcaagagtc tggccctggc ctggtcaagc ctagccaaac actgagcctg        60
acctgtaccg tgtccggcta cgccttcacc gcctacaata tccactgggt ccgacaggcc       120
cctggacagg gacttgaatg gatgggcagc ttcgacccct acgatggcgg cagcagctac       180
aaccagaagt tcaaggaccg gctgaccatc agcaaggaca ccagcaagaa ccaggtggtg       240
ctgaccatga ccaacatgga ccctgtggac accgccacct actactgtgc cagaggctgg       300
tactacttcg actactgggg ccacggcacc ctggtcacag ttagctctgc ctctacaaag       360 ggcccagcg tgttccctct ggctcctagc agcaagtcta caagcggagg aacagccgct       420
ctgggctgcc tcgtgaagga ttactttccc gagccagtga ccgtgtcctg aatagcggga       480
gcactgacaa gcggcgtgca cacctttcca gctgtgctgc aaagcagcgg cctgtactct       540
ctgagcagcg tcgtgacagt gccaagcagc tctctgggca cccagaccta catctgcaat       600
gtgaatcaca gcccagcaa caccaaggtg gacaagaagg tggaacccaa gagctgcgac       660
aagacccaca cctgtcctcc atgtcctgct ccagaagctg ctggcgcccc ttccgtgttt       720
ctgttccctc caaagcctaa ggacaccctg atgatcagca gaacccctga agtgacctgc       780
gtggtggtgg atgtgtccca cgaggatccc gaagtgaagt tcaattggta cgtggacggc       840
gtggaagtgc acaacgccaa gaccaagcct agagaggaac agtacaacag cacctacaga       900
gtggtgtctg tgctgaccgt gctgcaccag gattggctga cggcaaaga gtacaagtgc       960 aaggtgtcca caaggccct gcctgctcct atcgagaaaa ccatctccaa ggccaaggga      1020
cagcccaggg aaccccaggt ttacacactg cctccaagca gggacgagct gaccaagaat      1080
caggtgtccc tgacctgcct ggttaagggc ttctacccct ccgatatcgc cgtggaatgg      1140
gagagcaatg gccagcctga gaacaactac aagacaaccc tcctgtgct ggacagcgac      1200 ggctcattct tcctgtacag caagctgaca gtggacaagt ccagatggca gcagggcaac      1260
gtgttctcct gcagcgtgat gcacgaggcc ctgcacaacc actacaccca gaaaagcctg      1320
tctctgagcc ccggaaaagg cggcggagga tctggcggag gcggatctca agttcaactg      1380
gtgcaatccg gtggcggcgt tgtccagcct ggaagatctc tgagactgag ctgcaaggcc      1440
agcggctaca cattcacccg gtacaccatg cactgggttc gccaggctcc aggcaaaggc      1500
ttggagtgga tcggctacat caaccccagc cggggctaca ccaactacaa tcagaaagtg      1560
aaggaccgct tcacaatcag ccgggacaac tccaagaaca ccctgtacct gcagatggac      1620
tccctgagag ccgaggatac cgccgtgtac tactgcgccc ggtactacga cgatcactac      1680
agcctggatt attggggaca gggcaccacc gtgactgtgt caagcggtgg cggaggaagc      1740
ggaggcggcg gttctggtgg tggtggtagc ggaggtggtg gcagcgatat ccagatgaca      1800
cagagcccta gcagcctgtc tgccagcgtg ggagacagtg tgaccatcac atgtagcgcc      1860
agctccagcg tgtcctacat gaactggtat cagcaaaagc ccggcaaggc ccctaagcgg      1920
```

```
tggatctacg atacaagcaa gctggcctct ggcgtgccat ccagattttc tggcagcggc    1980
tctggcaccg acttcacctt caccataagc agcctgcagc ctgaggacat tgccacatat    2040
tactgccagc agtggtccag caatcctttc acctttggcc agggcacaaa gctcgagatc    2100
aag                                                                   2103

<210> SEQ ID NO 25
<211> LENGTH: 2103
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 25
caggttcagc tgcaagagtc tggccctggc ctggtcaagc ctagccaaac actgagcctg      60
acctgtaccg tgtccggcta cgccttcacc gcctacaata tccactgggt ccgacaggcc     120
cctggacagg gacttgaatg gatgggcagc ttcgacccct acgatggcgg cagcagctac     180
aaccagaagt tcaaggaccg gctgaccatc agcaaggaca ccagcaagaa ccaggtggtg     240
ctgaccatga ccaacatgga ccctgtggac accgccacct actactgtgc cagaggctgg     300
tactacttcg actactgggg ccacggcacc ctggtcacag ttagctctgc ctctacaaag     360
ggccccagcg tgttccctct ggctcctagc agcaagtcta caagcggagg aacagccgct     420
ctgggctgcc tcgtgaagga ttactttccc gagccagtga ccgtgtcctg gaatagcgga     480
gcactgacaa gcggcgtgca cacctttcca gctgtgctgc aaagcagcgg cctgtactct     540
ctgagcagcg tcgtgacagt gccaagcagc tctctgggca cccagaccta catctgcaat     600
gtgaatcaca gcccagcaa caccaaggtg acaagaagg tggaacccaa gagctgcgac     660
aagacccaca cctgtcctcc atgtcctgct ccagaagctg ctggcgcccc ttccgtgttt     720
ctgttccctc caaagcctaa ggacaccctg atgatcagca gaaccctga agtgacctgc     780 gtggtggtgg atgtgtccca cgaggatccc gaagtgaagt tcaattggta cgtggacggc     840
gtggaagtgc acaacgccaa gaccaagcct agagaggaac agtacaacag cacctacaga     900
gtggtgtctg tgctgaccgt gctgcaccag gattggctga cggcaaaga gtacaagtgc     960 aaggtgtcca caaggccct gcctgctcct atcgagaaaa ccatctccaa ggccaaggga    1020
cagcccaggg aaccccaggt ttacacactg cctccaagca gggacgagct gaccaagaat    1080
caggtgtccc tgacctgcct ggttaagggc ttctaccct ccgatatcgc cgtggaatgg    1140
gagagcaatg gccagcctga aacaactac aagacaaccc ctcctgtgct ggacagcgac    1200
ggctcattct tcctgtacag caagctgaca gtggacaagt ccagatggca gcagggcaac    1260
gtgttctcct gcagcgtgat gcacgaggcc ctgcacaacc actacaccca gaaaagcctg    1320
tctctgagcc ccggaaaagg cggcggagga tctggcggag gcggatctca agttcaactg    1380
gtgcagtctg gcgctgaagt gaagaaacct ggcgcctccg tgaaggtgtc ctgtaaagcc    1440
agcggctaca cattcacccg gtacaccatg cactgggttc gccaagctcc aggacaaggc    1500
ttggagtgga tgggctacat caaccccagc cggggctaca ccaactacaa tcaaaagttt    1560
aaggatcgcg tgacccctgac caccgacaag agcagctcta cagcctacat ggaactgagc    1620
agcctgcgga gcgaagatac cgccgtgtac tactgcgccc ggtactacga cgatcactac    1680
agcctggatt attggggaca gggcaccctc gtgactgtgt caagcggtgg cggaggaagc    1740
```

-continued

```
ggaggcggcg gttctggtgg tggtggtagc ggaggtggtg gcagcgatat ccagatgaca    1800
cagagcccta gcagcctgtc tgccagcgtg ggagacagag tgaccatcac atgtagcgcc    1860
agctccagcg tgtcctacat gaattggtat cagcaaaagc ccggcaaggc ccctaagcgg    1920
ctgatctacg atacaagcaa gctggcctct ggcgtgccat ccagattttc tggcagcggc    1980
tctggcaccg acttcaccct gacaatatct agcctgcagc ctgaggactt cgccacatat    2040
tactgccagc agtggtccag caatcccttc acctttggcc agggcaccaa gctggaaatc    2100
aag                                                                  2103

<210> SEQ ID NO 26
<211> LENGTH: 2133
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 26
caggttcagc tgcaagagtc tggccctggc ctggtcaagc ctagccaaac actgagcctg      60
acctgtaccg tgtccggcta cgccttcacc gcctacaata tccactgggt ccgacaggcc     120
cctggacagg gacttgaatg gatgggcagc ttcgacccct acgatggcgg cagcagctac     180
aaccagaagt tcaaggaccg gctgaccatc agcaaggaca ccagcaagaa ccaggtggtg     240
ctgaccatga ccaacatgga ccctgtggac accgccacct actactgtgc cagaggctgg     300
tactacttcg actactgggg ccacggcacc ctggtcacag ttagctctgc ctctacaaag     360 ggcccccagcg tgttccctct ggctcctagc agcaagtcta caagcggagg aacagccgct     420
ctgggctgcc tcgtgaagga ttactttccc gagccagtga ccgtgtcctg gaatagcgga     480
gcactgacaa gcggcgtgca cacctttcca gctgtgctgc aaagcagcgg cctgtactct     540
ctgagcagcg tcgtgacagt gccaagcagc tctctgggca cccagaccta catctgcaat     600
gtgaatcaca gcccagcaa caccaaggtg gacaagaagg tggaacccaa gagctgcgac     660
aagacccaca cctgtcctcc atgtcctgct ccagaagctg ctggcgcccc ttccgtgttt     720
ctgttccctc caaagcctaa ggacaccctg atgatcagca gaacccctga agtgacctgc     780
gtggtggtgg atgtgtccca cgaggatccc gaagtgaagt tcaattggta cgtggacggc     840
gtggaagtgc acaacgccaa gaccaagcct agagaggaac agtacaacag cacctacaga     900
gtggtgtctg tgctgaccgt gctgcaccag gattggctga cggcaaaga gtacaagtgc     960 aaggtgtcca acaaggccct gcctgctcct atcgagaaaa ccatctccaa ggccaaggga    1020
cagcccaggg aaccccaggt ttacacactg cctccaagca gggacgagct gaccaagaat    1080
caggtgtccc tgacctgcct ggttaagggc ttctacccct ccgatatcgc cgtggaatgg    1140
gagagcaatg ccagcctga aacaactac aagacaaccc ctcctgtgct ggacagcgac    1200
ggctcattct tcctgtacag caagctgaca gtggacaagt ccagatggca gcagggcaac    1260
gtgttctcct gcagcgtgat gcacgaggcc ctgcacaacc actacaccca gaaaagcctg    1320
tctctgagcc ccggaaaagg cggcggagga tctggcggag gcggatctga agttcagctg    1380
gttgaatctg gcggcggact ggttcaacct ggcggatctc tgagactgag ctgtgccgcc    1440
tccggcttca ccttcaatac ctacgccatg aattgggttc gacaagcccc aggcaaaggc    1500
ctggaatggg tcgccagaat cagaagcaag tacaacaact acgccacgta ctacgccgac    1560
agcgtgaagg gcagattcac catcagccgg gacgactcca agaacaccct gtacctgcag    1620
```

-continued

```
atgaactccc tgagagccga ggataccgcc gtgtactatt gtgtgcggca cggcaacttc      1680
ggcaacagct acgtgtccta ctttgcctat tggggacagg gcaccaccgt gactgtttct      1740
agcggtggcg gaggaagtgg tggcggcggt agcggaggtg gtggtagcgg aggcggaggt      1800
tctgagatcg tggttacaca gagccccgcc acactgagtg tgtctccagg cgaaagagcc      1860
actctgagct gcagatcttc tacaggcgcc gtgacagccg ccaattacgc caattgggtg      1920
caagagaagc ccggccaggc tttcagagga ctgattggcg gagccaacaa gagagcccct      1980
ggcgttccag ccagattttc tggcagtctg tctggcgacg aggctaccct gacaatcagc      2040
agcctgcaga gcgaggactt cgccgtgtat tactgcgccc tgttctacag caacctgtgg      2100
gtgttcggcc agggcacaaa gctggaaatc aag                                  2133
```

<210> SEQ ID NO 27
<211> LENGTH: 2103
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 27

```
caggttcagc tgcaagagtc tggccctggc ctggtcaagc ctagccaaac actgagcctg        60
acctgtaccg tgtccggcta cgccttcacc gcctacaata tccactgggt ccgacaggcc       120
cctggacagg gacttgaatg gatgggcagc ttcgacccct acgatggcgg cagcagctac       180
aaccagaagt tcaaggaccg gctgaccatc agcaaggaca ccagcaagaa ccaggtggtg       240
ctgaccatga ccaacatgga ccctgtggac accgccacct actactgtgc cagaggctgg       300
tactacttcg actactgggg ccacggcacc ctggtcacag ttagctctgc ctctacaaag       360
ggccccagcg tgttccctct ggctcctagc agcaagtcta caagcggagg aacagccgct       420
ctgggctgcc tcgtgaagga ttactttccc gagccagtga ccgtgtcctg aatagcggga       480
gcactgacaa gcggcgtgca cacctttcca gctgtgctgc aaagcagcgg cctgtactct       540
ctgagcagcg tcgtgacagt gccaagcagc tctctgggca cccagaccta catctgcaat       600
gtgaatcaca gcccagcaa caccaaggtg gacaagaagg tggaacccaa gagctgcgac        660
aagacccaca cctgtcctcc atgtcctgct ccagaagctg ctggcgcccc ttccgtgttt       720
ctgttccctc caaagcctaa ggacaccctg atgatcagca gaaccccctga agtgacctgc      780 gtggtggtgg atgtgtccca cgaggatccc gaagtgaagt tcaattggta cgtggacggc       840
gtggaagtgc acaacgccaa gaccaagcct agagaggaac agtacaacag cacctacaga       900
gtggtgtctg tgctgaccgt gctgcaccag gattggctga acggcaaaga gtacaagtgc       960
aaggtgtcca acaaggccct gcctgctcct atcgagaaaa ccatctccaa ggccaaggga      1020
cagcccaggg aaccccaggt ttacacactg cctccaagca gggacgagct gaccaagaat      1080
caggtgtccc tgacctgcct ggttaagggc ttctacccct ccgatatcgc cgtggaatgg      1140
gagagcaatg gccagcctga gaacaactac aagacaaccc ctcctgtgct ggacagcgac      1200
ggctcattct tcctgtacag caagctgaca gtggacaagt ccagatggca gcaggcaac       1260 gtgttctcct gcagcgtgat gcacgaggcc ctgcacaacc actacaccca gaaaagcctg      1320
tctctgagcc ccgaaaaagg cggcggagga tctggcggag cggatctca agttcaactg       1380 gtgcaatccg gtggcggcgt tgtccagcct ggaagatctc tgagactgag ctgcaaggcc      1440
```

-continued

```
agcggctaca cattcacccg gtacaccatg cactgggttc gccaggctcc aggcaaatgt    1500
ttggagtgga tcggctacat caaccccagc cggggctaca ccaactacaa tcagaaagtg    1560
aaggaccgct tcacaatcag ccgggacaac tccaagaaca ccctgtacct gcagatggac    1620
tccctgagag ccgaggatac cgccgtgtac tactgcgccc ggtactacga cgatcactac    1680
agcctggatt attggggaca gggcaccacc gtgactgtgt caagcggtgg cggaggaagc    1740
ggaggcggcg ttctggtggt tggtggtagc ggaggtggtg cagcgatat ccagatgaca     1800 cagagcccta gcagcctgtc tgccagcgtg ggagacagag tgaccatcac atgtagcgcc    1860
agctccagcg tgtcctacat gaactggtat cagcaaaagc ccggcaaggc ccctaagcgg    1920
tggatctacg atacaagcaa gctggcctct ggcgtgccat ccagatttc tggcagcggc     1980 tctggcaccg acttcacct caccataagc agcctgcagc ctgaggacat tgccacatat      2040
tactgccagc agtggtccag caatcctttc accttgggct gcggcacaaa gctcgagatc    2100
aag                                                                   2103
```

<210> SEQ ID NO 28
<211> LENGTH: 2103
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 28

```
caggttcagc tgcaagagtc tggccctggc ctggtcaagc ctagccaaac actgagcctg     60
acctgtaccg tgtccggcta cgccttcacc gcctacaata tccactgggt ccgacaggcc    120
cctggacagg gacttgaatg gatgggcagc ttcgacccct acgatggcgg cagcagctac    180
aaccagaagt tcaaggaccg gctgaccatc agcaaggaca ccagcaagaa ccaggtggtg    240
ctgaccatga ccaacatgga ccctgtggac accgccacct actactgtgc cagaggctgg    300
tactacttcg actactgggg ccacggcacc ctggtcacag ttagctctgc ctctacaaag    360
ggccccagcg tgttccctct ggctcctagc agcaagtcta caagcggagg aacagccgct    420
ctgggctgcc tcgtgaagga ttactttccc gagccagtga ccgtgtcctg gaatagcgga    480
gcactgacaa gcggcgtgca cacctttcca gctgtgctgc aaagcagcgg cctgtactct    540
ctgagcagcg tcgtgacagt gccaagcagc tctctgggca cccagaccta catctgcaat    600
gtgaatcaca agcccagcaa caccaaggtg gacaagaagg tggaacccaa gagctgcgac    660
aagacccaca cctgtcctcc atgtcctgct ccagaagctg ctggcgcccc ttccgtgttt    720
ctgttccctc caaagcctaa ggacaccctg atgatcagca gaacccctga agtgacctgc    780
gtggtggtgg atgtgtccca cgaggatccc gaagtgaagt tcaattggta cgtggacggc    840
gtggaagtgc acaacgccaa gaccaagcct agagaggaac agtacaacag cacctacaga    900
gtggtgtctg tgctgaccgt gctgcaccag gattggctga acggcaaaga gtacaagtgc    960
aaggtgtcca caaaggccct gcctgctcct atcgagaaaa ccatctccaa ggccaaggga    1020
cagcccaggg aacccccagt ttacacactg cctccaagca gggacgagct gaccaagaat    1080
caggtgtccc tgacctgcct ggttaagggc ttctacccct ccgatatcgc cgtggaatgg    1140
gagagcaatg gccagcctga gaacaactac aagacaaccc ctcctgtgct ggacagcgac    1200
ggctcattct tcctgtacag caagctgaca gtggacaagt ccagatggca gcagggcaac    1260
gtgttctcct gcagcgtgat gcacgaggcc ctgcacaacc actacaccca gaaaagcctg    1320
```

-continued

```
tctctgagcc ccggaaaagg cggcggagga tctggcggag gcggatctca agttcaactg    1380
gtgcagtctg gcgctgaagt gaagaaacct ggcgcctccg tgaaggtgtc ctgtaaagcc    1440
agcggctaca cattcacccg gtacaccatg cactgggttc gccaagctcc aggacaatgc    1500
ttggagtgga tgggctacat caaccccagc cggggctaca ccaactacaa tcaaaagttt    1560
aaggatcgcg tgaccctgac caccgacaag agcagctcta cagcctacat ggaactgagc    1620
agcctgcgga gcgaagatac cgccgtgtac tactgcgccc ggtactacga cgatcactac    1680
agcctggatt attggggaca gggcaccctc gtgactgtgt caagcggtgg cggaggaagc    1740
ggaggcggcg gttctggtgg tggtggtagc ggaggtggtg gcagcgatat ccagatgaca    1800
cagagcccta gcagcctgtc tgccagcgtg ggagacagag tgaccatcac atgtagcgcc    1860
agctccagcg tgtcctacat gaattggtat cagcaaaagc ccggcaaggc ccctaagcgg    1920
ctgatctacg atacaagcaa gctggcctct ggcgtgccat ccagattttc tggcagcggc    1980
tctggcaccg acttcaccct gacaatatct agcctgcagc ctgaggactt cgccacatat    2040
tactgccagc agtggtccag caatcccttc acctttggct gcggcaccaa gctggaaatc    2100
aag                                                                   2103
```

<210> SEQ ID NO 29
<211> LENGTH: 2133
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 29

```
caggttcagc tgcaagagtc tggccctggc ctggtcaagc ctagccaaac actgagcctg      60
acctgtaccg tgtccggcta cgccttcacc gcctacaata tccactgggt ccgacaggcc     120
cctggacagg gacttgaatg gatgggcagc ttcgacccct tacgatggcg gcagcagctac    180 aaccagaagt tcaaggaccg gctgaccatc agcaaggaca ccagcaagaa ccaggtggtg     240
ctgaccatga ccaacatgga ccctgtggac accgccacct actactgtgc cagaggctgg     300
tactacttcg actactgggg ccacggcacc ctggtcacag ttagctctgc ctctacaaag     360
ggccccagcg tgttccctct ggctcctagc agcaagtcta caagcggagg aacagccgct     420
ctgggctgcc tcgtgaagga ttactttccc gagccagtga ccgtgtcctg gaatagcgga     480
gcactgacaa gcggcgtgca cacctttcca gctgtgctgc aaagcagcgg cctgtactct     540
ctgagcagcg tcgtgacagt gccaagcagc tctctgggca cccagaccta catctgcaat     600
gtgaatcaca agcccagcaa caccaaggtg gacaagaagg tggaacccaa gagctgcgac     660
aagacccaca cctgtcctcc atgtcctgct ccagaagctg ctggcgcccc ttccgtgttt     720
ctgttccctc caaagcctaa ggacaccctg atgatcagca gaacccctga agtgacctgc     780
gtggtggtgg atgtgtccca cgaggatccc gaagtgaagt tcaattggta cgtggacggc     840
gtggaagtgc acaacgccaa gaccaagcct agagaggaac agtacaacag cacctacaga     900
gtggtgtctg tgctgaccgt gctgcaccag gattggctga acggcaaaga gtacaagtgc     960
aaggtgtcca acaaggccct gcctgctcct atcgagaaaa ccatctccaa ggccaaggga    1020
cagcccaggg aacccagggt ttacacactg cctccaagca gggacgagct gaccaagaat    1080
caggtgtccc tgacctgcct ggttaagggc ttctacccct ccgatatcgc cgtggaatgg    1140
```

-continued

```
gagagcaatg gccagcctga gaacaactac aagacaaccc ctcctgtgct ggacagcgac    1200
ggctcattct tcctgtacag caagctgaca gtggacaagt ccagatggca gcagggcaac    1260
gtgttctcct gcagcgtgat gcacgaggcc ctgcacaacc actacaccca gaaaagcctg    1320
tctctgagcc ccgaaaagg cggcggagga tctggcggag cggatctga agttcagctg    1380 gttgaatctg gcggcggact ggttcaacct ggcggatctc tgagactgag ctgtgccgcc    1440
tccggcttca ccttcaatac ctacgccatg aattgggttc gacaagcccc aggcaaatgc    1500
ctggaatggg tcgccagaat cagaagcaag tacaacaact acgccacgta ctacgccgac    1560
agcgtgaagg gcagattcac catcagccgg gacgactcca gaacaccct gtacctgcag    1620 atgaactccc tgagagccga ggataccgcc gtgtactatt gtgtgcggca cggcaacttc    1680
ggcaacagct acgtgtccta ctttgcctat tggggacagg gcaccaccgt gactgtttct    1740
agcggtggcg gaggaagtgg tggcggcggt agcggaggtg gtggtagcgg aggcggaggt    1800
tctgagatcg tggttacaca gagccccgcc acactgagtg tgtctccagg cgaaagagcc    1860
actctgagct gcagatcttc tacaggcgcc gtgacagccg ccaattacgc caattgggtg    1920
caagagaagc ccggccaggc tttcagagga ctgattggcg gagccaacaa gagagcccct    1980
ggcgttccag ccagattttc tggcagtctg tctggcgacg aggctaccct gacaatcagc    2040
agcctgcaga gcgaggactt cgccgtgtat tactgcgccc tgttctacag caacctgtgg    2100
gtgttcggct gcggcacaaa gctggaaatc aag    2133
```

<210> SEQ ID NO 30
<211> LENGTH: 1338
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 30

```
caggttcagc tgcaagagtc tggccctggc ctggtcaagc ctagccaaac actgagcctg    60
acctgtaccg tgtccggcta cgccttcacc gcctacaata tccactgggt ccgacaggcc    120
cctggacagg gacttgaatg gatgggcagc ttcgacccct acgatggcgg cagcagctac    180
aaccagaagt tcaaggaccg gctgaccatc agcaaggaca ccagcaagaa ccaggtggtg    240
ctgaccatga ccaacatgga ccctgtggac accgccacct actactgtgc cagaggctgg    300
tactacttcg actactgggg ccacggcacc ctggtcacag ttagctctgc ctctacaaag    360
ggccccagcg tgttccctct ggctcctagc agcaagtcta caagcggagg aacagccgct    420
ctgggctgcc tcgtgaagga ttactttccc gagccagtga ccgtgtcctg gaatagcgga    480
gcactgacaa gcggcgtgca cacctttcca gctgtgctgc aaagcagcgg cctgtactct    540
ctgagcagcg tcgtgacagt gccaagcagc tctctgggca cccagaccta catctgcaat    600
gtgaatcaca agcccagcaa caccaaggtg gacaagaagg tggaacccaa gagctgcgac    660
aagacccaca cctgtcctcc atgtcctgct ccagaagctg ctggcgcccc ttccgtgttt    720
ctgttccctc caaagcctaa ggacaccctg atgatcagca gaacccctga agtgacctgc    780
gtggtggtgg atgtgtccca cgaggatccc gaagtgaagt tcaattggta cgtggacggc    840
gtggaagtgc acaacgccaa gaccaagcct agagaggaac agtacaacag cacctacaga    900
gtggtgtctg tgctgaccgt gctgcaccag gattggctga acggcaaaga gtacaagtgc    960
aaggtgtcca acaaggccct gcctgctcct atcgagaaaa ccatctccaa ggccaaggga    1020
```

-continued

```
cagcccaggg aaccccaggt ttacacactg cctccaagca gggacgagct gaccaagaat      1080
caggtgtccc tgacctgcct ggttaagggc ttctacccct ccgatatcgc cgtggaatgg      1140
gagagcaatg gccagcctga gaacaactac aagacaaccc ctcctgtgct ggacagcgac      1200
ggctcattct tcctgtacag caagctgaca gtggacaagt ccagatggca gcagggcaac      1260
gtgttctcct gcagcgtgat gcacgaggcc ctgcacaacc actacaccca gaaaagcctg      1320
tctctgagcc ccggcaaa                                                    1338
```

<210> SEQ ID NO 31
<211> LENGTH: 1338
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 31

```
caggttcagc tgcaagagtc tggccctggc ctggtcaagc ctagccaaac actgagcctg        60
acctgtaccg tgtccggcta cgccttcacc gcctacaata tccactgggt ccgacaggcc       120
cctggacagg gacttgaatg gatgggcagc ttcgacccct acgatggcgg cagcagctac       180
aaccagaagt tcaaggaccg gctgaccatc agcaaggaca ccagcaagaa ccaggtggtg       240
ctgaccatga ccaacatgga ccctgtggac accgccacct actactgtgc cagaggctgg       300
tactacttcg actactgggg ccacggcacc ctggtcacag ttagctctgc ctctacaaag       360 ggcccagcg tgttccctct ggctcctagc agcaagtcta caagcggagg aacagccgct       420
ctgggctgcc tcgtgaagga ttactttccc gagccagtga ccgtgtcctg gaatagcgga       480
gcactgacaa gcggcgtgca cacctttcca gctgtgctgc aaagcagcgg cctgtactct       540
ctgagcagcg tcgtgacagt gccaagcagc tctctgggca cccagaccta catctgcaat       600
gtgaatcaca gcccagcaa caccaaggtg gacaagaagg tggaacccaa gagctgcgac       660
aagacccaca cctgtcctcc atgtcctgct ccagaagctg ctggcgcccc ttccgtgttt       720
ctgttccctc caaagcctaa ggacaccctg atgatcagca gaacccctga agtgacctgc       780
gtggtggtgg atgtgtccca cgaggatccc gaagtgaagt tcaattggta cgtggacggc       840
gtggaagtgc acaacgccaa gaccaagcct agagaggaac agtacaacag cacctacaga       900
gtggtgtctg tgctgaccgt gctgcaccag gattggctga acggcaaaga gtacaagtgc       960
aaggtgtcca acaaggccct gcctgctcct atcgagaaaa ccatctccaa ggccaaggga      1020
cagcccaggg aaccccaggt ttacacactg cctccaagca gggacgagct gaccaagaat      1080
caggtgtccc tgtggtgcct ggttaagggc ttctacccct ccgatatcgc cgtggaatgg      1140
gagagcaatg gccagcctga gaacaactac aagacaaccc ctcctgtgct ggacagcgac      1200
ggctcattct tcctgtacag caagctgaca gtggacaagt ccagatggca gcagggcaac      1260
gtgttctcct gcagcgtgat gcacgaggcc ctgcacaacc actacaccca gaaaagcctg      1320
tctctgagcc ccggcaaa                                                    1338
```

<210> SEQ ID NO 32
<211> LENGTH: 1431
<212> TYPE: DNA
<213> ORGANISM: Artificial Sequence
<220> FEATURE:

-continued

<221> NAME/KEY: source
<223> OTHER INFORMATION: /note="Description of Artificial Sequence:
      Synthetic polynucleotide"

<400> SEQUENCE: 32

```
caggttcagc tggttcaatc tggcggcgga gttgtgcagc ctggcagatc tctgagactg      60
agctgtaaag ccagcggcta caccttcacc agatacacca tgcactgggt ccgacaggcc     120
cctggcaaag gacttgagtg gatcggctac atcaacccca gccggggcta caccaactac     180
aaccagaaag tgaaggaccg gttcaccatc agccgggaca acagcaagaa caccctgtac     240
ctgcagatgg acagcctgag agccgaggat accgccgtgt actactgtgc ccggtactac     300
gacgaccact acagcctgga ttattggggc cagggcacca ccgtgacagt ttctagcgga     360
ggcggaggat caggtggcgg tggatctggc ggtggtggaa gtggtggtgg cggaagcgat     420
atccagatga cacagagccc tagcagcctg tctgccagcg tgggagacag agtgaccatc     480
acatgtagcg ccagcagcag cgtgtcctac atgaactggt atcagcagaa gcccggcaag     540
gcccctaaga gatggatcta cgacaccagc aagctggcct ctggcgtgcc aagcagattt     600
tctggcagcg gctctggcac cgacttcacc tttaccataa gcagcctgca gcctgaggac     660
attgccacct actactgcca gcagtggtcc agcaatccct tcacattcgg ccaggggacc     720
aagctggaaa tcaaagagcc caagagcagc gacaagaccc acacctgtcc tccatgtcct     780
gctccagaag ctgcaggcgc ccccttccgtg tttctgttcc ctccaaagcc taaggacacc     840
ctgatgatca gcaggacccc tgaagtgacc tgcgtggtgg tcgatgtgtc ccacgaggat     900
cccgaagtga agttcaattg gtacgtggac ggcgtggaag tgcacaacgc caagaccaag     960
cctagagagg aacagtacaa cagcacctac agagtggtgt ccgtgctgac cgtgctgcac    1020
caggattggc tgaacggcaa agagtacaag tgcaaggtgt ccaacaaggc cctgcctgct    1080
cctatcgaga aaaccatcag caaggccaag ggccagccta gggaacccca ggtttacaca    1140
ctgcctccaa gcagggacga gctgaccaag aatcaggtgt ccctgagctg tgccgtgaag    1200
ggcttctacc cttccgatat cgccgtggaa tgggagagca tggccagcc agagaacaac    1260 tacaagacaa cccctcctgt gctggacagc gacggctcat tcttcctggt gtccaagctg    1320
acagtggaca gagcagatg gcagcagggc aacgtgttca gctgcagcgt gatgcacgag    1380
gccctgcaca accactacac ccagaagtcc ctgtctctga gccctggcaa g            1431
```

<210> SEQ ID NO 33
<211> LENGTH: 1431
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 33

```
caggttcagc tggttcagtc tggcgccgaa gtgaagaaac ctggcgcctc tgtgaaggtg      60
tcctgcaagg cctctggcta cacattcacc cggtacacca tgcactgggt ccgacaggct     120
ccaggacaag gcttggagtg gatgggctac atcaacccca gccggggcta caccaactac     180
aaccagaaat tcaaggaccg cgtgaccctg accaccgaca gtctagcag caccgcctac     240 atggaactga gcagcctgag aagcgaggac accgccgtgt actactgtgc ccggtactac     300
gacgaccact acagcctgga ttattggggc cagggcaccc tggtcacagt ttctagcgga     360
ggcggaggat ctggtggcgg aggaagtggc ggaggcggta gtggtggtgg cggatctgat     420
```

-continued

```
atccagatga cacagagccc cagcagcctg tctgcctctg tgggagacag agtgaccatc      480
acctgtagcg ccagcagcag cgtgtcctac atgaattggt atcagcagaa gcccggcaag      540
gcccctaagc ggctgatcta cgatacaagc aaactggcca gcggcgtgcc cagcagattt      600
tctggttctg gcagcggcac cgacttcacc ctgacaatat ctagcctgca gccagaggac      660
ttcgccacct actactgcca gcagtggtcc agcaatccct tcacctttgg ccaggggacc      720
aagctggaaa tcaaagagcc caagagcagc gacaagaccc acacctgtcc tccatgtcct      780
gctccagaag ctgcaggcgc cccttccgtg tttctgttcc ctccaaagcc taaggacacc      840
ctgatgatca gcaggacccc tgaagtgacc tgcgtggtgg tcgatgtgtc ccacgaggac      900
ccagaagtga agttcaattg gtacgtggac ggcgtggaag tgcacaacgc caagaccaag      960
cctagagagg aacagtacaa cagcacctac agagtggtgt ccgtgctgac cgtgctgcac     1020
caggattggc tgaacggcaa agagtacaag tgcaaggtgt ccaacaaagc cctgcctgct     1080
cctatcgaga aaaccatcag caaggccaag ggccagccta gggaacccca ggtttacaca     1140
ctgcctccaa gcagggacga gctgaccaag aatcaggtgt ccctgagctg tgccgtgaag     1200
ggcttctacc cttccgatat cgccgtggaa tgggagagca tggccagcc agagaacaac     1260 tacaagacaa cccctcctgt gctggacagc gacggctcat cttcctggt gtccaagctg     1320 acagtggaca gagcagatg gcagcagggc aacgtgttca gctgcagcgt gatgcacgag     1380
gccctgcaca accactacac acagaagtcc ctgtctctga gccccggcaa a            1431
```

```
<210> SEQ ID NO 34
<211> LENGTH: 1461
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 34
gaagtgcagc tggttgagtc tggcggagga ctggttcaac ctggcggaag cctgagactg       60
tcttgtgccg ccagcggctt caccttcaac acctacgcca tgaactgggt ccgacaggcc      120
cctggcaaag gccttgaatg ggtcgccaga atcagaagca agtacaacaa ttacgccacc      180
tactacgccg acagcgtgaa gggcagattc accatcagcc gggacgacag caagaacacc      240
ctgtacctgc agatgaacag cctgagagcc gaggacaccg ccgtgtacta ttgtgtgcgg      300
cacggcaact cggcaacag ctacgtgtcc tacttcgcct attggggcca gggcaccacc      360
gtgacagttt ctagcggagg cggtggatct ggcggcggag gaagtggtgg cggaggtagt      420 ggcggaggc gatctgagat tgtggtcaca cagagcccg ccacactgag tgtttctcca      480
ggcgaaagag ccacactgtc ctgcaggtct agtacaggcg ctgtgaccgc cgccaactac      540
gccaattggg tgcaagagaa acccggccag gccttcagag gactgattgg cggagccaac      600
aaacgcgctc ctggcgtgcc agccagattt tctggatccc tgagcggcga cgaggccact      660
ctgactatta gcagcctgca gtccgaggac tttgccgtgt attactgcgc cctgttctac      720
agcaacctgt gggtgttcgg ccaggggacc aagctggaaa tcaaagagcc caagagcagc      780
gacaagaccc acacatgccc tccatgtcct gctccagaag ctgctggcgc cccttccgtg      840
tttctgttcc ctccaaagcc taaggacacc ctgatgatca gcagaacccc tgaagtgacc      900
tgcgtggtgg tggatgtgtc ccacgaggat cccgaagtga agttcaattg gtacgtggac      960
```

-continued

```
ggcgtggaag tgcacaacgc caagaccaag cctagagagg aacagtacaa cagcacctac     1020
agagtggtgt ccgtgctgac cgtgctgcac caggattggc tgaacggcaa agagtacaag     1080
tgcaaggtgt ccaacaaggc cctgcctgct cctatcgaga aaaccatcag caaggccaag     1140
ggccagccta gggaacccca ggtttacaca ctgcctccaa gcagggacga gctgaccaag     1200
aatcaggtgt ccctgagctg cgccgtgaag ggattctacc cttccgatat cgccgtggaa     1260
tgggagagca atggacagcc cgagaacaac tacaagacca cacctcctgt gctggacagc     1320
gacggctcat tcttcctggt gtccaagctg acagtggaca gagcagatg gcagcagggc     1380 aacgtgttca gctgcagcgt gatgcacgag gccctgcaca accactacac ccagaagtcc     1440
ctgtctctga gccctggcaa g     1461
```

```
<210> SEQ ID NO 35
<211> LENGTH: 1338
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 35
```

```
caggttcagc tgcaagagtc tggccctggc ctggtcaagc ctagccaaac actgagcctg      60
acctgtaccg tgtccggcta tgccttcgcc gcctacaata tccactgggt ccgacaggct     120
ccaggacagg gacttgagtg gatgggcagc ttcgacccct acgatggcgg cagcagctac     180
aaccagaagt tcaaggaccg gctgaccatc agcaaggaca ccagcaagaa ccaggtggtg     240
ctgaccatga ccaacatgga ccctgtggac accgccacct actactgtgc cagaggctgg     300
tactacttcg actactgggg ccacggcacc ctggtcacag ttagctctgc ctctacaaag     360 ggcccagcg tgttccctct ggctcctagc agcaagtcta agcggagg aacagccgct      420 ctgggctgcc tcgtgaagga ttactttccc gagccagtga ccgtgtcctg gaatagcgga     480
gcactgacaa gcggcgtgca cacctttcca gctgtgctgc aaagcagcgg cctgtactct     540
ctgagcagcg tcgtgacagt gccaagcagc tctctgggca cccagaccta catctgcaat     600
gtgaatcaca gcccagcaa caccaaggtg gacaagaagg tggaacccaa gagctgcgac     660
aagacccaca cctgtcctcc atgtcctgct ccagaagctg ctggcgcccc ttccgtgttt     720
ctgttccctc caaagcctaa ggacaccctg atgatcagca gaacccctga agtgacctgc     780
gtggtggtgg atgtgtccca cgaggatccc gaagtgaagt tcaattggta cgtggacggc     840
gtggaagtgc acaacgccaa gaccaagcct agagaggaac agtacaacag cacctacaga     900
gtggtgtctg tgctgaccgt gctgcaccag gattggctga cggcaaaga gtacaagtgc      960 aaggtgtcca acaaggccct gcctgctcct atcgagaaaa ccatctccaa ggccaaggga     1020
cagcccaggg aacccaggt ttacacactg cctccaagca gggacgagct gaccaagaat     1080
caggtgtccc tgtggtgcct ggttaagggc ttctacccct ccgatatcgc cgtggaatgg     1140
gagagcaatg ccagcctga gaacaactac aagacaaccc tcctgtgct ggacagcgac      1200 ggctcattct tcctgtacag caagctgaca gtggacaagt ccagatggca gcaggcaac      1260 gtgttctcct gcagcgtgat gcacgaggcc ctgcacaacc actacaccca gaaaagcctg     1320
tctctgagcc ccggcaaa     1338
```

```
<210> SEQ ID NO 36
<211> LENGTH: 1461
```

<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 36

```
gaagtgcagc tggttgagtc tggcggagga ctggttcaac ctggcggaag cctgagactg      60
tcttgtgccg ccagcggctt caccttcaac acctacgcca tgaactgggt ccgacaggcc     120
cctggcaaat gccttgaatg ggtcgccaga atcagaagca agtacaacaa ttacgccacc     180
tactacgccg acagcgtgaa gggcagattc accatcagcc gggacgacag caagaacacc     240
ctgtacctgc agatgaacag cctgagagcc gaggacaccg ccgtgtacta ttgtgtgcgg     300
cacggcaact cggcaacag ctacgtgtcc tacttcgcct attgggccca gggcaccacc     360
gtgacagttt ctagcggagg cggtggatct ggcggcggag gaagtggtgg cggaggtagt     420
ggcggaggcg gatctgagat tgtggtcaca cagagccccg ccacactgag tgtttctcca     480
ggcgaaagag ccacactgtc ctgcaggtct agtacaggcg ctgtgaccgc cgccaactac     540
gccaattggg tgcaagagaa acccggccag gccttcagag gactgattgg cggagccaac     600
aaacgcgctc ctggcgtgcc agccagattt tctggatccc tgagcggcga cgaggccact     660
ctgactatta gcagcctgca gtccgaggac tttgccgtgt attactgcgc cctgttctac     720
agcaacctgt gggtgttcgg ctgcgggacc aagctggaaa tcaaagagcc caagagcagc     780
gacaagaccc acacatgccc tccatgtcct gctccagaag ctgctggcgc cccttccgtg     840
tttctgttcc ctccaaagcc taaggacacc ctgatgatca gcagaacccc tgaagtgacc     900
tgcgtggtgg tggatgtgtc ccacgaggat cccgaagtga agttcaattg gtacgtggac     960
ggcgtggaag tgcacaacgc caagaccaag cctagagagg aacagtacaa cagcacctac    1020
agagtggtgt ccgtgctgac cgtgctgcac caggattggc tgaacggcaa agagtacaag    1080
tgcaaggtgt ccaacaaggc cctgcctgct cctatcgaga aaaccatcag caaggccaag    1140
ggccagccta gggaacccca ggtttacaca ctgcctccaa gcaggacga gctgaccaag    1200 aatcaggtgt ccctgagctg cgccgtgaag ggattctacc cttccgatat cgccgtggaa    1260
tgggagagca tggacagcc cgagaacaac tacaagacca cacctcctgt gctggacagc    1320
gacggctcat cttcctggt gtccaagctg acagtggaca gagcagatg gcagcaggc    1380 aacgtgttca gctgcagcgt gatgcacgag gccctgcaca accactacac ccagaagtcc    1440
ctgtctctga gccctggcaa g                                            1461
```

<210> SEQ ID NO 37
<211> LENGTH: 1338
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 37

```
caggttcagc tgcaagagtc tggccctggc ctggtcaagc ctagccaaac actgagcctg      60
acctgtaccg tgtccggcta tgccttcgcc gcctacaata tccactgggt ccgacaggct     120
ccaggacagg gacttgagtg gatgggcagc ttcgacccct acgatggcgg cagcagctac     180
aaccagaagt tcaaggaccg gctgaccatc agcaaggaca ccagcaagaa ccaggtggtg     240
```

-continued

```
ctgaccatga ccaacatgga ccctgtggac accgccacct actactgtgc cagaggctgg    300
tactacttcg actactgggg ccacggcacc ctggtcacag ttagctctgc ctctacaaag    360
ggccccagcg tgttccctct ggctcctagc agcaagtcta caagcggagg aacagccgct    420
ctgggctgcc tcgtgaagga ttactttccc gagccagtga ccgtgtcctg aatagcgga     480 gcactgacaa gcggcgtgca cacctttcca gctgtgctgc aaagcagcgg cctgtactct    540
ctgagcagcg tcgtgacagt gccaagcagc tctctgggca cccagaccta catctgcaat    600
gtgaatcaca agcccagcaa caccaaggtg gacaagaagg tggaacccaa gagctgcgac    660
aagacccaca cctgtcctcc atgtcctgct ccagaagctg ctggcgcccc ttccgtgttt    720
ctgttccctc caaagcctaa ggacaccctg atgatcagca gaacccctga agtgacctgc    780
gtggtggtgg atgtgtccca cgaggatccc gaagtgaagt tcaattggta cgtggacggc    840
gtggaagtgc acaacgccaa gaccaagcct agagaggaac agtacaacag cacctacaga    900
gtggtgtctg tgctgaccgt gctgcaccag gattggctga cggcaaaga gtacaagtgc      960 aaggtgtcca acaaggccct gcctgctcct atcgagaaa ccatctccaa ggccaaggga     1020
cagcccaggg aacccaggt ttacacactg cctccaagca gggacgagct gaccaagaat     1080
caggtgtccc tgacctgcct ggttaagggc ttctacccct ccgatatcgc cgtggaatgg    1140
gagagcaatg gccagcctga gaacaactac aagacaaccc ctcctgtgct ggacagcgac    1200
ggctcattct tcctgtacag caagctgaca gtggacaagt ccagatggca gcagggcaac    1260
gtgttctcct gcagcgtgat gcacgaggcc ctgcacaacc actacaccca gaaaagcctg    1320
tctctgagcc ccggcaaa                                                  1338
```

<210> SEQ ID NO 38
<211> LENGTH: 2133
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 38

```
gaagtgcagc tggttgagtc tggcggagga ctggttcaac ctggcggaag cctgagactg     60
tcttgtgccg ccagcggctt caccttcaac acctacgcca tgaactgggt ccgacaggcc    120
cctggcaaag gccttgaatg ggtcgccaga atcagaagca agtacaacaa ttacgccacc    180
tactacgccg acagcgtgaa gggcagattc accatcagcc gggacgacag caagaacacc    240
ctgtacctgc agatgaacag cctgagagcc gaggacaccg ccgtgtacta ttgtgtgcgg    300
cacggcaact cggcaacag ctacgtgtcc tacttcgcct attggggcca gggcaccacc     360
gtgacagttt ctagcggagg cggtggatct ggcggcggag gaagtggtgg cggaggtagt    420 ggcgaggcg gatctgagat tgtggtcaca cagagccccg ccacactgag tgtttctcca     480
ggcgaaagag ccacactgtc ctgcaggtct agtacaggcg ctgtgaccgc cgccaactac    540
gccaattggg tgcaagagaa acccggccag gccttcagag gactgattgg cggagccaac    600
aaacgcgctc ctggcgtgcc agccagattt tctggatccc tgagcggcga cgaggccact    660
ctgactatta gcagcctgca gtccgaggac tttgccgtgt attactgcgc cctgttctac    720
agcaacctgt gggtgttcgg ccagggggacc aagctggaaa tcaaaggtgg cggtggttca    780
ggtggcggcg gatctcaagt tcagctgcaa gagtctggcc ctggcctggt caagcctagc    840
caaacactga gcctgacctg taccgtgtcc ggctacgcct tcaccgccta caatatccac    900
```

-continued

```
tgggttcgac aagctcccgg acagggactt gagtggatgg gcagcttcga cccttacgat       960
ggcggcagca gctacaacca gaagttcaag gaccggctga ccatcagcaa ggacacctcc      1020
aagaaccagg tggtgctgac catgaccaac atggaccctg tggacaccgc tacctactac      1080
tgtgccagag gctggtacta cttcgattac tggggccacg gaaccctggt cacagtgtct      1140
agcgcctcta caaagggccc cagcgttttc ccactggctc ctagcagcaa gtctaccagc      1200
ggaggaacag ccgctctggg ctgtctggtc aaggactact ttcccgagcc agtgaccgtg      1260
tcctggaata gcggagcact gacaagcggc gtgcacacct tccagctgt gctgcaaagc       1320 agcggcctgt acagcctgtc tagcgtcgtg acagtgccaa gcagctctct gggcacccag      1380
acctacatct gcaatgtgaa tcacaagccc agcaacacca aggtggacaa gaaggtggaa      1440
cccaagagct gcgacaagac ccacacatgc cctccatgtc ctgctccaga agctgctggc      1500
gccccttccg tgtttctgtt ccctccaaag cctaaggaca ccctgatgat cagcagaacc      1560
cctgaagtga cctgcgtggt ggtggatgtg tcccacgagg atcccgaagt gaagttcaat      1620
tggtacgtgg acggcgtgga agtgcacaac gccaagacca gcctagaga ggaacagtac       1680 aacagcacct acagagtggt gtctgtgctg accgtgctgc accaggattg gctgaacggc      1740
aaagagtaca gtgcaaggt gtccaacaag gccctgcctg ctcctatcga gaaaaccatc       1800
tccaaggcca aggggcagcc cagggaacct caggtttaca cactgcctcc aagcagggac      1860
gagctgacca aaaatcaggt gtccctgagc tgcgccgtga agggattcta cccttccgat      1920
atcgccgtgg aatgggagag caatggacag cccgagaaca actacaagac cacacctcct      1980
gtgctggaca gcgacggctc attcttcctg gtgtccaagc tgacagtgga caagtccaga      2040
tggcagcagg gcaacgtgtt ctcctgcagc gtgatgcacg aggccctgca caaccactac      2100
acccagaaaa gcctgtctct gagccccggc aaa                                  2133
```

```
<210> SEQ ID NO 39
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic polynucleotide"

<400> SEQUENCE: 39
gatatcgtga tgacccagac acctctgagc ctgcctgtga cacctggcga acctgccagc        60
atcagctgta gagccagcaa gagcatcagc aagtacctgg cctggtatca gcagaagcct       120
ggacaggctc cccggctgct gatctatagc ggaagcacac tgcagagcgg catccctcct       180
agattttccg gcagcggcta cggcaccgat ttcacccctga ccatcaacaa catcgagagc      240
gaggacgccg cctactactt ctgccagcag cacgatgaga gcccctacac atttggcgag       300
ggcaccaagg tggaaatcaa gcggacagtg gccgctccta gcgtgttcat ctttccacct      360
agcgacgagc agctgaagtc tggcacagcc tctgtcgtgt gcctgctgaa caacttctac       420
cccagagaag ccaaggtgca gtggaaggtg gacaacgccc tgcagtccgg caatagccaa       480
gagagcgtga ccgagcagga cagcaaggac tctacctaca gcctgagcag caccctgaca       540
ctgagcaagg ccgactacga gaagcacaaa gtgtacgcct gcgaagtgac ccaccagggc       600
ctttctagcc ctgtgaccaa gagcttcaac cggggcgaat gt                         642
```

```
<210> SEQ ID NO 40
```

-continued

```
<211> LENGTH: 1407
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 40
gatatcgtga tgacccagac acctctgagc ctgcctgtga cacctggcga acctgccagc      60
atcagctgta gagccagcaa gagcatcagc aagtacctgg cctggtatca gcagaagcct     120
ggacaggctc cccggctgct gatctatagc ggaagcacac tgcagagcgg catccctcct     180
agattttccg gcagcggcta cggcaccgat ttcaccctga ccatcaacaa catcgagagc     240
gaggacgccg cctactactt ctgccagcag cacgatgaga gccctacac atttggcgag      300 ggcaccaagg tggaaatcaa gcggacagtg gccgctccta gcgtgttcat ctttccacct     360
agcgacgagc agctgaagtc tggcacagcc tctgtcgtgt gcctgctgaa caacttctac     420
cccagagaag ccaaggtgca gtggaaggtg gacaacgccc tgcagtccgg caatagccaa     480
gagagcgtga ccgagcagga cagcaaggac tctacctaca gcctgagcag caccctgaca     540
ctgagcaagg ccgactacga gaagcacaaa gtgtacgcct gcgaagtgac ccaccagggc     600
ctttctagcc ctgtgaccaa gagcttcaac agaggcgaat gtggcggcgg aggatctggc     660
ggaggcggat ctcaagttca gctggttcaa tccggtggcg gcgttgtgca gcctggcaga     720
tctctgagac tgagctgcaa ggcctccggc tacaccttca ccagatacac catgcactgg     780
gtccgacagg cccctggcaa aggacttgag tggatcggct acatcaaccc cagccggggc     840
tacaccaact acaaccagaa agtgaaggac cggttcacca tcagccggga caacagcaag     900
aacaccctgt acctgcagat ggactccctg agagccgagg ataccgccgt gtactactgt     960
gcccggtact acgacgacca ctactccctg gattattggg gccagggcac caccgtgaca    1020
gtttctagcg gtggcggagg aagcggaggc ggcggttcag gtggtggtgg tagcggaggt    1080
ggtggctccg atatccagat gacacagagc cctagcagcc tgtctgccag cgtgggagac    1140
agagtgacca tcacatgtag cgccagcagc tccgtgtcct acatgaactg gtatcaacaa    1200
aaacccggca aggcccctaa gcggtggatc tacgatacaa gcaagctggc ctctggcgtg    1260
cccagcagat tttctggctc tggcagcggc accgacttta cctttacaat cagctccctg    1320
cagcctgagg acattgccac ctactactgt cagcagtggt ccagcaatcc cttcaccttc    1380
ggccagggga caaagctcga gatcaag                                        1407

<210> SEQ ID NO 41
<211> LENGTH: 1407
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 41
gatatcgtga tgacccagac acctctgagc ctgcctgtga cacctggcga acctgccagc      60
atcagctgta gagccagcaa gagcatcagc aagtacctgg cctggtatca gcagaagcct     120
ggacaggctc cccggctgct gatctatagc ggaagcacac tgcagagcgg catccctcct     180
agattttccg gcagcggcta cggcaccgat ttcaccctga ccatcaacaa catcgagagc     240
gaggacgccg cctactactt ctgccagcag cacgatgaga gccctacac atttggcgag      300
```

-continued

```
ggcaccaagg tggaaatcaa gcggacagtg gccgctccta gcgtgttcat ctttccacct      360
agcgacgagc agctgaagtc tggcacagcc tctgtcgtgt gcctgctgaa caacttctac      420
cccagagaag ccaaggtgca gtggaaggtg gacaacgccc tgcagtccgg caatagccaa      480
gagagcgtga ccgagcagga cagcaaggac tctacctaca gcctgagcag caccctgaca      540
ctgagcaagg ccgactacga gaagcacaaa gtgtacgcct gcgaagtgac ccaccagggc      600
ctttctagcc ctgtgaccaa gagcttcaac agaggcgaat gtggcggcgg aggatctggc      660
ggaggcggat ctcaagttca gctggttcag tctggcgccg aagtgaagaa acctggcgcc      720
tccgtgaagg tgtcctgtaa agcctccggc tacacattca cccggtacac catgcactgg      780
gtccgacagg cacctggcca aggacttgag tggatgggct acatcaaccc cagccggggc      840
tacaccaact acaaccagaa attcaaggac cgcgtgaccc tgacaaccga caagtctagc      900
agcaccgcct acatggaact gagcagcctg agaagcgagg ataccgccgt gtactactgc      960
gcccggtact acgacgatca ctactccctg gattactggg gccagggcac actggtcaca     1020
gtttctagcg gtggcggagg aagcggaggc ggcggttcag gtggtggtgg tagcggaggt     1080
ggtggctccg atatccagat gacacagagc cctagcagcc tgtctgccag cgtgggagac     1140
agagtgacca tcacatgtag cgccagcagc tccgtgtcct acatgaattg gtatcaacaa     1200
aagcccggca aggcccctaa gcggctgatc tacgatacaa gcaagctggc ctctggcgtg     1260
cccagcagat tttctggctc tggcagcggc accgacttta cactcaccat aagcagcctg     1320
cagccagagg acttcgccac ctactattgc cagcagtggt ccagcaatcc cttcaccttt     1380
ggccagggaa caaagctcga gatcaag                                        1407
```

```
<210> SEQ ID NO 42
<211> LENGTH: 1437
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 42
```

```
gatatcgtga tgacccagac acctctgagc ctgcctgtga cacctggcga acctgccagc       60
atcagctgta gagccagcaa gagcatcagc aagtacctgg cctggtatca gcagaagcct      120
ggacaggctc cccggctgct gatctatagc ggaagcacac tgcagagcgg catccctcct      180
agattttccg gcagcggcta cggcaccgat ttcaccctga ccatcaacaa catcgagagc      240
gaggacgccg cctactactt ctgccagcag cacgatgaga gcccctacac atttggcgag      300
ggcaccaagg tggaaatcaa gcggacagtg gccgctccta gcgtgttcat ctttccacct      360
agcgacgagc agctgaagtc tggcacagcc tctgtcgtgt gcctgctgaa caacttctac      420
cccagagaag ccaaggtgca gtggaaggtg gacaacgccc tgcagtccgg caatagccaa      480
gagagcgtga ccgagcagga cagcaaggac tctacctaca gcctgagcag caccctgaca      540
ctgagcaagg ccgactacga gaagcacaaa gtgtacgcct gcgaagtgac ccaccagggc      600
ctttctagcc ctgtgaccaa gagcttcaac agaggcgaat gtggcggcgg aggatctggc      660
ggaggcggat ctgaagttca gctggttgaa tcaggcggcg gactggttca acctggcgga      720
tctctgagac tgagctgtgc cgccagcggc ttcaccttca atacctacgc catgaactgg      780
gtccgacagg cccctggcaa aggccttgaa tgggtcgcca gaatcagaag caagtacaac      840
```

-continued

```
aactacgcca cgtactacgc cgacagcgtg aagggcagat tcaccatcag ccgggacgac       900
agcaagaaca ccctgtacct gcagatgaac tccctgagag ccgaggatac cgccgtgtac       960
tattgtgtgc ggcacggcaa cttcggcaac agctacgtgt cctacttcgc ctattggggc      1020
cagggcacca ccgtgacagt ttctagcggt ggcggaggaa gcggaggcgg cggttcaggt      1080
ggtggtggta gcggaggtgg tggctctgag atcgtggtta cacagagccc cgccacactg      1140
agtgtgtctc aggcgaaag agccacactg tcctgcaggt ctagtacagg cgctgtgacc       1200
gccgccaact atgccaattg ggtgcaagag aaacccggcc aggccttcag aggactgatt      1260
ggcggagcca caaacgcgc tcctggcgtg ccagccagat tttctggaag cctgagcggc       1320
gacgaggcca ctctgactat tagcagcctg cagtctgagg acttcgccgt gtattactgc      1380
gccctgttct acagcaacct gtgggtgttc ggccagggga caaagctcga gatcaag         1437

<210> SEQ ID NO 43
<211> LENGTH: 1407
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 43
gatatcgtga tgacccagac acctctgagc ctgcctgtga cacctggcga acctgccagc        60
atcagctgta gagccagcaa gagcatcagc aagtacctgg cctggtatca gcagaagcct       120
ggacaggctc cccggctgct gatctatagc ggaagcacac tgcagagcgg catccctcct       180
agattttccg gcagcggcta cggcaccgat ttcaccctga ccatcaacaa catcgagagc       240
gaggacgccg cctactactt ctgccagcag cacgatgaga gcccctacac atttggcgag       300
ggcaccaagg tggaaatcaa gcggacagtg gccgctccta gcgtgttcat ctttccacct       360
agcgacgagc agctgaagtc tggcacagcc tctgtcgtgt gcctgctgaa caacttctac       420
cccagagaag ccaaggtgca gtggaaggtg gacaacgccc tgcagtccgg caatagccaa       480
gagagcgtga ccgagcagga cagcaaggac tctacctaca gcctgagcag caccctgaca       540
ctgagcaagg ccgactacga gaagcacaaa gtgtacgcct gcgaagtgac ccaccagggc       600
ctttctagcc ctgtgaccaa gagcttcaac agaggcgaat gtggcggcgg aggatctggc       660
ggaggcggat ctcaagttca gctggttcaa tccggtggcg gcgttgtgca gcctggcaga       720
tctctgagac tgagctgcaa ggcctccggc tacaccttca ccagatacac catgcactgg       780
gtccgacagg cccctggcaa atgccttgag tggatcggct acatcaaccc cagccggggc       840
tacaccaact acaaccagaa agtgaaggac cggttcacca tcagccggga caacagcaag       900
aacaccctgt acctgcagat ggactccctg agagccgagg ataccgccgt gtactactgt       960
gcccggtact acgacgacca ctactccctg gattattggg gccagggcac caccgtgaca      1020
gtttctagcg gtggcggagg aagcggaggc ggcggttcag gtggtggtgg tagcggaggt      1080
ggtggctccg atatccagat gacacagagc cctagcagcc tgtctgccag cgtgggagac      1140
agagtgacca tcacatgtag cgccagcagc tccgtgtcct acatgaactg gtatcaacaa      1200
aaacccggca aggcccctaa gcggtggatc tacgataaca gcaagctggc ctctggcgtg      1260
cccagcagat tttctggctc tggcagcggc accgacttta cctttacaat cagctccctg      1320
cagcctgagg acattgccac ctactactgt cagcagtggt ccagcaatcc cttcaccttc      1380
ggctgcggga caaagctcga gatcaag                                          1407
```

```
<210> SEQ ID NO 44
<211> LENGTH: 1407
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 44
gatatcgtga tgacccagac acctctgagc ctgcctgtga cacctggcga acctgccagc      60
atcagctgta gagccagcaa gagcatcagc aagtacctgg cctggtatca gcagaagcct     120
ggacaggctc cccggctgct gatctatagc ggaagcacac tgcagagcgg catccctcct     180
agattttccg gcagcggcta cggcaccgat ttcaccctga ccatcaacaa catcgagagc     240
gaggacgccg cctactactt ctgccagcag cacgatgaga gcccctacac atttggcgag     300
ggcaccaagg tggaaatcaa gcggacagtg gccgctccta gcgtgttcat ctttccacct     360
agcgacgagc agctgaagtc tggcacagcc tctgtcgtgt gcctgctgaa caacttctac     420
cccagagaag ccaaggtgca gtggaaggtg gacaacgccc tgcagtccgg caatagccaa     480
gagagcgtga ccgagcagga cagcaaggac tctacctaca gcctgagcag caccctgaca     540
ctgagcaagg ccgactacga gaagcacaaa gtgtacgcct gcgaagtgac ccaccagggc     600
ctttctagcc ctgtgaccaa gagcttcaac agaggcgaat gtggcggcgg aggatctggc     660
ggaggcggat ctcaagttca gctggttcag tctggcgccg aagtgaagaa acctggcgcc     720
tccgtgaagg tgtcctgtaa agcctccggc tacacattca cccggtacac catgcactgg     780
gtccgacagg cacctggcca atgccttgag tggatgggct acatcaaccc cagccggggc     840
tacaccaact acaaccagaa attcaaggac cgcgtgaccc tgacaaccga caagtctagc     900
agcaccgcct acatggaact gagcagcctg agaagcgagg ataccgccgt gtactactgc     960
gcccggtact acgacgatca ctactccctg gattactggg gccagggcac actggtcaca    1020
gtttctagcg gtggcggagg aagcggaggc ggcggttcag gtggtggtgg tagcggaggt    1080
ggtggctccg atatccagat gacacagagc cctagcagcc tgtctgccag cgtgggagac    1140
agagtgacca tcacatgtag cgccagcagc tccgtgtcct acatgaattg gtatcaacaa    1200
aagcccggca aggcccctaa gcggctgatc tacgatacaa gcaagctggc ctctggcgtg    1260
cccagcagat tttctggctc tggcagcggc accgacttta cactcaccat aagcagcctg    1320
cagccagagg acttcgccac ctactattgc cagcagtggt ccagcaatcc cttcaccttt    1380
ggctgcggaa caaagctcga gatcaag                                        1407

<210> SEQ ID NO 45
<211> LENGTH: 1437
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 45
gatatcgtga tgacccagac acctctgagc ctgcctgtga cacctggcga acctgccagc      60
atcagctgta gagccagcaa gagcatcagc aagtacctgg cctggtatca gcagaagcct     120
ggacaggctc cccggctgct gatctatagc ggaagcacac tgcagagcgg catccctcct     180
```

-continued

```
agattttccg gcagcggcta cggcaccgat ttcaccctga ccatcaacaa catcgagagc        240
gaggacgccg cctactactt ctgccagcag cacgatgaga gccccctacac atttggcgag       300 ggcaccaagg tggaaatcaa gcggacagtg gccgctccta gcgtgttcat ctttccacct        360
agcgacgagc agctgaagtc tggcacagcc tctgtcgtgt gcctgctgaa caacttctac        420
cccagagaag ccaaggtgca gtggaaggtg gacaacgccc tgcagtccgg caatagccaa        480
gagagcgtga ccgagcagga cagcaaggac tctacctaca gcctgagcag caccctgaca        540
ctgagcaagg ccgactacga gaagcacaaa gtgtacgcct gcgaagtgac ccaccagggc        600
ctttctagcc ctgtgaccaa gagcttcaac agaggcgaat gtggcggcgg aggatctggc        660
ggaggcggat ctgaagttca gctggttgaa tcaggcggcg gactggttca acctggcgga        720
tctctgagac tgagctgtgc cgccagcggc ttcaccttca atacctacgc catgaactgg        780
gtccgacagg cccctggcaa atgccttgaa tgggtcgcca gaatcagaag caagtacaac        840
aactacgcca cgtactacgc cgacagcgtg aagggcagat tcaccatcag ccgggacgac        900
agcaagaaca ccctgtacct gcagatgaac tccctgagag ccgaggatac cgccgtgtac        960
tattgtgtgc ggcacggcaa cttcggcaac agctacgtgt cctacttcgc ctattggggc       1020
cagggcacca ccgtgacagt ttctagcggt ggcggaggaa gcggaggcgg cggttcaggt       1080
ggtggtggta gcggaggtgg tggctctgag atcgtggtta cacagagccc cgccacactg       1140
agtgtgtctc aggcgaaag agccacactg tcctgcaggt ctagtacagg cgctgtgacc       1200
gccgccaact atgccaattg ggtgcaagag aaacccggcc aggccttcag aggactgatt       1260
ggcggagcca acaaacgcgc tcctggcgtg ccagccagat tttctggaag cctgagcggc       1320
gacgaggcca ctctgactat tagcagcctg cagtctgagg acttcgccgt gtattactgc       1380
gccctgttct acagcaacct gtgggtgttc ggctgcggga caaagctcga gatcaag        1437
```

<210> SEQ ID NO 46
<211> LENGTH: 1437
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 46

```
gaagtgcagc tggttgagtc tggcggagga ctggttcaac ctggcggaag cctgagactg         60
tcttgtgccg ccagcggctt caccttcaac acctacgcca tgaactgggt ccgacaggcc        120
cctggcaaag gccttgaatg gtgcgccaga atcagaagca agtacaacaa ttacgccacc        180
tactacgccg acagcgtgaa gggcagattc accatcagcc gggacgacag caagaacacc        240
ctgtacctgc agatgaacag cctgagagcc gaggacaccg ccgtgtacta ttgtgtgcgg        300
cacggcaact tcggcaacag ctacgtgtcc tacttcgcct attggggcca gggcaccacc        360
gtgacagttt ctagcggagg cggtggatct ggcggcggag gaagtggtgg cggaggtagt        420
ggcggaggcg gatctgagat tgtggtcaca cagagcccccg ccacactgag tgtttctcca        480
ggcgaaagag ccacactgtc ctgcaggtct agtacaggcg ctgtgaccgc cgccaactac        540
gccaattggg tgcaagagaa acccggccag gccttcagag gactgattgg cggagccaac        600
aaacgcgctc ctggcgtgcc agccagattt tctggatccc tgagcggcga cgaggccact        660
ctgactatta gcagcctgca gtccgaggac tttgccgtgt attactgcgc cctgttctac        720
agcaacctgt gggtgttcgg ccaggggacc aagctggaaa tcaaaggtgg cggtggttca        780
```

```
ggtggcggcg gaagcgatat tgtgatgacc cagacacctc tgagcctgcc tgtgacacct    840
ggcgaacctg ccagcatcag ctgtagagcc agcaagagca tcagcaagta cctggcctgg    900
tatcagcaga gccccggaca ggctcctcgg ctgctgatct atagcggcag cacactgcag    960
agcggcatcc ctcctagatt ttccggcagc ggctacggca ccgatttcac cctgaccatc    1020
aacaacatcg agagcgagga tgccgcctac tacttctgcc agcagcacga cgagagcccc    1080
tacacatttg gcgagggcac aaaggtcgag atcaagcgga cagtggccgc tcctagcgtg    1140
ttcatctttc cacctagcga cgagcagctg aagtctggca gcctctgt cgtgtgcctg    1200 ctgaacaact ctaccccag agaagccaag gtgcagtgga aggtggacaa cgccctgcag    1260
tctggcaact cccaagagag cgtgaccgag caggacagca aggactctac ctacagcctg    1320
tcctccacac tgaccctgag caaggccgac tacgagaagc acaaagtgta cgcctgcgaa    1380
gtgacccacc agggcctttc tagccctgtg accaagagct tcaaccgggg cgaatgt    1437
```

<210> SEQ ID NO 47
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

```
Gly Tyr Thr Phe Thr Arg Tyr Thr Met His
1               5                   10
```

<210> SEQ ID NO 48
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

```
Tyr Ile Asn Pro Ser Arg Gly Tyr Thr Asn Tyr Asn Gln Lys Val Lys
1               5                   10                  15

Asp
```

<210> SEQ ID NO 49
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

```
Ala Arg Tyr Tyr Asp Asp His Tyr Ser Leu Asp Tyr
1               5                   10
```

<210> SEQ ID NO 50
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 50

Ser Ala Ser Ser Ser Val Ser Tyr Met Asn
1               5                   10

<210> SEQ ID NO 51
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Asp Thr Ser Lys Leu Ala Ser
1               5

<210> SEQ ID NO 52
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Gln Gln Trp Ser Ser Asn Pro Phe Thr
1               5

<210> SEQ ID NO 53
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Tyr Ile Asn Pro Ser Arg Gly Tyr Thr Asn Tyr Asn Gln Lys Phe Lys
1               5                   10                  15

Asp

<210> SEQ ID NO 54
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Gly Phe Thr Phe Asn Thr Tyr Ala Met Asn
1               5                   10

<210> SEQ ID NO 55
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

-continued

<400> SEQUENCE: 55

Arg Ile Arg Ser Lys Tyr Asn Asn Tyr Ala Thr Tyr Tyr Ala Asp Ser
1               5                   10                  15

Val Lys Gly

<210> SEQ ID NO 56
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

Val Arg His Gly Asn Phe Gly Asn Ser Tyr Val Ser Tyr Phe Ala Tyr
1               5                   10                  15

<210> SEQ ID NO 57
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Arg Ser Ser Thr Gly Ala Val Thr Ala Ala Asn Tyr Ala Asn
1               5                   10

<210> SEQ ID NO 58
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Gly Ala Asn Lys Arg Ala Pro
1               5

<210> SEQ ID NO 59
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Ala Leu Phe Tyr Ser Asn Leu Trp Val
1               5

<210> SEQ ID NO 60
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

-continued

```
<400> SEQUENCE: 60

Gly Tyr Ala Phe Thr Ala Tyr Asn Ile His
1               5                   10

<210> SEQ ID NO 61
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Ser Phe Asp Pro Tyr Asp Gly Gly Ser Ser Tyr Asn Gln Lys Phe Lys
1               5                   10                  15

Asp

<210> SEQ ID NO 62
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

Ala Arg Gly Trp Tyr Tyr Phe Asp Tyr
1               5

<210> SEQ ID NO 63
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Arg Ala Ser Lys Ser Ile Ser Lys Tyr Leu Ala
1               5                   10

<210> SEQ ID NO 64
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

Ser Gly Ser Thr Leu Gln Ser
1               5

<210> SEQ ID NO 65
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 65

Gln Gln His Asp Glu Ser Pro Tyr Thr
1               5

<210> SEQ ID NO 66
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 66

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Asn Tyr Asn Gln Lys Val
    50                  55                  60

Lys Asp Arg Phe Thr Ile Ser Arg Asp Asn Ser Lys Asn Thr Leu Tyr
65                  70                  75                  80

Leu Gln Met Asp Ser Leu Arg Ala Glu Asp Thr Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Thr Val Thr Val Ser Ser
        115

<210> SEQ ID NO 67
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 67

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

Asn Trp Tyr Gln Gln Lys Pro Gly Lys Ala Pro Lys Arg Trp Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Phe Thr Phe Thr Ile Ser Ser Leu Gln Pro Glu
65                  70                  75                  80

Asp Ile Ala Thr Tyr Tyr Cys Gln Gln Trp Ser Ser Asn Pro Phe Thr
                85                  90                  95

Phe Gly Gln Gly Thr Lys Leu Glu Ile Lys
            100                 105

<210> SEQ ID NO 68
<211> LENGTH: 119
<212> TYPE: PRT

<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 68

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Gln Gly Leu Glu Trp Met
        35                  40                  45

Gly Tyr Ile Asn Pro Ser Arg Gly Tyr Thr Asn Tyr Asn Gln Lys Phe
    50                  55                  60

Lys Asp Arg Val Thr Leu Thr Thr Asp Lys Ser Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Leu Val Thr Val Ser Ser
        115

<210> SEQ ID NO 69
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 69

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

Asn Trp Tyr Gln Gln Lys Pro Gly Lys Ala Pro Lys Arg Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Asn Pro Phe Thr
                85                  90                  95

Phe Gly Gln Gly Thr Lys Leu Glu Ile Lys
            100                 105

<210> SEQ ID NO 70
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 70

Glu Val Gln Leu Val Glu Ser Gly Gly Gly Leu Val Gln Pro Gly Gly
1               5                   10                  15

```
Ser Leu Arg Leu Ser Cys Ala Ala Ser Gly Phe Thr Phe Asn Thr Tyr
            20              25              30

Ala Met Asn Trp Val Arg Gln Ala Pro Gly Lys Gly Leu Glu Trp Val
            35              40              45

Ala Arg Ile Arg Ser Lys Tyr Asn Asn Tyr Ala Thr Tyr Tyr Ala Asp
    50              55              60

Ser Val Lys Gly Arg Phe Thr Ile Ser Arg Asp Asp Ser Lys Asn Thr
65              70              75              80

Leu Tyr Leu Gln Met Asn Ser Leu Arg Ala Glu Asp Thr Ala Val Tyr
            85              90              95

Tyr Cys Val Arg His Gly Asn Phe Gly Asn Ser Tyr Val Ser Tyr Phe
            100             105             110

Ala Tyr Trp Gly Gln Gly Thr Thr Val Thr Val Ser Ser
    115             120             125
```

<210> SEQ ID NO 71
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 71

```
Glu Ile Val Val Thr Gln Ser Pro Ala Thr Leu Ser Val Ser Pro Gly
1               5               10              15

Glu Arg Ala Thr Leu Ser Cys Arg Ser Ser Thr Gly Ala Val Thr Ala
            20              25              30

Ala Asn Tyr Ala Asn Trp Val Gln Glu Lys Pro Gly Gln Ala Phe Arg
            35              40              45

Gly Leu Ile Gly Gly Ala Asn Lys Arg Ala Pro Gly Val Pro Ala Arg
    50              55              60

Phe Ser Gly Ser Leu Ser Gly Asp Glu Ala Thr Leu Thr Ile Ser Ser
65              70              75              80

Leu Gln Ser Glu Asp Phe Ala Val Tyr Tyr Cys Ala Leu Phe Tyr Ser
            85              90              95

Asn Leu Trp Val Phe Gly Gln Gly Thr Lys Leu Glu Ile Lys
            100             105             110
```

<210> SEQ ID NO 72
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 72

```
Gln Val Gln Leu Gln Glu Ser Gly Pro Gly Leu Val Lys Pro Ser Gln
1               5               10              15

Thr Leu Ser Leu Thr Cys Thr Val Ser Gly Tyr Ala Phe Thr Ala Tyr
            20              25              30

Asn Ile His Trp Val Arg Gln Ala Pro Gly Gln Gly Leu Glu Trp Met
            35              40              45

Gly Ser Phe Asp Pro Tyr Asp Gly Gly Ser Ser Tyr Asn Gln Lys Phe
    50              55              60
```

-continued

```
Lys Asp Arg Leu Thr Ile Ser Lys Asp Thr Ser Lys Asn Gln Val Val
65                  70                  75                  80

Leu Thr Met Thr Asn Met Asp Pro Val Asp Thr Ala Thr Tyr Tyr Cys
                85                  90                  95

Ala Arg Gly Trp Tyr Tyr Phe Asp Tyr Trp Gly His Gly Thr Leu Val
            100                 105                 110

Thr Val Ser Ser
        115
```

<210> SEQ ID NO 73
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 73

```
Asp Ile Val Met Thr Gln Thr Pro Leu Ser Leu Pro Val Thr Pro Gly
1               5                   10                  15

Glu Pro Ala Ser Ile Ser Cys Arg Ala Ser Lys Ser Ile Ser Lys Tyr
                20                  25                  30

Leu Ala Trp Tyr Gln Gln Lys Pro Gly Gln Ala Pro Arg Leu Leu Ile
            35                  40                  45

Tyr Ser Gly Ser Thr Leu Gln Ser Gly Ile Pro Pro Arg Phe Ser Gly
        50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Gln Gln His Asp Glu Ser Pro Tyr
                85                  90                  95

Thr Phe Gly Glu Gly Thr Lys Val Glu Ile Lys
            100                 105
```

<210> SEQ ID NO 74
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 74

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ala Phe Ala Ala Tyr
                20                  25                  30

Asn Ile His Trp Val Arg Gln Ala Pro Gly Gln Gly Leu Glu Trp Met
            35                  40                  45

Gly Ser Phe Asp Pro Tyr Asp Gly Gly Ser Ser Tyr Asn Gln Lys Phe
        50                  55                  60

Lys Asp Arg Leu Thr Ile Ser Lys Asp Thr Ser Lys Asn Gln Val Val
65                  70                  75                  80

Leu Thr Met Thr Asn Met Asp Pro Val Asp Thr Ala Thr Tyr Tyr Cys
                85                  90                  95
```

-continued

```
Ala Arg Gly Trp Tyr Tyr Phe Asp Tyr Trp Gly His Gly Thr Leu Val
            100             105             110

Thr Val Ser Ser
        115

<210> SEQ ID NO 75
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 75

Gln Val Gln Leu Gln Glu Ser Gly Pro Gly Leu Val Lys Pro Ser Gln
1               5               10              15

Thr Leu Ser Leu Thr Cys Thr Val Ser Gly Tyr Ala Phe Glu Ala Tyr
            20              25              30

Asn Ile His Trp Val Arg Gln Ala Pro Gly Gln Gly Leu Glu Trp Met
        35              40              45

Gly Ser Phe Asp Pro Tyr Asp Gly Gly Ser Ser Tyr Asn Gln Lys Phe
    50              55              60

Lys Asp Arg Leu Thr Ile Ser Lys Asp Thr Ser Lys Asn Gln Val Val
65              70              75              80

Leu Thr Met Thr Asn Met Asp Pro Val Asp Thr Ala Thr Tyr Tyr Cys
            85              90              95

Ala Arg Gly Trp Tyr Tyr Phe Asp Tyr Trp Gly His Gly Thr Leu Val
            100             105             110

Thr Val Ser Ser
        115

<210> SEQ ID NO 76
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 76

Gln Val Gln Leu Val Gln Ser Gly Gly Gly Val Val Gln Pro Gly Arg
1               5               10              15

Ser Leu Arg Leu Ser Cys Lys Ala Ser Gly Tyr Thr Phe Thr Arg Tyr
            20              25              30

Thr Met His Trp Val Arg Gln Ala Pro Gly Lys Cys Leu Glu Trp Ile
        35              40              45

Gly Tyr Ile Asn Pro Ser Arg Gly Tyr Thr Asn Tyr Asn Gln Lys Val
    50              55              60

Lys Asp Arg Phe Thr Ile Ser Arg Asp Asn Ser Lys Asn Thr Leu Tyr
65              70              75              80

Leu Gln Met Asp Ser Leu Arg Ala Glu Asp Thr Ala Val Tyr Tyr Cys
            85              90              95

Ala Arg Tyr Tyr Asp Asp His Tyr Ser Leu Asp Tyr Trp Gly Gln Gly
            100             105             110

Thr Thr Val Thr Val Ser Ser
        115
```

<210> SEQ ID NO 77
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 77

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

Asn Trp Tyr Gln Gln Lys Pro Gly Lys Ala Pro Lys Arg Trp Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Phe Thr Phe Thr Ile Ser Ser Leu Gln Pro Glu
65                  70                  75                  80

Asp Ile Ala Thr Tyr Tyr Cys Gln Gln Trp Ser Ser Asn Pro Phe Thr
                85                  90                  95

Phe Gly Cys Gly Thr Lys Leu Glu Ile Lys
            100                 105

<210> SEQ ID NO 78
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 78

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Gln Cys Leu Glu Trp Met
        35                  40                  45

Gly Tyr Ile Asn Pro Ser Arg Gly Tyr Thr Asn Tyr Asn Gln Lys Phe
    50                  55                  60

Lys Asp Arg Val Thr Leu Thr Thr Asp Lys Ser Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Leu Val Thr Val Ser Ser
        115

<210> SEQ ID NO 79
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

-continued

<400> SEQUENCE: 79

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

Asn Trp Tyr Gln Gln Lys Pro Gly Lys Ala Pro Lys Arg Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Asn Pro Phe Thr
                85                  90                  95

Phe Gly Cys Gly Thr Lys Leu Glu Ile Lys
                100                 105
```

<210> SEQ ID NO 80
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 80

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Cys Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Tyr Phe
                100                 105                 110

Ala Tyr Trp Gly Gln Gly Thr Thr Val Thr Val Ser Ser
        115                 120                 125
```

<210> SEQ ID NO 81
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 81

```
Glu Ile Val Val Thr Gln Ser Pro Ala Thr Leu Ser Val Ser Pro Gly
1               5                   10                  15

Glu Arg Ala Thr Leu Ser Cys Arg Ser Ser Thr Gly Ala Val Thr Ala
            20                  25                  30

Ala Asn Tyr Ala Asn Trp Val Gln Glu Lys Pro Gly Gln Ala Phe Arg
        35                  40                  45
```

-continued

```
Gly Leu Ile Gly Gly Ala Asn Lys Arg Ala Pro Gly Val Pro Ala Arg
    50                  55                  60

Phe Ser Gly Ser Leu Ser Gly Asp Glu Ala Thr Leu Thr Ile Ser Ser
65                  70                  75                  80

Leu Gln Ser Glu Asp Phe Ala Val Tyr Tyr Cys Ala Leu Phe Tyr Ser
                85                  90                  95

Asn Leu Trp Val Phe Gly Cys Gly Thr Lys Leu Glu Ile Lys
            100                 105                 110

<210> SEQ ID NO 82
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 82

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ala Phe Thr Ala Tyr
            20                  25                  30

Asn Ile His Trp Val Arg Gln Ala Pro Gly Gln Gly Leu Glu Trp Met
        35                  40                  45

Gly Ser Phe Asp Pro Tyr Asp Gly Gly Ser Ser Tyr Asn Gln Lys Phe
    50                  55                  60

Lys Asp Arg Leu Thr Ile Ser Lys Asp Thr Ser Lys Asn Gln Val Val
65                  70                  75                  80

Leu Thr Met Thr Asn Met Asp Pro Val Asp Thr Ala Thr Tyr Tyr Cys
                85                  90                  95

Ala Arg Gly Trp Tyr Tyr Phe Asp Tyr Trp Gly His Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
    275                 280                 285
```

```
Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Asp Glu Leu Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
        435                 440                 445
```

```
<210> SEQ ID NO 83
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 83

Asp Ile Val Met Thr Gln Thr Pro Leu Ser Leu Pro Val Thr Pro Gly
1               5                   10                  15

Glu Pro Ala Ser Ile Ser Cys Arg Ala Ser Lys Ser Ile Ser Lys Tyr
                20                  25                  30

Leu Ala Trp Tyr Gln Gln Lys Pro Gly Gln Ala Pro Arg Leu Leu Ile
        35                  40                  45

Tyr Ser Gly Ser Thr Leu Gln Ser Gly Ile Pro Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Gln Gln His Asp Glu Ser Pro Tyr
                85                  90                  95

Thr Phe Gly Glu Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190
```

-continued

```
Ala Cys Glu Val Thr His Gln Gly Leu Ser Ser Pro Val Thr Lys Ser
        195                 200                 205

Phe Asn Arg Gly Glu Cys
    210

<210> SEQ ID NO 84
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 84

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ala Phe Ala Ala Tyr
            20                  25                  30

Asn Ile His Trp Val Arg Gln Ala Pro Gly Gln Gly Leu Glu Trp Met
        35                  40                  45

Gly Ser Phe Asp Pro Tyr Asp Gly Gly Ser Ser Tyr Asn Gln Lys Phe
    50                  55                  60

Lys Asp Arg Leu Thr Ile Ser Lys Asp Thr Ser Lys Asn Gln Val Val
65                  70                  75                  80

Leu Thr Met Thr Asn Met Asp Pro Val Asp Thr Ala Thr Tyr Tyr Cys
                85                  90                  95

Ala Arg Gly Trp Tyr Tyr Phe Asp Tyr Trp Gly His Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320
```

-continued

```
Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 85
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 85

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ala Phe Glu Ala Tyr
            20                  25                  30

Asn Ile His Trp Val Arg Gln Ala Pro Gly Gln Gly Leu Glu Trp Met
            35                  40                  45

Gly Ser Phe Asp Pro Tyr Asp Gly Gly Ser Ser Tyr Asn Gln Lys Phe
            50                  55                  60

Lys Asp Arg Leu Thr Ile Ser Lys Asp Thr Ser Lys Asn Gln Val Val
65                  70                  75                  80

Leu Thr Met Thr Asn Met Asp Pro Val Asp Thr Ala Thr Tyr Tyr Cys
            85                  90                  95

Ala Arg Gly Trp Tyr Tyr Phe Asp Tyr Trp Gly His Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
            130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
            210                 215                 220
```

-continued

Cys Pro Pro Cys Pro Ala Pro Glu Leu Leu Gly Gly Pro Ser Val Phe
225             230             235             240

Leu Phe Pro Pro Lys Pro Lys Asp Thr Leu Met Ile Ser Arg Thr Pro
            245             250             255

Glu Val Thr Cys Val Val Val Asp Val Ser His Glu Asp Pro Glu Val
            260             265             270

Lys Phe Asn Trp Tyr Val Asp Gly Val Glu Val His Asn Ala Lys Thr
            275             280             285

Lys Pro Arg Glu Glu Gln Tyr Asn Ser Thr Tyr Arg Val Val Ser Val
        290             295             300

Leu Thr Val Leu His Gln Asp Trp Leu Asn Gly Lys Glu Tyr Lys Cys
305             310             315             320

Lys Val Ser Asn Lys Ala Leu Pro Ala Pro Ile Glu Lys Thr Ile Ser
            325             330             335

Lys Ala Lys Gly Gln Pro Arg Glu Pro Gln Val Tyr Thr Leu Pro Pro
            340             345             350

Ser Arg Asp Glu Leu Thr Lys Asn Gln Val Ser Leu Thr Cys Leu Val
            355             360             365

Lys Gly Phe Tyr Pro Ser Asp Ile Ala Val Glu Trp Glu Ser Asn Gly
        370             375             380

Gln Pro Glu Asn Asn Tyr Lys Thr Thr Pro Pro Val Leu Asp Ser Asp
385             390             395             400

Gly Ser Phe Phe Leu Tyr Ser Lys Leu Thr Val Asp Lys Ser Arg Trp
            405             410             415

Gln Gln Gly Asn Val Phe Ser Cys Ser Val Met His Glu Ala Leu His
            420             425             430

Asn His Tyr Thr Gln Lys Ser Leu Ser Leu Ser Pro Gly Lys
        435             440             445

<210> SEQ ID NO 86
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 86

Gln Val Gln Leu Gln Glu Ser Gly Pro Gly Leu Val Lys Pro Ser Gln
1               5               10              15

Thr Leu Ser Leu Thr Cys Thr Val Ser Gly Tyr Ala Phe Thr Ala Tyr
            20              25              30

Asn Ile His Trp Val Arg Gln Ala Pro Gly Gln Gly Leu Glu Trp Met
            35              40              45

Gly Ser Phe Asp Pro Tyr Asp Gly Gly Ser Ser Tyr Asn Gln Lys Phe
        50              55              60

Lys Asp Arg Leu Thr Ile Ser Lys Asp Thr Ser Lys Asn Gln Val Val
65              70              75              80

Leu Thr Met Thr Asn Met Asp Pro Val Asp Thr Ala Thr Tyr Tyr Cys
            85              90              95

Ala Arg Gly Trp Tyr Tyr Phe Asp Tyr Trp Gly His Gly Thr Leu Val
            100             105             110

Thr Val Ser Ser Ala Ser Thr Lys Gly Pro Ser Val Phe Pro Leu Ala
            115             120             125

```
Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
                195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Ala Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
    275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Asp Glu Leu Thr Lys Asn Gln Val Ser Leu Trp Cys Leu Val
    355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
                435                 440                 445
```

<210> SEQ ID NO 87
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 87

```
Gln Val Gln Leu Gln Glu Ser Gly Pro Gly Leu Val Lys Pro Ser Gln
1                   5                   10                  15

Thr Leu Ser Leu Thr Cys Thr Val Ser Gly Tyr Ala Phe Ala Ala Tyr
                20                  25                  30
```

```
Asn Ile His Trp Val Arg Gln Ala Pro Gly Gln Gly Leu Glu Trp Met
        35                  40                  45

Gly Ser Phe Asp Pro Tyr Asp Gly Gly Ser Ser Tyr Asn Gln Lys Phe
        50                  55                  60

Lys Asp Arg Leu Thr Ile Ser Lys Asp Thr Ser Lys Asn Gln Val Val
65                  70                  75                  80

Leu Thr Met Thr Asn Met Asp Pro Val Asp Thr Ala Thr Tyr Tyr Cys
                85                  90                  95

Ala Arg Gly Trp Tyr Tyr Phe Asp Tyr Trp Gly His Gly Thr Leu Val
                100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
                195                 200                 205

Lys Val Asp Lys Lys Val Glu Pro Lys Ser Cys Asp Lys Thr His Thr
        210                 215                 220

Cys Pro Pro Cys Pro Ala Pro Glu Ala Ala Gly Ala Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Asp Glu Leu Thr Lys Asn Gln Val Ser Leu Trp Cys Leu Val
        355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
        435                 440                 445
```

-continued

```
<210> SEQ ID NO 88
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 88

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ala Phe Glu Ala Tyr
            20                  25                  30

Asn Ile His Trp Val Arg Gln Ala Pro Gly Gln Gly Leu Glu Trp Met
        35                  40                  45

Gly Ser Phe Asp Pro Tyr Asp Gly Gly Ser Ser Tyr Asn Gln Lys Phe
    50                  55                  60

Lys Asp Arg Leu Thr Ile Ser Lys Asp Thr Ser Lys Asn Gln Val Val
65                  70                  75                  80

Leu Thr Met Thr Asn Met Asp Pro Val Asp Thr Ala Thr Tyr Tyr Cys
                85                  90                  95

Ala Arg Gly Trp Tyr Tyr Phe Asp Tyr Trp Gly His Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Ala Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
            340                 345                 350
```

-continued

```
Ser Arg Asp Glu Leu Thr Lys Asn Gln Val Ser Leu Trp Cys Leu Val
        355             360             365

Lys Gly Phe Tyr Pro Ser Asp Ile Ala Val Glu Trp Glu Ser Asn Gly
        370             375             380

Gln Pro Glu Asn Asn Tyr Lys Thr Thr Pro Pro Val Leu Asp Ser Asp
385             390             395             400

Gly Ser Phe Phe Leu Tyr Ser Lys Leu Thr Val Asp Lys Ser Arg Trp
            405             410             415

Gln Gln Gly Asn Val Phe Ser Cys Ser Val Met His Glu Ala Leu His
            420             425             430

Asn His Tyr Thr Gln Lys Ser Leu Ser Leu Ser Pro Gly Lys
        435             440             445
```

<210> SEQ ID NO 89
<211> LENGTH: 937
<212> TYPE: PRT
<213> ORGANISM: Homo sapiens

<400> SEQUENCE: 89

```
Met His Arg Pro Arg Arg Arg Gly Thr Arg Pro Pro Leu Leu Ala Leu
1               5               10              15

Leu Ala Ala Leu Leu Leu Ala Ala Arg Gly Ala Ala Ala Gln Glu Thr
            20              25              30

Glu Leu Ser Val Ser Ala Glu Leu Val Pro Thr Ser Ser Trp Asn Ile
        35              40              45

Ser Ser Glu Leu Asn Lys Asp Ser Tyr Leu Thr Leu Asp Glu Pro Met
        50              55              60

Asn Asn Ile Thr Thr Ser Leu Gly Gln Thr Ala Glu Leu His Cys Lys
65              70              75              80

Val Ser Gly Asn Pro Pro Pro Thr Ile Arg Trp Phe Lys Asn Asp Ala
            85              90              95

Pro Val Val Gln Glu Pro Arg Arg Leu Ser Phe Arg Ser Thr Ile Tyr
            100             105             110

Gly Ser Arg Leu Arg Ile Arg Asn Leu Asp Thr Thr Asp Thr Gly Tyr
        115             120             125

Phe Gln Cys Val Ala Thr Asn Gly Lys Glu Val Val Ser Ser Thr Gly
        130             135             140

Val Leu Phe Val Lys Phe Gly Pro Pro Thr Ala Ser Pro Gly Tyr
145             150             155             160

Ser Asp Glu Tyr Glu Glu Asp Gly Phe Cys Gln Pro Tyr Arg Gly Ile
            165             170             175

Ala Cys Ala Arg Phe Ile Gly Asn Arg Thr Val Tyr Met Glu Ser Leu
            180             185             190

His Met Gln Gly Glu Ile Glu Asn Gln Ile Thr Ala Ala Phe Thr Met
        195             200             205

Ile Gly Thr Ser Ser His Leu Ser Asp Lys Cys Ser Gln Phe Ala Ile
        210             215             220

Pro Ser Leu Cys His Tyr Ala Phe Pro Tyr Cys Asp Glu Thr Ser Ser
225             230             235             240

Val Pro Lys Pro Arg Asp Leu Cys Arg Asp Glu Cys Glu Ile Leu Glu
            245             250             255

Asn Val Leu Cys Gln Thr Glu Tyr Ile Phe Ala Arg Ser Asn Pro Met
            260             265             270
```

```
Ile Leu Met Arg Leu Lys Leu Pro Asn Cys Glu Asp Leu Pro Gln Pro
        275                 280                 285

Glu Ser Pro Glu Ala Ala Asn Cys Ile Arg Ile Gly Ile Pro Met Ala
    290                 295                 300

Asp Pro Ile Asn Lys Asn His Lys Cys Tyr Asn Ser Thr Gly Val Asp
305                 310                 315                 320

Tyr Arg Gly Thr Val Ser Val Thr Lys Ser Gly Arg Gln Cys Gln Pro
                325                 330                 335

Trp Asn Ser Gln Tyr Pro His Thr His Thr Phe Thr Ala Leu Arg Phe
            340                 345                 350

Pro Glu Leu Asn Gly Gly His Ser Tyr Cys Arg Asn Pro Gly Asn Gln
        355                 360                 365

Lys Glu Ala Pro Trp Cys Phe Thr Leu Asp Glu Asn Phe Lys Ser Asp
    370                 375                 380

Leu Cys Asp Ile Pro Ala Cys Asp Ser Lys Asp Ser Lys Glu Lys Asn
385                 390                 395                 400

Lys Met Glu Ile Leu Tyr Ile Leu Val Pro Ser Val Ala Ile Pro Leu
                405                 410                 415

Ala Ile Ala Leu Leu Phe Phe Phe Ile Cys Val Cys Arg Asn Asn Gln
            420                 425                 430

Lys Ser Ser Ser Ala Pro Val Gln Arg Gln Pro Lys His Val Arg Gly
        435                 440                 445

Gln Asn Val Glu Met Ser Met Leu Asn Ala Tyr Lys Pro Lys Ser Lys
    450                 455                 460

Ala Lys Glu Leu Pro Leu Ser Ala Val Arg Phe Met Glu Glu Leu Gly
465                 470                 475                 480

Glu Cys Ala Phe Gly Lys Ile Tyr Lys Gly His Leu Tyr Leu Pro Gly
                485                 490                 495

Met Asp His Ala Gln Leu Val Ala Ile Lys Thr Leu Lys Asp Tyr Asn
            500                 505                 510

Asn Pro Gln Gln Trp Thr Glu Phe Gln Gln Glu Ala Ser Leu Met Ala
        515                 520                 525

Glu Leu His His Pro Asn Ile Val Cys Leu Leu Gly Ala Val Thr Gln
    530                 535                 540

Glu Gln Pro Val Cys Met Leu Phe Glu Tyr Ile Asn Gln Gly Asp Leu
545                 550                 555                 560

His Glu Phe Leu Ile Met Arg Ser Pro His Ser Asp Val Gly Cys Ser
                565                 570                 575

Ser Asp Glu Asp Gly Thr Val Lys Ser Ser Leu Asp His Gly Asp Phe
            580                 585                 590

Leu His Ile Ala Ile Gln Ile Ala Ala Gly Met Glu Tyr Leu Ser Ser
            595                 600                 605

His Phe Phe Val His Lys Asp Leu Ala Ala Arg Asn Ile Leu Ile Gly
        610                 615                 620

Glu Gln Leu His Val Lys Ile Ser Asp Leu Gly Leu Ser Arg Glu Ile
625                 630                 635                 640

Tyr Ser Ala Asp Tyr Tyr Arg Val Gln Ser Lys Ser Leu Leu Pro Ile
                645                 650                 655

Arg Trp Met Pro Pro Glu Ala Ile Met Tyr Gly Lys Phe Ser Ser Asp
            660                 665                 670

Ser Asp Ile Trp Ser Phe Gly Val Val Leu Trp Glu Ile Phe Ser Phe
        675                 680                 685
```

-continued

```
Gly Leu Gln Pro Tyr Tyr Gly Phe Ser Asn Gln Glu Val Ile Glu Met
    690             695             700

Val Arg Lys Arg Gln Leu Leu Pro Cys Ser Glu Asp Cys Pro Pro Arg
705             710             715             720

Met Tyr Ser Leu Met Thr Glu Cys Trp Asn Glu Ile Pro Ser Arg Arg
                725             730             735

Pro Arg Phe Lys Asp Ile His Val Arg Leu Arg Ser Trp Glu Gly Leu
                740             745             750

Ser Ser His Thr Ser Ser Thr Thr Pro Ser Gly Gly Asn Ala Thr Thr
            755             760             765

Gln Thr Thr Ser Leu Ser Ala Ser Pro Val Ser Asn Leu Ser Asn Pro
    770             775             780

Arg Tyr Pro Asn Tyr Met Phe Pro Ser Gln Gly Ile Thr Pro Gln Gly
785             790             795             800

Gln Ile Ala Gly Phe Ile Gly Pro Pro Ile Pro Gln Asn Gln Arg Phe
                805             810             815

Ile Pro Ile Asn Gly Tyr Pro Ile Pro Pro Gly Tyr Ala Ala Phe Pro
                820             825             830

Ala Ala His Tyr Gln Pro Thr Gly Pro Pro Arg Val Ile Gln His Cys
            835             840             845

Pro Pro Pro Lys Ser Arg Ser Pro Ser Ser Ala Ser Gly Ser Thr Ser
    850             855             860

Thr Gly His Val Thr Ser Leu Pro Ser Ser Gly Ser Asn Gln Glu Ala
865             870             875             880

Asn Ile Pro Leu Leu Pro His Met Ser Ile Pro Asn His Pro Gly Gly
                885             890             895

Met Gly Ile Thr Val Phe Gly Asn Lys Ser Gln Lys Pro Tyr Lys Ile
                900             905             910

Asp Ser Lys Gln Ala Ser Leu Leu Gly Asp Ala Asn Ile His Gly His
        915             920             925

Thr Glu Ser Met Ile Ser Ala Glu Leu
    930             935
```

<210> SEQ ID NO 90
<211> LENGTH: 182
<212> TYPE: PRT
<213> ORGANISM: Homo sapiens

<400> SEQUENCE: 90

```
Met Glu Gln Gly Lys Gly Leu Ala Val Leu Ile Leu Ala Ile Ile Leu
1               5               10              15

Leu Gln Gly Thr Leu Ala Gln Ser Ile Lys Gly Asn His Leu Val Lys
                20              25              30

Val Tyr Asp Tyr Gln Glu Asp Gly Ser Val Leu Leu Thr Cys Asp Ala
            35              40              45

Glu Ala Lys Asn Ile Thr Trp Phe Lys Asp Gly Lys Met Ile Gly Phe
    50              55              60

Leu Thr Glu Asp Lys Lys Lys Trp Asn Leu Gly Ser Asn Ala Lys Asp
65              70              75              80

Pro Arg Gly Met Tyr Gln Cys Lys Gly Ser Gln Asn Lys Ser Lys Pro
                85              90              95

Leu Gln Val Tyr Tyr Arg Met Cys Gln Asn Cys Ile Glu Leu Asn Ala
                100             105             110

Ala Thr Ile Ser Gly Phe Leu Phe Ala Glu Ile Val Ser Ile Phe Val
            115             120             125
```

-continued

Leu Ala Val Gly Val Tyr Phe Ile Ala Gly Gln Asp Gly Val Arg Gln
    130                 135                 140

Ser Arg Ala Ser Asp Lys Gln Thr Leu Leu Pro Asn Asp Gln Leu Tyr
145                 150                 155                 160

Gln Pro Leu Lys Asp Arg Glu Asp Asp Gln Tyr Ser His Leu Gln Gly
                165                 170                 175

Asn Gln Leu Arg Arg Asn
            180

<210> SEQ ID NO 91
<211> LENGTH: 171
<212> TYPE: PRT
<213> ORGANISM: Homo sapiens

<400> SEQUENCE: 91

Met Glu His Ser Thr Phe Leu Ser Gly Leu Val Leu Ala Thr Leu Leu
1               5                   10                  15

Ser Gln Val Ser Pro Phe Lys Ile Pro Ile Glu Glu Leu Glu Asp Arg
                20                  25                  30

Val Phe Val Asn Cys Asn Thr Ser Ile Thr Trp Val Glu Gly Thr Val
        35                  40                  45

Gly Thr Leu Leu Ser Asp Ile Thr Arg Leu Asp Leu Gly Lys Arg Ile
    50                  55                  60

Leu Asp Pro Arg Gly Ile Tyr Arg Cys Asn Gly Thr Asp Ile Tyr Lys
65                  70                  75                  80

Asp Lys Glu Ser Thr Val Gln Val His Tyr Arg Met Cys Gln Ser Cys
                85                  90                  95

Val Glu Leu Asp Pro Ala Thr Val Ala Gly Ile Ile Val Thr Asp Val
                100                 105                 110

Ile Ala Thr Leu Leu Leu Ala Leu Gly Val Phe Cys Phe Ala Gly His
        115                 120                 125

Glu Thr Gly Arg Leu Ser Gly Ala Ala Asp Thr Gln Ala Leu Leu Arg
    130                 135                 140

Asn Asp Gln Val Tyr Gln Pro Leu Arg Asp Arg Asp Asp Ala Gln Tyr
145                 150                 155                 160

Ser His Leu Gly Gly Asn Trp Ala Arg Asn Lys
                165                 170

<210> SEQ ID NO 92
<211> LENGTH: 207
<212> TYPE: PRT
<213> ORGANISM: Homo sapiens

<400> SEQUENCE: 92

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
                20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

-continued

```
Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
            115                 120                 125

Ser Val Ala Thr Ile Val Ile Val Asp Ile Cys Ile Thr Gly Gly Leu
            130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                    165                 170                 175

Lys Glu Arg Pro Pro Pro Val Pro Asn Pro Asp Tyr Glu Pro Ile Arg
                180                 185                 190

Lys Gly Gln Arg Asp Leu Tyr Ser Gly Leu Asn Gln Arg Arg Ile
            195                 200                 205
```

```
<210> SEQ ID NO 93
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 93

Gly Gly Gly Gly Ser Gly Gly Gly Gly Ser
1               5                   10
```

```
<210> SEQ ID NO 94
<211> LENGTH: 22
<212> TYPE: PRT
<213> ORGANISM: Homo sapiens

<400> SEQUENCE: 94

Val Ala Thr Asn Gly Lys Glu Val Val Ser Ser Thr Gly Val Leu Phe
1               5                   10                  15

Val Lys Phe Gly Pro Cys
            20
```

```
<210> SEQ ID NO 95
<211> LENGTH: 16
<212> TYPE: PRT
<213> ORGANISM: Homo sapiens

<400> SEQUENCE: 95

Glu Val Val Ser Ser Thr Gly Val Leu Phe Val Lys Phe Gly Pro Cys
1               5                   10                  15
```

```
<210> SEQ ID NO 96
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 96

Gly Gly Gly Gly Ser Gly Gly Gly Ser Gly Gly Gly Gly Ser Gly
1               5                   10                  15

Gly Gly Gly Ser
            20
```

-continued

```
<210> SEQ ID NO 97
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 97

Gly Tyr Ala Phe Ala Ala Tyr Asn Ile His
1               5                   10

<210> SEQ ID NO 98
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 98

Gly Tyr Ala Phe Glu Ala Tyr Asn Ile His
1               5                   10

<210> SEQ ID NO 99
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 99

Arg Pro Ser Lys Ser Ile Ser Lys Tyr Leu Ala
1               5                   10

<210> SEQ ID NO 100
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 100

Asp Ile Val Met Thr Gln Thr Pro Leu Ser Leu Pro Val Thr Pro Gly
1               5                   10                  15

Glu Pro Ala Ser Ile Ser Cys Arg Pro Ser Lys Ser Ile Ser Lys Tyr
            20                  25                  30

Leu Ala Trp Tyr Gln Gln Lys Pro Gly Gln Ala Pro Arg Leu Leu Ile
        35                  40                  45

Tyr Ser Gly Ser Thr Leu Gln Ser Gly Ile Pro Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Gln Gln His Asp Glu Ser Pro Tyr
                85                  90                  95

Thr Phe Gly Glu Gly Thr Lys Val Glu Ile Lys
            100                 105
```

```
<210> SEQ ID NO 101
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 101

Asp Ile Val Met Thr Gln Thr Pro Leu Ser Leu Pro Val Thr Pro Gly
1               5                   10                  15

Glu Pro Ala Ser Ile Ser Cys Arg Pro Ser Lys Ser Ile Ser Lys Tyr
            20                  25                  30

Leu Ala Trp Tyr Gln Gln Lys Pro Gly Gln Ala Pro Arg Leu Leu Ile
        35                  40                  45

Tyr Ser Gly Ser Thr Leu Gln Ser Gly Ile Pro Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Gln Gln His Asp Glu Ser Pro Tyr
                85                  90                  95

Thr Phe Gly Glu Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 102
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 102

Ser Gly Ser Arg Leu Gln Ser
1               5

<210> SEQ ID NO 103
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

-continued

<400> SEQUENCE: 103

Asp Ile Val Met Thr Gln Thr Pro Leu Ser Leu Pro Val Thr Pro Gly
1               5                   10                  15

Glu Pro Ala Ser Ile Ser Cys Arg Ala Ser Lys Ser Ile Ser Lys Tyr
            20                  25                  30

Leu Ala Trp Tyr Gln Gln Lys Pro Gly Gln Ala Pro Arg Leu Leu Ile
        35                  40                  45

Tyr Ser Gly Ser Arg Leu Gln Ser Gly Ile Pro Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Gln Gln His Asp Glu Ser Pro Tyr
                85                  90                  95

Thr Phe Gly Glu Gly Thr Lys Val Glu Ile Lys
            100                 105

<210> SEQ ID NO 104
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 104

Asp Ile Val Met Thr Gln Thr Pro Leu Ser Leu Pro Val Thr Pro Gly
1               5                   10                  15

Glu Pro Ala Ser Ile Ser Cys Arg Ala Ser Lys Ser Ile Ser Lys Tyr
            20                  25                  30

Leu Ala Trp Tyr Gln Gln Lys Pro Gly Gln Ala Pro Arg Leu Leu Ile
        35                  40                  45

Tyr Ser Gly Ser Arg Leu Gln Ser Gly Ile Pro Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Gln Gln His Asp Glu Ser Pro Tyr
                85                  90                  95

Thr Phe Gly Glu Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 105

-continued

```
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 105

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ala Phe Glu Ala Tyr
            20                  25                  30

Asn Ile His Trp Val Arg Gln Ala Pro Gly Gln Gly Leu Glu Trp Met
        35                  40                  45

Gly Ser Phe Asp Pro Tyr Asp Gly Gly Ser Ser Tyr Asn Gln Lys Phe
    50                  55                  60

Lys Asp Arg Leu Thr Ile Ser Lys Asp Thr Ser Lys Asn Gln Val Val
65                  70                  75                  80

Leu Thr Met Thr Asn Met Asp Pro Val Asp Thr Ala Thr Tyr Tyr Cys
                85                  90                  95

Ala Arg Gly Trp Tyr Tyr Phe Asp Tyr Trp Gly His Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Ala Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365
```

-continued

```
Lys Gly Phe Tyr Pro Ser Asp Ile Ala Val Glu Trp Glu Ser Asn Gly
    370             375                 380

Gln Pro Glu Asn Asn Tyr Lys Thr Thr Pro Pro Val Leu Asp Ser Asp
385             390                 395                 400

Gly Ser Phe Phe Leu Tyr Ser Lys Leu Thr Val Asp Lys Ser Arg Trp
            405             410                 415

Gln Gln Gly Asn Val Phe Ser Cys Ser Val Met His Glu Ala Leu His
            420             425                 430

Asn His Tyr Thr Gln Lys Ser Leu Ser Leu Ser Pro Gly Lys
    435             440                 445

<210> SEQ ID NO 106
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 106

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ala Phe Thr Ala Tyr
            20                  25                  30

Asn Ile His Trp Val Arg Gln Ala Pro Gly Gln Gly Leu Glu Trp Met
        35                  40                  45

Gly Ser Phe Asp Pro Tyr Asp Gly Gly Ser Ser Tyr Asn Gln Lys Phe
    50                  55                  60

Lys Asp Arg Leu Thr Ile Ser Lys Asp Thr Ser Lys Asn Gln Val Val
65                  70                  75                  80

Leu Thr Met Thr Asn Met Asp Pro Val Asp Thr Ala Thr Tyr Tyr Cys
            85                  90                  95

Ala Arg Gly Trp Tyr Tyr Phe Asp Tyr Trp Gly His Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Ala Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
            260                 265                 270
```

```
Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Asp Glu Leu Thr Lys Asn Gln Val Ser Leu Ser Cys Ala Val
        355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Val Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
        435                 440                 445
```

```
<210> SEQ ID NO 107
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 107
```

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ala Phe Ala Ala Tyr
        20                  25                  30

Asn Ile His Trp Val Arg Gln Ala Pro Gly Gln Gly Leu Glu Trp Met
        35                  40                  45

Gly Ser Phe Asp Pro Tyr Asp Gly Gly Ser Ser Tyr Asn Gln Lys Phe
    50                  55                  60

Lys Asp Arg Leu Thr Ile Ser Lys Asp Thr Ser Lys Asn Gln Val Val
65                  70                  75                  80

Leu Thr Met Thr Asn Met Asp Pro Val Asp Thr Ala Thr Tyr Tyr Cys
                85                  90                  95

Ala Arg Gly Trp Tyr Tyr Phe Asp Tyr Trp Gly His Gly Thr Leu Val
                100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175
```

-continued

```
Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
            210                 215                 220

Cys Pro Pro Cys Pro Ala Pro Glu Ala Ala Gly Ala Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Ser Cys Ala Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Val Ser Lys Leu Thr Val Asp Lys Ser Arg Trp
            405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 108
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 108

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ala Phe Glu Ala Tyr
            20                  25                  30

Asn Ile His Trp Val Arg Gln Ala Pro Gly Gln Gly Leu Glu Trp Met
            35                  40                  45

Gly Ser Phe Asp Pro Tyr Asp Gly Gly Ser Ser Tyr Asn Gln Lys Phe
            50                  55                  60

Lys Asp Arg Leu Thr Ile Ser Lys Asp Thr Ser Lys Asn Gln Val Val
65                  70                  75                  80
```

```
Leu Thr Met Thr Asn Met Asp Pro Val Asp Thr Ala Thr Tyr Tyr Cys
             85                  90                  95

Ala Arg Gly Trp Tyr Tyr Phe Asp Tyr Trp Gly His Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
        210                 215                 220

Cys Pro Pro Cys Pro Ala Pro Glu Ala Ala Gly Ala Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Ser Cys Ala Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Val Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445
```

<210> SEQ ID NO 109
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

```
<400> SEQUENCE: 109

Glu Pro Lys Ser Ser Asp Lys Thr His Thr Cys Pro Pro Cys Pro Ala
1               5                   10                  15

Pro Glu Ala Ala Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
        50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Ser Cys Ala Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Val
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 110
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 110

Met Gly Trp Ser Cys Ile Ile Leu Phe Leu Val Ala Thr Ala Thr Gly
1               5                   10                  15

Val His Ser

<210> SEQ ID NO 111
<211> LENGTH: 508
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 111

Gln Leu Val Leu Thr Gln Ser Pro Ser Ala Ser Ala Ser Leu Gly Ser
1               5                   10                  15
```

-continued

```
Ser Val Lys Leu Thr Cys Thr Leu Ser Ser Gly His Lys Thr Asp Thr
        20                  25                  30

Ile Asp Trp Tyr Gln Gln Gln Pro Gly Lys Ala Pro Arg Tyr Leu Met
        35                  40                  45

Lys Leu Glu Gly Ser Gly Ser Tyr Asn Lys Gly Ser Gly Val Pro Asp
    50                  55                  60

Arg Phe Ser Gly Ser Ser Ser Gly Ala Asp Trp Tyr Leu Thr Ile Ser
65                  70                  75                  80

Ser Leu Gln Ser Glu Asp Glu Ala Asp Tyr Tyr Cys Gly Thr Asp Tyr
                85                  90                  95

Pro Gly Asn Tyr Leu Phe Gly Gly Gly Thr Gln Leu Thr Val Leu Gly
            100                 105                 110

Gly Gly Gly Ser Gly Gly Gly Gly Glu Val Gln Leu Val Glu Ser Gly
        115                 120                 125

Gly Gly Leu Val Gln Pro Gly Gly Ser Leu Arg Leu Ser Cys Ala Ala
    130                 135                 140

Ser Gly Phe Thr Phe Ser Thr Tyr Ala Met Asn Trp Val Arg Gln Ala
145                 150                 155                 160

Pro Gly Lys Gly Leu Glu Trp Val Gly Arg Ile Arg Ser Lys Tyr Asn
            165                 170                 175

Asn Tyr Ala Thr Tyr Tyr Ala Asp Ser Val Lys Gly Arg Phe Thr Ile
            180                 185                 190

Ser Arg Asp Asp Ser Lys Asn Ser Leu Tyr Leu Gln Met Asn Ser Leu
        195                 200                 205

Lys Thr Glu Asp Thr Ala Val Tyr Tyr Cys Val Arg His Gly Asn Phe
    210                 215                 220

Gly Asn Ser Tyr Val Ser Trp Phe Ala Tyr Trp Gly Gln Gly Thr Leu
225                 230                 235                 240

Val Thr Val Ser Ser Ala Ser Thr Lys Gly Glu Val Ala Ala Cys Glu
            245                 250                 255

Lys Glu Val Ala Ala Leu Glu Lys Glu Val Ala Ala Leu Glu Lys Glu
            260                 265                 270

Val Ala Ala Leu Glu Lys Gly Gly Gly Asp Lys Thr His Thr Cys Pro
        275                 280                 285

Pro Cys Pro Ala Pro Glu Ala Ala Gly Gly Pro Ser Val Phe Leu Phe
    290                 295                 300

Pro Pro Lys Pro Lys Asp Thr Leu Met Ile Ser Arg Thr Pro Glu Val
305                 310                 315                 320

Thr Cys Val Val Val Asp Val Ser His Glu Asp Pro Glu Val Lys Phe
            325                 330                 335

Asn Trp Tyr Val Asp Gly Val Glu Val His Asn Ala Lys Thr Lys Pro
            340                 345                 350

Arg Glu Glu Gln Tyr Asn Ser Thr Tyr Arg Val Val Ser Val Leu Thr
        355                 360                 365

Val Leu His Gln Asp Trp Leu Asn Gly Lys Glu Tyr Lys Cys Lys Val
    370                 375                 380

Ser Asn Lys Ala Leu Pro Ala Pro Ile Glu Lys Thr Ile Ser Lys Ala
385                 390                 395                 400

Lys Gly Gln Pro Arg Glu Pro Gln Val Tyr Thr Leu Pro Pro Ser Arg
            405                 410                 415

Glu Glu Met Thr Lys Asn Gln Val Ser Leu Trp Cys Leu Val Lys Gly
            420                 425                 430
```

-continued

```
Phe Tyr Pro Ser Asp Ile Ala Val Glu Trp Glu Ser Asn Gly Gln Pro
        435             440             445

Glu Asn Asn Tyr Lys Thr Thr Pro Pro Val Leu Asp Ser Asp Gly Ser
    450             455             460

Phe Phe Leu Tyr Ser Lys Leu Thr Val Asp Lys Ser Arg Trp Gln Gln
465             470             475             480

Gly Asn Val Phe Ser Cys Ser Val Met His Glu Ala Leu His Asn His
            485             490             495

Tyr Thr Gln Lys Ser Leu Ser Leu Ser Pro Gly Lys
        500             505

<210> SEQ ID NO 112
<211> LENGTH: 272
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 112

Gln Ala Val Val Thr Gln Glu Pro Ser Leu Thr Val Ser Pro Gly Gly
1               5               10              15

Thr Val Thr Leu Thr Cys Arg Ser Ser Thr Gly Ala Val Thr Thr Ser
            20              25              30

Asn Tyr Ala Asn Trp Val Gln Gln Lys Pro Gly Gln Ala Pro Arg Gly
        35              40              45

Leu Ile Gly Gly Thr Asn Lys Arg Ala Pro Trp Thr Pro Ala Arg Phe
    50              55              60

Ser Gly Ser Leu Leu Gly Gly Lys Ala Ala Leu Thr Ile Thr Gly Ala
65              70              75              80

Gln Ala Glu Asp Glu Ala Asp Tyr Tyr Cys Ala Leu Trp Tyr Ser Asn
            85              90              95

Leu Trp Val Phe Gly Gly Gly Thr Lys Leu Thr Val Leu Gly Gly Gly
            100             105             110

Gly Ser Gly Gly Gly Gly Gln Glu Gln Leu Val Glu Ser Gly Gly Gly
        115             120             125

Leu Val Gln Pro Gly Gly Ser Leu Arg Leu Ser Cys Ala Ala Ser Gly
    130             135             140

Phe Thr Phe Ser Asp Tyr Tyr Met Ser Trp Ile Arg Gln Ala Pro Gly
145             150             155             160

Lys Gly Leu Glu Trp Val Ala Thr Ile Tyr Pro Ser Ser Gly Lys Thr
            165             170             175

Tyr Tyr Ala Asp Ser Ala Lys Gly Arg Leu Thr Ile Ser Ser Asp Asn
            180             185             190

Ala Lys Asp Ser Leu Tyr Leu Gln Met Asn Ser Leu Arg Ala Glu Asp
        195             200             205

Thr Ala Val Tyr Tyr Cys Thr Arg Asp Ser Tyr Ala Asp Asp Ala Ala
    210             215             220

Leu Phe Asp Ile Trp Gly Gln Gly Thr Thr Val Thr Val Ser Ser Ala
225             230             235             240

Ser Thr Lys Gly Lys Val Ala Ala Cys Lys Glu Lys Val Ala Ala Leu
            245             250             255

Lys Glu Lys Val Ala Ala Leu Lys Glu Lys Val Ala Ala Leu Lys Glu
        260             265             270
```

-continued

```
<210> SEQ ID NO 113
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 113

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
            85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Glu Glu Met Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn Arg Tyr Thr Gln Lys Ser Leu Ser Leu Ser
    210                 215                 220

Pro Gly Lys
225

<210> SEQ ID NO 114
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: SITE
<222> LOCATION: (1)..(20)
<223> OTHER INFORMATION: /note="This sequence may encompass 1-4 'Gly Gly
      Gly Gly Ser' repeating units"

<400> SEQUENCE: 114

Gly Gly Gly Gly Ser Gly Gly Gly Gly Ser Gly Gly Gly Gly Ser Gly
1               5                   10                  15

Gly Gly Gly Ser
            20
```

ANTI-ROR1 / ANTI-CD3 BISPECIFIC BINDING MOLECULES

CROSS-REFERENCE TO RELATED APPLICATION

This application is a National Stage application of International Patent Application No. PCT/US2020/034281, filed May 22, 2020, which claims the benefit of priority to U.S. Provisional Patent Application No. 62/852,039, filed May 23, 2019, the contents of each of which are hereby incorporated by reference in their entireties.

SEQUENCE LISTING

The instant application contains a Sequence Listing that has been submitted electronically in ASCII format and is hereby incorporated by reference in its entirety. The electronic copy of the Sequence Listing, created on May 18, 2020, is named 024651_WO004_SL.txt and is 258,844 bytes in size.

BACKGROUND OF THE INVENTION

Receptor tyrosine kinase-like orphan receptor 1 (ROR1) is a cell surface protein that mediates signals from its ligand, the secreted glycoprotein Wnt5a. Consistent with its role in influencing the fate of stem cells during embryogenesis, ROR1 expression is observed on invasive malignancies that revert to an embryonic transcriptional program, but is not observed on normal adult tissues, offering a favorable selectivity profile as a therapeutic target. ROR1 is commonly expressed on the malignant cells of patients with acute lymphoblastic leukemia (ALL), acute myeloid leukemia (AML), chronic lymphoblastic leukemia (CLL), mantle cell lymphoma (MCL), follicular lymphoma (FL), marginal zone lymphoma (MZL), diffuse large B-cell lymphoma (DLBCL), and Richter's transformation or Richter's syndrome (RS). ROR1 is also present on the cell surfaces of multiple solid tumors, where it appears to be a marker of cancer stem cells. Because it is not expressed to appreciable levels in healthy adult tissues, but displays high levels of expression in multiple hematological and solid tumors, ROR1 is an attractive target for tumor-specific therapy.

Cluster of differentiation 3 (CD3) is a multimeric protein complex expressed on T cells in association with the T cell receptor complex (TCR), and is required for T cell activation. Functional CD3 is formed from the dimeric association of two of four distinct chains—epsilon, gamma, delta, and zeta—into one of the following three pairs of dimers: gamma/epsilon, delta/epsilon and zeta/zeta. Antibodies against CD3 have been shown to cluster CD3 on T cells, causing T cell activation. Accordingly, anti-CD3 antibodies have been proposed for therapeutic purposes involving the activation of T cells. For example, bispecific antibodies that are capable of binding CD3 and a target antigen have been proposed for therapeutic uses involving targeting T cell immune responses to tissues and cells expressing the target antigen. Recent approval of the CD19×CD3 bispecific T-cell engager (BiTE), blinatumomab, has validated this approach.

Numerous formats and compositions have been described for bispecific binding molecules. Multiple variables impact the in vivo potency of these molecules, including PK, targeted antigen epitopes, the relative affinities of the antigen-binding components, and the valency and spatial configuration of the paratopes. Currently, there is no reliable method for designing apriori a single molecule that optimizes all these parameters for a bispecific binding molecule, such as an antibody that specifically binds to both ROR1 and CD3. Bispecific constructs must be designed, made, and tested to systematically evaluate the impact of many of these parameters and to select optimal bispecific binding molecules for therapeutic uses such as cancer treatment.

In view of the above, there is a need for new and improved cancer therapeutics that combine the tumor specificity of the ROR1 antigen with the potent activity of redirected T cells.

SUMMARY OF THE INVENTION

The present invention is directed to novel bispecific binding molecules targeting ROR1 and CD3, as well as pharmaceutical compositions comprising one or more of these antibodies, and use of the antibodies and pharmaceutical compositions for treating cancer. Compared to currently available cancer treatments, including antibody treatments, it is contemplated that the bispecific binding molecules of the invention may provide a superior clinical response.

In some embodiments, the present disclosure provides a bispecific binding molecule comprising a first antigen-binding domain that specifically binds to an extracellular domain of human ROR1 and a second antigen-binding domain that specifically binds to an extracellular domain of human CD3.

In certain embodiments, the first antigen-binding domain competes for binding to human ROR1 with, or binds to the same epitope of human ROR1 as, an antibody comprising a heavy chain amino acid sequence set forth in SEQ ID NO: 82 and a light chain amino acid sequence set forth in SEQ ID NO: 83. In particular embodiments, the first antigen-binding domain comprises:

a) heavy chain (H)-CDR1-3 and light chain (L)-CDR1-3 comprising the amino acid sequences of SEQ ID NOs: 97, 61, 62, 63, 64, and 65, respectively;

b) H-CDR1-3 and L-CDR1-3 comprising the amino acid sequences of SEQ ID NOs: 60, 61, 62, 63, 64, and 65, respectively;

c) a heavy chain variable domain (VH) comprising an amino acid sequence at least 90% identical to SEQ ID NO: 72 and a light chain variable domain (VL) comprising an amino acid sequence at least 90% identical to SEQ ID NO: 73;

d) a VH comprising the amino acid sequence of SEQ ID NO: 74 and a VL comprising the amino acid sequence of SEQ ID NO: 73;

e) a VH comprising the amino acid sequence of SEQ ID NO: 72 and a VL comprising the amino acid sequence of SEQ ID NO: 73;

f) a heavy chain (HC) comprising the amino acid sequence of SEQ ID NO: 84 and a light chain (LC) comprising the amino acid sequence of SEQ ID NO: 83;

g) an HC comprising the amino acid sequence of SEQ ID NO: 82 and an LC comprising the amino acid sequence of SEQ ID NO: 83;

h) an HC comprising the amino acid sequence of SEQ ID NO: 87 and an LC comprising the amino acid sequence of SEQ ID NO: 83; or i) an HC comprising the amino acid sequence of SEQ ID NO: 86 and an LC comprising the amino acid sequence of SEQ ID NO: 83.

In certain embodiments, the second antigen-binding domain competes for binding to human CD3 with, or binds to the same epitope of human CD3 as, an antibody that comprises:

a) a heavy chain variable domain (VH) comprising the amino acid sequence of SEQ ID NO: 70 and a light chain variable domain (VL) comprising the amino acid sequence of SEQ ID NO: 71;

b) a VH comprising the amino acid sequence of SEQ ID NO: 66 and a VL comprising the amino acid sequence of SEQ ID NO: 67; or c) a VH comprising the amino acid sequence of SEQ ID NO: 68 and a VL comprising the amino acid sequence of SEQ ID NO: 69. In particular embodiments, the second antigen-binding domain comprises:

a) heavy chain (H)-CDR1-3 and light chain (L)-CDR1-3 comprising the amino acid sequences of SEQ ID NOs: 54, 55, 56, 57, 58, and 59, respectively;

b) H-CDR1-3 and L-CDR1-3 comprising the amino acid sequences of SEQ ID NOs: 47, 48, 49, 50, 51, and 52, respectively;

c) H-CDR1-3 and L-CDR1-3 comprising the amino acid sequences of SEQ ID NOs. 47, 53, 49, 50, 51, and 52, respectively;

d) a heavy chain variable domain (VH) comprising an amino acid sequence at least 90% identical to SEQ ID NO: 70 and a light chain variable domain (VL) comprising an amino acid sequence at least 90% identical to SEQ ID NO: 71;

e) a VH comprising an amino acid sequence at least 90% identical to SEQ ID NO: 66 and a VL comprising an amino acid sequence at least 90% identical to SEQ ID NO: 67;

f) a VH comprising an amino acid sequence at least 90% identical to SEQ ID NO: 68 and a VL comprising an amino acid sequence at least 90% identical to SEQ ID NO: 69;

g) a VH comprising the amino acid sequence of SEQ ID NO: 70 and a VL comprising the amino acid sequence of SEQ ID NO: 71;

h) a VH comprising the amino acid sequence of SEQ ID NO: 66 and a VL comprising the amino acid sequence of SEQ ID NO: 67;

i) a VH comprising the amino acid sequence of SEQ ID NO: 68 and a VL comprising the amino acid sequence of SEQ ID NO: 69;

j) a VH comprising the amino acid sequence of SEQ ID NO: 80 and a VL comprising the amino acid sequence of SEQ ID NO: 81;

k) a VH comprising the amino acid sequence of SEQ ID NO: 76 and a VL comprising the amino acid sequence of SEQ ID NO: 77; or l) a VH comprising the amino acid sequence of SEQ ID NO: 78 and a VL comprising the amino acid sequence of SEQ ID NO: 79.

In some embodiments, the present disclosure provides a bispecific binding molecule comprising:

a) a first antigen-binding domain that comprises heavy chain (H)-CDR1-3 and light chain (L)-CDR1-3 comprising the amino acid sequences of SEQ ID NOs: 97, 61, 62, 63, 64, and 65, respectively, and a second antigen-binding domain that comprises H-CDR1-3 and L-CDR1-3 comprising the amino acid sequences of SEQ ID NOs: 54, 55, 56, 57, 58, and 59, respectively;

b) a first antigen-binding domain that comprises H-CDR1-3 and L-CDR1-3 comprising the amino acid sequences of SEQ ID NOs: 60, 61, 62, 63, 64, and 65, respectively, and a second antigen-binding domain that comprises H-CDR1-3 and L-CDR1-3 comprising the amino acid sequences of SEQ ID NOs: 54, 55, 56, 57, 58, and 59, respectively;

c) a first antigen-binding domain that comprises H-CDR1-3 and L-CDR1-3 comprising the amino acid sequences of SEQ ID NOs: 60, 61, 62, 63, 64, and 65, respectively, and a second antigen-binding domain that comprises H-CDR1-3 and L-CDR1-3 comprising the amino acid sequences of SEQ ID NOs: 47, 53, 49, 50, 51, and 52, respectively;

d) a first antigen-binding domain that comprises H-CDR1-3 and L-CDR1-3 comprising the amino acid sequences of SEQ ID NOs: 97, 61, 62, 63, 64, and 65, respectively, and a second antigen-binding domain that comprises H-CDR1-3 and L-CDR1-3 comprising the amino acid sequences of SEQ ID NOs: 47, 48, 49, 50, 51, and 52, respectively;

e) a first antigen-binding domain that comprises H-CDR1-3 and L-CDR1-3 comprising the amino acid sequences of SEQ ID NOs: 97, 61, 62, 63, 64, and 65, respectively, and a second antigen-binding domain that comprises H-CDR1-3 and L-CDR1-3 comprising the amino acid sequences of SEQ ID NOs: 47, 53, 49, 50, 51, and 52, respectively; or f) a first antigen-binding domain that comprises H-CDR1-3 and L-CDR1-3 comprising the amino acid sequences of SEQ ID NOs: 60, 61, 62, 63, 64, and 65, respectively, and a second antigen-binding domain that comprises H-CDR1-3 and L-CDR1-3 comprising the amino acid sequences of SEQ ID NOs: 47, 48, 49, 50, 51, and 52, respectively.

In some embodiments, the present disclosure provides a bispecific binding molecule comprising:

a) a first antigen-binding domain that comprises a heavy chain variable domain (VH) and a light chain variable domain (VL) comprising the amino acid sequences of SEQ ID NOs: 74 and 73, respectively, and a second antigen-binding domain that comprises a VH and a VL comprising the amino acid sequences of SEQ ID NOs: 70 and 71, respectively;

b) a first antigen-binding domain that comprises a VH and a VL comprising the amino acid sequences of SEQ ID NOs: 72 and 73, respectively, and a second antigen-binding domain that comprises a VH and a VL comprising the amino acid sequences of SEQ ID NOs: 70 and 71, respectively;

c) a first antigen-binding domain that comprises a VH and a VL comprising the amino acid sequences of SEQ ID NOs: 72 and 73, respectively, and a second antigen-binding domain that comprises a VH and a VL comprising the amino acid sequences of SEQ ID NOs: 68 and 69, respectively;

d) a first antigen-binding domain that comprises a VH and a VL comprising the amino acid sequences of SEQ ID NOs: 74 and 73, respectively, and a second antigen-binding domain that comprises a VH and a VL comprising the amino acid sequences of SEQ ID NOs: 66 and 67, respectively;

e) a first antigen-binding domain that comprises a VH and a VL comprising the amino acid sequences of SEQ ID NOs: 74 and 73, respectively, and a second antigen-binding domain that comprises a VH and a VL comprising the amino acid sequences of SEQ ID NOs: 68 and 69, respectively; or f) a first antigen-binding domain that comprises a VH and a VL comprising the amino acid sequences of SEQ ID NOs: 72 and 73, respectively, and a second antigen-binding domain that comprises a VH and a VL comprising the amino acid sequences of SEQ ID NOs: 66 and 67, respectively.

In some embodiments, the present disclosure provides a bispecific binding molecule comprising:

a) a first antigen-binding domain that comprises a heavy chain variable domain (VH) and a light chain variable domain (VL) comprising the amino acid sequences of SEQ ID NOs: 74 and 73, respectively, and a second antigen-binding domain that comprises a VH and a VL comprising the amino acid sequences of SEQ ID NOs: 80 and 81, respectively;

b) a first antigen-binding domain that comprises a VH and a VL comprising the amino acid sequences of SEQ ID NOs: 72 and 73, respectively, and a second antigen-binding domain that comprises a VH and a VL comprising the amino acid sequences of SEQ ID NOs: 80 and 81, respectively;

c) a first antigen-binding domain that comprises a VH and a VL comprising the amino acid sequences of SEQ ID NOs: 72 and 73, respectively, and a second antigen-binding domain that comprises a VH and a VL comprising the amino acid sequences of SEQ ID NOs: 78 and 79, respectively;

d) a first antigen-binding domain that comprises a VH and a VL comprising the amino acid sequences of SEQ ID NOs: 74 and 73, respectively, and a second antigen-binding domain that comprises a VH and a VL comprising the amino acid sequences of SEQ ID NOs: 76 and 77, respectively;

e) a first antigen-binding domain that comprises a VH and a VL comprising the amino acid sequences of SEQ ID NOs: 74 and 73, respectively, and a second antigen-binding domain that comprises a VH and a VL comprising the amino acid sequences of SEQ ID NOs: 78 and 79, respectively; or f) a first antigen-binding domain that comprises a VH and a VL comprising the amino acid sequences of SEQ ID NOs: 72 and 73, respectively, and a second antigen-binding domain that comprises a VH and a VL comprising the amino acid sequences of SEQ ID NOs: 76 and 77, respectively.

In some embodiments, the present disclosure provides a bispecific binding molecule comprising:

a) a first antigen-binding domain that comprises a heavy chain (HC) and a light chain (LC) comprising the amino acid sequences of SEQ ID NOs: 84 and 83, respectively, and a second antigen-binding domain that comprises a VH and a VL comprising the amino acid sequences of SEQ ID NOs: 70 and 71, respectively;

b) a first antigen-binding domain that comprises an HC and an LC comprising the amino acid sequences of SEQ ID NOs: 82 and 83, respectively, and a second antigen-binding domain that comprises a VH and a VL comprising the amino acid sequences of SEQ ID NOs: 70 and 71, respectively;

c) a first antigen-binding domain that comprises an HC and an LC comprising the amino acid sequences of SEQ ID NOs: 82 and 83, respectively, and a second antigen-binding domain that comprises a VH and a VL comprising the amino acid sequences of SEQ ID NOs: 68 and 69, respectively;

d) a first antigen-binding domain that comprises an HC and an LC comprising the amino acid sequences of SEQ ID NOs: 84 and 83, respectively, and a second antigen-binding domain that comprises a VH and a VL comprising the amino acid sequences of SEQ ID NOs: 66 and 67, respectively;

e) a first antigen-binding domain that comprises an HC and an LC comprising the amino acid sequences of SEQ ID NOs: 84 and 83, respectively, and a second antigen-binding domain that comprises a VH and a VL comprising the amino acid sequences of SEQ ID NOs: 68 and 69, respectively;

f) a first antigen-binding domain that comprises an HC and an LC comprising the amino acid sequences of SEQ ID NOs: 82 and 83, respectively, and a second antigen-binding domain that comprises a VH and a VL comprising the amino acid sequences of SEQ ID NOs: 66 and 67, respectively;

g) a first antigen-binding domain that comprises an HC comprising the amino acid sequence of SEQ ID NO: 87, an HC comprising the amino acid sequence of SEQ ID NO: 107 or 109, and an LC comprising the amino acid sequence of SEQ ID NO: 83, and a second antigen-binding domain that comprises a VH and a VL comprising the amino acid sequences of SEQ ID NOs: 70 and 71, respectively;

h) a first antigen-binding domain that comprises an HC comprising the amino acid sequence of SEQ ID NO: 86, an HC comprising the amino acid sequence of SEQ ID NO: 106 or 109, and an LC comprising the amino acid sequence of SEQ ID NO: 83, and a second antigen-binding domain that comprises a VH and a VL comprising the amino acid sequences of SEQ ID NOs: 70 and 71, respectively;

i) a first antigen-binding domain that comprises an HC comprising the amino acid sequence of SEQ ID NO: 86, an HC comprising the amino acid sequence of SEQ ID NO: 106 or 109, and an LC comprising the amino acid sequence of SEQ ID NO: 83, and a second antigen-binding domain that comprises a VH and a VL comprising the amino acid sequences of SEQ ID NOs: 68 and 69, respectively;

j) a first antigen-binding domain that comprises an HC comprising the amino acid sequence of SEQ ID NO: 87, an HC comprising the amino acid sequence of SEQ ID NO: 107 or 109, and an LC comprising the amino acid sequence of SEQ ID NO: 83, and a second antigen-binding domain that comprises a VH and a VL comprising the amino acid sequences of SEQ ID NOs: 66 and 67, respectively;

k) a first antigen-binding domain that comprises an HC comprising the amino acid sequence of SEQ ID NO: 87, an HC comprising the amino acid sequence of SEQ ID NO: 107 or 109, and an LC comprising the amino acid sequence of SEQ ID NO: 83, and a second antigen-binding domain that comprises a VH and a VL comprising the amino acid sequences of SEQ ID NOs: 68 and 69, respectively; or l) a first antigen-binding domain that comprises an HC comprising the amino acid sequence of SEQ ID NO: 86, an HC comprising the amino acid sequence of SEQ ID NO: 106 or 109, and an LC comprising the amino acid sequence of SEQ ID NO: 83, and a second antigen-binding domain that comprises a VH and a VL comprising the amino acid sequences of SEQ ID NOs: 66 and 67, respectively.

In some embodiments, the present disclosure provides a bispecific binding molecule comprising:

a) a first antigen-binding domain that comprises a heavy chain (HC) and a light chain (LC) comprising the amino acid sequences of SEQ ID NOs: 84 and 83, respectively, and a second antigen-binding domain that comprises a VH and a VL comprising the amino acid sequences of SEQ ID NOs: 80 and 81, respectively;

b) a first antigen-binding domain that comprises an HC and an LC comprising the amino acid sequences of SEQ ID NOs: 82 and 83, respectively, and a second antigen-binding domain that comprises a VH and a VL comprising the amino acid sequences of SEQ ID NOs: 80 and 81, respectively;

c) a first antigen-binding domain that comprises an HC and an LC comprising the amino acid sequences of SEQ ID NOs: 82 and 83, respectively, and a second antigen-binding domain that comprises a VH and a VL comprising the amino acid sequences of SEQ ID NOs: 78 and 79, respectively;

d) a first antigen-binding domain that comprises an HC and an LC comprising the amino acid sequences of SEQ ID NOs: 84 and 83, respectively, and a second antigen-binding domain that comprises a VH and a VL comprising the amino acid sequences of SEQ ID NOs: 76 and 77, respectively;

e) a first antigen-binding domain that comprises an HC and an LC comprising the amino acid sequences of SEQ ID NOs: 84 and 83, respectively, and a second antigen-binding domain that comprises a VH and a VL comprising the amino acid sequences of SEQ ID NOs: 78 and 79, respectively;

f) a first antigen-binding domain that comprises an HC and an LC comprising the amino acid sequences of SEQ ID NOs: 82 and 83, respectively, and a second antigen-binding domain that comprises a VH and a VL comprising the amino acid sequences of SEQ ID NOs: 76 and 77, respectively;

g) a first antigen-binding domain that comprises an HC comprising the amino acid sequence of SEQ ID NO: 87, an HC comprising the amino acid sequence of SEQ ID NO: 107 or 109, and an LC comprising the amino acid sequence of SEQ ID NO: 83, and a second antigen-binding domain that comprises a VH and a VL comprising the amino acid sequences of SEQ ID NOs: 80 and 81, respectively;

h) a first antigen-binding domain that comprises an HC comprising the amino acid sequence of SEQ ID NO: 86, an HC comprising the amino acid sequence of SEQ ID NO: 106 or 109, and an LC comprising the amino acid sequence of SEQ ID NO: 83, and a second antigen-binding domain that comprises a VH and a VL comprising the amino acid sequences of SEQ ID NOs: 80 and 81, respectively;

i) a first antigen-binding domain that comprises an HC comprising the amino acid sequence of SEQ ID NO: 86, an HC comprising the amino acid sequence of SEQ ID NO: 106 or 109, and an LC comprising the amino acid sequence of SEQ ID NO: 83, and a second antigen-binding domain that comprises a VH and a VL comprising the amino acid sequences of SEQ ID NOs: 78 and 79, respectively;

j) a first antigen-binding domain that comprises an HC comprising the amino acid sequence of SEQ ID NO: 87, an HC comprising the amino acid sequence of SEQ ID NO: 107 or 109, and an LC comprising the amino acid sequence of SEQ ID NO: 83, and a second antigen-binding domain that comprises a VH and a VL comprising the amino acid sequences of SEQ ID NOs: 76 and 77, respectively;

k) a first antigen-binding domain that comprises an HC comprising the amino acid sequence of SEQ ID NO: 87, an HC comprising the amino acid sequence of SEQ ID NO: 107 or 109, and an LC comprising the amino acid sequence of SEQ ID NO: 83, and a second antigen-binding domain that comprises a VH and a VL comprising the amino acid sequences of SEQ ID NOs: 78 and 79, respectively; or l) a first antigen-binding domain that comprises an HC comprising the amino acid sequence of SEQ ID NO: 86, an HC comprising the amino acid sequence of SEQ ID NO: 106 or 109, and an LC comprising the amino acid sequence of SEQ ID NO: 83, and a second antigen-binding domain that comprises a VH and a VL comprising the amino acid sequences of SEQ ID NOs: 76 and 77, respectively.

In certain embodiments, a bispecific binding molecule of the present disclosure comprises the amino acid sequences of SEQ ID NOs: 14 and 19, SEQ ID NOs: 7 and 19, SEQ ID NOs: 7 and 18, or SEQ ID NOs: 7 and 23. In certain embodiments, a bispecific binding molecule of the present disclosure comprises:

a) the amino acid sequences of SEQ ID NOs: 1 and 16;

b) the amino acid sequences of SEQ ID NOs: 2 and 16;

c) the amino acid sequences of SEQ ID NOs: 3 and 16;

d) the amino acid sequences of SEQ ID NOs: 4 and 16;

e) the amino acid sequences of SEQ ID NOs: 5 and 16;

f) the amino acid sequences of SEQ ID NOs: 6 and 16;

g) the amino acid sequences of SEQ ID NOs: 7 and 17;

h) the amino acid sequences of SEQ ID NOs: 7 and 20;

i) the amino acid sequences of SEQ ID NOs: 7 and 21;

j) the amino acid sequences of SEQ ID NOs: 7 and 22;

k) the amino acid sequences of SEQ ID NOs: 8, 9, and 16;

l) the amino acid sequences of SEQ ID NOs: 8, 10, and 16;

m) the amino acid sequences of SEQ ID NOs: 8, 11, and 16;

n) the amino acid sequences of SEQ ID NOs: 12, 11, and 16;

o) the amino acid sequences of SEQ ID NOs: 12, 13, and 16; or p) the amino acid sequences of SEQ ID NOs: 8, 15, and 16.

In some embodiments, a bispecific binding molecule described herein may have any of the following valencies for the first and second antigen-binding domains:

a) the first antigen-binding domain has a valency of 2 and the second antigen-binding domain has a valency of 2;

b) the first antigen-binding domain has a valency of 1 and the second antigen-binding domain has a valency of 1; or c) the first antigen-binding domain has a valency of 2 and the second antigen-binding domain has a valency of 1.

In some embodiments, a bispecific binding molecule described herein may comprise a human IgG1 constant region; said constant region may contain the amino acid substitutions L234A, L235A, and/or G237A, wherein the residues are numbered according to the EU system.

In some embodiments, the second antigen-binding domain of a bispecific binding molecule described herein is an scFv.

In some embodiments of a bispecific binding molecule described herein, a heavy or light chain amino acid sequence of the second antigen-binding domain is fused to a heavy or light chain amino acid sequence of the first antigen-binding domain via a peptide linker. In certain embodiments, the peptide linker has the amino acid sequence of GGGGSGGGGS (SEQ ID NO: 93). In particular embodiments, the heavy or light chain amino acid sequence of the second antigen-binding domain may be fused to, e.g.:

a) the carboxy-terminus of the light chain of the first antigen-binding domain; or b) the amino-terminus of the light chain of the first antigen-binding domain.

In certain embodiments, a bispecific binding molecule described herein has at least one (e.g., 1, 2, 3, 4, 5, 6, 7, 8, 9, 10, 11, or 12) of the following properties:

a) has a $K_D$ for immobilized ROR1 of 0.5 nM or less as determined by ELISA;

b) has a $K_D$ for soluble b-ROR1 of 0.4 nM or less as determined by ELISA;

c) demonstrates reduced internalization in ROR1-transfected MEC cells and/or Jurkat cells as compared to an antibody comprising the heavy and light chain amino acid sequences of SEQ ID NOs: 82 and 83, respectively;

d) induces LDH release in PBMC-exposed ROR1-transfected MEC cells at 1 μg/mL or less;

e) induces LDH release in PBMC-exposed JeKo-1 cells at 1 μg/mL or less;

f) induces LDH release in PBMC-exposed Mino cells at 1 μg/mL or less;

g) induces LDH release in PBMC-exposed MDA-MB-468 cells at 1 μg/mL or less;

h) upregulates CD69 on the surface of T cells co-cultured with ROR1-transfected MEC cells at 1 μg/mL or less as determined by flow cytometry;

i) upregulates CD69 on the surface of T cells co-cultured with JeKo-1 cells at 1 μg/mL or less as determined by flow cytometry;

j) upregulates CD69 on the surface of T cells co-cultured with Mino cells at 1 μg/mL or less as determined by flow cytometry;

k) upregulates CD69 on the surface of T cells co-cultured with MDA-MB-468 cells at 1 μg/mL or less as determined by flow cytometry; and l) induces release of IFN-γ, TNF-α, IL-10, IL-6, IL-4, and IL-2 from T cells co-cultured with Jeko-1 or ROR1-transfected MEC cells at 1 μg/mL or less.

The present disclosure also provides an immunoconjugate comprising a bispecific binding molecule described herein conjugated to a cytotoxic agent.

The present disclosure also provides a pharmaceutical composition comprising a bispecific binding molecule described herein and a pharmaceutically acceptable excipient.

The present disclosure also provides one or more isolated nucleic acid molecules comprising nucleotide sequences that encode the heavy and light chain variable domains (VH and VL) of the first antigen-binding domain, and further comprising nucleotide sequences that encode the VH and VL of the second antigen-binding domain, of a bispecific binding molecule described herein. In some embodiments, the isolated nucleic acid molecule(s) comprise:

a) the nucleotide sequences of SEQ ID NOs: 37 and 42;
b) the nucleotide sequences of SEQ ID NOs: 30 and 42;
c) the nucleotide sequences of SEQ ID NOs: 30 and 41;
d) the nucleotide sequences of SEQ ID NOs: 30 and 46;
e) the nucleotide sequences of SEQ ID NOs: 24 and 39;
f) the nucleotide sequences of SEQ ID NOs: 25 and 39;
g) the nucleotide sequences of SEQ ID NOs: 26 and 39;
h) the nucleotide sequences of SEQ ID NOs: 27 and 39;
i) the nucleotide sequences of SEQ ID NOs: 28 and 39;
j) the nucleotide sequences of SEQ ID NOs: 29 and 39;
k) the nucleotide sequences of SEQ ID NOs: 30 and 40;
l) the nucleotide sequences of SEQ ID NOs: 30 and 43;
m) the nucleotide sequences of SEQ ID NOs: 30 and 44;

n) the nucleotide sequences of SEQ ID NOs: 30 and 45;
o) the nucleotide sequences of SEQ ID NOs: 31, 32, and 39;
p) the nucleotide sequences of SEQ ID NOs: 31, 33 and 39;
q) the nucleotide sequences of SEQ ID NOs: 31, 34, and 39;
r) the nucleotide sequences of SEQ ID NOs: 35, 34, and 39;
s) the nucleotide sequences of SEQ ID NOs: 35, 36, and 39; or
t) the nucleotide sequences of SEQ ID NOs: 31, 38, and 39.

The present disclosure also provides a vector comprising isolated nucleic acid molecule(s) described herein.

The present disclosure also provides a host cell comprising nucleotide sequences that encode the heavy and light chain variable domains (VH and VL) of the first antigen-binding domain, and further comprising nucleotide sequences that encode the VH and VL of the second antigen-binding domain, of a bispecific binding molecule described herein. In some embodiments, the host cell comprises the nucleotide sequences of:

a) SEQ ID NOs: 37 and 42;
b) SEQ ID NOs: 30 and 42;
c) SEQ ID NOs: 30 and 41;
d) SEQ ID NOs: 30 and 46;
e) SEQ ID NOs: 24 and 39;
f) SEQ ID NOs: 25 and 39;
g) SEQ ID NOs: 26 and 39;
h) SEQ ID NOs: 27 and 39;
i) SEQ ID NOs: 28 and 39;
j) SEQ ID NOs: 29 and 39;
k) SEQ ID NOs: 30 and 40;
l) SEQ ID NOs: 30 and 43;
m) SEQ ID NOs: 30 and 44;
n) SEQ ID NOs: 30 and 45;
o) SEQ ID NOs: 31, 32, and 39;
p) SEQ ID NOs: 31, 33 and 39;
q) SEQ ID NOs: 31, 34, and 39;
r) SEQ ID NOs: 35, 34, and 39;
s) SEQ ID NOs: 35, 36, and 39; or
t) SEQ ID NOs: 31, 38, and 39.

The present invention also provides a method for producing a bispecific binding molecule described herein, comprising providing a host cell as described herein, cultivating said host cell under conditions suitable for expression of the bispecific binding molecule, and isolating the resulting bispecific binding molecule.

The present disclosure also provides a method for treating cancer in a patient, comprising administering to the patient a bispecific binding molecule described herein. Further, the present disclosure provides the use of a bispecific binding molecule described herein for the manufacture of a medicament for treating cancer in a patient, and a bispecific binding molecule described herein for use in treating cancer in a patient. In some embodiments, the cancer is a ROR1-positive cancer. In some embodiments, the cancer is a leukemia, a lymphoma, or a solid tumor. In some embodiments, the cancer is acute myeloid leukemia, acute lymphoblastic leukemia, chronic lymphocytic leukemia, T-cell leukemia, mantle cell lymphoma, diffuse large B-cell lymphoma, follicular lymphoma, Burkitt's lymphoma, T cell non-Hodgkin lymphoma, lymphoplasmacytoid lymphoma, Waldenström macroglobulinemia, multiple myeloma, marginal zone lymphoma, small lymphocytic lymphoma, or a non-Hodgkin lymphoma that has undergone Richter's transformation. In some embodiments, the cancer is colon cancer, non-small cell lung cancer, glioblastoma, hepatocellular carcinoma, pancreatic cancer, Ewing sarcoma, osteosarcoma, head and neck cancer, ovarian cancer, breast cancer, or triple negative breast cancer. In certain embodiments, the patient may be treated with one or more additional therapeutic agents, such as a Bruton's tyrosine kinase (BTK) inhibitor, a B-cell lymphoma 2 (Bcl-2) inhibitor, a mammalian target of rapamycin (mTOR) inhibitor, and/or a phosphoinositide 3-kinase (PI3K) inhibitor. In particular embodiments, the additional therapeutic agent is ibrutinib, acalabrutinib, venetoclax, everolimus, sapanisertib, or idelalisib.

The present disclosure also provides a kit comprising a bispecific binding molecule as described herein. Further, the present disclosure provides an article of manufacture comprising a bispecific binding molecule as described herein, wherein said article of manufacture is suitable for treating cancer in a patient.

BRIEF DESCRIPTION OF THE DRAWINGS

FIG. 22 is a pair of graphs quantitating LDH release from MDA-MB-468 cells (Panel A) and cell surface levels of CD69 on CD8+ cells (Panel B), where MDA-MB-468 cells are incubated with human PBMCs and bispecific constructs 9, 18, and 20.

Figure 23:
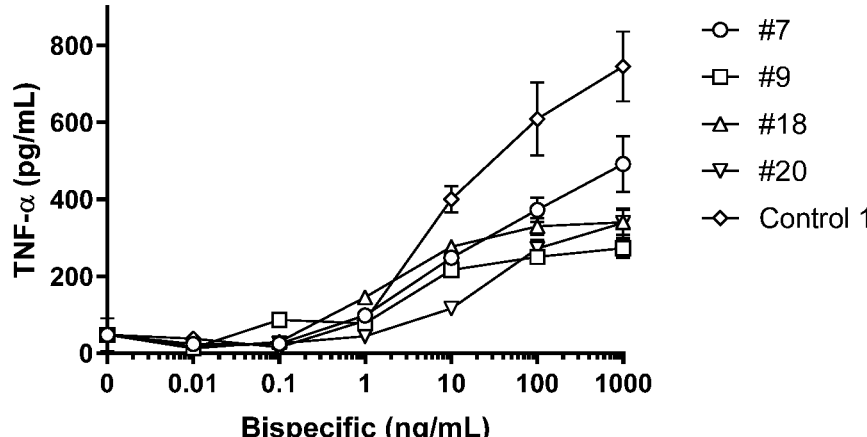
Figure 23:
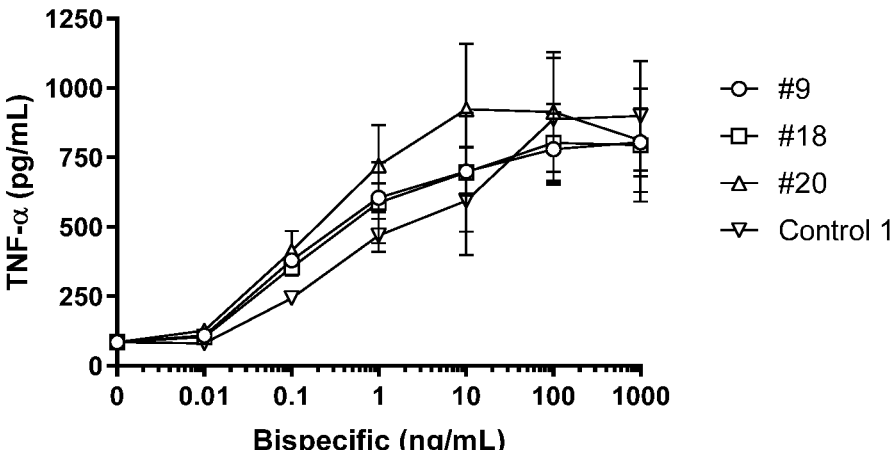
Figure 23:
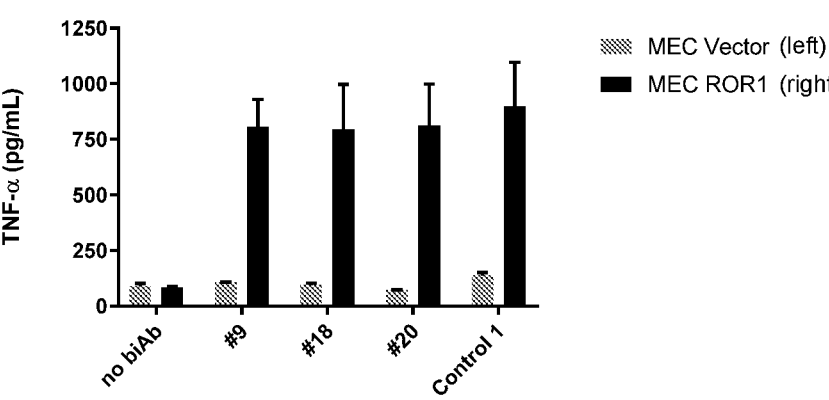

FIG. 23 is a set of graphs quantitating release of TNF-α from JeKo-1 cells (Panel A), ROR1-transfected MEC cells (Panel B), and from mock-transfected, ROR1⁻MEC cells (Panel C) following activation of T cells with designated target cells and bispecific constructs 7, 9, 18, and 20 (Panel A) or 9, 18, 20 (Panels B and C). Mock-transfected, ROR1⁻ MEC cells (Panel C) were treated with a single concentration (1 µg/mL) of the bispecific constructs. "Control 1" is an unrelated ROR1×CD3 bispecific construct.

Figure 24:
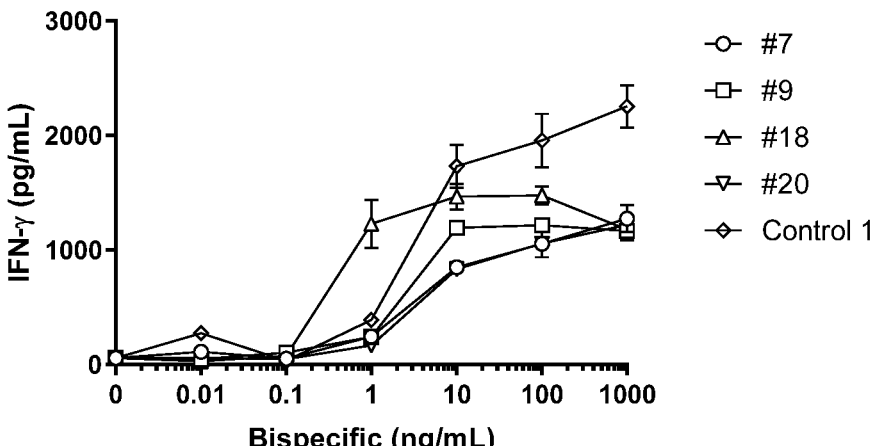
Figure 24:
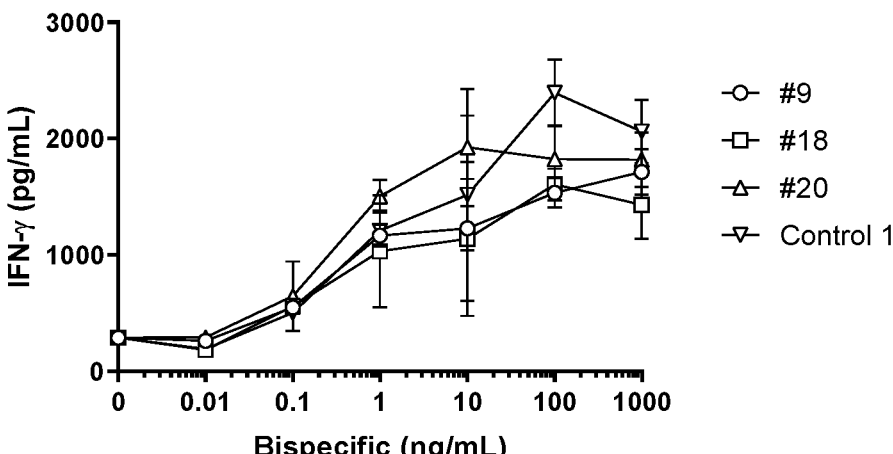
Figure 24:
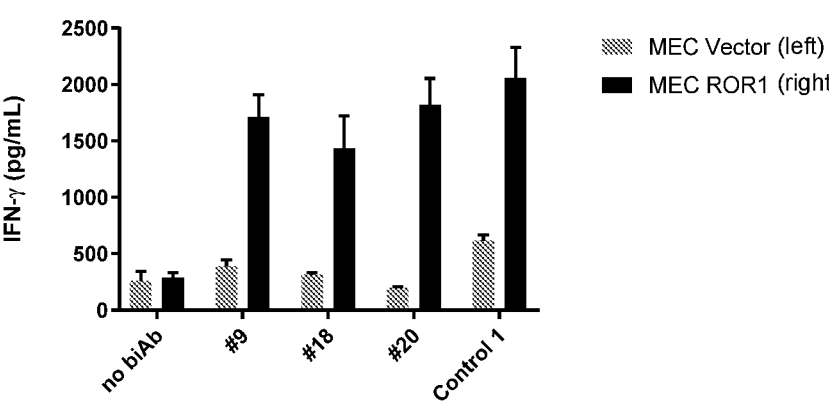

FIG. 24 is a set of graphs quantitating release of IFN-γ from JeKo-1 cells (Panel A), ROR1-transfected MEC cells (Panel B), and from mock-transfected, ROR1⁻MEC cells (Panel C) following activation of T cells with designated target cells and bispecific constructs 7, 9, 18, and 20 (Panel A) or 9, 18, and 20 (Panels B and C). Mock-transfected, ROR1⁻MEC cells (Panel C) were treated with a single concentration (1 µg/mL) of the bispecific constructs. "Control 1" is an unrelated ROR1×CD3 bispecific construct.

Figure 25:
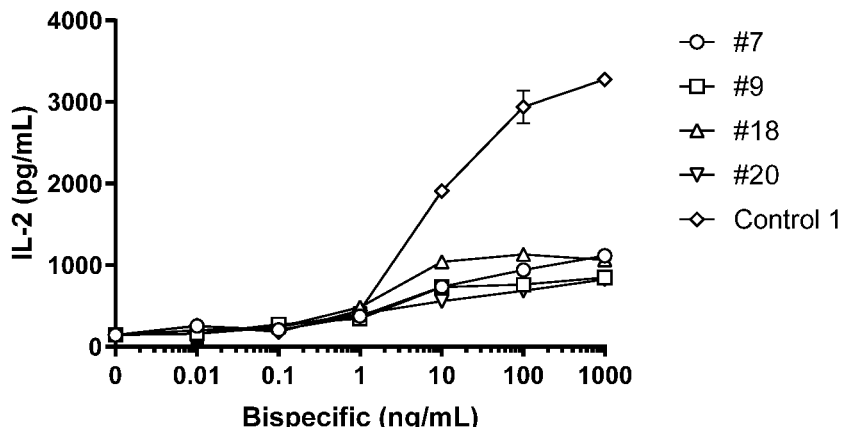
Figure 25:
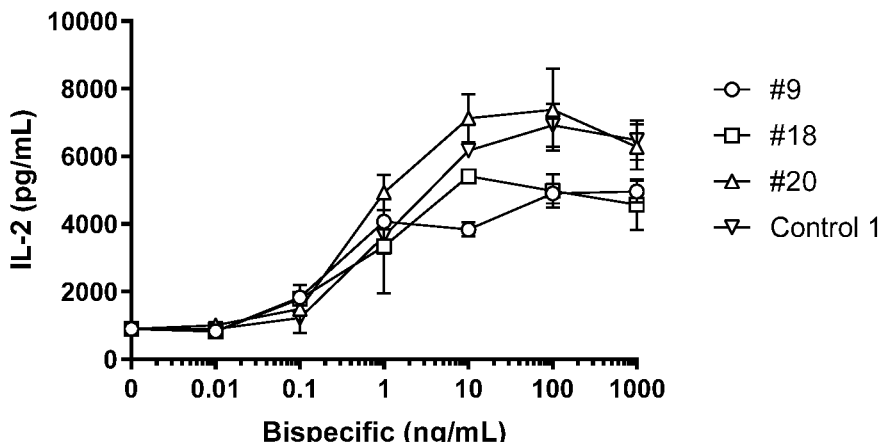
Figure 25:
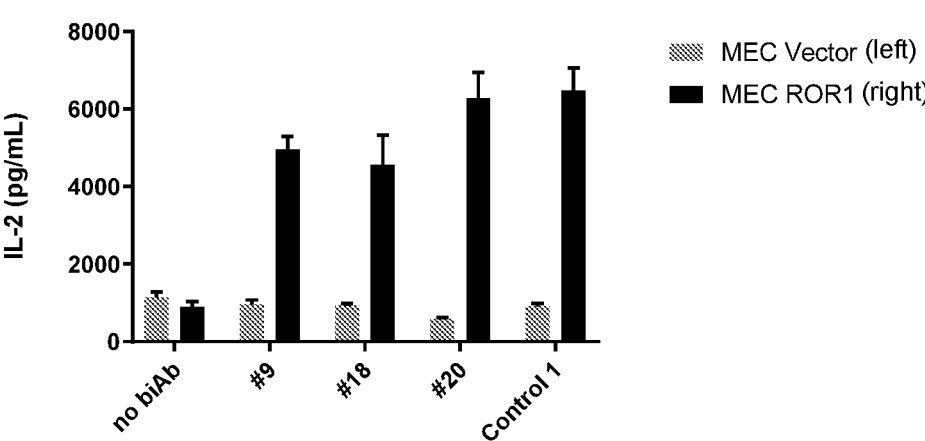

FIG. 25 is a set of graphs quantitating release of IL-2 from JeKo-1 cells (Panel A), ROR1-transfected MEC cells (Panel B), and from mock-transfected, ROR1⁻MEC cells (Panel C) following activation of T cells with designated target cells and bispecific constructs 7, 9, 18, and 20 (Panel A) or 9, 18, and 20 (Panels B and C). Mock-transfected, ROR1⁻MEC cells (Panel C) were treated with a single concentration (1 µg/mL) of the bispecific constructs. "Control 1" is an unrelated ROR1×CD3 bispecific construct.

Figure 26:
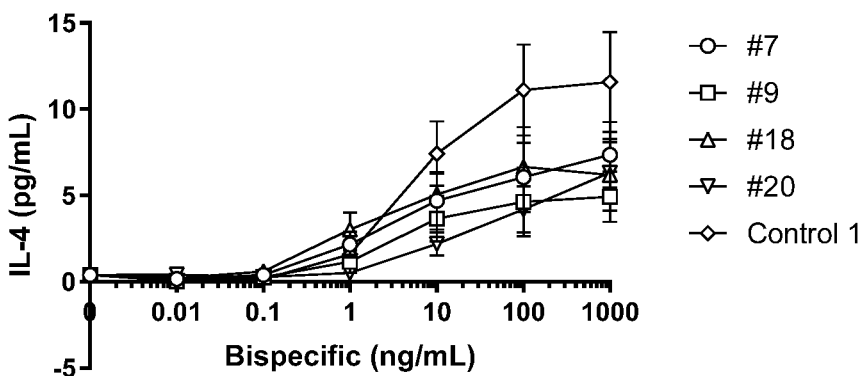
Figure 26:
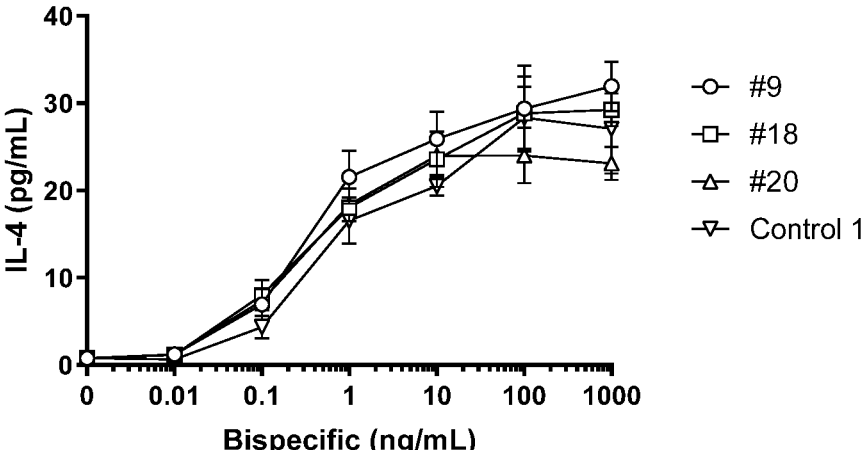
Figure 26:
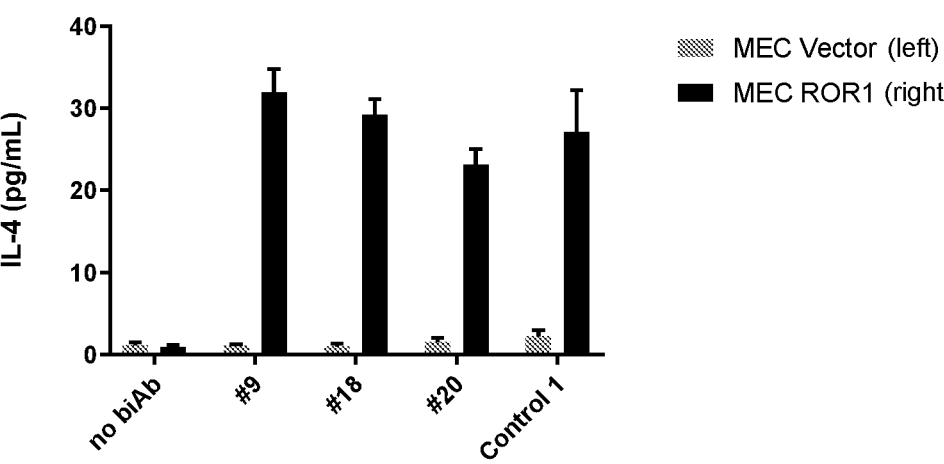

FIG. 26 is a set of graphs quantitating release of IL-4 from JeKo-1 cells (Panel A), ROR1-transfected MEC cells (Panel B), and from mock-transfected, ROR1⁻MEC cells (Panel C) following activation of T cells with designated target cells and bispecific constructs 7, 9, 18, and 20 (Panel A) or 9, 18, and 20 (Panels B and C). Mock-transfected, ROR1⁻MEC cells (Panel C) were treated with a single concentration (1 µg/mL) of the bispecific constructs. "Control 1" is an unrelated ROR1×CD3 bispecific construct.

Figure 27:
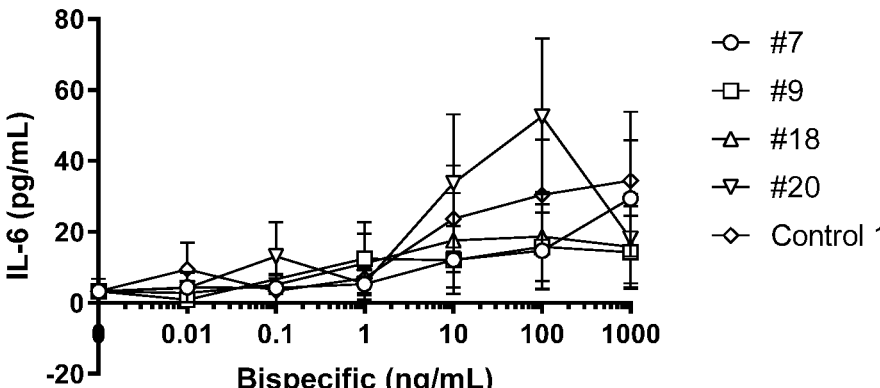
Figure 27:
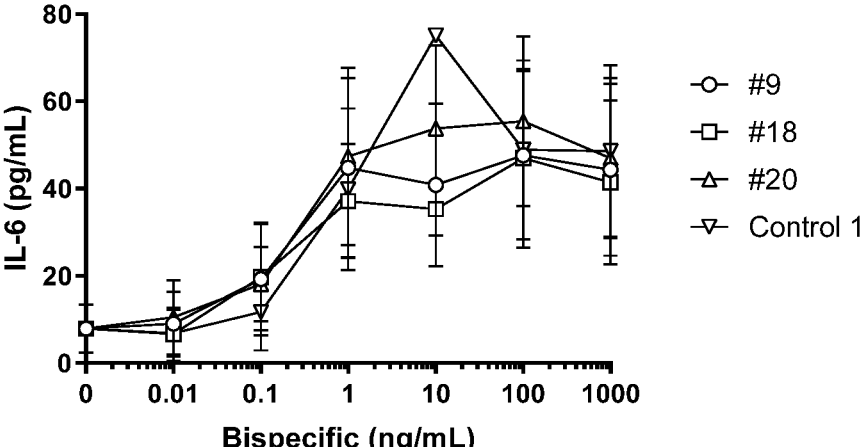
Figure 27:
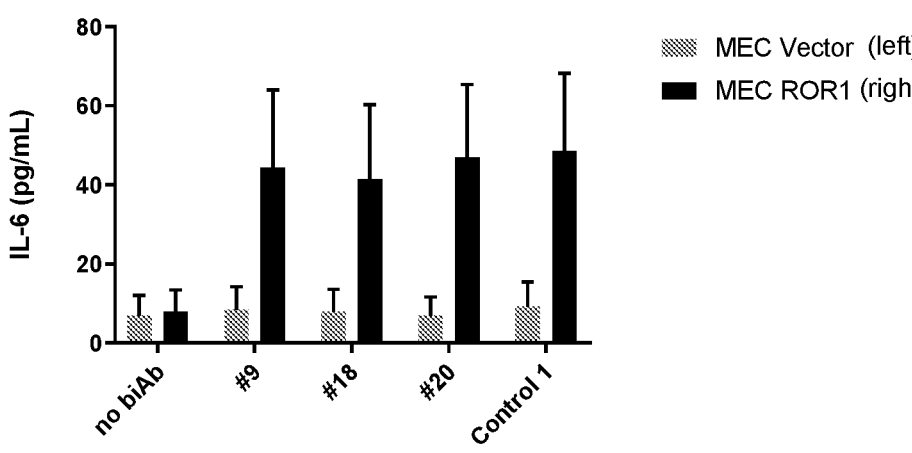

FIG. 27 is a set of graphs quantitating release of IL-6 from JeKo-1 cells (Panel A), ROR1-transfected MEC cells (Panel B), and from mock-transfected, ROR1⁻MEC cells (Panel C) following activation of T cells with designated target cells and bispecific constructs 7, 9, 18, and 20 (Panel A) or 9, 18, and 20 (Panels B and C) Mock-transfected, ROR1⁻MEC cells (Panel C) were treated with a single concentration (1 µg/mL) of the bispecific constructs. "Control 1" is an unrelated ROR1×CD3 bispecific construct.

Figure 28:
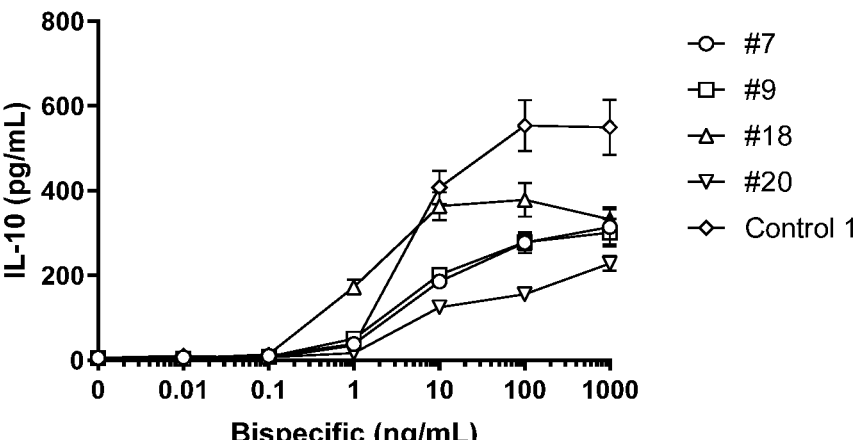
Figure 28:
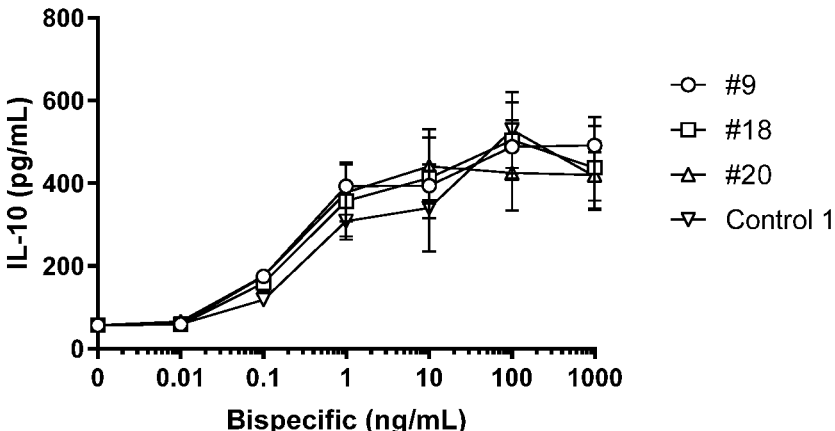
Figure 28:
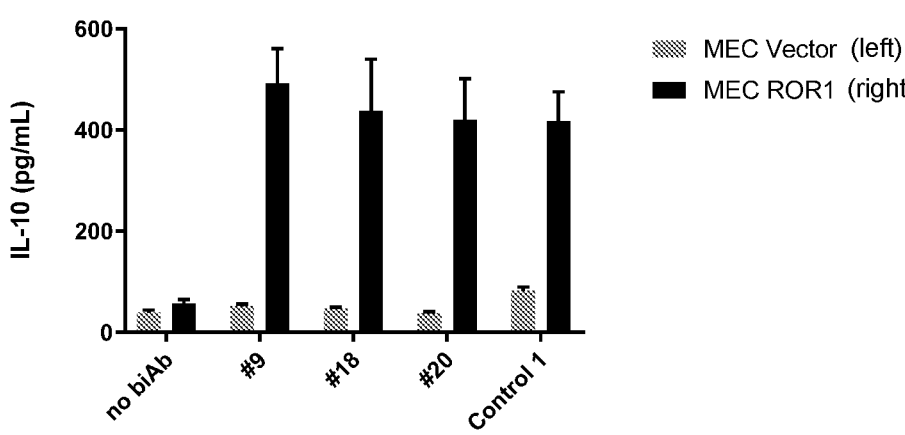

FIG. 28 is a set of graphs quantitating release of IL-10 from JeKo-1 cells (Panel A), ROR1-transfected MEC cells (Panel B), and from mock-transfected, ROR1⁻MEC cells (Panel C) following activation of T cells with designated target cells and bispecific constructs 7, 9, 18, and 20 (Panel A) or 9, 18, and 20 (Panels B and C). Mock-transfected, ROR1⁻MEC cells (Panel C) were treated with a single concentration (1 µg/mL) of the bispecific constructs. "Control 1" is an unrelated ROR1×CD3 bispecific construct.

FIG. 29 is a table showing SEQ ID NOs for the indicated sequences of anti-ROR1 and anti-CD3 antigen-binding domains.

DETAILED DESCRIPTION OF THE INVENTION

The present disclosure provides new bispecific binding molecules that bind to ROR and CD3. In some embodiments, binding of the bispecific binding molecules to ROR and CD3 brings T cells in proximity to ROR1-positive tumor cells, thus treating cancer by invoking T cell cytotoxicity. Unless otherwise stated, as used herein, "ROR1" refers to human RORL. A human ROR1 polypeptide sequence is available under UniProt Accession No. Q01973-1 (SEQ ID NO: 89). Unless otherwise stated, as used herein, "CD3" refers to human CD3. CD3 is comprised of a gamma chain, a delta chain, and two epsilon chains. A human CD3 gamma polypeptide sequence is available under GenBank Accession Number NP_000064.1 (SEQ ID NO: 90). A human CD3 delta polypeptide sequence is available under GenBank Accession Number NP_000723.1 (SEQ ID NO: 91). A human CD3 epsilon polypeptide sequence is available under GenBank Accession Number NP_000724.1 (SEQ ID NO: 92).

In some embodiments, the antigen-binding domains of a bispecific binding molecule of the present disclosure are derived from an anti-ROR1 antibody and an anti-CD3 antibody. The term "antibody" (Ab) or "immunoglobulin" (Ig), as used herein, may refer to a tetramer comprising two heavy (H) chains (about 50-70 kDa) and two light (L) chains (about 25 kDa) interconnected by disulfide bonds. Each heavy chain is comprised of a heavy chain variable domain (VH) and a heavy chain constant region (CH). Each light chain is composed of a light chain variable domain (VL) and a light chain constant region (CL). The VH and VL domains can be subdivided further into regions of hypervariability, termed "complementarity determining regions" (CDRs), interspersed with regions that are more conserved, termed "framework regions" (FRs). Each VH and VL is composed of three CDRs (H-CDR herein designates a CDR from the heavy chain; and L-CDR herein designates a CDR from the light chain) and four FRs, arranged from amino-terminus to carboxyl-terminus in the following order: FR1, CDR1, FR2, CDR2, FR3, CDR3, FR4.

The precise amino acid sequence boundaries of a given CDR or FR can be readily determined using any of several well-known schemes, including those described by Kabat et al., 5th Ed., Public Health Service, National Institutes of Health, Bethesda, MD (1991) ("Kabat" numbering scheme); Al-Lazikani et al., *JMB* 273,927-948 (1997) ("Chothia" numbering scheme); MacCallum et al., *J. Mol. Biol.* 262: 732-745 (1996) ("contact" numbering scheme); Lefranc et al., *Dev Comp Immunol.* 27(1):55-77 (2003) ("IMGT" numbering scheme); and Honegger and Plückthun, *J Mol Biol,* 309(3):657-70 (2001) ("Aho" numbering scheme).

The boundaries of a given CDR or FR may vary depending on the scheme used for identification. For example, the Kabat scheme is based on sequence alignments, while the Chothia scheme is based on structural information. Numbering for both the Kabat and Chothia schemes is based upon the most common antibody region sequence lengths, with insertions accommodated by insertion letters, for example, "30a." The two schemes place certain insertions and deletions ("indels") at different positions, resulting in differential numbering. The contact scheme is based on analysis of complex crystal structures and is similar in many respects to the Chothia numbering scheme. Unless indicated otherwise, the CDRs of the antibodies referred to herein may be identified according to any of the Kabat, Chothia, IMGT, contact, and Aho methods.

In some embodiments, the anti-ROR1 antibody and/or the anti-CD3 antibody from which a bispecific binding molecule of the present disclosure is derived are monoclonal antibodies. In some embodiments, the anti-ROR1 and/or anti-CD3 antibodies are chimeric, humanized, or fully human antibodies.

The term "affinity" refers to a measure of the attraction between an antigen and an antibody or an antigen-binding fragment thereof, or a related molecule such as a bispecific binding molecule. The intrinsic attractiveness of the antibody for the antigen is typically expressed as the binding affinity equilibrium constant ($K_D$) of a particular antibody-antigen interaction. An antibody is said to specifically bind to an antigen when the $K_D$ is $\leq 1$ mM, preferably $\leq 100$ nM. A $K_D$ binding affinity constant can be measured, e.g., by surface plasmon resonance (BIAcore™) or Bio-Layer Interferometry, for example using the *IBIS* MX96 SPR system from IBIS Technologies or the Octet® system from ForteBio.

The term "paratope" refers to the antigen-binding site of an antibody (i.e., the part of the antibody that recognizes and binds to an antigen epitope).

The term "epitope" as used herein refers to a portion (determinant) of an antigen that specifically binds to an antibody or a related molecule such as a bispecific binding molecule. Epitopic determinants generally consist of chemically active surface groupings of molecules such as amino acids or carbohydrate or sugar side chains and generally have specific three-dimensional structural characteristics, as well as specific charge characteristics. An epitope may be "linear" or "conformational." In a linear epitope, all of the points of interaction between a protein (e.g., an antigen) and an interacting molecule (such as an antibody) occur linearly along the primary amino acid sequence of the protein. In a conformational epitope, the points of interaction occur across amino acid residues on the protein that are separated from one another in the primary amino acid sequence. Once a desired epitope on an antigen is determined, it is possible to generate antibodies to that epitope using techniques well known in the art. For example, an antibody to a linear epitope may be generated, e.g., by immunizing an animal with a peptide having the amino acid residues of the linear epitope. An antibody to a conformational epitope may be generated, e.g., by immunizing an animal with a mini-domain containing the relevant amino acid residues of the conformational epitope. An antibody to a particular epitope can also be generated, e.g., by immunizing an animal with the target molecule of interest (e.g., ROR1 or CD3) or a relevant portion thereof, then screening for binding to the epitope.

One can determine whether an antibody binds to the same epitope of ROR1 or CD3 as or competes for binding with a bi specific binding molecule of the present disclosure by using methods known in the art, including, without limitation, competition assays, epitope binning, and alanine scanning. In one embodiment, one allows the bi specific binding molecule of the present disclosure to bind to ROR1 or CD3 under saturating conditions, and then measures the ability of the test antibody to bind to said antigen. If the test antibody is able to bind to said antigen at the same time as the reference bispecific binding molecule, then the test antibody binds to a different epitope than the reference bi specific binding molecule. However, if the test antibody is not able to bind to the antigen at the same time, then the test antibody binds to the same epitope, an overlapping epitope, or an epitope that is in close proximity to the epitope bound by the bispecific binding molecule of the present disclosure. This experiment can be performed using, e.g., ELISA, RIA, BIACORE™, SPR, Bio-Layer Interferometry or flow cytometry. To test whether a bi specific binding molecule of the present disclosure cross-competes with another antibody for binding to ROR1 or CD3, one may use the competition method described above in two directions, i.e., determining if the known antibody blocks the test antibody and vice versa. Such cross-competition experiments may be performed, e.g., using an IBIS JVIX96 SPR instrument or the Octet® system.

The term "antigen-binding portion" or "antigen-binding fragment" of an antibody, as used herein, refers to one or more portions or fragments of an antibody that retain the ability to specifically bind to an antigen (e.g., human ROR1 or CD3, or a portion thereof). It has been shown that certain fragments of a full-length antibody can perform the antigen-binding function of the antibody. Examples of binding fragments encompassed within the term "antigen-binding portion" include (i) a Fab fragment: a monovalent fragment consisting of the $V_L$, $V_H$, $C_L$ and $C_H 1$ domains; (ii) a $F(ab')_2$ fragment: a bivalent fragment comprising two Fab fragments linked by a disulfide bridge at the hinge region; (iii) an Fd fragment consisting of the $V_H$ and $C_H 1$ domains; (iv) a Fv fragment consisting of the $V_L$ and $V_H$ domains of a single arm of an antibody, (v) a dAb fragment, which consists of a $V_H$ domain; and (vi) an isolated complementarity determining region (CDR) capable of specifically binding to an antigen. Furthermore, although the two domains of the Fv fragment, $V_L$ and $V_H$, are encoded by separate genes, they can be joined, using recombinant methods, by a synthetic linker that enables them to be made as a single protein chain in which the $V_L$ and $V_H$ domains pair to form monovalent molecules (known as single chain variable fragments (scFv)). Also within the present disclosure are antigen-binding molecules comprising a $V_H$ and/or a $V_L$. In the case of a $V_H$, the molecule may also comprise one or more of a CH1, hinge, CH2, or CH3 region. Such single chain antibodies are also intended to be encompassed within the term "antigen-binding portion" of an antibody. Other forms of single chain antibodies, such as diabodies, are also encompassed. Diabodies are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen-binding sites.

Unless otherwise indicated, all antibody amino acid residue numbers referred to in this disclosure are those under the Honegger numbering scheme (Honegger and Pluckthun, *J Mol Biol,* 309(3):657-70 (2001)).

Anti-ROR1/Anti-CD3 Bispecifc Binding Molecules

The present disclosure relates to a bispecific binding molecule comprising a first antigen-binding domain that specifically binds to an extracellular domain of human ROR1 and a second antigen-binding domain that specifically binds to an extracellular domain of human CD3.

In some embodiments, the first antigen-binding domain binds to an epitope on an extracellular portion of the ROR1 protein such as an epitope in one or more of the immunoglobulin (Ig)-like, Frizzled, and Kringle domains. In certain embodiments, the first antigen-binding domain binds to an amino acid sequence of ROR1 shown in SEQ ID NO: 94 or 95 (not including the terminal cysteine, which is added for convenience of conjugation).

In some embodiments, the first antigen-binding domain competes for binding to human ROR1 with, and/or binds to the same epitope of human ROR1 as, an anti-ROR1 antibody described in PCT Patent Application PCT/US2013/32572. In some embodiments, the first antigen-binding domain competes for binding to human ROR1 with, and/or binds to the same epitope of human ROR1 as, an antibody comprising a heavy chain amino acid sequence set forth in SEQ ID NO: 82 and a light chain amino acid sequence set forth in SEQ ID NO: 83 ("Ab1").

In some embodiments, the first antigen-binding domain comprises the heavy chain (H)-CDR1-3 in the amino acid sequence of SEQ ID NO: 82 and the light chain (L)-CDR1-3 in the amino acid sequence of SEQ ID NO: 83, wherein the CDRs are determined by the Kabat, Chothia, IMGT, or contact method, or any combination thereof.

In some embodiments, the first antigen-binding domain comprises H-CDR1-3 and L-CDR1-3 comprising the amino acid sequences of:

SEQ ID NOs: 60, 61, 62, 63, 64, and 65, respectively;
SEQ ID NOs: 97, 61, 62, 63, 64, and 65, respectively;
SEQ ID NOs: 98, 61, 62, 63, 64, and 65, respectively;
SEQ ID NOs: 60, 61, 62, 99, 64, 65, respectively;
SEQ ID NOs: 60, 61, 62, 63, 102, 65, respectively;
SEQ ID NOs: 97, 61, 62, 99, 64, 65, respectively;
SEQ ID NOs: 97, 61, 62, 63, 102, 65, respectively;
SEQ ID NOs: 98, 61, 62, 99, 64, 65, respectively; or
SEQ ID NOs: 98, 61, 62, 63, 102, 65, respectively.

In some embodiments, the first antigen-binding domain comprises a heavy chain variable domain (VH) comprising an amino acid sequence that is at least 90% (e.g., at least 92%, at least 95%, at least 96%, at least 97%, at least 98%, or at least 99%) identical to SEQ ID NO: 72 and a light chain variable domain (VL) comprising an amino acid sequence at least 90% (e.g., at least 92%, at least 95%, at least 96%, at least 97%, at least 98%, or at least 99%) identical to SEQ ID NO: 73.

In some embodiments, the first antigen-binding domain comprises:

a VH comprising the amino acid sequence of SEQ ID NO: 72 and a VL comprising the amino acid sequence of SEQ ID NO: 73;
a VH comprising the amino acid sequence of SEQ ID NO: 74 and a VL comprising the amino acid sequence of SEQ ID NO: 73;
a VH comprising the amino acid sequence of SEQ ID NO: 75 and a VL comprising the amino acid sequence of SEQ ID NO: 73;
a VH comprising the amino acid sequence of SEQ ID NO: 72 and a VL comprising the amino acid sequence of SEQ ID NO: 100;
a VH comprising the amino acid sequence of SEQ ID NO: 72 and a VL comprising the amino acid sequence of SEQ ID NO: 103;
a VH comprising the amino acid sequence of SEQ ID NO: 74 and a VL comprising the amino acid sequence of SEQ ID NO: 100;
a VH comprising the amino acid sequence of SEQ ID NO: 74 and a VL comprising the amino acid sequence of SEQ ID NO: 103;
a VH comprising the amino acid sequence of SEQ ID NO: 75 and a VL comprising the amino acid sequence of SEQ ID NO: 100; or
a VH comprising the amino acid sequence of SEQ ID NO: 75 and a VL comprising the amino acid sequence of SEQ ID NO: 103.

In some embodiments, the first antigen-binding domain comprises a heavy chain (HC) comprising an amino acid sequence that is at least 90% (e.g., at least 92%, at least 95%, at least 96%, at least 97%, at least 98%, or at least 99%) identical to SEQ ID NO: 82 and a light chain (LC) comprising an amino acid sequence at least 90% (e.g., at least 92%, at least 95%, at least 96%, at least 97%, at least 98%, or at least 991%) identical to SEQ ID NO: 83.

In some embodiments, the first antigen-binding domain comprises:

an HC comprising the amino acid sequence of SEQ ID NO: 82 and an LC comprising the amino acid sequence of SEQ ID NO: 83;
an HC comprising the amino acid sequence of SEQ ID NO: 84 and an LC comprising the amino acid sequence of SEQ ID NO: 83;
an HC comprising the amino acid sequence of SEQ ID NO: 85 and an LC comprising the amino acid sequence of SEQ ID NO: 83;
an HC comprising the amino acid sequence of SEQ ID NO: 82 and an LC comprising the amino acid sequence of SEQ ID NO: 101;
an HC comprising the amino acid sequence of SEQ ID NO: 82 and an LC comprising the amino acid sequence of SEQ ID NO: 104;
an HC comprising the amino acid sequence of SEQ ID NO: 84 and an LC comprising the amino acid sequence of SEQ ID NO: 101;
an HC comprising the amino acid sequence of SEQ ID NO: 84 and an LC comprising the amino acid sequence of SEQ ID NO: 104;
an HC comprising the amino acid sequence of SEQ ID NO: 85 and an LC comprising the amino acid sequence of SEQ ID NO: 101; or
an HC comprising the amino acid sequence of SEQ ID NO: 85 and an LC comprising the amino acid sequence of SEQ ID NO: 104.

In certain embodiments, the HC sequence is modified to reduce or eliminate effector function. For example, the IgG1 portion of the HC sequence may comprise "LALA" (L234A/L235A), or "LALAGA" (L234A/L235A/G237A) mutations (wherein all residues are numbered according to the EU numbering scheme).

In some embodiments, the first antigen-binding domain comprises:

an HC comprising the amino acid sequence of SEQ ID NO: 7 and an LC comprising the amino acid sequence of SEQ ID NO: 83;
an HC comprising the amino acid sequence of SEQ ID NO: 14 and an LC comprising the amino acid sequence of SEQ ID NO: 83;
an HC comprising the amino acid sequence of SEQ ID NO: 105 and an LC comprising the amino acid sequence of SEQ ID NO: 83;
an HC comprising the amino acid sequence of SEQ ID NO: 7 and an LC comprising the amino acid sequence of SEQ ID NO: 101;
an HC comprising the amino acid sequence of SEQ ID NO: 7 and an LC comprising the amino acid sequence of SEQ ID NO: 104;
an HC comprising the amino acid sequence of SEQ ID NO: 14 and an LC comprising the amino acid sequence of SEQ ID NO: 101;
an HC comprising the amino acid sequence of SEQ ID NO: 14 and an LC comprising the amino acid sequence of SEQ ID NO: 104;
an HC comprising the amino acid sequence of SEQ ID NO: 105 and an LC comprising the amino acid sequence of SEQ ID NO: 101; or
an HC comprising the amino acid sequence of SEQ ID NO: 105 and an LC comprising the amino acid sequence of SEQ ID NO: 104.

In some embodiments, the first antigen-binding domain comprises:

an HC comprising the amino acid sequence of SEQ ID NO: 86, an HC comprising the amino acid sequence of SEQ ID NO: 106, and an LC comprising the amino acid sequence of SEQ ID NO: 83;

an HC comprising the amino acid sequence of SEQ ID NO: 87, an HC comprising the amino acid sequence of SEQ ID NO: 107, and an LC comprising the amino acid sequence of SEQ ID NO: 83;

an HC comprising the amino acid sequence of SEQ ID NO: 88, an HC comprising the amino acid sequence of SEQ ID NO: 108, and an LC comprising the amino acid sequence of SEQ ID NO: 83;

an HC comprising the amino acid sequence of SEQ ID NO: 86, an HC comprising the amino acid sequence of SEQ ID NO: 106, and an LC comprising the amino acid sequence of SEQ ID NO: 101;

an HC comprising the amino acid sequence of SEQ ID NO: 86, an HC comprising the amino acid sequence of SEQ ID NO: 106, and an LC comprising the amino acid sequence of SEQ ID NO: 104;

an HC comprising the amino acid sequence of SEQ ID NO: 87, an HC comprising the amino acid sequence of SEQ ID NO: 107, and an LC comprising the amino acid sequence of SEQ ID NO: 101;

an HC comprising the amino acid sequence of SEQ ID NO: 87, an HC comprising the amino acid sequence of SEQ ID NO: 107, and an LC comprising the amino acid sequence of SEQ ID NO: 104;

an HC comprising the amino acid sequence of SEQ ID NO: 88, an HC comprising the amino acid sequence of SEQ ID NO: 108, and an LC comprising the amino acid sequence of SEQ ID NO: 101; or an HC comprising the amino acid sequence of SEQ ID NO: 88, an HC comprising the amino acid sequence of SEQ ID NO: 108, and an LC comprising the amino acid sequence of SEQ ID NO: 104.

In some embodiments, the first antigen-binding domain comprises:

an HC comprising the amino acid sequence of SEQ ID NO: 86, an HC comprising the amino acid sequence of SEQ ID NO: 109, and an LC comprising the amino acid sequence of SEQ ID NO: 83;

an HC comprising the amino acid sequence of SEQ ID NO: 87, an HC comprising the amino acid sequence of SEQ ID NO: 109, and an LC comprising the amino acid sequence of SEQ ID NO: 83;

an HC comprising the amino acid sequence of SEQ ID NO: 88, an HC comprising the amino acid sequence of SEQ ID NO: 109, and an LC comprising the amino acid sequence of SEQ ID NO: 83;

an HC comprising the amino acid sequence of SEQ ID NO: 86, an HC comprising the amino acid sequence of SEQ ID NO: 109, and an LC comprising the amino acid sequence of SEQ ID NO: 101;

an HC comprising the amino acid sequence of SEQ ID NO: 86, an HC comprising the amino acid sequence of SEQ ID NO: 109, and an LC comprising the amino acid sequence of SEQ ID NO: 104;

an HC comprising the amino acid sequence of SEQ ID NO: 87, an HC comprising the amino acid sequence of SEQ ID NO: 109, and an LC comprising the amino acid sequence of SEQ ID NO: 101;

an HC comprising the amino acid sequence of SEQ ID NO: 87, an HC comprising the amino acid sequence of SEQ ID NO: 109, and an LC comprising the amino acid sequence of SEQ ID NO: 104;

an HC comprising the amino acid sequence of SEQ ID NO: 88, an HC comprising the amino acid sequence of SEQ ID NO: 109, and an LC comprising the amino acid sequence of SEQ ID NO: 101; or an HC comprising the amino acid sequence of SEQ ID NO: 88, an HC comprising the amino acid sequence of SEQ ID NO: 109, and an LC comprising the amino acid sequence of SEQ ID NO: 104.

In some embodiments, the first antigen-binding domain comprises the six CDRs, the heavy and light chain variable domains, and/or the heavy and light chain amino acid sequences of an anti-ROR1 antibody as described in PCT/US2013/32572.

In some embodiments, the second antigen-binding domain binds to a Group I or Group II epitope of CD3 as defined in Tunnacliffe et al., *International Immunology* 1:546-550 (1989)).

In some embodiments, the second antigen-binding domain competes for binding to human CD3 with, and/or binds to the same epitope of human CD3 as, anti-CD3 antibody OKT3 or SP34. In some embodiments, the second antigen-binding domain competes for binding to human CD3 with, and/or binds to the same epitope of human CD3 as, an antibody that comprises:

a VH comprising the amino acid sequence of SEQ ID NO: 66 and a VL comprising the amino acid sequence of SEQ ID NO: 67;

a VH comprising the amino acid sequence of SEQ ID NO: 68 and a VL comprising the amino acid sequence of SEQ ID NO: 69; or a VH comprising the amino acid sequence of SEQ ID NO: 70 and a VL comprising the amino acid sequence of SEQ ID NO: 71.

In some embodiments, the second antigen-binding domain comprises the H-CDR1-3 and L-CDR1-3 in the amino acid sequences of:

SEQ ID NOs: 66 and 67, respectively;

SEQ ID NOs: 68 and 69, respectively; or

SEQ ID NOs: 70 and 71, respectively; wherein the CDRs are determined by the Kabat, Chothia, IMGT, or contact method, or any combination thereof.

In some embodiments, the second antigen-binding domain comprises H-CDR1-3 and L-CDR1-3 comprising the amino acid sequences of:

SEQ ID NOs: 47, 48, 49, 50, 51, and 52, respectively;

SEQ ID NOs: 47, 53, 49, 50, 51, and 52, respectively; or

SEQ ID NOs: 54, 55, 56, 57, 58, and 59, respectively.

In some embodiments, the second antigen-binding domain comprises:

a VH comprising an amino acid sequence at least 90% (e.g., at least 92%, at least 95%, at least 96%, at least 97%, at least 98%, or at least 991%) identical to SEQ ID NO. 66 and a VL comprising an amino acid sequence at least 90% (e.g., at least 92%, at least 95%, at least 96%, at least 97%, at least 98%, or at least 99%) identical to SEQ ID NO: 67;

a VH comprising an amino acid sequence at least 90% (e.g., at least 92%, at least 95%, at least 96%, at least 97%, at least 98%, or at least 990%) identical to SEQ ID NO: 68 and a VL comprising an amino acid sequence at least 90% (e.g., at least 92%, at least 95%, at least 96%, at least 97%, at least 98%, or at least 99%) identical to SEQ ID NO: 69; or a VH comprising an amino acid sequence that is at least 90% (e.g., at least 92%, at least 95%, at least 96%, at least 97%, at least 98%, or at least 990%) identical to SEQ ID NO: 70 and a VL comprising an amino acid sequence at least 90% (e.g., at least 92%, at least 95%, at least 96%, at least 97%, at least 98%, or at least 99%) identical to SEQ ID NO: 71.

In some embodiments, the second antigen-binding domain comprises:

a VH comprising the amino acid sequence of SEQ ID NO: 66 and a VL comprising the amino acid sequence of SEQ ID NO: 67;

a VH comprising the amino acid sequence of SEQ ID NO: 68 and a VL comprising the amino acid sequence of SEQ ID NO: 69;

a VH comprising the amino acid sequence of SEQ ID NO: 70 and a VL comprising the amino acid sequence of SEQ ID NO: 71;

a VH comprising the amino acid sequence of SEQ ID NO: 76 and a VL comprising the amino acid sequence of SEQ ID NO: 77;

a VH comprising the amino acid sequence of SEQ ID NO: 78 and a VL comprising the amino acid sequence of SEQ ID NO: 79; or a VH comprising the amino acid sequence of SEQ ID NO: 80 and a VL comprising the amino acid sequence of SEQ ID NO: 81.

In some embodiments, the second antigen-binding domain comprises the six CDRs and/or the heavy and light chain variable domains of an anti-CD3 antibody as described in U.S. Patent Publication 2018/0112011.

The present disclosure also contemplates any combination of the above-described first and second antigen-binding domains.

In some embodiments, a bispecific binding molecule of the present disclosure comprises:

a first antigen-binding domain that comprises H-CDR1-3 and L-CDR1-3 comprising the amino acid sequences of SEQ ID NOs: 97, 61, 62, 63, 64, and 65, respectively, and a second antigen-binding domain that comprises H-CDR1-3 and L-CDR1-3 comprising the amino acid sequences of SEQ ID NOs: 54, 55, 56, 57, 58, and 59, respectively;

a first antigen-binding domain that comprises H-CDR1-3 and L-CDR1-3 comprising the amino acid sequences of SEQ ID NOs: 60, 61, 62, 63, 64, and 65, respectively, and a second antigen-binding domain that comprises H-CDR1-3 and L-CDR1-3 comprising the amino acid sequences of SEQ ID NOs: 54, 55, 56, 57, 58, and 59, respectively;

a first antigen-binding domain that comprises H-CDR1-3 and L-CDR1-3 comprising the amino acid sequences of SEQ ID NOs: 60, 61, 62, 63, 64, and 65, respectively, and a second antigen-binding domain that comprises H-CDR1-3 and L-CDR1-3 comprising the amino acid sequences of SEQ ID NOs: 47, 53, 49, 50, 51, and 52, respectively;

a first antigen-binding domain that comprises H-CDR1- and L-CDR1-3 comprising the amino acid sequences of SEQ ID NOs: 97, 61, 62, 63, 64, and 65, respectively, and a second antigen-binding domain that comprises H-CDR1-3 and L-CDR1-3 comprising the amino acid sequences of SEQ ID NOs: 47, 48, 49, 50, 51, and 52, respectively;

a first antigen-binding domain that comprises H-CDR1-3 and L-CDR1-3 comprising the amino acid sequences of SEQ ID NOs: 97, 61, 62, 63, 64, and 65, respectively, and a second antigen-binding domain that comprises H-CDR1-3 and L-CDR1-3 comprising the amino acid sequences of SEQ ID NOs: 47, 53, 49, 50, 51, and 52, respectively;

a first antigen-binding domain that comprises H-CDR1-3 and L-CDR1-3 comprising the amino acid sequences of SEQ ID NOs: 60, 61, 62, 63, 64, and 65, respectively, and a second antigen-binding domain that comprises H-CDR1-3 and L-CDR1-3 comprising the amino acid sequences of SEQ ID NOs: 47, 48, 49, 50, 51, and 52, respectively;

a first antigen-binding domain that comprises H-CDR1-3 and L-CDR1-3 comprising the amino acid sequences of SEQ ID NOs: 98, 61, 62, 63, 64, and 65, respectively, and a second antigen-binding domain that comprises H-CDR1-3 and L-CDR1-3 comprising the amino acid sequences of SEQ ID NOs: 54, 55, 56, 57, 58, and 59, respectively;

a first antigen-binding domain that comprises H-CDR1-3 and L-CDR1-3 comprising the amino acid sequences of SEQ ID NOs: 98, 61, 62, 63, 64, and 65, respectively, and a second antigen-binding domain that comprises H-CDR1-3 and L-CDR1-3 comprising the amino acid sequences of SEQ ID NOs: 47, 48, 49, 50, 51, and 52, respectively;

a first antigen-binding domain that comprises H-CDR1-3 and L-CDR1-3 comprising the amino acid sequences of SEQ ID NOs: 98, 61, 62, 63, 64, and 65, respectively, and a second antigen-binding domain that comprises H-CDR1-3 and L-CDR1-3 comprising the amino acid sequences of SEQ ID NOs: 47, 53, 49, 50, 51, and 52, respectively;

a first antigen-binding domain that comprises H-CDR1-3 and L-CDR1-3 comprising the amino acid sequences of SEQ ID NOs: 60, 61, 62, 99, 64, and 65, respectively, and a second antigen-binding domain that comprises H-CDR1-3 and L-CDR1-3 comprising the amino acid sequences of SEQ ID NOs: 54, 55, 56, 57, 58, and 59, respectively;

a first antigen-binding domain that comprises H-CDR1-3 and L-CDR1-3 comprising the amino acid sequences of SEQ ID NOs: 60, 61, 62, 99, 64, and 65, respectively, and a second antigen-binding domain that comprises H-CDR1-3 and L-CDR1-3 comprising the amino acid sequences of SEQ ID NOs: 47, 48, 49, 50, 51, and 52, respectively;

a first antigen-binding domain that comprises H-CDR1-3 and L-CDR1-3 comprising the amino acid sequences of SEQ ID NOs: 60, 61, 62, 99, 64, and 65, respectively, and a second antigen-binding domain that comprises H-CDR1-3 and L-CDR1-3 comprising the amino acid sequences of SEQ ID NOs: 47, 53, 49, 50, 51, and 52, respectively;

a first antigen-binding domain that comprises H-CDR1-3 and L-CDR1-3 comprising the amino acid sequences of SEQ ID NOs: 60, 61, 62, 63, 102, and 65, respectively, and a second antigen-binding domain that comprises H-CDR1-3 and L-CDR1-3 comprising the amino acid sequences of SEQ ID NOs: 54, 55, 56, 57, 58, and 59, respectively;

a first antigen-binding domain that comprises H-CDR1-3 and L-CDR1-3 comprising the amino acid sequences of SEQ ID NOs: 60, 61, 62, 63, 102, and 65, respectively, and a second antigen-binding domain that comprises H-CDR1-3 and L-CDR1-3 comprising the amino acid sequences of SEQ ID NOs: 47, 48, 49, 50, 51, and 52, respectively;

a first antigen-binding domain that comprises H-CDR1-3 and L-CDR1-3 comprising the amino acid sequences of SEQ ID NOs: 60, 61, 62, 63, 102, and 65, respectively, and a second antigen-binding domain that comprises H-CDR1-3 and L-CDR1-3 comprising the amino acid sequences of SEQ ID NOs: 47, 53, 49, 50, 51, and 52, respectively;

a first antigen-binding domain that comprises H-CDR1-3 and L-CDR1-3 comprising the amino acid sequences of SEQ ID NOs: 97, 61, 62, 99, 64, and 65, respectively, and a second antigen-binding domain that comprises H-CDR1-3 and L-CDR1-3 comprising the amino acid sequences of SEQ ID NOs: 54, 55, 56, 57, 58, and 59, respectively;

a first antigen-binding domain that comprises H-CDR1-3 and L-CDR1-3 comprising the amino acid sequences of SEQ ID NOs: 97, 61, 62, 99, 64, and 65, respectively, and a second antigen-binding domain that comprises H-CDR1-3 and L-CDR1-3 comprising the amino acid sequences of SEQ ID NOs: 47, 48, 49, 50, 51, and 52, respectively;

a first antigen-binding domain that comprises H-CDR1-3 and L-CDR1-3 comprising the amino acid sequences of SEQ ID NOs: 97, 61, 62, 99, 64, and 65, respectively, and a second antigen-binding domain that comprises H-CDR1-3 and L-CDR1-3 comprising the amino acid sequences of SEQ ID NOs: 47, 53, 49, 50, 51, and 52, respectively;

a first antigen-binding domain that comprises H-CDR1-3 and L-CDR1-3 comprising the amino acid sequences of SEQ ID NOs: 97, 61, 62, 63, 102, and 65, respectively, and a second antigen-binding domain that comprises H-CDR1-3 and L-CDR1-3 comprising the amino acid sequences of SEQ ID NOs: 54, 55, 56, 57, 58, and 59, respectively;

a first antigen-binding domain that comprises H-CDR1-3 and L-CDR1-3 comprising the amino acid sequences of SEQ ID NOs: 97, 61, 62, 63, 102, and 65, respectively, and a second antigen-binding domain that comprises H-CDR1-3 and L-CDR1-3 comprising the amino acid sequences of SEQ ID NOs: 47, 48, 49, 50, 51, and 52, respectively;

a first antigen-binding domain that comprises H-CDR1-3 and L-CDR1-3 comprising the amino acid sequences of SEQ ID NOs: 97, 61, 62, 63, 102, and 65, respectively, and a second antigen-binding domain that comprises H-CDR1-3 and L-CDR1-3 comprising the amino acid sequences of SEQ ID NOs: 47, 53, 49, 50, 51, and 52, respectively;

a first antigen-binding domain that comprises H-CDR1-3 and L-CDR1-3 comprising the amino acid sequences of SEQ ID NOs: 98, 61, 62, 99, 64, and 65, respectively, and a second antigen-binding domain that comprises H-CDR1-3 and L-CDR1-3 comprising the amino acid sequences of SEQ ID NOs: 54, 55, 56, 57, 58, and 59, respectively;

a first antigen-binding domain that comprises H-CDR1-3 and L-CDR1-3 comprising the amino acid sequences of SEQ ID NOs: 98, 61, 62, 99, 64, and 65, respectively, and a second antigen-binding domain that comprises H-CDR1-3 and L-CDR1-3 comprising the amino acid sequences of SEQ ID NOs: 47, 48, 49, 50, 51, and 52, respectively;

a first antigen-binding domain that comprises H-CDR1-3 and L-CDR1-3 comprising the amino acid sequences of SEQ ID NOs: 98, 61, 62, 99, 64, and 65, respectively, and a second antigen-binding domain that comprises H-CDR1-3 and L-CDR1-3 comprising the amino acid sequences of SEQ ID NOs: 47, 53, 49, 50, 51, and 52, respectively;

a first antigen-binding domain that comprises H-CDR1-3 and L-CDR1-3 comprising the amino acid sequences of SEQ ID NOs: 98, 61, 62, 63, 102, and 65, respectively, and a second antigen-binding domain that comprises H-CDR1-3 and L-CDR1-3 comprising the amino acid sequences of SEQ ID NOs: 54, 55, 56, 57, 58, and 59, respectively;

a first antigen-binding domain that comprises H-CDR1-3 and L-CDR1-3 comprising the amino acid sequences of SEQ ID NOs: 98, 61, 62, 63, 102, and 65, respectively, and a second antigen-binding domain that comprises H-CDR1-3 and L-CDR1-3 comprising the amino acid sequences of SEQ ID NOs: 47, 48, 49, 50, 51, and 52, respectively; or a first antigen-binding domain that comprises H-CDR1-3 and L-CDR1-3 comprising the amino acid sequences of SEQ ID NOs: 98, 61, 62, 63, 102, and 65, respectively, and a second antigen-binding domain that comprises H-CDR1-3 and L-CDR1-3 comprising the amino acid sequences of SEQ ID NOs: 47, 53, 49, 50, 51, and 52, respectively.

In some embodiments, a bispecific binding molecule of the present disclosure comprises:

a first antigen-binding domain that comprises a VH and a VL at least 90% (e.g., at least 92%, at least 95%, at least 96%, at least 97%, at least 98%, or at least 99%) identical to the amino acid sequences of SEQ ID NOs: 74 and 73, respectively, and a second antigen-binding domain that comprises a VH and a VL at least 90% (e.g., at least 92%, at least 95%, at least 96%, at least 97%, at least 98%, or at least 99%) identical to the amino acid sequences of SEQ ID NOs: 70 and 71, respectively;

a first antigen-binding domain that comprises a VH and a VL at least 90% (e.g., at least 92%, at least 95%, at least 96%, at least 97%, at least 98%, or at least 99%) identical to the amino acid sequences of SEQ ID NOs: 72 and 73, respectively, and a second antigen-binding domain that comprises a VH and a VL at least 90% (e.g., at least 92%, at least 95%, at least 96%, at least 97%, at least 98%, or at least 99%) identical to the amino acid sequences of SEQ ID NOs: 70 and 71, respectively;

a first antigen-binding domain that comprises a VH and a VL at least 90% (e.g., at least 92%, at least 95%, at least 96%, at least 97%, at least 98%, or at least 99%) identical to the amino acid sequences of SEQ ID NOs: 72 and 73, respectively, and a second antigen-binding domain that comprises a VH and a VL at least 90% (e.g., at least 92%, at least 95%, at least 96%, at least 97%, at least 98%, or at least 99%) identical to the amino acid sequences of SEQ ID NOs: 68 and 69, respectively;

a first antigen-binding domain that comprises a VH and a VL at least 90% (e.g., at least 92%, at least 95%, at least 96%, at least 97%, at least 98%, or at least 99%) identical to the amino acid sequences of SEQ ID NOs: 74 and 73, respectively, and a second antigen-binding domain that comprises a VH and a VL at least 90% (e.g., at least 92%, at least 95%, at least 96%, at least 97%, at least 98%, or at least 990%) identical to the amino acid sequences of SEQ ID NOs: 66 and 67, respectively;

a first antigen-binding domain that comprises a VH and a VL at least 90% (e.g., at least 92%, at least 95%, at least 96%, at least 97%, at least 98%, or at least 99%) identical to the amino acid sequences of SEQ ID NOs: 74 and 73, respectively, and a second antigen-binding domain that comprises a VH and a VL at least 90% (e.g., at least 92%, at least 95%, at least 96%, at least 97%, at least 98%, or at least 99° %) identical to the amino acid sequences of SEQ ID NOs: 68 and 69, respectively;

a first antigen-binding domain that comprises a VH and a VL at least 90% (e.g., at least 92%, at least 95%, at least 96%, at least 97%, at least 98%, or at least 99%) identical to the amino acid sequences of SEQ ID NOs: 72 and 73, respectively, and a second antigen-binding domain that comprises a VH and a VL at least 90% (e.g., at least 92%, at least 95%, at least 96%, at least 97%, at least 98%, or at least 99%) identical to the amino acid sequences of SEQ ID NOs: 66 and 67, respectively;

a first antigen-binding domain that comprises a VH and a VL at least 90% (e.g., at least 92%, at least 95%, at least 96%, at least 97%, at least 98%, or at least 99%10) identical to the amino acid sequences of SEQ ID NOs: 75 and 73, respectively, and a second antigen-binding domain that comprises a VH and a VL at least 90% (e.g., at least 92%, at least 95%, at least 96%, at least 97%, at least 98%, or at least 99%) identical to the amino acid sequences of SEQ ID NOs: 70 and 71, respectively;

a first antigen-binding domain that comprises a VH and a VL at least 90% (e.g., at least 92%, at least 95%, at least 96%, at least 97%, at least 98%, or at least 99/%) identical to the amino acid sequences of SEQ ID NOs: 75 and 73, respectively, and a second antigen-binding domain that comprises a VH and a VL at least 90% (e.g., at least 92%, at least 95%, at least 96%, at least 97%, at least 98%, or at least 99%) identical to the amino acid sequences of SEQ ID NOs: 66 and 67, respectively;

a first antigen-binding domain that comprises a VH and a VL at least 90% (e.g., at least 92%, at least 95%, at least 96%, at least 97%, at least 98%, or at least 99%) identical to the amino acid sequences of SEQ ID NOs: 75 and 73, respectively, and a second antigen-binding domain that comprises a VH and a VL at least 90% (e.g., at least 92%, at least 95%, at least 96%, at least 97%, at least 98%, or at least 99%) identical to the amino acid sequences of SEQ ID NOs: 68 and 69, respectively;

a first antigen-binding domain that comprises a VH and a VL at least 90% (e.g., at least 92%, at least 95%, at least 96%, at least 97%, at least 98%, or at least 99%) identical to the amino acid sequences of SEQ ID NOs: 72 and 100, respectively, and a second antigen-binding domain that comprises a VH and a VL at least 90% (e.g., at least 92%, at least 95%, at least 96%, at least 97%, at least 98%, or at least 99%) identical to the amino acid sequences of SEQ ID NOs: 70 and 71, respectively;

a first antigen-binding domain that comprises a VH and a VL at least 90% (e.g., at least 92%, at least 95%, at least 96%, at least 97%, at least 98%, or at least 99%) identical to the amino acid sequences of SEQ ID NOs: 72 and 100, respectively, and a second antigen-binding domain that comprises a VH and a VL at least 90% (e.g., at least 92%, at least 95%, at least 96%, at least 97%, at least 98%, or at least 99%) identical to the amino acid sequences of SEQ ID NOs: 66 and 67, respectively;

a first antigen-binding domain that comprises a VH and a VL at least 90% (e.g., at least 92%, at least 95%, at least 96%, at least 97%, at least 98%, or at least 99%) identical to the amino acid sequences of SEQ ID NOs: 72 and 100, respectively, and a second antigen-binding domain that comprises a VH and a VL at least 90% (e.g., at least 92%, at least 95%, at least 96%, at least 97%, at least 98%, or at least 99%) identical to the amino acid sequences of SEQ ID NOs: 68 and 69, respectively;

a first antigen-binding domain that comprises a VH and a VL at least 90% (e.g., at least 92%, at least 95%, at least 96%, at least 97%, at least 98%, or at least 990%) identical to the amino acid sequences of SEQ ID NOs: 72 and 103, respectively, and a second antigen-binding domain that comprises a VH and a VL at least 90% (e.g., at least 92%, at least 95%, at least 96%, at least 97%, at least 98%, or at least 99%) identical to the amino acid sequences of SEQ ID NOs: 70 and 71, respectively;

a first antigen-binding domain that comprises a VH and a VL at least 90% (e.g., at least 92%, at least 95%, at least 96%, at least 97%, at least 98%, or at least 99%) identical to the amino acid sequences of SEQ ID NOs: 72 and 103, respectively, and a second antigen-binding domain that comprises a VH and a VL at least 90% (e.g., at least 92%, at least 95%, at least 96%, at least 97%, at least 98%, or at least 99%) identical to the amino acid sequences of SEQ ID NOs: 66 and 67, respectively;

a first antigen-binding domain that comprises a VH and a VL at least 90% (e.g., at least 92%, at least 95%, at least 96%, at least 97%, at least 98%, or at least 99%) identical to the amino acid sequences of SEQ ID NOs: 72 and 103, respectively, and a second antigen-binding domain that comprises a VH and a VL at least 90% (e.g., at least 92%, at least 95%, at least 96%, at least 97%, at least 98%, or at least 99%) identical to the amino acid sequences of SEQ ID NOs: 68 and 69, respectively;

a first antigen-binding domain that comprises a VH and a VL at least 90% (e.g., at least 92%, at least 95%, at least 96%, at least 97%, at least 98%, or at least 990%) identical to the amino acid sequences of SEQ ID NOs: 74 and 100, respectively, and a second antigen-binding domain that comprises a VH and a VL at least 90% (e.g., at least 92%, at least 95%, at least 96%, at least 97%, at least 98%, or at least 99%) identical to the amino acid sequences of SEQ ID NOs: 70 and 71, respectively;

a first antigen-binding domain that comprises a VH and a VL at least 90% (e.g., at least 92%, at least 95%, at least 96%, at least 97%, at least 98%, or at least 99%) identical to the amino acid sequences of SEQ ID NOs: 74 and 100, respectively, and a second antigen-binding domain that comprises a VH and a VL at least 90% (e.g., at least 92%, at least 95%, at least 96%, at least 97%, at least 98%, or at least 99%) identical to the amino acid sequences of SEQ ID NOs: 66 and 67, respectively;

a first antigen-binding domain that comprises a VH and a VL at least 90% (e.g., at least 92%, at least 95%, at least 96%, at least 97%, at least 98%, or at least 99%) identical to the amino acid sequences of SEQ ID NOs:

74 and 100, respectively, and a second antigen-binding domain that comprises a VH and a VL at least 90% (e.g., at least 92%, at least 95%, at least 96%, at least 97%, at least 98%, or at least 99%) identical to the amino acid sequences of SEQ ID NOs: 68 and 69, respectively;

a first antigen-binding domain that comprises a VH and a VL at least 90% (e.g., at least 92%, at least 95%, at least 96%, at least 97%, at least 98%, or at least 99%) identical to the amino acid sequences of SEQ ID NOs: 74 and 103, respectively, and a second antigen-binding domain that comprises a VH and a VL at least 90% (e.g., at least 92%, at least 95%, at least 96%, at least 97%, at least 98%, or at least 99° %) identical to the amino acid sequences of SEQ ID NOs: 70 and 71, respectively;

a first antigen-binding domain that comprises a VH and a VL at least 90% (e.g., at least 92%, at least 95%, at least 96%, at least 97%, at least 98%, or at least 99%) identical to the amino acid sequences of SEQ ID NOs: 74 and 103, respectively, and a second antigen-binding domain that comprises a VH and a VL at least 90% (e.g., at least 92%, at least 95%, at least 96%, at least 97%, at least 98%, or at least 99%) identical to the amino acid sequences of SEQ ID NOs: 66 and 67, respectively;

a first antigen-binding domain that comprises a VH and a VL at least 90% (e.g., at least 92%, at least 95%, at least 96%, at least 97%, at least 98%, or at least 99%) identical to the amino acid sequences of SEQ ID NOs: 74 and 103, respectively, and a second antigen-binding domain that comprises a VH and a VL at least 90% (e.g., at least 92%, at least 95%, at least 96%, at least 97%, at least 98%, or at least 99%) identical to the amino acid sequences of SEQ ID NOs: 68 and 69, respectively;

a first antigen-binding domain that comprises a VH and a VL at least 90% (e.g., at least 92%, at least 95%, at least 96%, at least 97%, at least 98%, or at least 99/%) identical to the amino acid sequences of SEQ ID NOs: 75 and 100, respectively, and a second antigen-binding domain that comprises a VH and a VL at least 90% (e.g., at least 92%, at least 95%, at least 96%, at least 97%, at least 98%, or at least 99%) identical to the amino acid sequences of SEQ ID NOs: 70 and 71, respectively;

a first antigen-binding domain that comprises a VH and a VL at least 90% (e.g., at least 92%, at least 95%, at least 96%, at least 97%, at least 98%, or at least 99%) identical to the amino acid sequences of SEQ ID NOs: 75 and 100, respectively, and a second antigen-binding domain that comprises a VH and a VL at least 90% (e.g., at least 92%, at least 95%, at least 96%, at least 97%, at least 98%, or at least 99%) identical to the amino acid sequences of SEQ ID NOs: 66 and 67, respectively;

a first antigen-binding domain that comprises a VH and a VL at least 90% (e.g., at least 92%, at least 95%, at least 96%, at least 97%, at least 98%, or at least 99%) identical to the amino acid sequences of SEQ ID NOs: 75 and 100, respectively, and a second antigen-binding domain that comprises a VH and a VL at least 90% (e.g., at least 92%, at least 95%, at least 96%, at least 97%, at least 98%, or at least 99%) identical to the amino acid sequences of SEQ ID NOs: 68 and 69, respectively;

a first antigen-binding domain that comprises a VH and a VL at least 90% (e.g., at least 92%, at least 95%, at least 96%, at least 97%, at least 98%, or at least 99%) identical to the amino acid sequences of SEQ ID NOs: 75 and 103, respectively, and a second antigen-binding domain that comprises a VH and a VL at least 90% (e.g., at least 92%, at least 95%, at least 96%, at least 97%, at least 98%, or at least 99%) identical to the amino acid sequences of SEQ ID NOs: 70 and 71, respectively;

a first antigen-binding domain that comprises a VH and a VL at least 90% (e.g., at least 92%, at least 95%, at least 96%, at least 97%, at least 98%, or at least 99%) identical to the amino acid sequences of SEQ ID NOs: 75 and 103, respectively, and a second antigen-binding domain that comprises a VH and a VL at least 90% (e.g., at least 92%, at least 95%, at least 96%, at least 97%, at least 98%, or at least 99%) identical to the amino acid sequences of SEQ ID NOs: 66 and 67, respectively; or a first antigen-binding domain that comprises a VH and a VL at least 90% (e.g., at least 92%, at least 95%, at least 96%, at least 97%, at least 98%, or at least 99%) identical to the amino acid sequences of SEQ ID NOs: 75 and 103, respectively, and a second antigen-binding domain that comprises a VH and a VL at least 90% (e.g., at least 92%, at least 95%, at least 96%, at least 97%, at least 98%, or at least 99%) identical to the amino acid sequences of SEQ ID NOs: 68 and 69, respectively.

In some embodiments, a bispecific binding molecule of the present disclosure comprises:

a first antigen-binding domain that comprises a VH and a VL comprising the amino acid sequences of SEQ ID NOs: 74 and 73, respectively, and a second antigen-binding domain that comprises a VH and a VL comprising the amino acid sequences of SEQ ID NOs: 70 and 71 or 80 and 81, respectively;

a first antigen-binding domain that comprises a VH and a VL comprising the amino acid sequences of SEQ ID NOs: 72 and 73, respectively, and a second antigen-binding domain that comprises a VH and a VL comprising the amino acid sequences of SEQ ID NOs: 70 and 71 or 80 and 81, respectively;

a first antigen-binding domain that comprises a VH and a VL comprising the amino acid sequences of SEQ ID NOs: 72 and 73, respectively, and a second antigen-binding domain that comprises a VH and a VL comprising the amino acid sequences of SEQ ID NOs: 68 and 69 or 78 and 79, respectively;

a first antigen-binding domain that comprises a VH and a VL comprising the amino acid sequences of SEQ ID NOs: 74 and 73, respectively, and a second antigen-binding domain that comprises a VH and a VL comprising the amino acid sequences of SEQ ID NOs: 66 and 67 or 76 and 77, respectively;

a first antigen-binding domain that comprises a VH and a VL comprising the amino acid sequences of SEQ ID NOs: 74 and 73, respectively, and a second antigen-binding domain that comprises a VH and a VL comprising the amino acid sequences of SEQ ID NOs: 68 and 69 or 78 and 79, respectively;

a first antigen-binding domain that comprises a VH and a VL comprising the amino acid sequences of SEQ ID NOs: 72 and 73, respectively, and a second antigen-binding domain that comprises a VH and a VL comprising the amino acid sequences of SEQ ID NOs: 66 and 67 or 76 and 77, respectively;

a first antigen-binding domain that comprises a VH and a VL comprising the amino acid sequences of SEQ ID NOs: 75 and 73, respectively, and a second antigen-binding domain that comprises a VH and a VL comprising the amino acid sequences of SEQ ID NOs: 70 and 71 or 80 and 81, respectively;

a first antigen-binding domain that comprises a VH and a VL comprising the amino acid sequences of SEQ ID NOs: 75 and 73, respectively, and a second antigen-binding domain that comprises a VH and a VL comprising the amino acid sequences of SEQ ID NOs: 66 and 67 or 76 and 77, respectively;

a first antigen-binding domain that comprises a VH and a VL comprising the amino acid sequences of SEQ ID NOs: 75 and 73, respectively, and a second antigen-binding domain that comprises a VH and a VL comprising the amino acid sequences of SEQ ID NOs: 68 and 69 or 78 and 79, respectively;

a first antigen-binding domain that comprises a VH and a VL comprising the amino acid sequences of SEQ ID NOs: 72 and 100, respectively, and a second antigen-binding domain that comprises a VH and a VL comprising the amino acid sequences of SEQ ID NOs: 70 and 71 or 80 and 81, respectively;

a first antigen-binding domain that comprises a VH and a VL comprising the amino acid sequences of SEQ ID NOs: 72 and 100, respectively, and a second antigen-binding domain that comprises a VH and a VL comprising the amino acid sequences of SEQ ID NOs: 66 and 67 or 76 and 77, respectively;

a first antigen-binding domain that comprises a VH and a VL comprising the amino acid sequences of SEQ ID NOs: 72 and 100, respectively, and a second antigen-binding domain that comprises a VH and a VL comprising the amino acid sequences of SEQ ID NOs: 68 and 69 or 78 and 79, respectively;

a first antigen-binding domain that comprises a VH and a VL comprising the amino acid sequences of SEQ ID NOs: 72 and 103, respectively, and a second antigen-binding domain that comprises a VH and a VL comprising the amino acid sequences of SEQ ID NOs: 70 and 71 or 80 and 81, respectively;

a first antigen-binding domain that comprises a VH and a VL comprising the amino acid sequences of SEQ ID NOs: 72 and 103, respectively, and a second antigen-binding domain that comprises a VH and a VL comprising the amino acid sequences of SEQ ID NOs: 66 and 67 or 76 and 77, respectively;

a first antigen-binding domain that comprises a VH and a VL comprising the amino acid sequences of SEQ ID NOs: 72 and 103, respectively, and a second antigen-binding domain that comprises a VH and a VL comprising the amino acid sequences of SEQ ID NOs: 68 and 69 or 78 and 79, respectively;

a first antigen-binding domain that comprises a VH and a VL comprising the amino acid sequences of SEQ ID NOs: 74 and 100, respectively, and a second antigen-binding domain that comprises a VH and a VL comprising the amino acid sequences of SEQ ID NOs: 70 and 71 or 80 and 81, respectively;

a first antigen-binding domain that comprises a VH and a VL comprising the amino acid sequences of SEQ ID NOs: 74 and 100, respectively, and a second antigen-binding domain that comprises a VH and a VL comprising the amino acid sequences of SEQ ID NOs: 66 and 67 or 76 and 77, respectively;

a first antigen-binding domain that comprises a VH and a VL comprising the amino acid sequences of SEQ ID NOs: 74 and 100, respectively, and a second antigen-binding domain that comprises a VH and a VL comprising the amino acid sequences of SEQ ID NOs: 68 and 69 or 78 and 79, respectively;

a first antigen-binding domain that comprises a VH and a VL comprising the amino acid sequences of SEQ ID NOs: 74 and 103, respectively, and a second antigen-binding domain that comprises a VH and a VL comprising the amino acid sequences of SEQ ID NOs: 70 and 71 or 80 and 81, respectively;

a first antigen-binding domain that comprises a VH and a VL comprising the amino acid sequences of SEQ ID NOs: 74 and 103, respectively, and a second antigen-binding domain that comprises a VH and a VL comprising the amino acid sequences of SEQ ID NOs: 66 and 67 or 76 and 77, respectively;

a first antigen-binding domain that comprises a VH and a VL comprising the amino acid sequences of SEQ ID NOs: 74 and 103, respectively, and a second antigen-binding domain that comprises a VH and a VL comprising the amino acid sequences of SEQ ID NOs: 68 and 69 or 78 and 79, respectively;

a first antigen-binding domain that comprises a VH and a VL comprising the amino acid sequences of SEQ ID NOs: 75 and 100, respectively, and a second antigen-binding domain that comprises a VH and a VL comprising the amino acid sequences of SEQ ID NOs: 70 and 71 or 80 and 81, respectively;

a first antigen-binding domain that comprises a VH and a VL comprising the amino acid sequences of SEQ ID NOs: 75 and 100, respectively, and a second antigen-binding domain that comprises a VH and a VL comprising the amino acid sequences of SEQ ID NOs: 66 and 67 or 76 and 77, respectively;

a first antigen-binding domain that comprises a VH and a VL comprising the amino acid sequences of SEQ ID NOs: 75 and 100, respectively, and a second antigen-binding domain that comprises a VH and a VL comprising the amino acid sequences of SEQ ID NOs: 68 and 69 or 78 and 79, respectively;

a first antigen-binding domain that comprises a VH and a VL comprising the amino acid sequences of SEQ ID NOs: 75 and 103, respectively, and a second antigen-binding domain that comprises a VH and a VL comprising the amino acid sequences of SEQ ID NOs: 70 and 71 or 80 and 81, respectively;

a first antigen-binding domain that comprises a VH and a VL comprising the amino acid sequences of SEQ ID NOs: 75 and 103, respectively, and a second antigen-binding domain that comprises a VH and a VL comprising the amino acid sequences of SEQ ID NOs: 66 and 67 or 76 and 77, respectively; or a first antigen-binding domain that comprises a VH and a VL comprising the amino acid sequences of SEQ ID NOs: 75 and 103, respectively, and a second antigen-binding domain that comprises a VH and a VL comprising the amino acid sequences of SEQ ID NOs: 68 and 69 or 78 and 79, respectively.

In some embodiments, a bispecific binding molecule of the present disclosure comprises:

a first antigen-binding domain that comprises an HC and an LC comprising the amino acid sequences of SEQ ID NOs: 84 and 83, respectively, and a second antigen-binding domain that comprises a VH and a VL comprising the amino acid sequences of SEQ ID NOs: 70 and 71 or 80 and 81, respectively;

a first antigen-binding domain that comprises an HC and an LC comprising the amino acid sequences of SEQ ID NOs: 82 and 83, respectively, and a second antigen-binding domain that comprises a VH and a VL comprising the amino acid sequences of SEQ ID NOs: 70 and 71 or 80 and 81, respectively;

a first antigen-binding domain that comprises an HC and an LC comprising the amino acid sequences of SEQ ID NOs: 82 and 83, respectively, and a second antigen-binding domain that comprises a VH and a VL comprising the amino acid sequences of SEQ ID NOs: 68 and 69 or 78 and 79, respectively;

a first antigen-binding domain that comprises an HC and an LC comprising the amino acid sequences of SEQ ID NOs: 84 and 83, respectively, and a second antigen-binding domain that comprises a VH and a VL comprising the amino acid sequences of SEQ ID NOs: 66 and 67 or 76 and 77, respectively;

a first antigen-binding domain that comprises an HC and an LC comprising the amino acid sequences of SEQ ID NOs: 84 and 83, respectively, and a second antigen-binding domain that comprises a VH and a VL comprising the amino acid sequences of SEQ ID NOs: 68 and 69 or 78 and 79, respectively;

a first antigen-binding domain that comprises an HC and an LC comprising the amino acid sequences of SEQ ID NOs: 82 and 83, respectively, and a second antigen-binding domain that comprises a VH and a VL comprising the amino acid sequences of SEQ ID NOs: 66 and 67 or 76 and 77, respectively;

a first antigen-binding domain that comprises an HC and an LC comprising the amino acid sequences of SEQ ID NOs: 85 and 83, respectively, and a second antigen-binding domain that comprises a VH and a VL comprising the amino acid sequences of SEQ ID NOs: 70 and 71 or 80 and 81, respectively;

a first antigen-binding domain that comprises an HC and an LC comprising the amino acid sequences of SEQ ID NOs: 85 and 83, respectively, and a second antigen-binding domain that comprises a VH and a VL comprising the amino acid sequences of SEQ ID NOs: 66 and 67 or 76 and 77, respectively;

a first antigen-binding domain that comprises an HC and an LC comprising the amino acid sequences of SEQ ID NOs: 85 and 83, respectively, and a second antigen-binding domain that comprises a VH and a VL comprising the amino acid sequences of SEQ ID NOs: 68 and 69 or 78 and 79, respectively;

a first antigen-binding domain that comprises an HC and an LC comprising the amino acid sequences of SEQ ID NOs: 82 and 101, respectively, and a second antigen-binding domain that comprises a VH and a VL comprising the amino acid sequences of SEQ ID NOs: 70 and 71 or 80 and 81, respectively;

a first antigen-binding domain that comprises an HC and an LC comprising the amino acid sequences of SEQ ID NOs: 82 and 101, respectively, and a second antigen-binding domain that comprises a VH and a VL comprising the amino acid sequences of SEQ ID NOs: 66 and 67 or 76 and 77, respectively;

a first antigen-binding domain that comprises an HC and an LC comprising the amino acid sequences of SEQ ID NOs: 82 and 101, respectively, and a second antigen-binding domain that comprises a VH and a VL comprising the amino acid sequences of SEQ ID NOs: 68 and 69 or 78 and 79, respectively;

a first antigen-binding domain that comprises an HC and an LC comprising the amino acid sequences of SEQ ID NOs: 82 and 104, respectively, and a second antigen-binding domain that comprises a VH and a VL comprising the amino acid sequences of SEQ ID NOs: 70 and 71 or 80 and 81, respectively;

a first antigen-binding domain that comprises an HC and an LC comprising the amino acid sequences of SEQ ID NOs: 82 and 104, respectively, and a second antigen-binding domain that comprises a VH and a VL comprising the amino acid sequences of SEQ ID NOs: 66 and 67 or 76 and 77, respectively;

a first antigen-binding domain that comprises an HC and an LC comprising the amino acid sequences of SEQ ID NOs: 82 and 104, respectively, and a second antigen-binding domain that comprises a VH and a VL comprising the amino acid sequences of SEQ ID NOs: 68 and 69 or 78 and 79, respectively;

a first antigen-binding domain that comprises an HC and an LC comprising the amino acid sequences of SEQ ID NOs: 84 and 101, respectively, and a second antigen-binding domain that comprises a VH and a VL comprising the amino acid sequences of SEQ ID NOs: 70 and 71 or 80 and 81, respectively;

a first antigen-binding domain that comprises an HC and an LC comprising the amino acid sequences of SEQ ID NOs: 84 and 101, respectively, and a second antigen-binding domain that comprises a VH and a VL comprising the amino acid sequences of SEQ ID NOs: 66 and 67 or 76 and 77, respectively;

a first antigen-binding domain that comprises an HC and an LC comprising the amino acid sequences of SEQ ID NOs: 84 and 101, respectively, and a second antigen-binding domain that comprises a VH and a VL comprising the amino acid sequences of SEQ ID NOs: 68 and 69 or 78 and 79, respectively;

a first antigen-binding domain that comprises an HC and an LC comprising the amino acid sequences of SEQ ID NOs: 84 and 104, respectively, and a second antigen-binding domain that comprises a VH and a VL comprising the amino acid sequences of SEQ ID NOs: 70 and 71 or 80 and 81, respectively;

a first antigen-binding domain that comprises an HC and an LC comprising the amino acid sequences of SEQ ID NOs: 84 and 104, respectively, and a second antigen-binding domain that comprises a VH and a VL comprising the amino acid sequences of SEQ ID NOs: 66 and 67 or 76 and 77, respectively;

a first antigen-binding domain that comprises an HC and an LC comprising the amino acid sequences of SEQ ID NOs: 84 and 104, respectively, and a second antigen-binding domain that comprises a VH and a VL comprising the amino acid sequences of SEQ ID NOs: 68 and 69 or 78 and 79, respectively;

a first antigen-binding domain that comprises an HC and an LC comprising the amino acid sequences of SEQ ID NOs: 85 and 101, respectively, and a second antigen-binding domain that comprises a VH and a VL comprising the amino acid sequences of SEQ ID NOs: 70 and 71 or 80 and 81, respectively;

a first antigen-binding domain that comprises an HC and an LC comprising the amino acid sequences of SEQ ID NOs: 85 and 101, respectively, and a second antigen-binding domain that comprises a VH and a VL comprising the amino acid sequences of SEQ ID NOs: 66 and 67 or 76 and 77, respectively;

a first antigen-binding domain that comprises an HC and an LC comprising the amino acid sequences of SEQ ID NOs: 85 and 101, respectively, and a second antigen-binding domain that comprises a VH and a VL comprising the amino acid sequences of SEQ ID NOs: 68 and 69 or 78 and 79, respectively;

a first antigen-binding domain that comprises an HC and an LC comprising the amino acid sequences of SEQ ID NOs: 85 and 104, respectively, and a second antigen-binding domain that comprises a VH and a VL comprising the amino acid sequences of SEQ ID NOs: 70 and 71 or 80 and 81, respectively;

a first antigen-binding domain that comprises an HC and an LC comprising the amino acid sequences of SEQ ID NOs: 85 and 104, respectively, and a second antigen-binding domain that comprises a VH and a VL comprising the amino acid sequences of SEQ ID NOs: 66 and 67 or 76 and 77, respectively; or a first antigen-binding domain that comprises an HC and an LC comprising the amino acid sequences of SEQ ID NOs: 85 and 104, respectively, and a second antigen-binding domain that comprises a VH and a VL comprising the amino acid sequences of SEQ ID NOs: 68 and 69 or 78 and 79, respectively.

In certain embodiments, the HC sequence is modified to reduce or eliminate effector function. For example, the IgG1 portion of the HC sequence may comprise L235E, "LALA" (L234A/L235A), or "LALAGA" (L234A/L235A/G237A) mutations (wherein all residues are numbered according to the EU numbering scheme).

In some embodiments, a bispecific binding molecule of the present disclosure comprises:

a first antigen-binding domain that comprises an HC and an LC comprising the amino acid sequences of SEQ ID NOs: 14 and 83, respectively, and a second antigen-binding domain that comprises a VH and a VL comprising the amino acid sequences of SEQ ID NOs: 70 and 71 or 80 and 81, respectively;

a first antigen-binding domain that comprises an HC and an LC comprising the amino acid sequences of SEQ ID NOs: 7 and 83, respectively, and a second antigen-binding domain that comprises a VH and a VL comprising the amino acid sequences of SEQ ID NOs: 70 and 71 or 80 and 81, respectively;

a first antigen-binding domain that comprises an HC and an LC comprising the amino acid sequences of SEQ ID NOs: 7 and 83, respectively, and a second antigen-binding domain that comprises a VH and a VL comprising the amino acid sequences of SEQ ID NOs: 68 and 69 or 78 and 79, respectively;

a first antigen-binding domain that comprises an HC and an LC comprising the amino acid sequences of SEQ ID NOs: 14 and 83, respectively, and a second antigen-binding domain that comprises a VH and a VL comprising the amino acid sequences of SEQ ID NOs: 66 and 67 or 76 and 77, respectively;

a first antigen-binding domain that comprises an HC and an LC comprising the amino acid sequences of SEQ ID NOs: 14 and 83, respectively, and a second antigen-binding domain that comprises a VH and a VL comprising the amino acid sequences of SEQ ID NOs: 68 and 69 or 78 and 79, respectively;

a first antigen-binding domain that comprises an HC and an LC comprising the amino acid sequences of SEQ ID NOs: 7 and 83, respectively, and a second antigen-binding domain that comprises a VH and a VL comprising the amino acid sequences of SEQ ID NOs: 66 and 67 or 76 and 77, respectively;

a first antigen-binding domain that comprises an HC and an LC comprising the amino acid sequences of SEQ ID NOs: 105 and 83, respectively, and a second antigen-binding domain that comprises a VH and a VL comprising the amino acid sequences of SEQ ID NOs: 70 and 71 or 80 and 81, respectively;

a first antigen-binding domain that comprises an HC and an LC comprising the amino acid sequences of SEQ ID NOs: 105 and 83, respectively, and a second antigen-binding domain that comprises a VH and a VL comprising the amino acid sequences of SEQ ID NOs: 66 and 67 or 76 and 77, respectively;

a first antigen-binding domain that comprises an HC and an LC comprising the amino acid sequences of SEQ ID NOs: 105 and 83, respectively, and a second antigen-binding domain that comprises a VH and a VL comprising the amino acid sequences of SEQ ID NOs: 68 and 69 or 78 and 79, respectively;

a first antigen-binding domain that comprises an HC and an LC comprising the amino acid sequences of SEQ ID NOs: 7 and 101, respectively, and a second antigen-binding domain that comprises a VH and a VL comprising the amino acid sequences of SEQ ID NOs: 70 and 71 or 80 and 81, respectively;

a first antigen-binding domain that comprises an HC and an LC comprising the amino acid sequences of SEQ ID NOs: 7 and 101, respectively, and a second antigen-binding domain that comprises a VH and a VL comprising the amino acid sequences of SEQ ID NOs: 66 and 67 or 76 and 77, respectively;

a first antigen-binding domain that comprises an HC and an LC comprising the amino acid sequences of SEQ ID NOs: 7 and 101, respectively, and a second antigen-binding domain that comprises a VH and a VL comprising the amino acid sequences of SEQ ID NOs: 68 and 69 or 78 and 79, respectively;

a first antigen-binding domain that comprises an HC and an LC comprising the amino acid sequences of SEQ ID NOs: 7 and 104, respectively, and a second antigen-binding domain that comprises a VH and a VL comprising the amino acid sequences of SEQ ID NOs: 70 and 71 or 80 and 81, respectively;

a first antigen-binding domain that comprises an HC and an LC comprising the amino acid sequences of SEQ ID NOs: 7 and 104, respectively, and a second antigen-binding domain that comprises a VH and a VL comprising the amino acid sequences of SEQ ID NOs: 66 and 67 or 76 and 77, respectively;

a first antigen-binding domain that comprises an HC and an LC comprising the amino acid sequences of SEQ ID NOs: 7 and 104, respectively, and a second antigen-binding domain that comprises a VH and a VL comprising the amino acid sequences of SEQ ID NOs: 68 and 69 or 78 and 79, respectively;

a first antigen-binding domain that comprises an HC and an LC comprising the amino acid sequences of SEQ ID NOs: 14 and 101, respectively, and a second antigen-binding domain that comprises a VH and a VL comprising the amino acid sequences of SEQ ID NOs: 70 and 71 or 80 and 81, respectively;

a first antigen-binding domain that comprises an HC and an LC comprising the amino acid sequences of SEQ ID NOs: 14 and 101, respectively, and a second antigen-binding domain that comprises a VH and a VL comprising the amino acid sequences of SEQ ID NOs: 66 and 67 or 76 and 77, respectively;

a first antigen-binding domain that comprises an HC and an LC comprising the amino acid sequences of SEQ ID NOs: 14 and 101, respectively, and a second antigen-binding domain that comprises a VH and a VL comprising the amino acid sequences of SEQ ID NOs: 68 and 69 or 78 and 79, respectively;

a first antigen-binding domain that comprises an HC and an LC comprising the amino acid sequences of SEQ ID NOs: 14 and 104, respectively, and a second antigen-binding domain that comprises a VH and a VL comprising the amino acid sequences of SEQ ID NOs: 70 and 71 or 80 and 81, respectively;

a first antigen-binding domain that comprises an HC and an LC comprising the amino acid sequences of SEQ ID NOs: 14 and 104, respectively, and a second antigen-binding domain that comprises a VH and a VL comprising the amino acid sequences of SEQ ID NOs: 66 and 67 or 76 and 77, respectively;

a first antigen-binding domain that comprises an HC and an LC comprising the amino acid sequences of SEQ ID NOs: 14 and 104, respectively, and a second antigen-binding domain that comprises a VH and a VL comprising the amino acid sequences of SEQ ID NOs: 68 and 69 or 78 and 79, respectively;

a first antigen-binding domain that comprises an HC and an LC comprising the amino acid sequences of SEQ ID NOs: 105 and 101, respectively, and a second antigen-binding domain that comprises a VH and a VL comprising the amino acid sequences of SEQ ID NOs: 70 and 71 or 80 and 81, respectively;

a first antigen-binding domain that comprises an HC and an LC comprising the amino acid sequences of SEQ ID NOs: 105 and 101, respectively, and a second antigen-binding domain that comprises a VH and a VL comprising the amino acid sequences of SEQ ID NOs: 66 and 67 or 76 and 77, respectively;

a first antigen-binding domain that comprises an HC and an LC comprising the amino acid sequences of SEQ ID NOs: 105 and 101, respectively, and a second antigen-binding domain that comprises a VH and a VL comprising the amino acid sequences of SEQ ID NOs: 68 and 69 or 78 and 79, respectively;

a first antigen-binding domain that comprises an HC and an LC comprising the amino acid sequences of SEQ ID NOs: 105 and 104, respectively, and a second antigen-binding domain that comprises a VH and a VL comprising the amino acid sequences of SEQ ID NOs: 70 and 71 or 80 and 81, respectively;

a first antigen-binding domain that comprises an HC and an LC comprising the amino acid sequences of SEQ ID NOs: 105 and 104, respectively, and a second antigen-binding domain that comprises a VH and a VL comprising the amino acid sequences of SEQ ID NOs: 66 and 67 or 76 and 77, respectively; or a first antigen-binding domain that comprises an HC and an LC comprising the amino acid sequences of SEQ ID NOs: 105 and 104, respectively, and a second antigen-binding domain that comprises a VH and a VL comprising the amino acid sequences of SEQ ID NOs: 68 and 69 or 78 and 79, respectively.

In some embodiments, a bispecific binding molecule of the present disclosure comprises:

a first antigen-binding domain that comprises an HC comprising the amino acid sequence of SEQ ID NO: 87, an HC comprising the amino acid sequence of SEQ ID NO: 107, and an LC comprising the amino acid sequence of SEQ ID NO: 83, and a second antigen-binding domain that comprises a VH and a VL comprising the amino acid sequences of SEQ ID NOs: 70 and 71 or 80 and 81, respectively;

a first antigen-binding domain that comprises an HC comprising the amino acid sequence of SEQ ID NO: 86, an HC comprising the amino acid sequence of SEQ ID NO: 106, and an LC comprising the amino acid sequence of SEQ ID NO: 83, and a second antigen-binding domain that comprises a VH and a VL comprising the amino acid sequences of SEQ ID NOs: 70 and 71 or 80 and 81, respectively;

a first antigen-binding domain that comprises an HC comprising the amino acid sequence of SEQ ID NO: 86, an HC comprising the amino acid sequence of SEQ ID NO: 106, and an LC comprising the amino acid sequence of SEQ ID NO: 83, and a second antigen-binding domain that comprises a VH and a VL comprising the amino acid sequences of SEQ ID NOs: 68 and 69 or 78 and 79, respectively;

a first antigen-binding domain that comprises an HC comprising the amino acid sequence of SEQ ID NO: 87, an HC comprising the amino acid sequence of SEQ ID NO: 107, and an LC comprising the amino acid sequence of SEQ ID NO: 83, and a second antigen-binding domain that comprises a VH and a VL comprising the amino acid sequences of SEQ ID NOs: 66 and 67 or 76 and 77, respectively;

a first antigen-binding domain that comprises an HC comprising the amino acid sequence of SEQ ID NO: 87, an HC comprising the amino acid sequence of SEQ ID NO: 107, and an LC comprising the amino acid sequence of SEQ ID NO: 83, and a second antigen-binding domain that comprises a VH and a VL comprising the amino acid sequences of SEQ ID NOs: 68 and 69 or 78 and 79, respectively;

a first antigen-binding domain that comprises an HC comprising the amino acid sequence of SEQ ID NO: 86, an HC comprising the amino acid sequence of SEQ ID NO: 106, and an LC comprising the amino acid sequence of SEQ ID NO: 83, and a second antigen-binding domain that comprises a VH and a VL comprising the amino acid sequences of SEQ ID NOs: 66 and 67 or 76 and 77, respectively;

a first antigen-binding domain that comprises an HC comprising the amino acid sequence of SEQ ID NO: 88, an HC comprising the amino acid sequence of SEQ ID NO: 108, and an LC comprising the amino acid sequence of SEQ ID NO: 83, and a second antigen-binding domain that comprises a VH and a VL comprising the amino acid sequences of SEQ ID NOs: 70 and 71 or 80 and 81, respectively;

a first antigen-binding domain that comprises an HC comprising the amino acid sequence of SEQ ID NO: 88, an HC comprising the amino acid sequence of SEQ ID NO: 108, and an LC comprising the amino acid sequence of SEQ ID NO: 83, and a second antigen-binding domain that comprises a VH and a VL comprising the amino acid sequences of SEQ ID NOs: 66 and 67 or 76 and 77, respectively;

a first antigen-binding domain that comprises an HC comprising the amino acid sequence of SEQ ID NO: 88, an HC comprising the amino acid sequence of SEQ ID NO: 108, and an LC comprising the amino acid sequence of SEQ ID NO: 83, and a second antigen-binding domain that comprises a VH and a VL comprising the amino acid sequences of SEQ ID NOs: 68 and 69 or 78 and 79, respectively;

a first antigen-binding domain that comprises an HC comprising the amino acid sequence of SEQ ID NO: 86, an HC comprising the amino acid sequence of SEQ ID NO: 106, and an LC comprising the amino acid sequence of SEQ ID NO: 101, and a second antigen-binding domain that comprises a VH and a VL comprising the amino acid sequences of SEQ ID NOs: 70 and 71 or 80 and 81, respectively;

a first antigen-binding domain that comprises an HC comprising the amino acid sequence of SEQ ID NO: 86, an HC comprising the amino acid sequence of SEQ ID NO: 106, and an LC comprising the amino acid sequence of SEQ ID NO: 101, and a second antigen-binding domain that comprises a VH and a VL comprising the amino acid sequences of SEQ ID NOs: 66 and 67 or 76 and 77, respectively;

a first antigen-binding domain that comprises an HC comprising the amino acid sequence of SEQ ID NO: 86, an HC comprising the amino acid sequence of SEQ ID NO: 106, and an LC comprising the amino acid sequence of SEQ ID NO: 101, and a second antigen-binding domain that comprises a VH and a VL comprising the amino acid sequences of SEQ ID NOs: 68 and 69 or 78 and 79, respectively;

a first antigen-binding domain that comprises an HC comprising the amino acid sequence of SEQ ID NO: 86, an HC comprising the amino acid sequence of SEQ ID NO: 106, and an LC comprising the amino acid sequence of SEQ ID NO: 104, and a second antigen-binding domain that comprises a VH and a VL comprising the amino acid sequences of SEQ ID NOs: 70 and 71 or 80 and 81, respectively;

a first antigen-binding domain that comprises an HC comprising the amino acid sequence of SEQ ID NO: 86, an HC comprising the amino acid sequence of SEQ ID NO: 106, and an LC comprising the amino acid sequence of SEQ ID NO: 104, and a second antigen-binding domain that comprises a VH and a VL comprising the amino acid sequences of SEQ ID NOs: 66 and 67 or 76 and 77, respectively;

a first antigen-binding domain that comprises an HC comprising the amino acid sequence of SEQ ID NO: 86, an HC comprising the amino acid sequence of SEQ ID NO: 106, and an LC comprising the amino acid sequence of SEQ ID NO: 104, and a second antigen-binding domain that comprises a VH and a VL comprising the amino acid sequences of SEQ ID NOs: 68 and 69 or 78 and 79, respectively;

a first antigen-binding domain that comprises an HC comprising the amino acid sequence of SEQ ID NO: 87, an HC comprising the amino acid sequence of SEQ ID NO: 107, and an LC comprising the amino acid sequence of SEQ ID NO: 101, and a second antigen-binding domain that comprises a VH and a VL comprising the amino acid sequences of SEQ ID NOs: 70 and 71 or 80 and 81, respectively;

a first antigen-binding domain that comprises an HC comprising the amino acid sequence of SEQ ID NO: 87, an HC comprising the amino acid sequence of SEQ ID NO: 107, and an LC comprising the amino acid sequence of SEQ ID NO: 101, and a second antigen-binding domain that comprises a VH and a VL comprising the amino acid sequences of SEQ ID NOs: 66 and 67 or 76 and 77, respectively;

a first antigen-binding domain that comprises an HC comprising the amino acid sequence of SEQ ID NO: 87, an HC comprising the amino acid sequence of SEQ ID NO: 107, and an LC comprising the amino acid sequence of SEQ ID NO: 101, and a second antigen-binding domain that comprises a VH and a VL comprising the amino acid sequences of SEQ ID NOs: 68 and 69 or 78 and 79, respectively;

a first antigen-binding domain that comprises an HC comprising the amino acid sequence of SEQ ID NO: 87, an HC comprising the amino acid sequence of SEQ ID NO: 107, and an LC comprising the amino acid sequence of SEQ ID NO: 104, and a second antigen-binding domain that comprises a VH and a VL comprising the amino acid sequences of SEQ ID NOs: 70 and 71 or 80 and 81, respectively;

a first antigen-binding domain that comprises an HC comprising the amino acid sequence of SEQ ID NO: 87, an HC comprising the amino acid sequence of SEQ ID NO: 107, and an LC comprising the amino acid sequence of SEQ ID NO: 104, and a second antigen-binding domain that comprises a VH and a VL comprising the amino acid sequences of SEQ ID NOs: 66 and 67 or 76 and 77, respectively;

a first antigen-binding domain that comprises an HC comprising the amino acid sequence of SEQ ID NO: 87, an HC comprising the amino acid sequence of SEQ ID NO: 107, and an LC comprising the amino acid sequence of SEQ ID NO: 104, and a second antigen-binding domain that comprises a VH and a VL comprising the amino acid sequences of SEQ ID NOs: 68 and 69 or 78 and 79, respectively;

a first antigen-binding domain that comprises an HC comprising the amino acid sequence of SEQ ID NO: 88, an HC comprising the amino acid sequence of SEQ ID NO: 108, and an LC comprising the amino acid sequence of SEQ ID NO: 101, and a second antigen-binding domain that comprises a VH and a VL comprising the amino acid sequences of SEQ ID NOs: 70 and 71 or 80 and 81, respectively;

a first antigen-binding domain that comprises an HC comprising the amino acid sequence of SEQ ID NO: 88, an HC comprising the amino acid sequence of SEQ ID NO: 108, and an LC comprising the amino acid sequence of SEQ ID NO: 101, and a second antigen-binding domain that comprises a VH and a VL comprising the amino acid sequences of SEQ ID NOs: 66 and 67 or 76 and 77, respectively;

a first antigen-binding domain that comprises an HC comprising the amino acid sequence of SEQ ID NO: 88, an HC comprising the amino acid sequence of SEQ ID NO: 108, and an LC comprising the amino acid sequence of SEQ ID NO: 101, and a second antigen-binding domain that comprises a VH and a VL comprising the amino acid sequences of SEQ ID NOs: 68 and 69 or 78 and 79, respectively;

a first antigen-binding domain that comprises an HC comprising the amino acid sequence of SEQ ID NO: 88, an HC comprising the amino acid sequence of SEQ ID NO: 108, and an LC comprising the amino acid sequence of SEQ ID NO: 104, and a second antigen-binding domain that comprises a VH and a VL comprising the amino acid sequences of SEQ ID NOs: 70 and 71 or 80 and 81, respectively;

a first antigen-binding domain that comprises an HC comprising the amino acid sequence of SEQ ID NO: 88, an HC comprising the amino acid sequence of SEQ ID NO: 108, and an LC comprising the amino acid sequence of SEQ ID NO: 104, and a second antigen-binding domain that comprises a VH and a VL comprising the amino acid sequences of SEQ ID NOs: 66 and 67 or 76 and 77, respectively; or a first antigen-binding domain that comprises an HC comprising the amino acid sequence of SEQ ID NO: 88, an HC comprising the amino acid sequence of SEQ ID NO: 108, and an LC comprising the amino acid sequence of SEQ ID NO: 104, and a second antigen-binding domain that comprises a VH and a VL comprising the amino acid sequences of SEQ ID NOs: 68 and 69 or 78 and 79, respectively.

In some embodiments, a bispecific binding molecule of the present disclosure comprises:

a first antigen-binding domain that comprises an HC comprising the amino acid sequence of SEQ ID NO: 87, an HC comprising the amino acid sequence of SEQ ID NO: 109, and an LC comprising the amino acid sequence of SEQ ID NO: 83, and a second antigen-binding domain that comprises a VH and a VL comprising the amino acid sequences of SEQ ID NOs: 70 and 71 or 80 and 81, respectively;

a first antigen-binding domain that comprises an HC comprising the amino acid sequence of SEQ ID NO: 86, an HC comprising the amino acid sequence of SEQ ID NO: 109, and an LC comprising the amino acid sequence of SEQ ID NO: 83, and a second antigen-binding domain that comprises a VH and a VL comprising the amino acid sequences of SEQ ID NOs: 70 and 71 or 80 and 81, respectively;

a first antigen-binding domain that comprises an HC comprising the amino acid sequence of SEQ ID NO: 86, an HC comprising the amino acid sequence of SEQ ID NO: 109, and an LC comprising the amino acid sequence of SEQ ID NO: 83, and a second antigen-binding domain that comprises a VH and a VL comprising the amino acid sequences of SEQ ID NOs: 68 and 69 or 78 and 79, respectively;

a first antigen-binding domain that comprises an HC comprising the amino acid sequence of SEQ ID NO: 87, an HC comprising the amino acid sequence of SEQ ID NO: 109, and an LC comprising the amino acid sequence of SEQ ID NO: 83, and a second antigen-binding domain that comprises a VH and a VL comprising the amino acid sequences of SEQ ID NOs: 66 and 67 or 76 and 77, respectively;

a first antigen-binding domain that comprises an HC comprising the amino acid sequence of SEQ ID NO: 87, an HC comprising the amino acid sequence of SEQ ID NO: 109, and an LC comprising the amino acid sequence of SEQ ID NO: 83, and a second antigen-binding domain that comprises a VH and a VL comprising the amino acid sequences of SEQ ID NOs: 68 and 69 or 78 and 79, respectively;

a first antigen-binding domain that comprises an HC comprising the amino acid sequence of SEQ ID NO: 86, an HC comprising the amino acid sequence of SEQ ID NO: 109, and an LC comprising the amino acid sequence of SEQ ID NO: 83, and a second antigen-binding domain that comprises a VH and a VL comprising the amino acid sequences of SEQ ID NOs: 66 and 67 or 76 and 77, respectively;

a first antigen-binding domain that comprises an HC comprising the amino acid sequence of SEQ ID NO: 88, an HC comprising the amino acid sequence of SEQ ID NO: 109, and an LC comprising the amino acid sequence of SEQ ID NO: 83, and a second antigen-binding domain that comprises a VH and a VL comprising the amino acid sequences of SEQ ID NOs: 70 and 71 or 80 and 81, respectively;

a first antigen-binding domain that comprises an HC comprising the amino acid sequence of SEQ ID NO: 88, an HC comprising the amino acid sequence of SEQ ID NO: 109, and an LC comprising the amino acid sequence of SEQ ID NO: 83, and a second antigen-binding domain that comprises a VH and a VL comprising the amino acid sequences of SEQ ID NOs: 66 and 67 or 76 and 77, respectively;

a first antigen-binding domain that comprises an HC comprising the amino acid sequence of SEQ ID NO: 88, an HC comprising the amino acid sequence of SEQ ID NO: 109, and an LC comprising the amino acid sequence of SEQ ID NO: 83, and a second antigen-binding domain that comprises a VH and a VL comprising the amino acid sequences of SEQ ID NOs: 68 and 69 or 78 and 79, respectively;

a first antigen-binding domain that comprises an HC comprising the amino acid sequence of SEQ ID NO: 86, an HC comprising the amino acid sequence of SEQ ID NO: 109, and an LC comprising the amino acid sequence of SEQ ID NO: 101, and a second antigen-binding domain that comprises a VH and a VL comprising the amino acid sequences of SEQ ID NOs: 70 and 71 or 80 and 81, respectively;

a first antigen-binding domain that comprises an HC comprising the amino acid sequence of SEQ ID NO: 86, an HC comprising the amino acid sequence of SEQ ID NO: 109, and an LC comprising the amino acid sequence of SEQ ID NO: 101, and a second antigen-binding domain that comprises a VH and a VL comprising the amino acid sequences of SEQ ID NOs: 66 and 67 or 76 and 77, respectively;

a first antigen-binding domain that comprises an HC comprising the amino acid sequence of SEQ ID NO: 86, an HC comprising the amino acid sequence of SEQ ID NO: 109, and an LC comprising the amino acid sequence of SEQ ID NO: 101, and a second antigen-binding domain that comprises a VH and a VL comprising the amino acid sequences of SEQ ID NOs: 68 and 69 or 78 and 79, respectively;

a first antigen-binding domain that comprises an HC comprising the amino acid sequence of SEQ ID NO: 86, an HC comprising the amino acid sequence of SEQ ID NO: 109, and an LC comprising the amino acid sequence of SEQ ID NO: 104, and a second antigen-binding domain that comprises a VH and a VL comprising the amino acid sequences of SEQ ID NOs: 70 and 71 or 80 and 81, respectively;

a first antigen-binding domain that comprises an HC comprising the amino acid sequence of SEQ ID NO: 86, an HC comprising the amino acid sequence of SEQ ID NO: 109, and an LC comprising the amino acid sequence of SEQ ID NO: 104, and a second antigen-binding domain that comprises a VH and a VL comprising the amino acid sequences of SEQ ID NOs: 66 and 67 or 76 and 77, respectively;

a first antigen-binding domain that comprises an HC comprising the amino acid sequence of SEQ ID NO: 86, an HC comprising the amino acid sequence of SEQ ID NO: 109, and an LC comprising the amino acid sequence of SEQ ID NO: 104, and a second antigen-binding domain that comprises a VH and a VL comprising the amino acid sequences of SEQ ID NOs: 68 and 69 or 78 and 79, respectively;

a first antigen-binding domain that comprises an HC comprising the amino acid sequence of SEQ ID NO: 87, an HC comprising the amino acid sequence of SEQ ID NO: 109, and an LC comprising the amino acid sequence of SEQ ID NO: 101, and a second antigen-binding domain that comprises a VH and a VL comprising the amino acid sequences of SEQ ID NOs: 70 and 71 or 80 and 81, respectively;

a first antigen-binding domain that comprises an HC comprising the amino acid sequence of SEQ ID NO: 87, an HC comprising the amino acid sequence of SEQ ID NO: 109, and an LC comprising the amino acid sequence of SEQ ID NO: 101, and a second antigen-binding domain that comprises a VH and a VL comprising the amino acid sequences of SEQ ID NOs: 66 and 67 or 76 and 77, respectively;

a first antigen-binding domain that comprises an HC comprising the amino acid sequence of SEQ ID NO: 87, an HC comprising the amino acid sequence of SEQ ID NO: 109, and an LC comprising the amino acid sequence of SEQ ID NO: 101, and a second antigen-binding domain that comprises a VH and a VL comprising the amino acid sequences of SEQ ID NOs: 68 and 69 or 78 and 79, respectively;

a first antigen-binding domain that comprises an HC comprising the amino acid sequence of SEQ ID NO: 87, an HC comprising the amino acid sequence of SEQ ID NO: 109, and an LC comprising the amino acid sequence of SEQ ID NO: 104, and a second antigen-binding domain that comprises a VH and a VL comprising the amino acid sequences of SEQ ID NOs: 70 and 71 or 80 and 81, respectively;

a first antigen-binding domain that comprises an HC comprising the amino acid sequence of SEQ ID NO: 87, an HC comprising the amino acid sequence of SEQ ID NO: 109, and an LC comprising the amino acid sequence of SEQ ID NO: 104, and a second antigen-binding domain that comprises a VH and a VL comprising the amino acid sequences of SEQ ID NOs: 66 and 67 or 76 and 77, respectively;

a first antigen-binding domain that comprises an HC comprising the amino acid sequence of SEQ ID NO: 87, an HC comprising the amino acid sequence of SEQ ID NO: 109, and an LC comprising the amino acid sequence of SEQ ID NO: 104, and a second antigen-binding domain that comprises a VH and a VL comprising the amino acid sequences of SEQ ID NOs: 68 and 69 or 78 and 79, respectively;

a first antigen-binding domain that comprises an HC comprising the amino acid sequence of SEQ ID NO: 88, an HC comprising the amino acid sequence of SEQ ID NO: 109, and an LC comprising the amino acid sequence of SEQ ID NO: 101, and a second antigen-binding domain that comprises a VH and a VL comprising the amino acid sequences of SEQ ID NOs: 70 and 71 or 80 and 81, respectively;

a first antigen-binding domain that comprises an HC comprising the amino acid sequence of SEQ ID NO: 88, an HC comprising the amino acid sequence of SEQ ID NO: 109, and an LC comprising the amino acid sequence of SEQ ID NO: 101, and a second antigen-binding domain that comprises a VH and a VL comprising the amino acid sequences of SEQ ID NOs: 66 and 67 or 76 and 77, respectively;

a first antigen-binding domain that comprises an HC comprising the amino acid sequence of SEQ ID NO: 88, an HC comprising the amino acid sequence of SEQ ID NO: 109, and an LC comprising the amino acid sequence of SEQ ID NO: 101, and a second antigen-binding domain that comprises a VH and a VL comprising the amino acid sequences of SEQ ID NOs: 68 and 69 or 78 and 79, respectively;

a first antigen-binding domain that comprises an HC comprising the amino acid sequence of SEQ ID NO: 88, an HC comprising the amino acid sequence of SEQ ID NO: 109, and an LC comprising the amino acid sequence of SEQ ID NO: 104, and a second antigen-binding domain that comprises a VH and a VL comprising the amino acid sequences of SEQ ID NOs: 70 and 71 or 80 and 81, respectively;

a first antigen-binding domain that comprises an HC comprising the amino acid sequence of SEQ ID NO: 88, an HC comprising the amino acid sequence of SEQ ID NO: 109, and an LC comprising the amino acid sequence of SEQ ID NO: 104, and a second antigen-binding domain that comprises a VH and a VL comprising the amino acid sequences of SEQ ID NOs: 66 and 67 or 76 and 77, respectively; or a first antigen-binding domain that comprises an HC comprising the amino acid sequence of SEQ ID NO: 88, an HC comprising the amino acid sequence of SEQ ID NO: 109, and an LC comprising the amino acid sequence of SEQ ID NO: 104, and a second antigen-binding domain that comprises a VH and a VL comprising the amino acid sequences of SEQ ID NOs: 68 and 69 or 78 and 79, respectively.

In some embodiments, a bispecific binding molecule of the present disclosure comprises:

the amino acid sequences of SEQ ID NOs: 1 and 16;
the amino acid sequences of SEQ ID NOs: 2 and 16;
the amino acid sequences of SEQ ID NOs: 3 and 16;
the amino acid sequences of SEQ ID NOs: 4 and 16;
the amino acid sequences of SEQ ID NOs: 5 and 16;
the amino acid sequences of SEQ ID NOs: 6 and 16;
the amino acid sequences of SEQ ID NOs: 7 and 17;
the amino acid sequences of SEQ ID NOs: 7 and 18;
the amino acid sequences of SEQ ID NOs: 7 and 19;
the amino acid sequences of SEQ ID NOs: 7 and 20;
the amino acid sequences of SEQ ID NOs: 7 and 21;
the amino acid sequences of SEQ ID NOs: 7 and 22;
the amino acid sequences of SEQ ID NOs: 8, 9, and 16;
the amino acid sequences of SEQ ID NOs: 8, 10, and 16;
the amino acid sequences of SEQ ID NOs: 8, 11, and 16;
the amino acid sequences of SEQ ID NOs: 12, 11, and 16;
the amino acid sequences of SEQ ID NOs: 12, 13, and 16;
the amino acid sequences of SEQ ID NOs: 14 and 19;
the amino acid sequences of SEQ ID NOs: 8, 15, and 16; or
the amino acid sequences of SEQ ID NOs: 7 and 23.

In some embodiments, a bispecific binding molecule of the present disclosure comprises one or two first antigen-binding domains as described above. In some embodiments, a bispecific binding molecule of the present disclosure comprises one or two second antigen-binding domains as described above.

In some embodiments, the first antigen-binding domain in a bispecific binding molecule of the present disclosure has a valency of 1 or 2. In some embodiments, the second antigen-binding domain in a bispecific binding molecule of the present disclosure has a valency of 1 or 2. Any combination of valencies of the first and second antigen-binding domains is contemplated; for example, the first and second antigen-binding domains may have valencies of 2 and 2, respectively; 1 and 1, respectively; 2 and 1, respectively; or 1 and 2, respectively.

In some embodiments, a bispecific binding molecule of the present disclosure may comprise a human IgG, IgM, IgE, IgA, or IgD constant region. In certain embodiments, the human constant region is of the IgG isotype, e.g., of IgG subclass IgG1, IgG2a or IgG2b, IgG3, or IgG4. In some embodiments, the bispecific binding molecule of the present disclosure may comprise a human a constant region. The class of a bispecific binding molecule described herein may be changed or switched with another class or subclass. For example, a constant region that was originally IgM may be class switched to IgG. Further, the class switching may be used to convert one IgG subclass to another, e.g., from IgG1 to IgG2. A u light chain constant region can be changed, e.g., to a λ light chain constant region.

In certain embodiments, a bispecific binding molecule of the present disclosure may comprise a human IgG constant region. In particular embodiments, the IgG constant region may include mutations that reduce or eliminate effector function (see, e.g., Wang et al., *Protein Cell* 9(1):63-73 (2018)). For example, a bispecific binding molecule of the present disclosure may comprise a human IgG1 constant region with the mutation L235E, "LALA" mutations (L234A/L235A), or "LALAGA" mutations (L234A/L235A/G237A), all numbered according to the EU numbering scheme).

The class (isotype) and subclass of bispecific binding molecules of the present disclosure may be determined by any method known in the art. In general, the class and subclass of an antibody may be determined using antibodies that are specific for a particular class and subclass of antibody. Such antibodies are available commercially. The class and subclass can be determined by ELISA, Western Blot as well as other techniques. Alternatively, the class and subclass may be determined by sequencing all or a portion of the constant regions of the heavy and/or light chains of the antibodies, comparing their amino acid sequences to the known amino acid sequences of various classes and subclasses of immunoglobulins, and determining the class and subclass of the antibodies.

In some embodiments, a bispecific binding molecule of the present disclosure is a homodimer. In some embodiments, a bispecific binding molecule of the present disclosure is a heterotrimer (light chain combined with heavy chain heterodimer), wherein the heavy chain heterodimer is, e.g., in a format described in Brinkmann and Kontermann, *MABS* 9:182-212 (2017). For example, a "knobs-into-holes," HA-TF, ZW1, CH3 charge pair, EW-RVT, LUZ-Y, Strand Exchange Engineered Domain body (SEEDbody), Biclonic, DuoBody, BEAT, 7.8.60, 20.8.34, Triomab/Quadroma, or CrossMAb strategy may be used to promote heterodimerization (e.g., over homodimerization) of the polypeptide comprising the Fc region of the immunoglobulin in the architecture of a bispecific binding molecule of the present disclosure. In certain embodiments, a "knobs-into-holes" approach may be used, wherein a "knob" variant of a domain is obtained by replacing an amino acid with a small side chain (for example, alanine, asparagine, aspartic acid, glycine, serine, threonine or valine) with another amino acid with a larger side chain (for example, arginine, phenylalanine, tyrosine, or tryptophan). A "hole" variant of a domain is obtained by replacing an amino acid with a large side chain (for example, arginine, phenylalanine, tyrosine, or tryptophan) with another amino acid with a smaller side chain (for example, alanine, asparagine, aspartic acid, glycine, serine, threonine or valine). In certain embodiments, the knob and/or hole mutations are in the CH3 domain.

In some embodiments, an antigen-binding fragment of an anti-ROR1 antibody and/or an antigen-binding fragment of an anti-CD3 antibody may be used in making a bispecific binding molecule of the present disclosure. Examples of antibody fragments include, but are not limited to, Fv, Fab, Fab', Fab'-SH, F(ab')₂; recombinant IgG (rIgG) fragments; diabodies; linear antibodies; single-chain antibody molecules (e.g., scFv or sFv); and single domain antibodies (e.g., sdAb, sdFv, nanobodies). In certain embodiments, the fragments are single-chain antibody fragments comprising a variable heavy chain region and/or a variable light chain region, such as scFvs.

In particular embodiments, the first antigen-binding domain, the second antigen-binding domain, or both, are single chain antibodies (scFv) comprising a heavy chain variable domain (VH) of an antibody linked to a light chain variable domain (VL) of the whole antibody, wherein the fusion protein retains the same antigen specificity as the antibody. The VH and VL may be linked via a peptide linker. In certain embodiments, the second antigen-binding domain is an scFv that specifically binds to CD3.

To create a single chain antibody (scFv), the VH- and VL-encoding DNA fragments are operatively linked to another fragment encoding a flexible linker, e.g., encoding the amino acid sequence (Gly4-Ser)4 (SEQ ID NO: 96), such that the VH and VL sequences can be expressed as a contiguous single-chain protein, with the VL and VH domains joined by the flexible linker. The single chain antibody may be monovalent, if only a single VH and VL are used; bivalent, if two VH and VL are used; or polyvalent, if more than two VH and VL are used.

In some embodiments, an amino acid sequence of the first antigen-binding domain is fused to an amino acid sequence of the second antigen-binding domain, e.g., via a peptide linker, to form a fusion polypeptide. In certain embodiments, the second antigen-binding domain is an scFv, and is fused to a heavy or light chain amino acid sequence of the first antigen-binding domain. For example, the second antigen-binding domain may be fused to:

the amino-terminus of the heavy chain of the first antigen-binding domain;

the amino-terminus of the light chain of the first antigen-binding domain;

the carboxy-terminus of the heavy chain of the first antigen-binding domain; and/or the carboxy-terminus of the light chain of the first antigen-binding domain.

Figure 1:
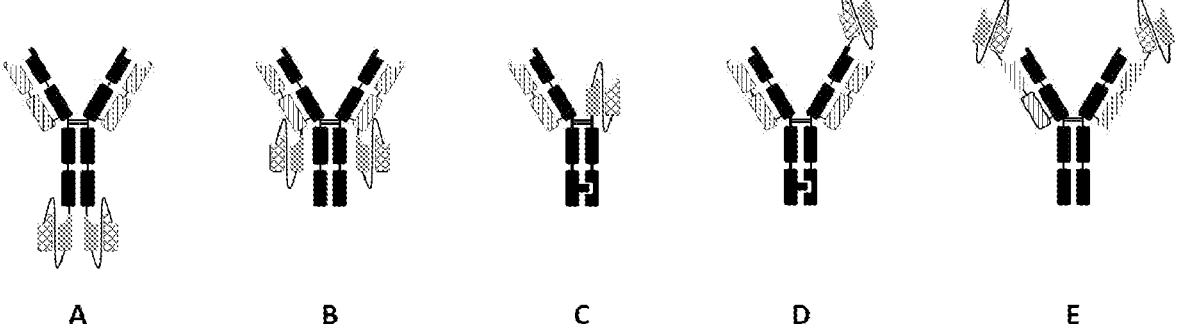
FIG. 1 is a schematic diagram illustrating exemplary configurations of bispecific binding molecules of the present disclosure.

In some embodiments, a bispecific binding molecule of the present disclosure is configured as shown in any of schematics A-E in FIG. 1.

In certain embodiments, the peptide linker conjugating the first and second antigen-binding domains is between 5-30, 5-25, 5-15, 10-30, 10-20, or 10-15 amino acids in length. In certain embodiments, the peptide linker comprises amino acids that allow for peptide linker solubility, such as, for example, serine and threonine. In certain embodiments, the linker may be charged (see, e.g., U.S. Pat. No. 9,856, 327). In certain embodiments, the peptide linker comprises amino acids that allow for peptide linker flexibility, such as, for example, glycine, or for peptide linker rigidity. In certain embodiments, the sequence of the peptide linker conjugating the first and second antigen-binding domains is (Gly4-Ser) X, wherein X may be 1, 2, 3, or 4 (SEQ ID NO: 114). In particular embodiments, the sequence of the peptide linker is GGGGSGGGGS (SEQ ID NO: 93).

In some embodiments, a second antigen-binding domain as described herein comprises one or more mutations (e.g., replacement of amino acid residues with cysteines) to stabilize disulfide binding, e.g., to prevent or reduce aggregation of the bispecific binding molecule.

In some embodiments, a bispecific binding molecule of the present disclosure has a $K_D$ for immobilized ROR1 of 100 nM, 50 nM, 40 nM, 30 nM, 20 nM, 10 nM, 5 nM, 2 nM, 1 nM, 0.9 nM, 0.8 nM, 0.7 nM, 0.6 nM, 0.5 nM, 0.4 nM, 0.3 nM, 0.2 nM, 0.1 nM, 0.09 nM, 0.08 nM, 0.07 nM, 0.06 nM, 0.05 nM, 0.04 nM, 0.03 nM, 0.02 nM, 0.01 nM, 0.005 nM, or 0.001 nM or less (e.g., 0.5 nM or less) as determined by ELISA.

In some embodiments, a bispecific binding molecule of the present disclosure has a $K_D$ for soluble b-ROR1 of 100 nM, 50 nM, 40 nM, 30 nM, 20 nM, 10 nM, 5 nM, 2 nM, 1 nM, 0.9 nM, 0.8 nM, 0.7 nM, 0.6 nM, 0.5 nM, 0.4 nM, 0.3 nM, 0.2 nM, 0.1 nM, 0.09 nM, 0.08 nM, 0.07 nM, 0.06 nM, 0.05 nM, 0.04 nM, 0.03 nM, 0.02 nM, 0.01 nM, 0.005 nM, or 0.001 nM or less (e.g., 0.4 nM or less) as determined by ELISA.

In some embodiments, a bispecific binding molecule of the present disclosure has a $K_D$ for CD3 of 100 nM, 50 nM, 40 nM, 30 nM, 20 nM, 10 nM, 5 nM, 2 nM, 1 nM, 0.9 nM, 0.8 nM, 0.7 nM, 0.6 nM, 0.5 nM, 0.4 nM, 0.3 nM, 0.2 nM, 0.1 nM, 0.09 nM, 0.08 nM, 0.07 nM, 0.06 nM, 0.05 nM, 0.04 nM, 0.03 nM, 0.02 nM, 0.01 nM, 0.005 nM, or 0.001 nM or less (e.g., 5 nM or less) as determined by ELISA.

In some embodiments, a bispecific binding molecule of the present disclosure induces LDH release in PBMC-exposed ROR1-transfected MEC cells at 10 µg/mL, 5 µg/mL, 1 µg/mL, 100 ng/mL, 50 ng/mL, 20 ng/mL, 10 ng/mL, 9 ng/mL, 8 ng/mL, 7 ng/mL, 6 ng/mL, 5 ng/mL, 4 ng/mL, 3 ng/mL, 2 ng/mL, 1 ng/mL, 0.9 ng/mL, 0.8 ng/mL, 0.7 ng/mL, 0.6 ng/mL, 0.5 ng/mL, 0.4 ng/mL, 0.3 ng/mL, 0.2 ng/mL, 0.1 ng/mL, 0.05 ng/mL, or 0.01 ng/mL or less.

In some embodiments, a bispecific binding molecule of the present disclosure induces LDH release in PBMC-exposed JeKo-1 cells at 10 µg/mL, 5 µg/mL, 1 µg/mL, 100 ng/mL, 50 ng/mL, 20 ng/mL, 10 ng/mL, 9 ng/mL, 8 ng/mL, 7 ng/mL, 6 ng/mL, 5 ng/mL, 4 ng/mL, 3 ng/mL, 2 ng/mL, 1 ng/mL, 0.9 ng/mL, 0.8 ng/mL, 0.7 ng/mL, 0.6 ng/mL, 0.5 ng/mL, 0.4 ng/mL, 0.3 ng/mL, 0.2 ng/mL, 0.1 ng/mL, 0.05 ng/mL, or 0.01 ng/mL or less.

In some embodiments, a bispecific binding molecule of the present disclosure induces LDH release in PBMC-exposed Mino cells at 10 µg/mL, 5 µg/mL, 1 µg/mL, 100 ng/mL, 50 ng/mL, 20 ng/mL, 10 ng/mL, 9 ng/mL, 8 ng/mL, 7 ng/mL, 6 ng/mL, 5 ng/mL, 4 ng/mL, 3 ng/mL, 2 ng/mL, 1 ng/mL, 0.9 ng/mL, 0.8 ng/mL, 0.7 ng/mL, 0.6 ng/mL, 0.5 ng/mL, 0.4 ng/mL, 0.3 ng/mL, 0.2 ng/mL, 0.1 ng/mL, or 0.05 ng/mL, 0.01 ng/mL or less.

In some embodiments, a bispecific binding molecule of the present disclosure induces LDH release in PBMC-exposed MDA-MB-468 cells at 10 µg/mL, 5 µg/mL, 1 µg/mL, 100 ng/mL, 50 ng/mL, 20 ng/mL, 10 ng/mL, 9 ng/mL, 8 ng/mL, 7 ng/mL, 6 ng/mL, 5 ng/mL, 4 ng/mL, 3 ng/mL, 2 ng/mL, 1 ng/mL, 0.9 ng/mL, 0.8 ng/mL, 0.7 ng/mL, 0.6 ng/mL, 0.5 ng/mL, 0.4 ng/mL, 0.3 ng/mL, 0.2 ng/mL, 0.1 ng/mL, 0.05 ng/mL, or 0.01 ng/mL or less.

In some embodiments, a bispecific binding molecule of the present disclosure induces ROR1-dependent killing of ROR1-transfected MEC cells, JeKo-1 cells, Mino cells, MDA-MB-468 cells, or any combination thereof, by PBMCs in vitro.

In some embodiments, a bispecific binding molecule of the present disclosure upregulates CD69 on the surface of T cells incubated with ROR1-transfected MEC cells at 50 µg/mL, 10 µg/mL, 5 µg/mL, 1 µg/mL, 100 ng/mL, 50 ng/mL, 20 ng/mL, 10 ng/mL, 9 ng/mL, 8 ng/mL, 7 ng/mL, 6 ng/mL, 5 ng/mL, 4 ng/mL, 3 ng/mL, 2 ng/mL, 1 ng/mL, 0.9 ng/mL, 0.8 ng/mL, 0.7 ng/mL, 0.6 ng/mL, 0.5 ng/mL, 0.4 ng/mL, 0.3 ng/mL, 0.2 ng/mL, 0.1 ng/mL, 0.05 ng/mL, or 0.01 ng/mL or less as determined by flow cytometry.

In some embodiments, a bispecific binding molecule of the present disclosure upregulates CD69 on the surface of T cells incubated with JeKo-1 cells at 50 µg/mL, 10 µg/mL, 5 µg/mL, 1 µg/mL, 100 ng/mL, 50 ng/mL, 20 ng/mL, 10 ng/mL, 9 ng/mL, 8 ng/mL, 7 ng/mL, 6 ng/mL, 5 ng/mL, 4 ng/mL, 3 ng/mL, 2 ng/mL, 1 ng/mL, 0.9 ng/mL, 0.8 ng/mL, 0.7 ng/mL, 0.6 ng/mL, 0.5 ng/mL, 0.4 ng/mL, 0.3 ng/mL, 0.2 ng/mL, 0.1 ng/mL, 0.05 ng/mL, or 0.01 ng/mL or less as determined by flow cytometry.

In some embodiments, a bispecific binding molecule of the present disclosure upregulates CD69 on the surface of T cells incubated with Mino cells at 50 µg/mL, 10 µg/mL, 5 µg/mL, 1 µg/mL, 100 ng/mL, 50 ng/mL, 20 ng/mL, 10 ng/mL, 9 ng/mL, 8 ng/mL, 7 ng/mL, 6 ng/mL, 5 ng/mL, 4 ng/mL, 3 ng/mL, 2 ng/mL, 1 ng/mL, 0.9 ng/mL, 0.8 ng/mL, 0.7 ng/mL, 0.6 ng/mL, 0.5 ng/mL, 0.4 ng/mL, 0.3 ng/mL, 0.2 ng/mL, 0.1 ng/mL, 0.05 ng/mL, or 0.01 ng/mL or less as determined by flow cytometry.

In some embodiments, a bispecific binding molecule of the present disclosure upregulates CD69 on the surface of T cells incubated with MDA-MB-468 cells at 50 µg/mL, 10 µg/mL, 5 µg/mL, 1 µg/mL, 100 ng/mL, 50 ng/mL, 20 ng/mL, 10 ng/mL, 9 ng/mL, 8 ng/mL, 7 ng/mL, 6 ng/mL, 5 ng/mL, 4 ng/mL, 3 ng/mL, 2 ng/mL, 1 ng/mL, 0.9 ng/mL, 0.8 ng/mL, 0.7 ng/mL, 0.6 ng/mL, 0.5 ng/mL, 0.4 ng/mL, 0.3 ng/mL, 0.2 ng/mL, 0.1 ng/mL, 0.05 ng/mL, or 0.01 ng/mL or less as determined by flow cytometry.

In some embodiments, a bispecific binding molecule of the present disclosure induces release of IFN-γ, TNF-α, IL-10, IL-6, IL-4, and IL-2 from T cells co-cultured with JeKo-1 or ROR1-transfected MEC cells at 10 µg/mL, 5 µg/mL, 1 µg/mL, 100 ng/mL, 50 ng/mL, 20 ng/mL, 10 ng/mL, 9 ng/mL, 8 ng/mL, 7 ng/mL, 6 ng/mL, 5 ng/mL, 4 ng/mL, 3 ng/mL, 2 ng/mL, 1 ng/mL, 0.9 ng/mL, 0.8 ng/mL, 0.7 ng/mL, 0.6 ng/mL, 0.5 ng/mL, 0.4 ng/mL, 0.3 ng/mL, 0.2 ng/mL, 0.1 ng/mL, 0.05 ng/mL, or 0.01 ng/mL or less.

In some embodiments, a bispecific binding molecule of the present disclosure has at least one of the following properties:

a) has a $K_D$ for immobilized ROR1 of 0.5 nM or less as determined by ELISA;

b) has a $K_D$ for soluble b-ROR1 of 0.4 nM or less as determined by ELISA;

c) demonstrates reduced internalization in ROR1-transfected MEC cells and/or Jurkat cells as compared to an antibody comprising the heavy and light chain amino acid sequences of SEQ ID NOs: 82 and 83, respectively;

d) induces LDH release in PBMC-exposed ROR1-transfected MEC cells at 1 µg/mL or less;

e) induces LDH release in PBMC-exposed JeKo-1 cells at 1 µg/mL or less;

f) induces LDH release in PBMC-exposed Mino cells at 1 µg/mL or less;

g) induces LDH release in PBMC-exposed MDA-MB-468 cells at 1 µg/mL or less;

h) upregulates CD69 on the surface of T cells co-cultured with ROR1-transfected MEC cells at 1 µg/mL or less as determined by flow cytometry;

i) upregulates CD69 on the surface of T cells co-cultured with JeKo-1 cells at 1 µg/mL or less as determined by flow cytometry;

j) upregulates CD69 on the surface of T cells co-cultured with Mino cells at 1 µg/mL or less as determined by flow cytometry;

k) upregulates CD69 on the surface of T cells co-cultured with MDA-MB-468 cells at 1 µg/mL or less as determined by flow cytometry; and l) induces release of IFN-$\gamma$, TNF-$\alpha$, IL-10, IL-6, IL-4, and IL-2 from T cells co-cultured with JeKo-1 or ROR1-transfected MEC cells at 1 µg/mL or less.

In certain embodiments, a bispecific binding molecule of the present disclosure has 1, 2, 3, 4, 5, 6, 7, 8, 9, 10, 11, or 12 of said properties. In particular embodiments, a bispecific binding molecule of the present disclosure has all of said properties.

In some embodiments, a bispecific binding molecule of the present disclosure induces T cell cytotoxicity against ROR1-positive cells.

Nucleic Acid Molecules and Vectors

The present disclosure also provides nucleic acid molecules and sequences encoding bispecific binding molecules described herein. In some embodiments, different nucleic acid molecules encode different polypeptides that form the bispecific binding molecule. In other embodiments, the same nucleic acid molecule encodes more than one, or all, of the polypeptides that form the bispecific binding molecule.

A reference to a nucleotide sequence encompasses its complement unless otherwise specified. Thus, a reference to a nucleic acid having a particular sequence should be understood to encompass its complementary strand, with its complementary sequence. The term "polynucleotide" as referred to herein means a polymeric form of nucleotides of at least 10 bases in length, either ribonucleotides or deoxynucleotides or a modified form of either type of nucleotide. The term includes single- and double-stranded forms.

In any of the above embodiments, the nucleic acid molecules may be isolated. Nucleic acid molecules referred to herein as "isolated" or "purified" are nucleic acids which (1) have been separated away from the nucleic acids of the genomic DNA or cellular RNA of their source of origin; and/or (2) do not occur in nature.

In some embodiments, a nucleic acid molecule of the present disclosure comprises nucleotide sequences that encode:

H-CDR1-3 and/or L-CDR1-3 of the first antigen-binding domain

H-CDR1-3 and/or L-CDR1-3 of the second antigen-binding domain;

VH and/or VL of the first antigen-binding domain;

VH and/or VL of the second antigen-binding domain; and/or

HC and/or LC of the first antigen-binding domain;

of a bispecific binding molecule of the present disclosure.

In some embodiments, a nucleic acid molecule of the present disclosure comprises nucleotide sequences that encode H-CDR1-3 and L-CDR1-3 of the first antigen-binding domain, and further comprises nucleotide sequences that encode H-CDR1-3 and L-CDR1-3 of the second antigen-binding domain, of a bispecific binding molecule of the present disclosure. In some embodiments, a nucleic acid molecule of the present disclosure comprises nucleotide sequences that encode the VH and VL of the first antigen-binding domain, and further comprises nucleotide sequences that encode the VH and VL of the second antigen-binding domain, of a bispecific binding molecule of the present disclosure. In some embodiments, a nucleic acid molecule of the present disclosure comprises nucleotide sequences that encode the HC and LC of the first antigen-binding domain, and further comprises nucleotide sequences that encode the VH and VL of the second antigen-binding domain, of a bispecific binding molecule of the present disclosure.

In some embodiments, a nucleic acid molecule of the present disclosure comprises one or more nucleotide sequences selected from the group consisting of SEQ ID NOs: 24-46.

In certain embodiments, a nucleic acid molecule of the present disclosure comprises:

the nucleotide sequences of SEQ ID NOs: 24 and 39;

the nucleotide sequences of SEQ ID NOs: 25 and 39;

the nucleotide sequences of SEQ ID NOs: 26 and 39;

the nucleotide sequences of SEQ ID NOs: 27 and 39;

the nucleotide sequences of SEQ ID NOs: 28 and 39;

the nucleotide sequences of SEQ ID NOs: 29 and 39;

the nucleotide sequences of SEQ ID NOs: 30 and 40;

the nucleotide sequences of SEQ ID NOs: 30 and 41;

the nucleotide sequences of SEQ ID NOs: 30 and 42;

the nucleotide sequences of SEQ ID NOs: 30 and 43;

the nucleotide sequences of SEQ ID NOs: 30 and 44;

the nucleotide sequences of SEQ ID NOs: 30 and 45;

the nucleotide sequences of SEQ ID NOs: 31, 32, and 39;

the nucleotide sequences of SEQ ID NOs: 31, 33 and 39;

the nucleotide sequences of SEQ ID NOs: 31, 34, and 39;

the nucleotide sequences of SEQ ID NOs: 35, 34, and 39;

the nucleotide sequences of SEQ ID NOs: 35, 36, and 39;

the nucleotide sequences of SEQ ID NOs: 37 and 42;

the nucleotide sequences of SEQ ID NOs: 31, 38, and 39; or the nucleotide sequences of SEQ ID NOs: 30 and 46.

In a further aspect, the present disclosure provides a vector suitable for expressing one or more of the polypeptides that form a bispecific binding molecule as described herein. The term "vector", as used herein, means a nucleic acid molecule capable of transporting another nucleic acid to which it has been linked. In some embodiments, the vector is a plasmid, i.e., a circular double stranded piece of DNA into which additional DNA segments may be ligated. In some embodiments, the vector is a viral vector, wherein additional DNA segments may be ligated into the viral genome. In some embodiments, the vectors are capable of autonomous replication in a host cell into which they are introduced (e.g., bacterial vectors having a bacterial origin of replication and episomal mammalian vectors). In other embodiments, the vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors").

In some embodiments, a nucleic acid molecule of the present disclosure can comprise a nucleotide sequence encoding an amino acid sequence from the first antigen-binding domain joined in-frame to a nucleotide sequence encoding an amino acid sequence from the second antigen-binding domain.

In some embodiments, the bispecific binding molecules of the present disclosure are expressed by inserting DNAs encoding polypeptide components of the bispecific binding molecules into expression vectors such that the DNAs are operatively linked to necessary expression control sequences such as transcriptional and translational control sequences. Expression vectors include plasmids, retroviruses, adenoviruses, adeno-associated viruses (AAVs), plant viruses such as cauliflower mosaic virus, tobacco mosaic virus, cosmids, YACs, EBV derived episomes, and the like. The coding sequence may be ligated into a vector such that transcriptional and translational control sequences within the vector serve their intended function of regulating the transcription and translation of the coding sequence. The expression vector and expression control sequences may be chosen to be compatible with the expression host cell used. Nucleotide sequences that encode different polypeptide components of a bispecific binding molecule of the present disclosure may be inserted into the same or separate vectors, and may be operatively linked to the same or different expression control sequences (e.g., promoters). In one embodiment, two or more coding sequences are inserted into the same expression vector and may be operatively linked to the same expression control sequences (e.g., a common promoter), to separate identical expression control sequences (e.g., promoters), or to different expression control sequences (e.g., promoters). The coding sequences may be inserted into the expression vector by standard methods (e.g., ligation of complementary restriction sites on the antibody gene fragment and vector, or blunt end ligation if no restriction sites are present).

Host Cells and Methods of Bispecific Binding Molecule Production

An additional aspect of the present disclosure relates to methods for producing the bispecific binding molecules of the present disclosure. In some embodiments, a method for producing a bispecific binding molecule as defined herein comprises providing a recombinant host cell capable of expressing the bispecific binding molecule (e.g., a host cell as described herein), cultivating said host cell under conditions suitable for expression of the bispecific binding molecule, and isolating the resulting bispecific binding molecule.

Mammalian cell lines available as hosts for expression are well known in the art and include many immortalized cell lines available from the American Type Culture Collection (ATCC). These include, inter alia, Chinese hamster ovary (CHO) cells, NS0 cells, SP2 cells, HEK-293T cells, 293 Freestyle cells (Invitrogen), NIH-3T3 cells, HeLa cells, baby hamster kidney (BHK) cells, African green monkey kidney cells (COS), human hepatocellular carcinoma cells (e.g., Hep G2), A549 cells, and a number of other cell lines. Other cell lines that may be used are insect cell lines, such as Sf9 or Sf21 cells, and yeast cell lines. Cell lines may be selected based on their expression levels.

In some embodiments, a host cell of the present disclosure comprises nucleotide sequences that encode:

H-CDR1-3 and/or L-CDR1-3 of the first antigen-binding domain

H-CDR1-3 and/or L-CDR1-3 of the second antigen-binding domain;

VH and/or VL of the first antigen-binding domain;

VH and/or VL of the second antigen-binding domain; and/or

HC and/or LC of the first antigen-binding domain;

of a bispecific binding molecule of the present disclosure.

In some embodiments, a host cell of the present disclosure comprises nucleotide sequences that encode H-CDR1-3 and L-CDR1-3 of the first antigen-binding domain, and further comprises nucleotide sequences that encode H-CDR1-3 and L-CDR1-3 of the second antigen-binding domain, of a bispecific binding molecule of the present disclosure. In some embodiments, a host cell of the present disclosure comprises nucleotide sequences that encode the VH and VL of the first antigen-binding domain, and further comprises nucleotide sequences that encode the VH and VL of the second antigen-binding domain, of a bispecific binding molecule of the present disclosure. In some embodiments, a host cell of the present disclosure comprises nucleotide sequences that encode the HC and LC of the first antigen-binding domain, and further comprises nucleotide sequences that encode the VH and VL of the second antigen-binding domain, of a bispecific binding molecule of the present disclosure.

In some embodiments, a host cell of the present disclosure comprises one or more nucleotide sequences selected from the group consisting of SEQ ID NOs: 24-46.

In certain embodiments, a host cell of the present disclosure comprises:

the nucleotide sequences of SEQ ID NOs: 24 and 39;
the nucleotide sequences of SEQ ID NOs: 25 and 39;
the nucleotide sequences of SEQ ID NOs: 26 and 39;
the nucleotide sequences of SEQ ID NOs: 27 and 39;
the nucleotide sequences of SEQ ID NOs: 28 and 39;
the nucleotide sequences of SEQ ID NOs: 29 and 39;
the nucleotide sequences of SEQ ID NOs: 30 and 40;
the nucleotide sequences of SEQ ID NOs: 30 and 41;
the nucleotide sequences of SEQ ID NOs: 30 and 42;
the nucleotide sequences of SEQ ID NOs: 30 and 43;
the nucleotide sequences of SEQ ID NOs: 30 and 44;
the nucleotide sequences of SEQ ID NOs: 30 and 45;
the nucleotide sequences of SEQ ID NOs: 31, 32, and 39;
the nucleotide sequences of SEQ ID NOs: 31, 33 and 39;
the nucleotide sequences of SEQ ID NOs: 31, 34, and 39;
the nucleotide sequences of SEQ ID NOs: 35, 34, and 39;
the nucleotide sequences of SEQ ID NOs: 35, 36, and 39;
the nucleotide sequences of SEQ ID NOs: 37 and 42;
the nucleotide sequences of SEQ ID NOs: 31, 38, and 39;
    or
the nucleotide sequences of SEQ ID NOs: 30 and 46.

Pharmaceutical Compositions

Another aspect of the present disclosure is a pharmaceutical composition comprising as an active ingredient (or as the sole active ingredient) a bispecific binding molecule of the present disclosure. The pharmaceutical composition may comprise any bispecific binding molecule as described herein. In some embodiments, the compositions are intended for amelioration, prevention, and/or treatment of cancer described herein (e.g., a ROR1-positive cancer).

Generally, a bispecific binding molecule of the present disclosure is suitable to be administered as a formulation in association with one or more pharmaceutically acceptable excipient(s), e.g., as described below.

The term "excipient" is used herein to describe any ingredient other than the compound(s) of the present disclosure. The choice of excipient(s) will to a large extent depend on factors such as the particular mode of administration, the effect of the excipient on solubility and stability, and the nature of the dosage form. As used herein, "pharmaceutically acceptable excipient" includes any and all solvents, dispersion media, coatings, antibacterial and antifungal agents, isotonic and absorption delaying agents, and the like that are physiologically compatible. Some examples of pharmaceutically acceptable excipients are water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Additional examples of pharmaceutically acceptable substances are wetting agents or minor amounts of auxiliary substances such as wetting or emulsifying agents, preservatives or buffers, which enhance the shelf life or effectiveness of the bispecific binding molecule.

Pharmaceutical compositions of the present disclosure and methods for their preparation will be readily apparent to those skilled in the art. Such compositions and methods for their preparation may be found, for example, in Remington's Pharmaceutical Sciences, 19th Edition (Mack Publishing Company, 1995). Pharmaceutical compositions are preferably manufactured under GMP (good manufacturing practices) conditions.

A pharmaceutical composition of the present disclosure may be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

Any method for administering peptides, proteins or antibodies accepted in the art may suitably be employed for the bispecific binding molecules of the present disclosure.

The pharmaceutical compositions of the present disclosure are typically suitable for parenteral administration. As used herein, "parenteral administration" of a pharmaceutical composition includes any route of administration characterized by physical breaching of a tissue of a subject and administration of the pharmaceutical composition through the breach in the tissue, thus generally resulting in the direct administration into the blood stream, into muscle, or into an internal organ. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal, intravenous, intraarterial, intrathecal, intraventricular, intraurethral, intracranial, intratumoral, and intrasynovial injection or infusions; and kidney dialytic infusion techniques. Regional perfusion is also contemplated. Particular embodiments include the intravenous and the subcutaneous routes.

Formulations of a pharmaceutical composition suitable for parenteral administration (e.g., intravenous administration) typically comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules or in multi-dose containers containing a preservative. Formulations for parenteral administration include, but are not limited to, suspensions, solutions, emulsions in oily or aqueous vehicles, pastes, and the like. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition. Parenteral formulations also include aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. Exemplary parenteral administration forms include solutions or suspensions in sterile aqueous solutions, for example, aqueous propylene glycol or dextrose solutions. Such dosage forms can be suitably buffered, if desired. Other parentally-administrable formulations which are useful include those which comprise the active ingredient in microcrystalline form, or in a liposomal preparation. Formulations for parenteral administration may be formulated to be immediate and/or modified release. Modified release formulations include delayed-, sustained-, pulsed-, controlled-, targeted and programmed release. Therapeutic Uses of Bispecifc Binding Molecules In some embodiments, a bispecific binding molecule of the present disclosure is used to treat cancer, such as a ROR1-positive cancer, in a patient. The patient may be a mammal, e.g., a human. ROR1 has been shown to express across many types of tumors, including lymphomas and solid tumors. High proportions of human cancers express ROR1. For example, Zhang et al. showed that 54% of ovarian cancers, 57% of colon cancers, 77% of lung cancers, 90% of lymphomas, 89% of skin cancers, 83% of pancreatic cancers, 73% of testicular cancers, 43% of bladder cancers, 96% of uterus cancers, 90% of prostate cancers, and 83% of adrenal cancers that they examined had moderate-to-strong staining with the anti-ROR1 antibody 4A5 (Zhang et al., *Am J Pathol.* 181(6):1903-10 (2012)). Daneshmanesh et al. similarly found near universal expression of ROR1 in chronic lymphocytic leukemia (CLL) and hairy cell leukemia (HCL) and varying degrees of expression in other lymphoid cancers such as mantle cell lymphoma (MCL), diffuse large B-cell lymphoma (DLBCL)/marginal zone lymphoma (MZL), follicular lymphoma (FL), chronic myeloid leukemia (CML), acute myeloid leukemia (AML), and myeloma (Daneshmanesh et al., *Leuk Lymphoma* 54(4): 843-50 (2013)). Multiple groups have demonstrated expression of ROR1 in a subset of B-cell acute lymphoblastic leukemia (ALL) (see, e.g., Dave et al., *PLoS One* 7:e52655 (2012)). ROR1 is also expressed in substantial proportions of cases of hepatocellular cancer (HCC) or non-small cell lung cancer (NSCLC) (U.S. Patent Publication 2018/ 0369406). Further, it has been shown that ROR1 expression increases in aggressive cancers and correlates with poor prognosis; thus, bispecific binding molecules of the present disclosure are particularly well suited to treat aggressive or advanced cancers.

"Treat", "treating" and "treatment" refer to a method of alleviating or abrogating a biological disorder and/or at least one of its attendant symptoms. As used herein, to "alleviate" a disease, disorder or condition means reducing the severity and/or occurrence frequency of the symptoms of the disease, disorder, or condition. Further, references herein to "treatment" include references to curative, palliative and prophylactic treatment. Treatment of cancer encompasses inhibiting cancer growth (including causing partial or complete cancer regression), inhibiting cancer progression or metastasis, preventing cancer recurrence or residual disease, and/or prolonging the patient's survival.

A bispecific binding molecule may be administered in a therapeutically effective amount to a patient with a cancer described herein. "Therapeutically effective amount" refers to the amount of the therapeutic agent being administered that will relieve to some extent one or more of the symptoms of the disorder being treated. A therapeutically effective amount of an anti-cancer therapeutic may, for example, result in tumor shrinkage, increased survival, elimination of cancer cells, decreased disease progression, reversal of metastasis, or other clinical endpoints desired by healthcare professionals.

In some embodiments, a cancer treatable by a bispecific binding molecule described herein is a ROR1-expressing (i.e., ROR1-positive) cancer. The cancer can be identified as ROR1-expressing by any suitable method of determining gene or protein expression, for example, by histology, flow cytometry, RT-PCR, or RNA-Seq. The cancer cells used for the determination may be obtained through tumor biopsy or through collection of circulating tumor cells. In certain embodiments, if an antibody-based assay such as flow cytometry or immunohistochemistry is used, ROR1-expressing cancers are any cancers with cells that show anti-ROR1 antibody reactivity greater than that of an isotype control antibody. In certain embodiments, if an RNA-based assay is used, ROR1-expressing cancers are those that show an elevated level of ROR1 RNA compared to a negative control cell or cancer that does not express ROR1.

In certain embodiments, bispecific binding molecules of the present disclosure are used to treat hematological malignancies (e.g., leukemias and/or lymphomas). In certain embodiments, bispecific binding molecules of the present disclosure are used to treat solid tumors. The cancer to be treated may be selected from, e.g., lymphoma, small lymphocytic lymphoma, marginal zone lymphoma, marginal cell B-cell lymphoma, Burkitt's lymphoma, mantle cell lymphoma, follicular lymphoma, diffuse large B-cell lymphoma, a non-Hodgkin lymphoma that has undergone Richter's transformation, T cell non-Hodgkin lymphoma, lymphoplasmacytoid lymphoma, Waldenström macroglobulinemia, acute lymphoblastic leukemia, acute myeloid leukemia, chronic lymphocytic leukemia, T cell leukemia, sarcoma, osteosarcoma, Ewing sarcoma, renal cell carcinoma, hepatocellular carcinoma, colon cancer, colorectal cancer, breast cancer, epithelial squamous cell cancer, glioblastoma, melanoma, myeloma, multiple myeloma, stomach cancer, brain cancer, lung cancer, non-small cell lung cancer, pancreatic cancer, cervical cancer, ovarian cancer, liver cancer, bladder cancer, prostate cancer, testicular cancer, thyroid cancer, and head and neck cancer. In certain embodiments, the cancer is selected from mantle cell lymphoma, breast cancer, lung cancer, bone osteosarcoma, and Ewing sarcoma.

In some embodiments, the cancer to be treated can be a cancer that is refractory to other therapeutics (for example, triple negative breast cancer). The cancer may be, e.g., at an early, intermediate, late, or metastatic stage.

In some embodiments, a patient to be treated with a bispecific binding molecule of the present disclosure has received prior cancer treatment. In other aspects, the patient has not received prior cancer treatment.

A bispecific binding molecule of the present disclosure may be administered without additional therapeutic treatments, i.e., as a stand-alone therapy (monotherapy). Alternatively, treatment with a bispecific binding molecule of the present disclosure may include at least one additional therapeutic treatment (combination therapy). In some embodiments, a bispecific binding molecule may be co-administered or formulated with another medication/drug for the treatment of cancer. The additional treatment may comprise, e.g., a chemotherapeutic, anti-neoplastic, or anti-angiogenic agent, a different anti-cancer antibody, and/or radiation therapy.

In certain embodiments, a bispecific binding molecule of the present disclosure is used in combination with an additional therapeutic agent or biologically active molecule (e.g., to treat a cancer described herein). Examples of biologically active molecules include, but are not limited to, peptides, proteins, enzymes, small molecule drugs, prodrugs, carbohydrates, imaging agents, lipids, nucleosides, radionuclides, oligonucleotides, toxins, cells, antibiotics, fungicides, antiviral agents, anti-inflammatory agents, anti-tumor agents, cardiovascular agents, anti-anxiety agents, hormones, growth factors, steroidal agents, microbially derived toxins, and the like. In some embodiments, the additional therapeutic agent is a vascular endothelial growth factor (VEGF) inhibitor, a Bruton's tyrosine kinase (BTK) inhibitor, an inhibitor of the mammalian target of rapamycin (mTOR), a phosphoinositide 3-kinase (PI3K) inhibitor, a Janus kinase/signal transducers and activators of transcription (Jak/STAT) signaling inhibitor, a B-cell lymphoma 2 (Bcl-2) inhibitor, a spleen tyrosine kinase (SYK) inhibitor, a microtubule inhibitor, an epithelial growth factor receptor (EGFR) inhibitor, a poly ADP ribose polymerase (PARP) inhibitor, an anaplastic lymphoma kinase (ALK) inhibitor, a DNA-repair inhibitor, a DNA cross-linker, a nucleoside analog, or an immunomodulatory agent. In some embodiments, the additional therapeutic agent is an antibody such as rituximab (anti-CD20) or bevacizumab (anti-VEGF); a Bruton's tyrosine kinase inhibitor such as acalabrutinib or ibrutinib; an mTOR inhibitor such as sapanisertib, everolimus or BEZ235; a PI3K inhibitor such as idelalisib or buparlisib; a Jak/STAT signaling inhibitor such as ruxolitinib; a Bcl-2 inhibitor such as ABT-199/venetoclax, Bcl-2i-1, or Bcl-2i-2; a SYK inhibitor such as fostamatinib; a microtubule inhibitor such as paclitaxel or vincristine; an EGFR inhibitor such as erlotinib; a PARP inhibitor such as olaparib; an ALK inhibitor such as crizotinib; a DNA-repair inhibitor such as carboplatin; a DNA cross-linker such as oxaliplatin/cisplatin; a nucleoside analog such as gemcitabine; or an immunomodulatory drug (IMiD) such as lenalidomide or pomalidomide. In certain embodiments, the additional therapeutic agent is ibrutinib, acalabrutinib, venetoclax, Bcl-2i-1, Bcl-2i-2, everolimus, sapanisertib, idelalisib, pacritinib, buparlisib, BEZ235, ruxolitinib, fostamatinib, rituximab, rituximab-CHOP, lenalidomide, pomalidomide, paclitaxel, vincristine, erlotinib, crizotinib, carboplatin, oxaliplatin/cisplatin, bevacizumab, or gemcitabine.

In certain embodiments, a bispecific binding molecule of the invention is used in combination with an immune checkpoint modulator that enhances the patient's immune system (e.g., to treat a cancer as described herein). For example, the conjugate is used with an immune checkpoint inhibitor such as an antibody or antibody derivative, an antisense oligonucleotide, a small interfering RNA, an aptamer, or a peptide, targeting programmed death-ligand 1 (PD-L1, also known as B7-H1, CD274), programmed death 1 (PD-1), CTLA-4, PD-L2 (B7-DC, CD273), LAG3, TIM3, 2B4, A2aR, B7H1, B7H3, B7H4, BTLA, CD2, CD27, CD28, CD30, CD40, CD70, CD80, CD86, CD137, CD160, CD226, CD276, DR3, GAL9, GITR, HAVCR2, HVEM, IDO1, IDO2, ICOS (inducible T cell costimulator), KIR, LAIR1, LIGHT, MARCO (macrophage receptor with collagenous structure), PS (phosphatidylserine), OX-40, SLAM, TIGHT, VISTA, VTCN1, or any combination thereof.

In certain embodiments, a bispecific binding molecule of the present disclosure is administered to a patient in combination with T cells (e.g., T cells autologous or allogeneic to the patient). In particular embodiments, where the patient is human, the T cells are also human. In some embodiments, the bispecific binding molecule is bound to the T cells before administration to the patient.

It is understood that bispecific binding molecules of the present disclosure may be used in a method of treatment as described herein, may be for use in a treatment as described herein, and/or may be used in the manufacture of a medicament for a treatment as described herein. The present disclosure also provides kits and articles of manufacture comprising bispecific binding molecules of the present disclosure as described herein.

Articles of Manufacture and Kits

The present disclosure also provides articles of manufacture, e.g., kits, comprising one or more containers (e.g., single-use or multi-use containers) containing a pharmaceutical composition of the bispecific binding molecule of the present disclosure, optionally an additional biologically active molecule (e.g., another therapeutic agent), and instructions for use. The bispecific binding molecule and optional additional biologically active molecule can be packaged separately in suitable packing such as a vial or ampule made from non-reactive glass or plastic. In certain embodiments, the vial or ampule holds lyophilized powder comprising the bispecific binding molecule and/or additional biologically active molecule. In certain embodiments, the vial or ampule holds a concentrated stock (e.g., 2×, 5×, 10× or more) of the bispecific binding molecule or biologically active molecule. In certain embodiments, the articles of manufacture such as kits include a medical device for administering the bispecific binding molecule and/or biologically active molecule (e.g., a syringe and a needle); and/or an appropriate diluent (e.g., sterile water and normal saline). The present disclosure also includes methods for manufacturing said articles.

Unless otherwise defined herein, scientific and technical terms used in connection with the present disclosure shall have the meanings that are commonly understood by those of ordinary skill in the art. Exemplary methods and materials are described below, although methods and materials similar or equivalent to those described herein can also be used in the practice or testing of the present disclosure. In case of conflict, the present specification, including definitions, will control.

Generally, nomenclature used in connection with, and techniques of, cell and tissue culture, molecular biology, immunology, microbiology, genetics, analytical chemistry, synthetic organic chemistry, medicinal and pharmaceutical chemistry, and protein and nucleic acid chemistry and hybridization described herein are those well-known and commonly used in the art. Enzymatic reactions and purification techniques are performed according to manufacturer's specifications, as commonly accomplished in the art or as described herein.

Further, unless otherwise required by context, singular terms shall include pluralities and plural terms shall include the singular. Throughout this specification and embodiments, the words "have" and "comprise," or variations such as "has," "having," "comprises," or "comprising," will be understood to imply the inclusion of a stated integer or group of integers but not the exclusion of any other integer or group of integers.

All publications and other references mentioned herein are incorporated by reference in their entirety. Although a number of documents are cited herein, this citation does not constitute an admission that any of these documents forms part of the common general knowledge in the art.

In order that this invention may be better understood, the following examples are set forth. These examples are for purposes of illustration only and are not to be construed as limiting the scope of the invention in any manner.

EXAMPLES

The following examples illustrate representative embodiments of the present invention and are not meant to be limiting in any way.

Example 1: Design and Expression of Anti-ROR1/Anti-CD3 Bispecific Binding Molecules Multiple variables impact the in vivo potency of bispecific binding molecules, including PK, epitopes, the relative affinities of the binding components, and the valency and spatial configuration of the paratopes. Currently, there is no reliable method for designing apriori a single molecule that optimizes all these parameters. Accordingly, multiple anti-ROR1/anti-CD3 bispecific constructs were designed, made, and tested to systematically evaluate the impact of many of these parameters.

To identify the structure that provides the optimal configuration, specifically the most active relative spatial placement of the ROR1 and CD3 binding components, a variety of constructs were designed as summarized in FIG. 1. Although a variety of bispecific formats have been described (see, e.g., Brinkmann and Kontermann, *MABS* 9:182-212 (2017)), the present efforts focused on formats that contain antibody Fc component in order to enable favorable PK and use well-established Protein A-based antibody purification approaches.

The ROR1 binding component used in the bispecific binding molecules has been demonstrated to be highly selective for human ROR1 and has proven to be safe in human clinical trials (see, e.g., Choi et al., *Cell Stem Cell* 22:951-959 (2018)). Further, bispecific binding molecules were tested with CD3 binding components specific for two distinct CD3 epitopes, using anti-CD3 scFv sequences based on the SP34 and OKT3 antibodies. CD3 antibodies have been classified based on distinct characteristics of their epitopes (Tunnacliffe et al., *International Immunology* 1:546-550 (1989)). Using this system, SP34 is classified as Group I while OKT3 is classified as Group II.

For certain constructs, use of wild-type antibody Fc sequences enabled the evaluation of bispecific constructs that are bivalent for both ROR1 and CD3 (FIGS. 1, A, B, and E). For other constructs, the use of knobs-into-holes mutations in the Fc region enabled the expression of bispecific binding molecules with different valencies for ROR1 and CD3. For example, one construct is bivalent for ROR1 and monovalent for CD3 (FIG. 1, D) while another construct is monovalent for both ROR1 and CD3 (FIG. 1, C).

Finally, ROR1 paratopes with altered affinities and valencies were tested in combination with the different CD3 paratopes to evaluate the effect of CD3 and ROR1 paratopes with differing relative affinities/avidities.

Based on these design parameters, multiple bispecific constructs were expressed, purified and characterized.

Materials and Methods

Codon-optimized DNA encoding the bispecific constructs with a leader sequence of SEQ ID NO: 110 was cloned into the pcDNA3.4 vector, then introduced into Expi293™ cells by transient transfection. The cells were grown in 40 mL cultures containing Expi293™ Expression Medium (ThermoFisher cat. #A1435103). Subsequently, antibody was purified from the culture supernatant in a single step using HiTrap® MabSelect SuRe™ (GE Healthcare cat. #11-0034-93). Purified antibody was stored in PBS, pH 7.2, and purity was characterized by SDS-PAGE. The purity of constructs consisting of three distinct polypeptide chains was further characterized by SEC using a TSKgel G3000SWxl 7.8 mm×380 mm column. The mobile phase was 0.IM phosphate buffer, 0.IM Na$_2$SO$_4$, pH 6.7, and the column was run at a flow rate of 0.7 mL/min.

Results

The sequences of the anti-ROR1/anti-CD3 bispecific binding molecules are summarized in Table 1 (protein) and Table 2 (DNA).

TABLE 1

| | Summary of Bispecific Construct Polypeptide Sequences | | | | | |
|---|---|---|---|---|---|---|
| Construct | Polypeptide 1 (Heavy Chain 1) SEQ ID | Polypeptide 2 (Heavy Chain 2) SEQ ID | Polypeptide 3 (Light Chain) SEQ ID | CD3 Valency | ROR1 Valency | Schematic (FIG. 1) |
| 1 | 1 | | 16 | 2 | 2 | A |
| 2 | 2 | | 16 | 2 | 2 | A |
| 3 | 3 | | 16 | 2 | 2 | A |
| 4 | 4 | | 16 | 2 | 2 | A |
| 5 | 5 | | 16 | 2 | 2 | A |
| 6 | 6 | | 16 | 2 | 2 | A |
| 7 | 7 | | 17 | 2 | 2 | B |
| 8 | 7 | | 18 | 2 | 2 | B |
| 9 | 7 | | 19 | 2 | 2 | B |
| 10 | 7 | | 20 | 2 | 2 | B |
| 11 | 7 | | 21 | 2 | 2 | B |
| 12 | 7 | | 22 | 2 | 2 | B |
| 13 | 8 | 9 | 16 | 1 | 1 | C |
| 14 | 8 | 10 | 16 | 1 | 1 | C |
| 15 | 8 | 11 | 16 | 1 | 1 | C |
| 16 | 12 | 11 | 16 | 1 | 1 | C |
| 17 | 12 | 13 | 16 | 1 | 1 | C |
| 18 | 14 | | 19 | 2 | 2 | B |
| 19 | 8 | 15 | 16 | 1 | 2 | D |
| 20 | 7 | | 23 | 2 | 2 | E |

TABLE 2

| | Summary of Bispecific Construct DNA Sequences | | | | | |
|---|---|---|---|---|---|---|
| Construct | Heavy Chain 1 SEQ ID | Heavy Chain 2 SEQ ID | Light Chain SEQ ID | CD3 Valency | ROR1 Valency | Schematic (FIG. 1) |
| 1 | 24 | | 39 | 2 | 2 | A |
| 2 | 25 | | 39 | 2 | 2 | A |
| 3 | 26 | | 39 | 2 | 2 | A |
| 4 | 27 | | 39 | 2 | 2 | A |
| 5 | 28 | | 39 | 2 | 2 | A |
| 6 | 29 | | 39 | 2 | 2 | A |
| 7 | 30 | | 40 | 2 | 2 | B |
| 8 | 30 | | 41 | 2 | 2 | B |
| 9 | 30 | | 42 | 2 | 2 | B |
| 10 | 30 | | 43 | 2 | 2 | B |
| 11 | 30 | | 44 | 2 | 2 | B |
| 12 | 30 | | 45 | 2 | 2 | B |
| 13 | 31 | 32 | 39 | 1 | 1 | C |
| 14 | 31 | 33 | 39 | 1 | 1 | C |
| 15 | 31 | 34 | 39 | 1 | 1 | C |
| 16 | 35 | 34 | 39 | 1 | 1 | C |
| 17 | 35 | 36 | 39 | 1 | 1 | C |
| 18 | 37 | | 42 | 2 | 2 | B |
| 19 | 31 | 38 | 39 | 1 | 2 | D |
| 20 | 30 | | 46 | 2 | 2 | E |

The majority of the constructs expressed well (17/20 expressed >1 mg; 14/20 expressed >2 mg) and in most cases were substantially purified in a single step using Protein A chromatography (Table 3), as determined by SDS-PAGE.

TABLE 3

Summary of Expression and Purification of Bispecific Constructs

| Construct | Yield (mg) | Concentration (mg/mL) | Purity (%) |
|---|---|---|---|
| 1 | 2.72 | 0.34 | 90 |
| 2 | 5.32 | 0.76 | 95 |
| 3 | 1.36 | 0.68 | 95 |
| 4 | 3.52 | 0.44 | 60 |
| 5 | 5.49 | 0.61 | 55 |
| 6 | 0.38 | 0.19 | 90 |
| 7 | 7.84 | 3.92 | 95 |
| 8 | 5.50 | 5.50 | 95 |
| 9 | 1.93 | 1.29 | 95 |
| 10 | 3.28 | 0.41 | 65 |
| 11 | 3.78 | 0.63 | 70 |
| 12 | 0.19 | 0.12 | 65 |
| 13 | 8.47 | 1.21 | 73 |
| 14 | 9.08 | 4.54 | 95 |
| 15 | 9.20 | 1.15 | 65 |
| 16 | 7.42 | 1.06 | 80 |
| 17 | 4.60 | 0.92 | 79 |
| 18 | 0.89 | 0.59 | 90 |
| 19 | 4.60 | 0.92 | 60 |
| 20 | 1.32 | 0.88 | 85 |

Constructs that did not contain disulfide-stabilized anti-CD3 scFv were generally of higher purity (>90%) after Protein A chromatography (Table 3, compare constructs 2 and 5).

SEC analysis was performed on constructs consisting of three distinct polypeptide chains. In general, following a single Protein A purification step, constructs consisting of two distinct chains (wild-type Fc) were obtained in higher purity than constructs consisting of three distinct chains (heteromeric Fc) (Table 3, compare purity of samples 1-3 and 7-9 with samples 13-17).

Collectively, these data demonstrate that most of the constructs express well and are >90% pure after a single Protein A purification step.

Example 2: Binding of Anti-ROR1/Anti-CD3 Bispecific Binding Molecules to ROR1

Bispecific binding molecules with different configurations, ROR1 affinities, and ROR1 valencies were evaluated for binding to human ROR1 to determine the impact of these parameters on cytotoxicity. The binding of bispecific constructs 1-20 to human ROR1 was characterized using ROR1-transfected MEC cells, JeKo-1 cells, and recombinant ROR1 extracellular domain (ECD).

Materials and Methods

ROR1 Binding Assay Using Cells and Flow Cytometry

ROR1 binding was quantitated using both ROR1-transfected MEC cells and JeKo-1 cells. For each condition, 2.5E5 cells were used. The cells were placed in 50 μL of PBS with 2% FBS. Next, the cells were diluted with an equal volume of 2× stock of the test bispecific binding molecule. The cells and antibody were co-incubated on ice for 20 min. The cells were then washed 3 times with 300 μL of FACS buffer and were resuspended in 100 μL of anti-human Fc-PE conjugate antibody (Invitrogen cat. #12499882) and incubated on ice with reduced light for 20 min. Subsequently, the cells were washed 3 times with 300 μL of FACS buffer and fixed with 2% paraformaldehyde for 10 min at 25° C. The cells then were washed 2 times with 300 μL of FACS buffer and analyzed on a Miltenyi MACSQuant Analyzer.

ROR1 Binding Assays Using Recombinant ROR1-ECD and ELISA

The binding of bispecific binding molecules to recombinant ROR1 was assessed by ELISA using two different configurations. In the first configuration, ROR1 protein was immobilized on 96-well plates and the bispecific constructs were titrated (details below). The bispecific binding molecules were also characterized for ROR1 binding using a second configuration in which the bispecific binding molecules were immobilized on the 96-well plates and soluble biotinylated ROR1 (b-ROR1) was titrated (details below).

Immobilized ROR1 ELISA

A 96-well Costar-3366 plate was coated with 50 μL/well of 2 μg/mL human TL1A (Acro Biosystems cat. #R01-H522Y) in PBS overnight at 4° C. The plate was rinsed once with PBS containing 0.05% Tween 20 (PBS-T) and blocked with 100 μL/well of 5% non-fat milk in PBS (5% M-P) for 1 h at 25° C. Antibody samples were serially diluted 2-fold using 5% M-P and were incubated for 1 h at 25° C. (50 μL/well). The plate was washed three times with PBS-T and 50 μL/well anti-human kappa, HRP conjugate (Southern Biotech cat. #2060-05) diluted 10,000-fold in 5% M-P was added for 1 h at 25° C. The plate was washed three times with PBS-T, developed with 50 μL/well 1-Step Ultra TMB-ELISA (Thermo Scientific cat. #34028). The reaction was terminated by the addition of 2 N $H_2SO_4$ and the A450 was determined using a Spectramax plate reader.

Soluble ROR1 ESA

To biotinylate ROR1, 200 μg of human ROR1 (Acro Biosystems cat. #R01-H522Y) was resuspended in 2 mL water to 100 μg/mL and was then combined with EZ-Link Sulfo-NHS-LC-Biotin (Thermo Scientific cat. #21327) at a 1:5 molar ratio and incubated at 25° C. for 2 h. The reaction was terminated by the addition of 31 μL of 750 mM arginine hydrochloride and was stored at 4° C.

To measure the binding of bispecific constructs to soluble ROR1, a 96-well Costar-3366 plate was coated with 50 μL/well of 2 μg/mL goat anti-human kappa (Southern Biotech cat. #2060-01) in PBS overnight at 4° C. The plate was rinsed once with PBS-T, blocked with 100 μL/well 5% M-P for 1 h at 25° C., rinsed once with PBS-T, and 2 μg/mL of the bispecific binding molecule was added and incubated for 1 h at 25° C. The plate was washed three times with PBS-T. Biotinylated ROR1 was diluted serially, 3-fold in 5% M-P and was incubated for 1 h at 25° C. (50 μL/well). The plate was washed three times with PBS-T. To detect the binding of b-ROR1, 50 μL/well Neutravidin-HRP (Pierce cat. #31030) diluted 1:5000 in 1% BSA-PBS was added for 1 h at 25° C. The plate was washed three times with PBS-T, then developed with 50 μL/well 1-Step Ultra TMB-ELISA (Thermo Scientific cat. #34028). The reaction was terminated by the addition of 2 N $H_2SO_4$ and the A450 was determined using a Spectramax plate reader.

Results

Figure 2:
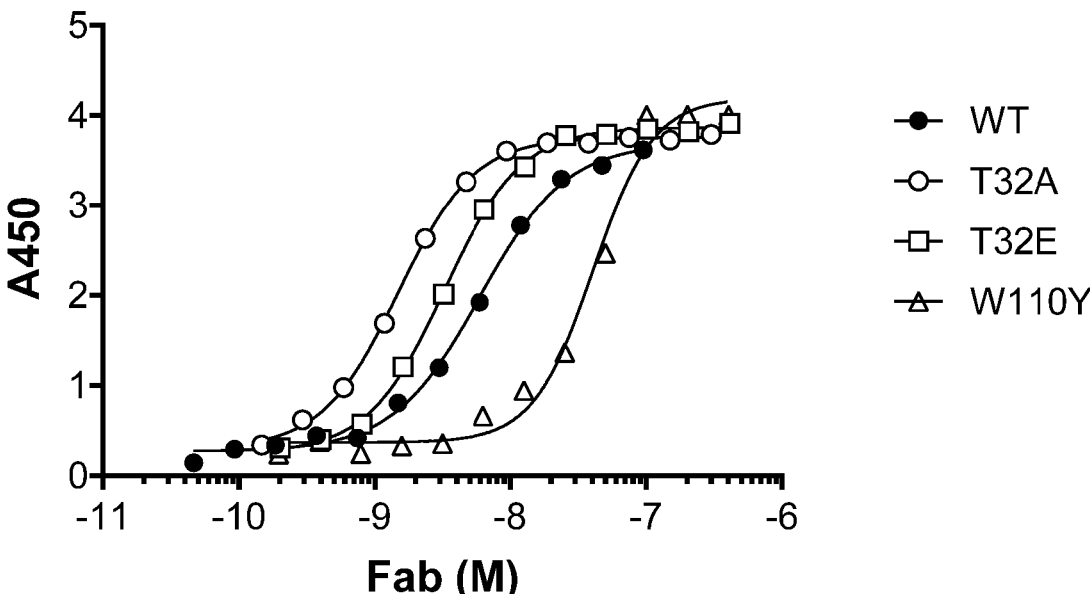
FIG. 2 is a pair of graphs illustrating the binding to human ROR1 of a parental Ab1 Fab (WT) and three heavy chain variants (Ab2 (T32A), Ab3 (T32E), and W110Y), as determined by ELISA (Panel A) and by flow cytometry analysis of binding to live ROR1-transfected MEC cells (Panel B).
Figure 2:
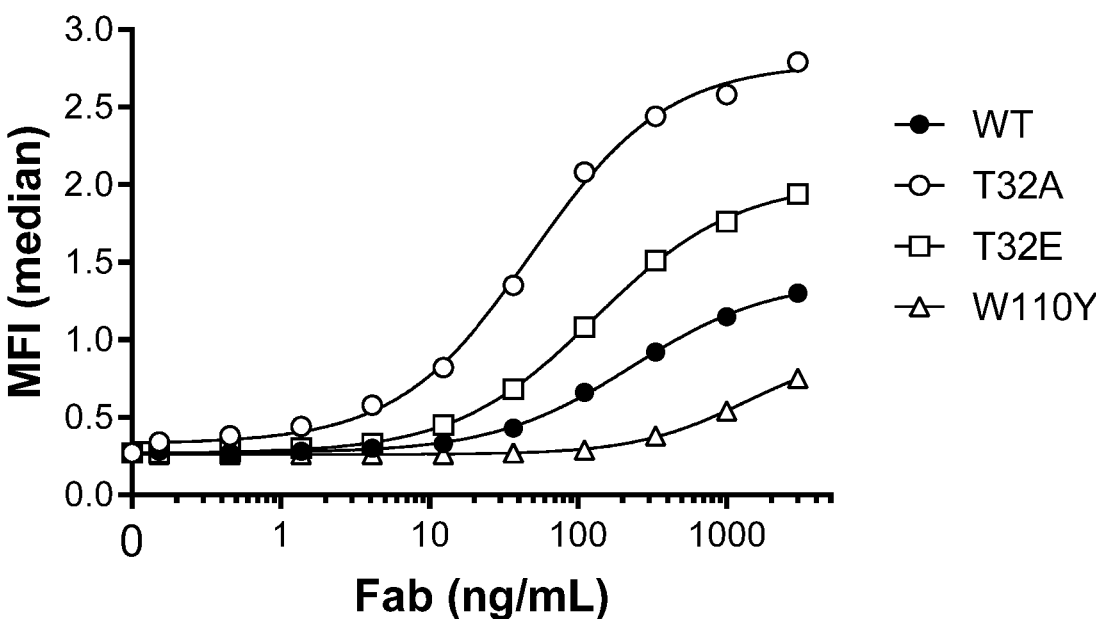

Three anti-ROR1 Fab variants, each differing from the parental antibody by a single amino acid in H-CDR2, were characterized for binding to human ROR using ELISA-based screening and live cell binding. Two of the variants, T32A and T32E, displayed higher affinity than the parental Fab (FIG. 2, Panel A, open circles and squares versus closed circles) while the other variant, W110Y, displayed lower affinity (FIG. 2, Panel A, triangles). The relative affinities of these variants were further characterized using live ROR1- transfected MEC cells. Similar to the ELISA-based screen, variants T32A and T32E displayed higher affinity (FIG. 2, Panel B, open circles and squares versus closed circles) while W110Y had diminished binding (FIG. 2, Panel B, triangles). No binding of any of the variants was detected when control empty vector transfected MEC cells were used (not shown), demonstrating the specificity of the variants for RORL. The relative binding strengths of the variants were very similar, regardless of the assay format. For example, the T32A variant was 4- to 4.7-fold higher affinity than the parental antibody while the W110Y variant was 5.9- to 6.8-fold lower affinity than the parental antibody. These very closely related variants differ from one another by one to two amino acids, display a 27-fold range of binding activity to ROR1, and enable the design of anti-ROR1/anti-CD3 bispecific binding molecules with a range of affinities for ROR1 as well as CD3.

Figure 3:
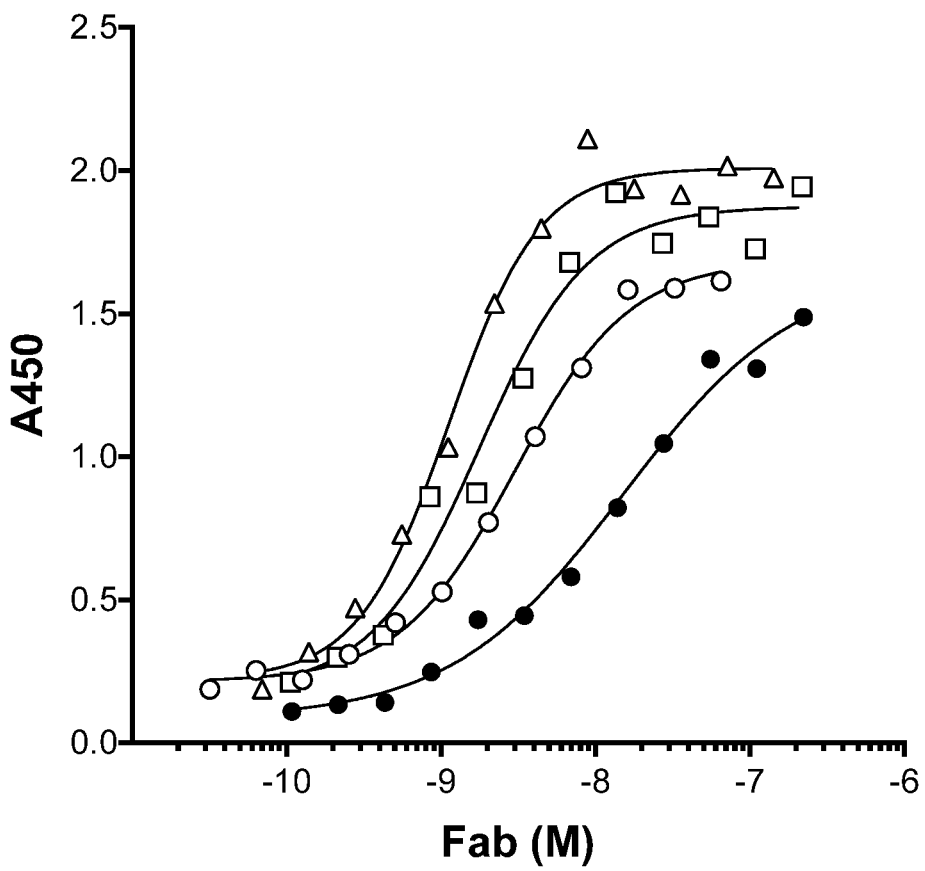
FIG. 3 is a graph illustrating the binding to human ROR1 of a parental Ab1 Fab (WT) and three variants (Ab2 (T32A), Ab6 (T32A (HC)+A25P (LC)), and Ab7 (T32A (HC)+T69R (LC))), as determined by ELISA using prolonged wash conditions.

Next, two additional anti-ROR1 Fab variants, each containing a distinct light chain CDR mutation combined with the heavy chain T32A mutation, were characterized for binding to human ROR using a modified version of the ELISA-based screen described previously. Specifically, the first wash step following the binding of the Fabs to immobilized ROR1 was altered by placing the plates in a large volume of PBS-T for a prolonged one hour dissociation step. This enabled variants with slow dissociation rates to be distinguished from one another. Using the modified ELISA, two variants, T32A (HC)+A25P (LC) and T32A (HC)+T69R (LC) displayed stronger binding than T32A (FIG. 3). As described previously, the T32A variant displayed >5-fold improvement in binding relative to the parental (WT), while T32A (HC)+A25P (LC) and T32A (HC)+T69R (LC) displayed further improvements in binding relative to the parental Fab (>8- and >13-fold, respectively). These very closely related variants differ from one another by 1-3 amino acids, display an 80- to 90-fold range of binding activity to ROR1, and enable the design of anti-ROR1/anti-CD3 bispecific binding molecules with a range of affinities for ROR1 as well as CD3.

The bispecific binding molecules were tested for ROR binding using three assays: (1) binding to live cells and detection by flow cytometry, (2) binding to immobilized ROR1 as determined by ELISA, and (3) binding to soluble, biotinylated ROR as determined by ELISA. Regardless of the screening format employed, all constructs bound ROR1 selectively (FIGS. 4-7).

Figure 4:
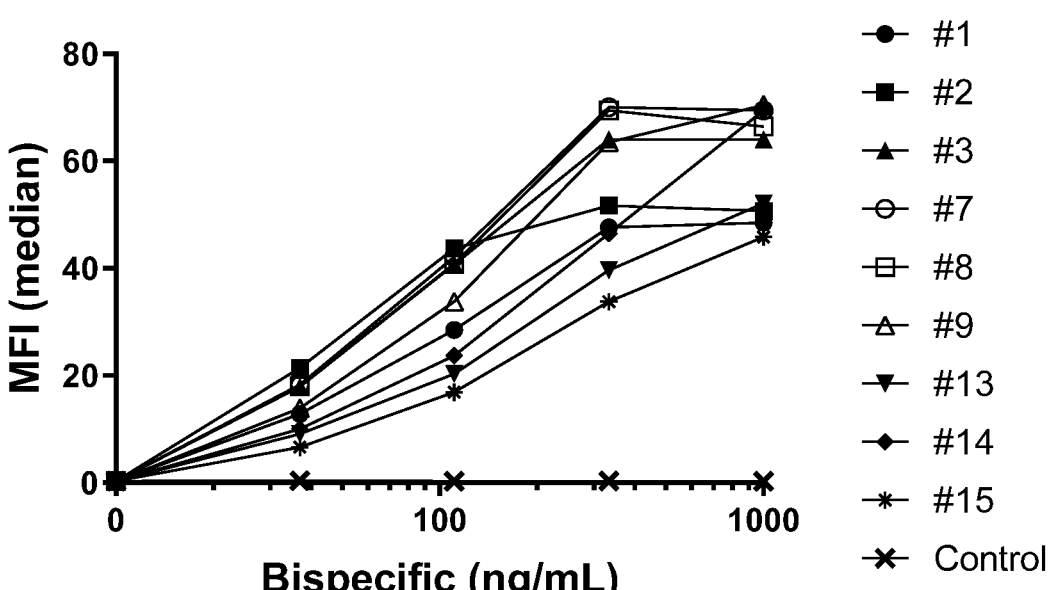
FIG. 4 is a pair of graphs showing the selectivity of bispecific constructs 1-3, 7-9, and 13-15 for ROR1, as demonstrated by flow cytometry analysis of binding to ROR1-transfected MEC cells (Panel A) and control MEC cells (Panel B). Non-specific human IgG was included as a control ("Control").
Figure 4:
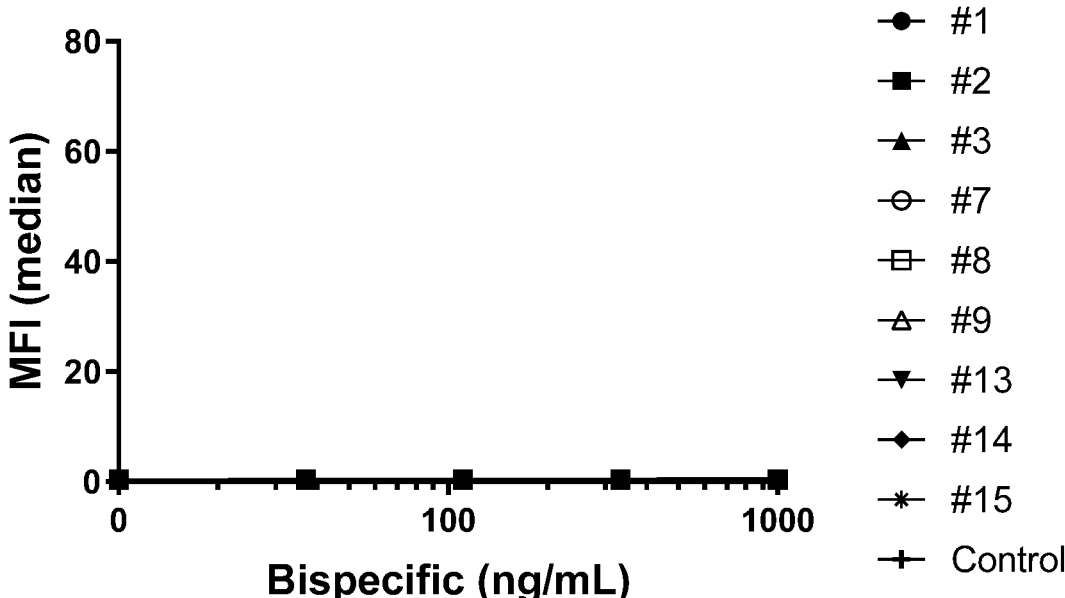

Selectivity for ROR was demonstrated by measuring binding to ROR1-transfected MEC cells and control MEC cells. Binding of the bispecific binding molecules to ROR1-transfected cells was concentration dependent (FIG. 4, Panel A) and no binding to the control cells was observed at any concentration (FIG. 4, Panel B). Non-specific human IgG was included as a control ("Control") for both cell lines.

Variation in the binding strength of the bispecific constructs to ROR1-transfected MEC cells was observed (FIG. 4, Panel A). For example, ROR1 bivalent constructs bound more tightly than ROR monovalent constructs (FIG. 4, Panel A, compare constructs 1-3 and 7-9 with 13-15). This difference in binding strength was most apparent at lower concentrations (<100 ng/mL).

Figure 5:
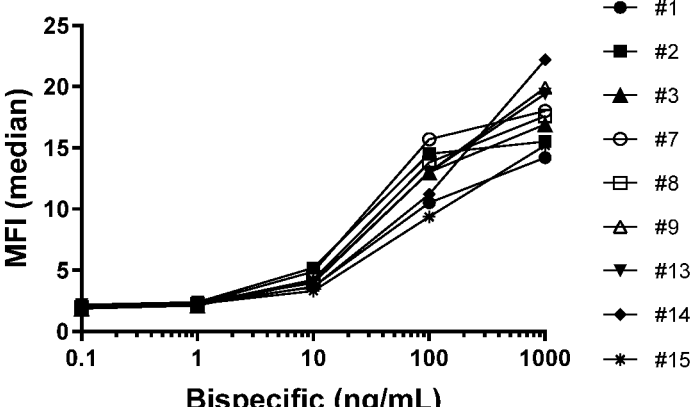
FIG. 5 is a set of graphs showing the influence of ROR1 expression levels on binding of bispecific constructs 1-3, 7-9, and 13-15 (Panel A), 4-6 and 10-12 (Panel B), and 3, 9, and 15-20 (Panel C). Binding was assessed by flow cytometry using JeKo-1 cells, which express lower levels of ROR1 (~13,000 copies/cell) than ROR1-transfected MEC cells (~56,000 copies/cell).
Figure 5:
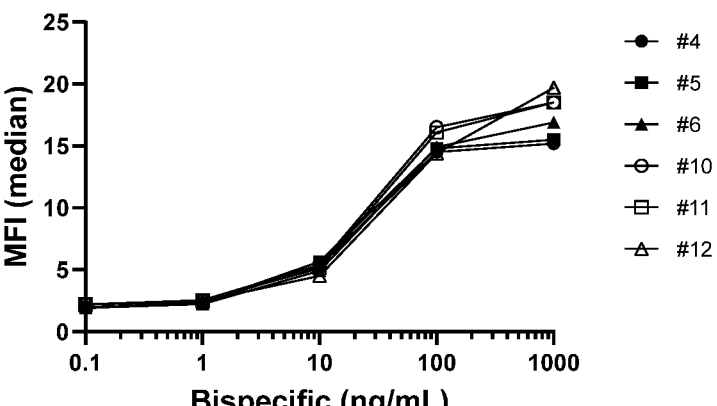
Figure 5:
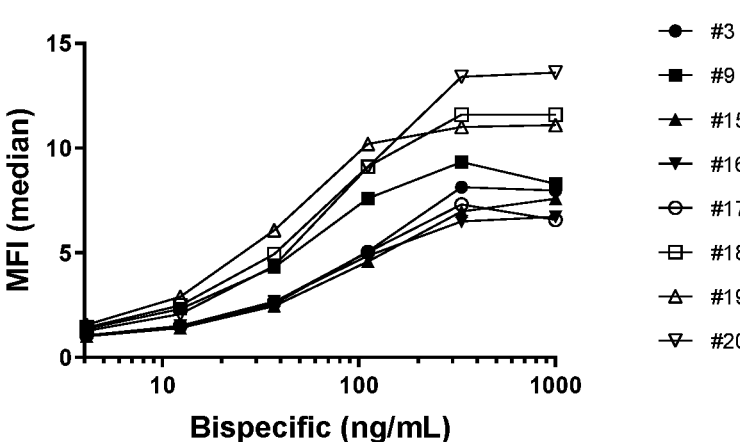

The influence of ROR expression levels on binding of the bispecific constructs was assessed by flow cytometry using JeKo-1 cells. JeKo-1 cells express lower levels of ROR (~13,000 copies/cell) than the ROR1-transfected MEC cells (~56,000 copies/cell). All constructs bound JeKo-1 cells (FIG. 5). Relative binding trends observed using the ROR1-transfected MEC cells were observed with JeKo-1 cells.

Specifically, monovalent ROR1 constructs generally bound more weakly than the bivalent constructs (FIG. 5, Panel A, compare constructs 14 and 15 with other constructs; FIG. 5, Panel C, compare constructs 15-17 with other constructs).

Figure 6:
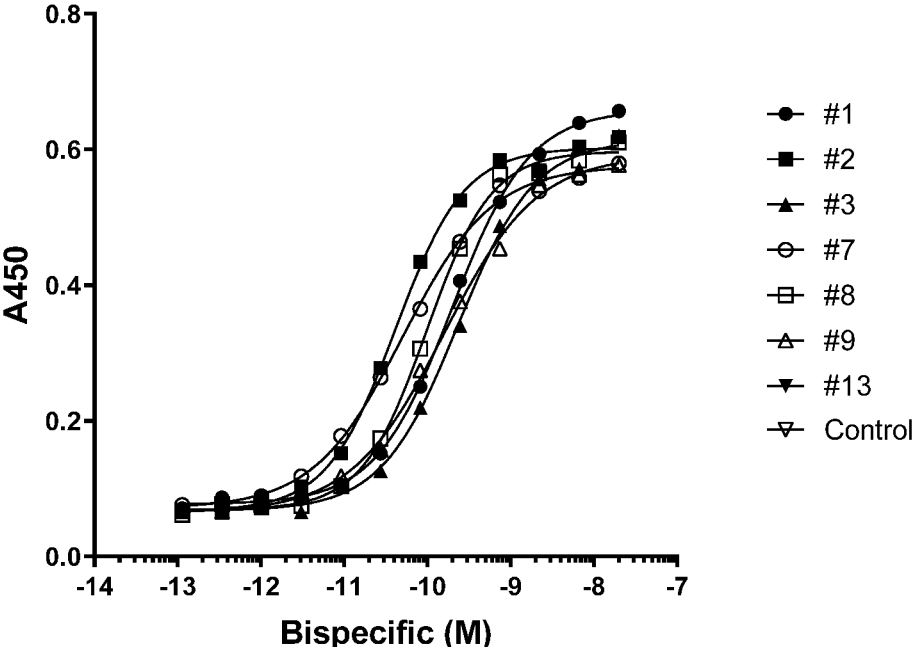
FIG. 6 is a pair of graphs showing the binding of bispecific constructs to immobilized human ROR1 as characterized by ELISA.
Figure 6:
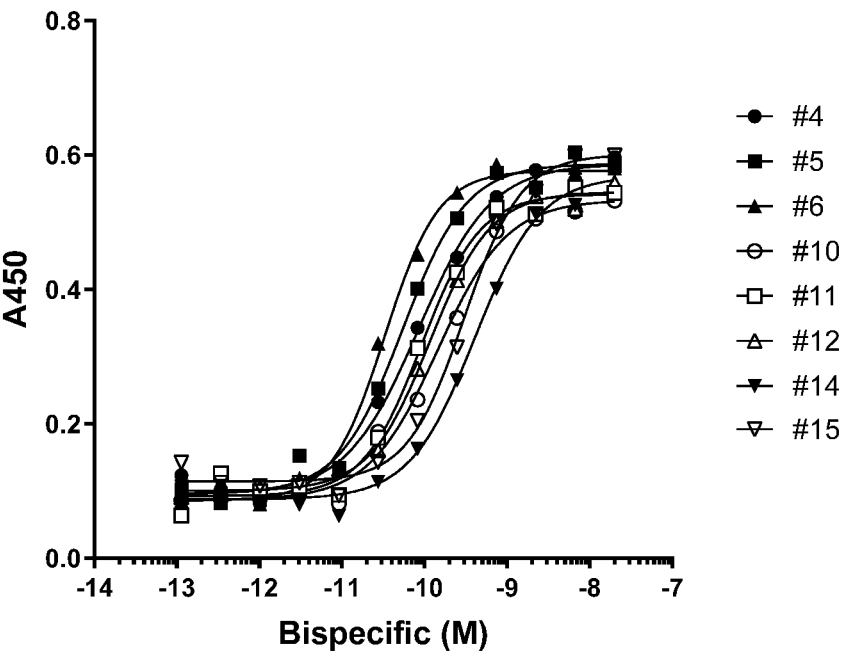
Figure 7:
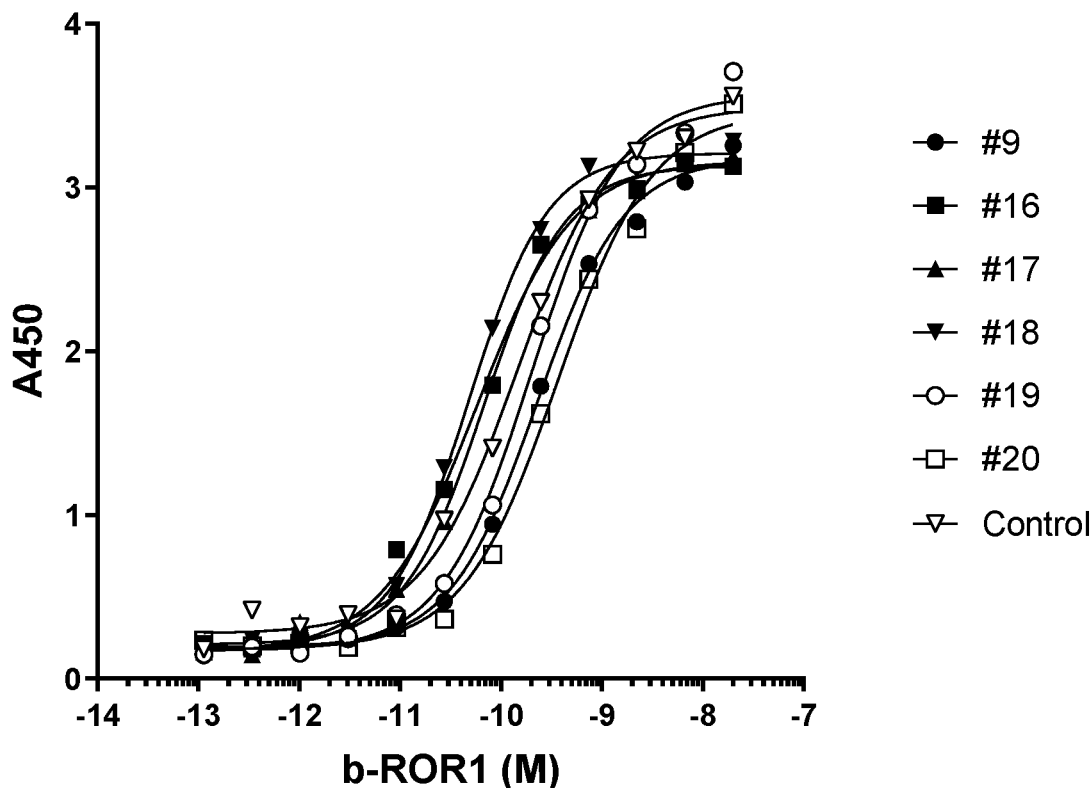
FIG. 7 is a graph showing the binding of bispecific constructs to soluble, biotinylated human ROR1 as characterized by ELISA.

Next, the binding of bispecific binding molecules to ROR was characterized by ELISA using recombinantly-expressed extracellular domain of RORL. ROR was immobilized on a microtiter plate, the bispecific binding molecules were titrated, and binding was quantitated with an anti-human kappa-HRP reagent. Consistent with the cell binding data, all constructs bound ROR1 in a concentration-dependent manner (FIG. 6). Moreover, monovalent ROR1 constructs 13-15 bound less tightly than all but two of the bivalent constructs. The binding activities of the bivalent bispecific binding molecules were similar to the parental anti-ROR1 IgG (Control), demonstrating that appending scFv domains to the Ig molecule did not inhibit ROR1 binding. The relative affinities of the bispecific constructs tested in this format are summarized in Table 4.

The stronger binding observed with bivalent constructs versus monovalent constructs in cell assays and ELISAs in which the antigen is immobilized is consistent with an avidity effect. To determine if this was the case, binding to soluble monomeric ROR1 was assessed by immobilizing the bispecific binding molecules on a microtiter plate coated with goat anti-human kappa antibody and titrating biotinylated RORL. All bispecific binding molecules were active in this format (FIG. 7), and in most cases, there were no notable differences between monovalent and bivalent constructs. These results are consistent with an avidity effect, depending on the assay format used. Weaker binding was observed with both variants in which the anti-CD3 scFv was amended to the amino terminus of the heavy or light chain (constructs 19 and 20, respectively), suggesting that placement of the CD3 paratope in close proximity to the ROR1 paratope may inhibit ROR1 binding to some extent.

Bispecific binding molecule constructs containing a higher affinity ROR1 binding domain (constructs 16-18) bound biotinylated ROR1 with higher affinity than the corresponding constructs that utilized the wild-type (lower affinity) ROR1 binding domain (constructs 9, 19, 20). Bispecific construct 18 (bivalent, higher affinity ROR1) bound more tightly than the corresponding construct 9 (bivalent, lower affinity ROR1). Likewise, bispecific constructs 16 and 17 (monovalent, higher affinity ROR1) bound more tightly than construct 15 (monovalent, lower affinity ROR1). These data are summarized in Table 4. Additionally, bispecific binding molecules with the higher affinity ROR1 binding domain bound soluble ROR1 with higher affinity than the parental IgG (Control).

TABLE 4

| Bispecific Binding Molecule Affinities for ROR1 | | |
| --- | --- | --- |
| | $K_D$ (nM) | |
| Construct | Immobilized ROR1 | Soluble b-ROR1 |
| 1 | 0.200 | 0.193 |
| 2 | 0.041 | 0.129 |
| 3 | 0.233 | 0.147 |
| 4 | 0.085 | 0.105 |
| 5 | 0.055 | 0.070 |
| 6 | 0.033 | 0.082 |
| 7 | 0.050 | 0.118 |
| 8 | 0.098 | 0.151 |
| 9 | 0.158 | 0.268, 0.229 |

TABLE 4-continued

Bispecific Binding Molecule Affinities for ROR1

| | $K_D$ (nM) | |
| --- | --- | --- |
| Construct | Immobilized ROR1 | Soluble b-ROR1 |
| 10 | 0.144 | 0.094 |
| 11 | 0.092 | 0.073 |
| 12 | 0.116 | 0.086 |
| 13 | 0.194 | 0.226 |
| 14 | 0.408 | 0.109 |
| 15 | 0.301 | 0.157 |
| 16 | | 0.057 |
| 17 | | 0.068 |
| 18 | | 0.048 |
| 19 | | 0.200 |
| 20 | | 0.366 |
| Control | 0.037 | 0.158, 0.145 |

Example 3: ROR1 Internalization by Anti-ROR1/Anti-CD3 Bispecific Binding Molecules Internalization and recycling of ROR1 and bispecific binding molecules that recognize ROR1 may impact therapeutic efficacy in vivo. For example, binding, internalization and degradation of ROR1 prior to engagement of T cells might be expected to diminish cytotoxicity. Anti-ROR1/anti-CD3 bispecific binding molecules with five distinct configurations were characterized for binding and internalization.

Simultaneous with characterizing the internalization of the various bispecific constructs, cell surface expression of ROR1 was examined using two different ROR1 antibodies. One antibody (UC961) recognizes the same ROR1 epitope as the bispecific binding molecules while the other (4A5) recognizes a non-overlapping ROR1 epitope.

In addition, cell surface binding of bispecific binding molecules was assessed following a 24 h incubation at 37° C. to determine if prolonged exposure influenced cell surface levels of the various binding molecules.

The internalization of ROR1 bispecific binding molecules and the recycling/re-expression of ROR1 was characterized using ROR1-transfected MEC cells and flow cytometry.

Materials and Methods

Measurement of Internalization of Bispecific Binding Molecules

Internalization of bispecific binding molecules was measured using a pulse-chase methodology that quantitates non-internalized, cell surface antibody at 0, 30, 60, 120, 180, and 240 minutes using flow cytometry. ROR1-transfected MEC cells were washed with cold PBS and resuspended at $1\times10^7$ per mL in cold incubation buffer (RPMI with 2% FBS—Fisher/Gibco cat. #16140071). Then, $3.5\times10^6$ cells were aliquoted to microcentrifuge tubes for each bispecific construct tested. An equal volume (350 μL) of bispecific binding molecule was combined with the cells to make a final concentration of 30 μg/mL. Based on previous binding studies, it was expected that 30 μg/mL would be saturating for the higher affinity/avidity of the bivalent ROR1 constructs (constructs 1-12). Cells and antibody were incubated on ice for 20 minutes, washed five times with 1 mL of cold FACS buffer (PBS with 2% FBS), and resuspended in 1.4 mL of incubation buffer. Subsequently, the samples were incubated at 37° C. for 0, 30, 60, 120, 180, and 240 minutes after which time 200 μL of each sample was transferred to ice to halt internalization.

Samples for each construct and timepoint were split in half (100 μL each) and spun down. Half of the samples were resuspended in 100 μL secondary antibody (goat anti-human IgG-PE, Fc-gamma specific—eBiosciences cat. #12-4998) to detect bound bispecific constructs. The other half was stained with 100 μL cocktail of UC961-PE and 4A5-AlexaFluor647. UC961 binds the same epitope as the bispecific constructs, thus detecting free ROR1 not bound by the bispecific binding molecules. 4A5 binds ROR1 at a different epitope, and therefore does not compete with the bispecific binding molecules for binding. Thus, 4A5 detects total cell surface ROR1 (bound and free). Both staining sets remained in incubation buffer for 20 minutes on ice in the dark. Cells were washed three times with FACS buffer and resuspended in 100 μL of fix buffer (2% paraformaldehyde in PBS) for 10 minutes at 25° C. Subsequently, fixed cells were washed once with FACS buffer and analyzed.

The median fluorescent intensity (MFI) was quantified for each stain. Several control conditions were used. The PE and A1647 MFI were measured for unstained control cells to use for background fluorescence subtraction. Cells not exposed to the bispecific constructs were stained with secondary antibody PE, to account for non-specific staining of the secondary antibody (secondary negative control), and with UC961-PE to obtain maximal UC961 binding control. Quantification of surface bispecific binding molecule, unoccupied cell surface ROR1 epitope, and total ROR1 was performed as follows:

$$\text{Surface } biAb = \frac{[(PE\ MFI \text{ of secondary at time point } x) - (PE\ MFI \text{ of secondary negative control})]}{[(PE\ MFI \text{ of secondary at time point } 0) - (PE\ MFI \text{ of secondary negative control})]}$$

$$\text{Total } RORl = \frac{[(A1647\ MFI \text{ of 4A5 at time point } x) - (A1647\ MFI \text{ of unstained cells})]}{[(A1647\ MFI \text{ of 4A5 at time point } 0) - (A1647\ MFI \text{ of unstained cells})]}$$

$$\text{Unoccupied epitope} = \frac{[(PE\ MFI \text{ of UC961 at time point } x) - (PE\ MFI \text{ of unstained cells})]}{[(PE\ MFI \text{ of maximal U961 binding control}) - (PE\ MFI \text{ of unstained cells})]}$$

Results

Previous experiments with the anti-ROR1 antibody used for constructing the bispecific binding molecules described herein demonstrated: (1) that the antibody was rapidly internalized, and (2) ROR1 re-appeared on the cell surface without bound antibody. This cell surface expression was either a result of ROR1 recycling from endosomal compartments or reflects rapid upregulation of ROR1 through de novo synthesis or trafficking of intracellular stores (see, e.g., U.S. Patent Publication 2018/0369406). The different bispecific constructs displayed variable internalization and ROR1 recycling/re-expression patterns (FIG. 8 and FIG. 9).

Figure 8:
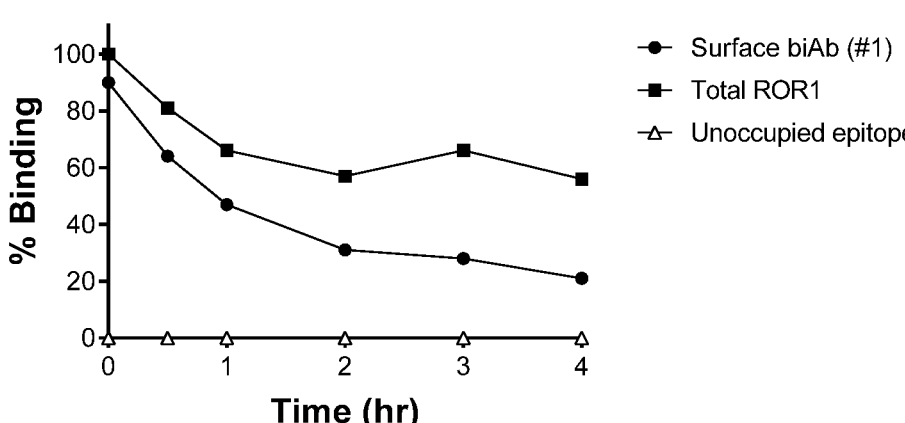
FIG. 8 is a set of graphs showing cell surface levels of bispecific binding molecules bound to ROR1 ("Surface biAb"), cell surface levels of free ROR1 not bound by bispecific binding molecules ("Unoccupied epitope"), and total cell surface ROR1 ("Total ROR1"), for ROR1-transfected MEC cells incubated with construct 1 (Panel A), construct 7 (Panel B), and construct 13 (Panel C).
Figure 8:
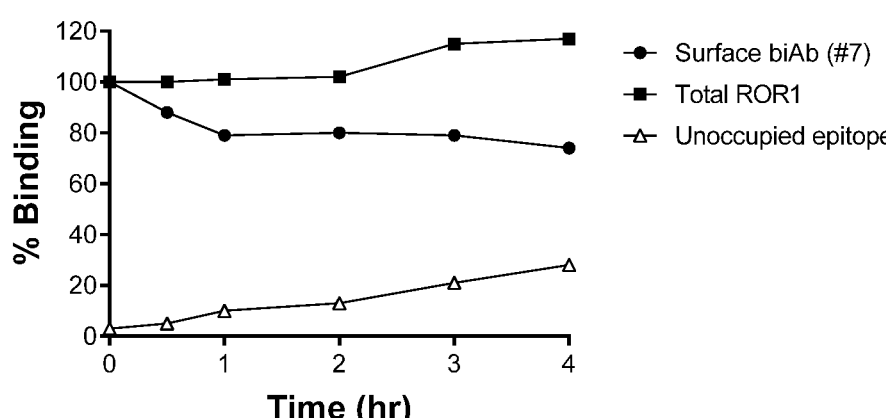
Figure 8:
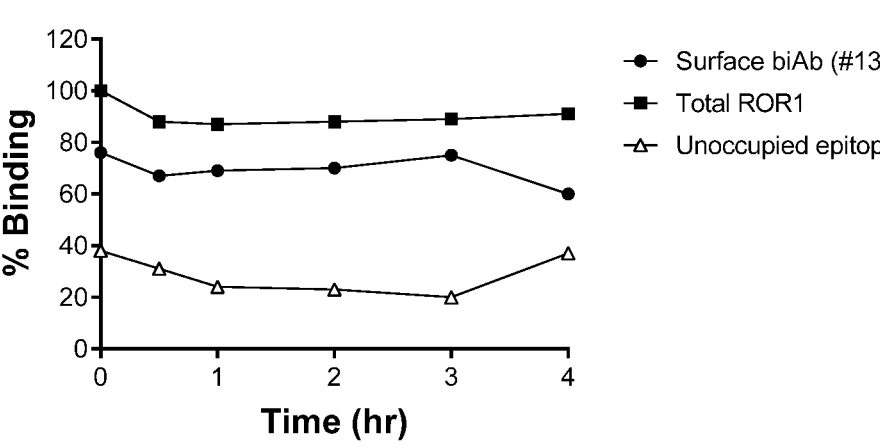
Figure 9:
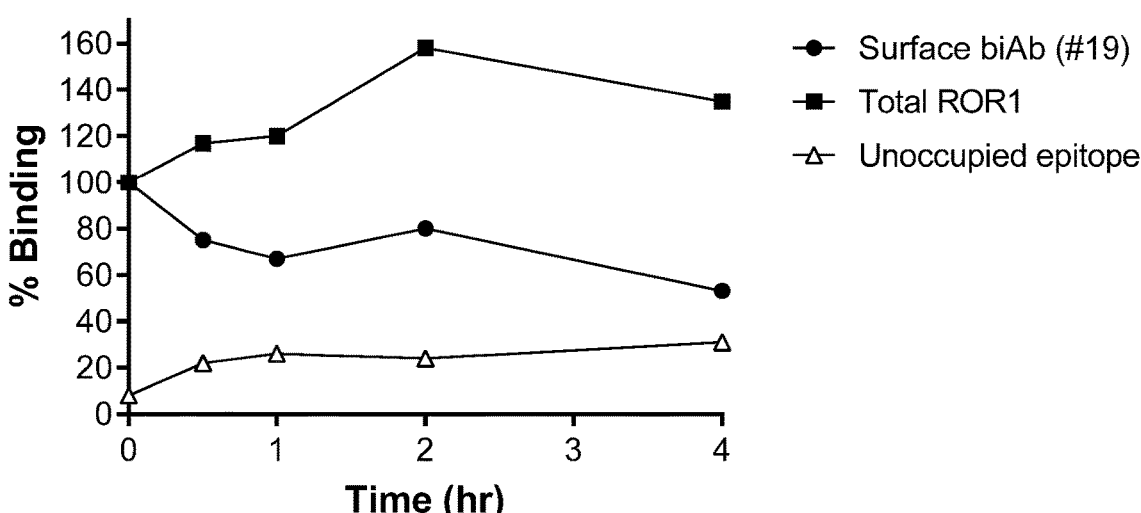
FIG. 9 is a pair of graphs showing cell surface levels of bispecific binding molecules bound to ROR1 ("Surface biAb"), cell surface levels of free ROR1 not bound by bispecific binding molecules ("Unoccupied epitope"), and total cell surface ROR1 ("Total ROR1"), for ROR1-transfected MEC cells incubated with construct 19 (Panel A) and construct 20 (Panel B).
Figure 9:
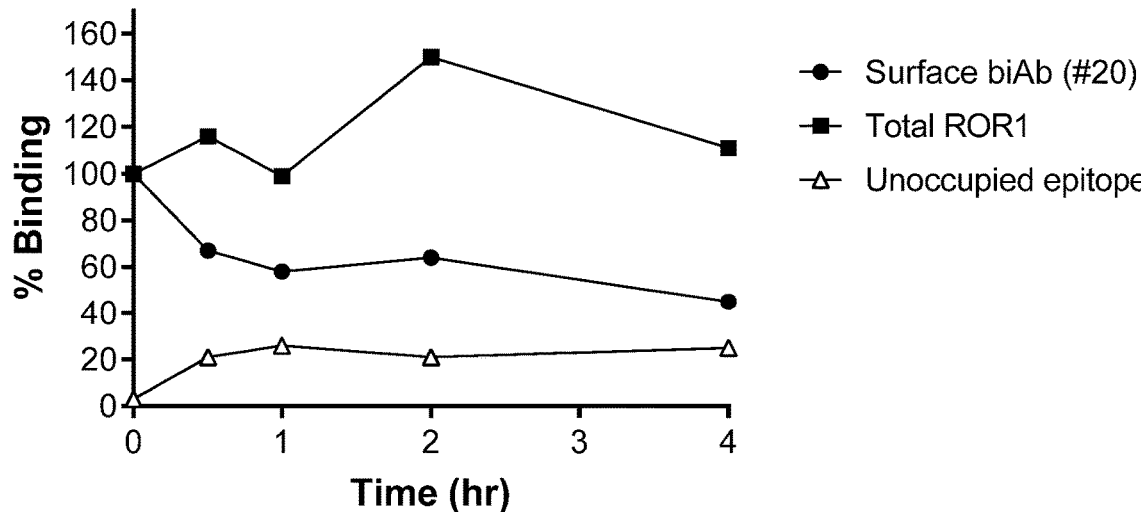

Placement of anti-CD3 scFv at the carboxy-terminus of the heavy chain (configuration A, construct 1) led to rapid internalization (FIG. 8, Panel A, circles). At time zero, the available ROR1 bispecific epitope was saturated, since no free epitope was detected. ROR1 was not recycled to the cell surface or re-expressed at significant levels during the experimental time course, as total ROR1 surface levels decreased (FIG. 8, Panel A, squares) and there was no detection of the free ROR1 epitope recognized by the bispecific binding molecule (FIG. 8, Panel A, triangles). These data are consistent with internalization of the bispecific binding molecule-ROR1 complex and trafficking to lysosomes. Very similar internalization and trafficking was observed with bispecific binding molecule constructs 2 and 3 (not shown).

Placement of anti-CD3 scFv at the carboxy-terminus of the light chain (configuration B, construct 7) inhibited internalization significantly (FIG. 8, Panel B, compare extent of internalization relative to construct 3 in FIG. 8, Panel A). At time 0, the construct has fully saturated its epitope. Total cell surface ROR1 levels appeared relatively constant (FIG. 8, Panel B, squares). In addition, the free ROR1 epitope recognized by the bispecific increased in a time-dependent manner (FIG. 8, Panel B, triangles), consistent with either dissociation of the bispecific binding molecule from the cell surface or recycling/re-expression of RORL. Very similar internalization and trafficking was observed with bispecific binding molecule constructs 8 and 9 (not shown).

Monovalent anti-ROR1 (configuration C, construct 13) also was not internalized efficiently (FIG. 8, Panel C). Previous studies demonstrated that binding of bivalent constructs was saturating at 30 µg/mL (FIG. 4, Panel A and FIG. 5). However, binding of monovalent anti-ROR1 bispecific binding molecules at 30 µg/mL did not appear to saturate cell surface ROR1 in this experiment. At time 0 the binding extent of construct 13 was only ~80% of that of the corresponding saturated MFI of constructs 1 and 7 at time 0 (FIG. 8, Panel C, compare circles with squares at time 0). Additionally, free ROR1 epitope recognized by construct 13 was also detected at time 0 (FIG. 8, Panel C, triangles). In summary, the levels of monovalent bispecific binding molecule construct 13, total cell surface ROR1 and unoccupied bispecific epitope all remained relatively constant over the duration of the experiment. Collectively, these data are consistent with little internalization of the bispecific binding molecule 13. Very similar internalization and trafficking was observed with construct 15 (not shown).

Placement of anti-CD3 scFv at the amino-terminus of one heavy chain (configuration D, construct 19) led to partial internalization (FIG. 9, Panel A, circles). ROR1 was recycled to the cell surface or re-expressed at significant levels during the experimental time course, as total ROR1 surface levels increased (FIG. 9, Panel A, squares) and there was increased, time-dependent detection of the ROR1 epitope recognized by the bispecific binding molecule (FIG. 9, Panel A, triangles). Placement of an anti-CD3 scFv moiety at the amino-terminus of one heavy chain resulted in internalization and trafficking very similar to bispecific binding molecules with configuration B (anti-CD3 scFv fused to the carboxy-terminus of the light chain).

Placement of anti-CD3 scFv at the amino-terminus of the light chain (configuration E, construct 20) led to partial internalization (FIG. 9, Panel B, circles). ROR1 was recycled to the cell surface or re-expressed at significant levels during the experimental time course, as total ROR1 surface levels increased (FIG. 9, Panel B, squares) and there was increased, time-dependent detection of the ROR1 epitope recognized by the bispecific binding molecule (FIG. 9, Panel B, triangles). Placement of an anti-CD3 scFv moiety at the amino-terminus of the light chain resulted in internalization and trafficking very similar to bispecific binding molecules with configuration B (anti-CD3 scFv fused to the carboxy-terminus of the light chain).

Figure 10:
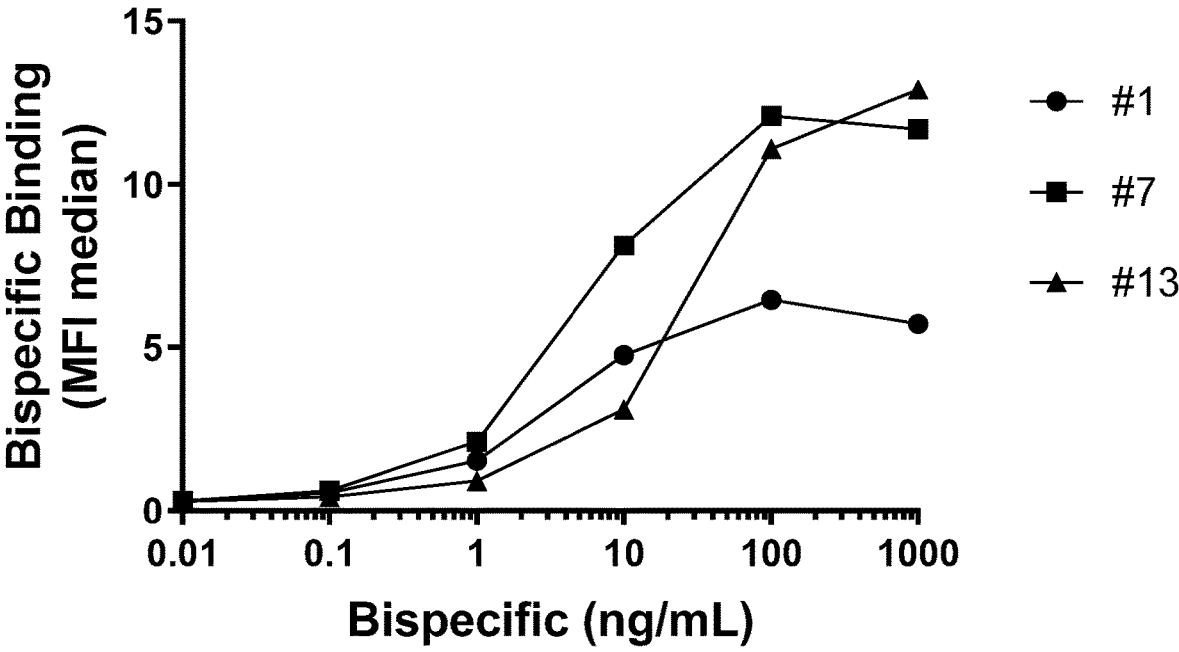
FIG. 10 is a graph showing quantitation of bispecific constructs 1, 7, and 13 on the surface of ROR-1 transfected MEC cells after incubation for 24 h.

To determine the long term impact of ROR1 trafficking and expression on the levels of bispecific binding molecules bound to the cell surface, cells were incubated with the bispecific binding molecule for 24 h, washed, and cell surface bispecific binding molecule was measured. Quantitation of surface bispecific binding molecule after 24 h incubation revealed that bispecific binding molecules with anti-CD3 scFv fused to the carboxy-terminus of the heavy chain (FIG. 10, construct 1, circles) were present at lower levels than bispecific binding molecules with the anti-CD3 scFv fused to the carboxy-terminus of the light chain (FIG. 10, construct 7, squares) or bispecific binding molecules with the anti-CD3 scFv fused to the amino-terminus of the Fc (FIG. 10, construct 13, triangles). Diminished cell surface levels of constructs in which anti-CD3 scFv is fused to the carboxy-terminus of the heavy chain, but not other bispecific configurations, suggests down-regulation of surface ROR1 and is consistent with the observations made in the internalization experiments (FIG. 8).

Example 4: CD3 Binding and Internalization of Anti-ROR1/Anti-CD3 Bispecific Binding Molecules The number of TCR-CD3 complexes on the surface of T cells reflects the combination of synthesis and secretion of new protein, internalization, recycling and degradation. Treatment with anti-CD3 antibody OKT3 has been shown to selectively remove CD3 from the surface by internalization.

Three anti-CD3 sequences were used as scFv constructs in anti-ROR1/anti-CD3 bispecific binding molecules. Two of the sequences are different humanized versions of OKT3 (Ab8 and Ab9) while the third sequence is a third party humanized version of a different anti-CD3 antibody, SP34 (Ab10). As noted above, OKT3 and SP34 bind distinct epitopes, and anti-CD3 antibodies have been classified based on distinct characteristics of their epitopes (Tunnacliffe et al., *International Immunology* 1:546-550 (1989)). Using this system, SP34 is classified as Group I while OKT3 is classified as Group II. The SP34-based sequence, but not the OKT3-based sequences, are expected to be cross-reactive with cynomolgus CD3.

The various CD3 paratopes were evaluated in five distinct configurations (FIG. 1, A-E) and the binding of monovalent anti-CD3 bispecific constructs (FIGS. 1, C and D) was compared with certain bivalent anti-CD3 constructs (FIGS. 1, A, B and E). Disulfide-stabilized versions of all three scFv sequences were also evaluated in the various bispecific configurations.

The internalization of the various bispecific constructs in the absence of ROR1 engagement was assessed. The binding and internalization of the bispecific binding molecules was characterized using Jurkat cells and flow cytometry.

Materials and Methods

CD3 Binding Assay

To quantitate CD3 binding, 2.5E5 Jurkat cells were used for each condition. A 2× stock of the cells was made by resuspending the cells to 5E6/mL by placing in 50 µL of PBS with 2% FBS. Next, the cells were diluted with an equal volume of 2× stock of the test bispecific binding molecule. The cells and antibody were co-incubated on ice for 20 min. The cells were then washed 3 times with 300 µL of FACS buffer and were resuspended in 100 µL of goat anti-human Fc-PE conjugate antibody (Invitrogen cat. #12499882) at 1:500 dilution and incubated on ice with reduced light for 20 min. The cells were then washed 3 times with 300 µL of FACS buffer and fixed with 2% paraformaldehyde for 10 min at 25° C. The cells were washed 2 times with 300 μL of FACS buffer and analyzed on a Miltenyi MACSQuant Analyzer.

CD3 Internalization Assay

To quantitate internalization of the bispecific binding molecules, 2.5E5 Jurkat cells were co-incubated with 1 μg/mL of the bispecific binding molecule on ice for 20 min. The cells were then washed 3 times 300 μL with ice-cold FACS buffer and were resuspended in culture media and incubated at 37° C. At various times, cells were removed, washed with 300 μL ice-cold FACS buffer and processed as described above.

Results

Figure 11:
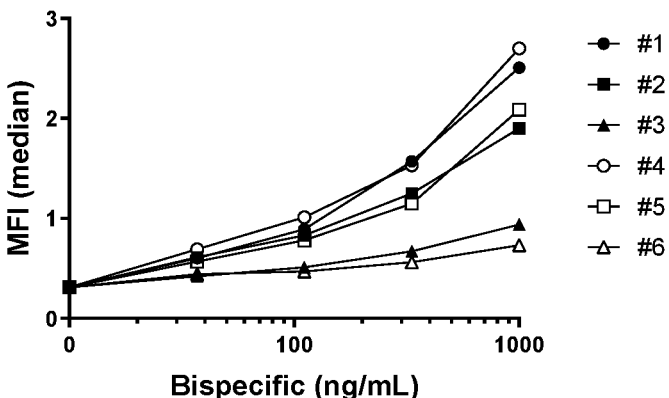
FIG. 11 is a set of graphs illustrating the binding to Jurkat cells of bispecific constructs 1-6 (Panel A), 7-12 (Panel B), and 13-15 (Panel C) as demonstrated by flow cytometry analysis. Non-specific human IgG was included as a control ("Control").
Figure 11:
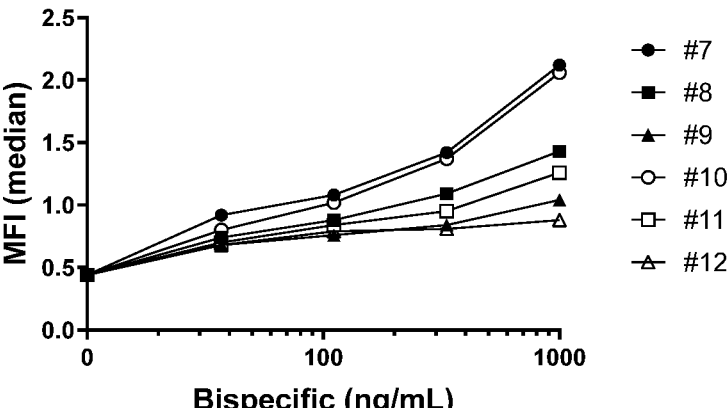
Figure 11:
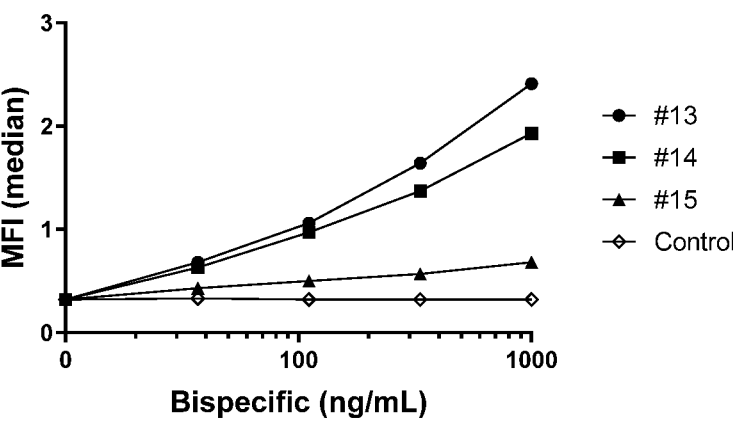

Five different bispecific configurations (FIG. 1) were evaluated. CD3 binding was preserved with both OKT3- and SP34-based sequences in all the bispecific configurations tested, as demonstrated by binding to Jurkat cells. The constructs bound to varying extents (FIG. 11 and FIG. 12).

For all bispecific configurations tested with either OKT3 and SP34 sequences (constructs 1-15), the OKT3-based sequences bound with higher affinity than the SP34-based sequences. For example, constructs 1 and 2 bound more tightly than 3 (FIG. 11, Panel A), constructs 7 and 8 bound more tightly than 9 (FIG. 11, Panel B) and constructs 13 and 14 bound more tightly than 15 (FIG. 11, Panel C). Non-specific human IgG was included as a control ("Control").

Introduction of cysteine residues to create disulfide-stabilized variants of the anti-CD3 scFv did not negatively impact binding. Binding of the disulfide-stabilized variants was indistinguishable from the corresponding non-disulfide stabilized sequence (FIG. 11, Panel A, compare constructs 1-3 with 4-6, respectively and FIG. 11, Panel B, compare constructs 7-9 with 10-12, respectively).

Figure 12:
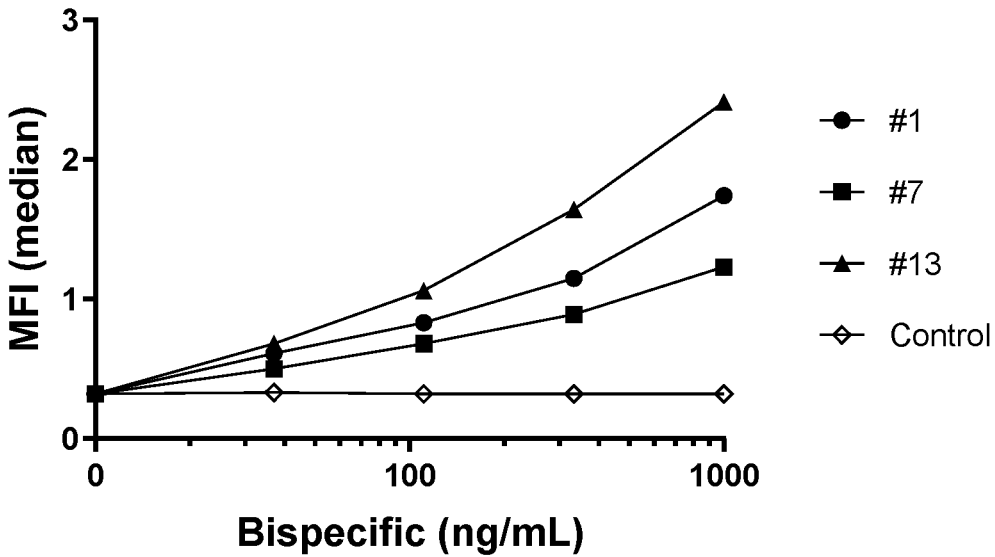
FIG. 12 is a pair of graphs illustrating the binding to Jurkat cells of bispecific constructs 1, 7, and 13 (Panel A), and bispecific constructs 3, 9, and 15-10 (Panel B), as demonstrated by flow cytometry analysis. Non-specific human IgG was included as a control in one experiment (Panel A, "Control") while an unrelated ROR1×CD3 bispecific construct (U.S. Patent Publication 2017/0233472) was included as a control in the second experiment (Panel B, "control 1").
Figure 12:
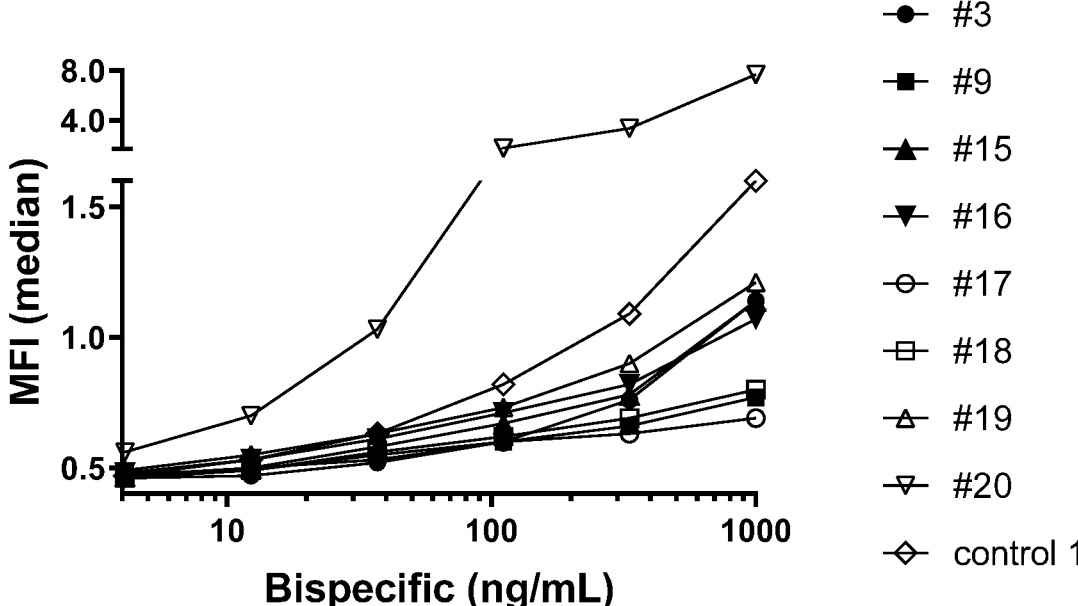

The configuration of the bispecific binding molecule had a profound effect on the binding of the anti-CD3 scFv (FIG. 12). The strongest binding to Jurkat cells was observed when the anti-CD3 scFv moiety was placed on the amino-terminus of the light chain (FIG. 12, Panel B, construct 20) or heavy chain (FIG. 12, Panel B, construct 19). Conversely, weaker binding was observed when the anti-CD3 scFv was placed at the carboxy-terminus of the light chain (FIG. 12, Panel B, constructs 9 and 18). A single anti-CD3 scFv moiety placed at the amino-terminus of one heavy chain (monovalent CD3 binding; FIG. 12, Panel B, construct 19) bound as well, or better than, placement of two anti-CD3 scFv moieties at the carboxy-terminus of the heavy chain (bivalent CD3 binding; FIG. 12, Panel B, construct 3) or light chain (bivalent CD3 binding; FIG. 12, Panel B, constructs 9 and 18). Non-specific human IgG was included as a control in one experiment (FIG. 12, Panel A, "Control") while an unrelated ROR1×CD3 bispecific construct (U.S. Patent Publication 2017/0233472; SEQ ID NOs: 111-113) was included as a control in the second experiment (FIG. 12, Panel B, "control 1").

Similar trends were observed with a subset of these bispecific configurations using OKT3 sequences. Specifically, monovalent anti-CD3 scFv fused to the amino-terminus of the Fc bound strongest (FIG. 12, Panel A, construct 13), followed by constructs in which the scFv was fused to the carboxy-terminus of the heavy chain (FIG. 12, Panel A, construct 1), followed by constructs in which the scFv was fused to the carboxy-terminus of the light chain (FIG. 12, Panel A, construct 7).

It is noteworthy that the configuration of the bispecific binding molecule appears to be a more important determinant of CD3 binding strength than the CD3 paratope valency. This surprising effect is highlighted by the observation that monovalent anti-CD3 constructs fused to the amino terminus of the heavy chain (FIG. 12, Panel B, construct 19) or Fc (FIG. 12, Panel A, construct 13 and FIG. 12, Panel B, constructs 15 and 16) bound as well or better than bivalent anti-CD3 constructs fused to the carboxy-terminus of the heavy and light chains (FIG. 12, Panel B, constructs 3, 9 and 18).

Collectively, these data demonstrate that there are three different approaches to modulating the strength of CD3 binding. First, SP34- and OKT3-based sequences display differing binding strengths when compared to one another in the same bispecific formats. Second, the binding strength of both SP34- and OKT3-based sequences is influenced by the configuration of the bispecific binding molecule. Finally, the use of heteromeric Fc constructs enables either monovalent or bivalent anti-CD3 bispecific binding molecules.

Figure 13:
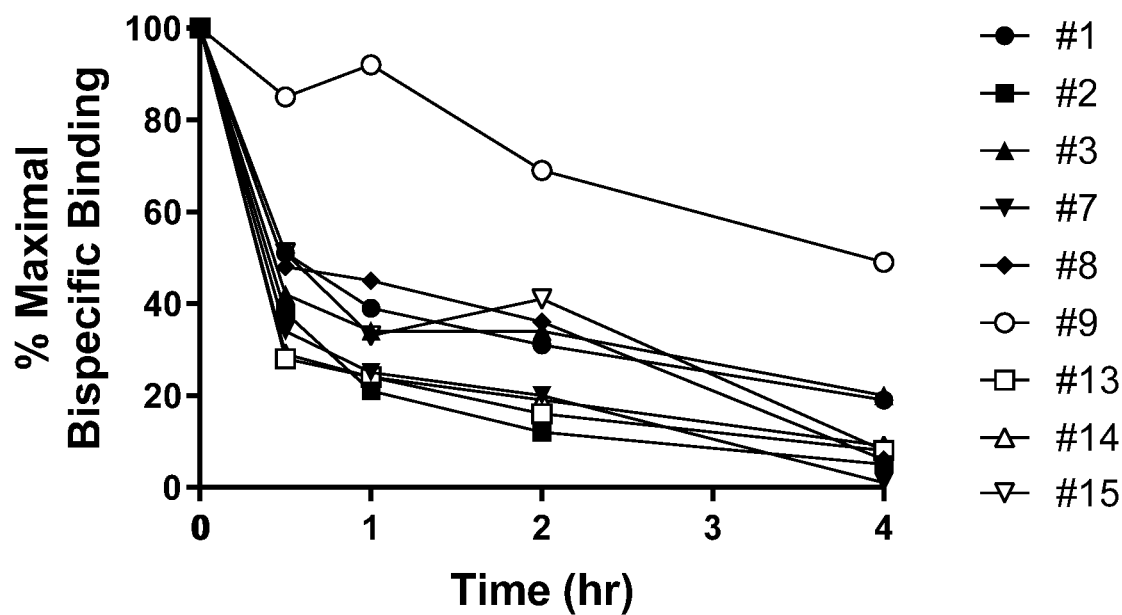
FIG. 13 is a graph quantitating levels of bispecific constructs 1-3, 7-9, and 13-15 on the surface of Jurkat cells over time following binding to CD3 in the absence of ROR1.

T cell activation by anti-CD3 antibodies may result in increased internalization of CD3. Once internalized, the CD3 may enter a recycling pathway and be re-expressed at the cell surface or may be sorted to the lysosomes and degraded. Internalization and degradation of CD3 induced by bispecific binding molecule in the absence of tumor antigen (ROR1) engagement may inhibit the cytotoxic activity of the bispecific binding molecule in vivo. Consequently, the bispecific binding molecules were characterized for internalization following binding to CD3 in the absence of ROR1 (FIG. 13).

Following the binding of bispecific binding molecule and washing at 4° C., Jurkat cells were incubated at 37° C. Subsequently, the amount of bispecific binding molecule on the cell surface was quantitated at various time points. Because the bispecific binding molecules initially bound with different strengths (FIG. 11 and FIG. 12), the internalization was reported as a percentage of binding observed at time 0. The level of surface bispecific binding molecule quantitated in this manner reflects a combination of internalization and dissociation. Nonetheless, for reasons outlined below, it appeared that the primary factor influencing surface levels was internalization and not dissociation of the bispecific binding molecules.

The level of surface bispecific binding molecule diminished in a time-dependent manner for all bispecific constructs tested, though the extent of loss varied. Rapid internalization (>50%) was observed within the first 30 min for eight of nine constructs tested, followed by a slower, but continuous internalization over the next 3.5 h. Construct 9, consisting of an SP34-based sequence fused to the carboxy-terminus of the light chain, was internalized the least over the duration of the experiment, with approximately 50% of the bispecific binding molecule still detectable on the cell surface after 4 h. In addition, constructs 1 and 3, consisting of the anti-CD3 scFv moiety fused to the carboxy-terminus of the heavy chain, displayed intermediate internalization, with ~20% still detectable on the cell surface after 4 h incubation.

As discussed previously, it is possible that the decreased staining of cell surface bispecific binding molecule observed over time reflects dissociation of the bispecific binding molecule from the surface as opposed to internalization. However, two of the bispecific constructs that displayed the least loss of signal over time, constructs 3 and 9, were among the weakest binding constructs characterized (FIG. 11, Panel A and Panel B, respectively) while the binding of construct 13, which displayed very strong binding at time 0 (FIG. 11, Panel C), stained weakly at 4 h (8% of initial signal). Collectively, these data suggest that certain configurations consisting of SP34-based anti-CD3 scFv moieties may internalize to a lesser extent than configurations consisting of OKT3-based scFv moieties.

Example 5: Redirected T Cell Toxicity of Anti-ROR1/Anti-CD3 Bispecific Binding Molecules In Vitro The twenty anti-ROR1/anti-CD3 bispecific binding molecules were tested to evaluate the impact of multiple parameters on antibody potency in T-cell mediated cytotoxicity assays. Variables examined included anti-CD3 epitope and valency, anti-ROR1 affinity and valency, and various configurations of the CD3 and ROR1 binding components.

The killing activity of the constructs was tested against a panel of hematological and solid tumor cancer cells with varying levels of ROR1 expression. In addition to characterizing the killing activity of the bispecific binding molecules, activation of T cells was assessed using CD69 as a marker. Cytokine release by activated T cells was also characterized.

Materials and Methods

Cytotoxicity Assay with Human PBMCs

For the cytotoxicity assay, target cells were resuspended to 4E5 cells/mL in RPMI (without phenol red), 10% FBS containing penicillin-streptomycin. Subsequently, 2E4 cells/well (50 µL/well) were transferred to a 96-well plate and placed in an incubator at 37° C. for 1 h. Round bottom plates were used for suspension cells and flat bottom plates for adherent cell lines. Human PBMCs were isolated as described below. The PBMCs were resuspended to 2E6 cells/mL, and subsequently, 2E5 cells/well (100 µL/well) were added to the wells containing the target cells. Unless indicated otherwise, the ratio of PBMCs (effector cells) to tumor cells (target) used was 10:1 (E:T ratio). The target cells and PBMCs were mixed and placed in an incubator at 37° C. for 1 h. The bispecific binding molecules were diluted to the appropriate concentration in media and 50 µL was added to the mixture of target cells and PBMCs and then placed in an incubator for 24 h at 37° C. The following controls were included for each experiment: (1) media only (Media), (2) media adjusted for lysis buffer (Adj), (3) PBMCs only (PBMCs), (4) target cell only for spontaneous release of LDH (SR), (5) target cell only for maximal release of LDH (MR), and (6) target cells and PBMCs without bispecific binding molecule (AICC).

Isolation of PBMCs

The lower chamber of SepMate-50 (StemCell Technologies) conical tubes was filled with 15 mL of Ficoll. Blood was obtained from de-identified normal donors in heparin blood collection tubes and was mixed in a 1:1 ratio with sterile PBS at 25° C. The diluted blood was layered on the top chamber of the SepMate-50 tubes and was centrifuged at 1200×g for 15 min at 25° C. with brakes. To obtain the PBMCs (top chamber contents), the SepMate-50 tubes were inverted quickly into a fresh 50 mL conical tube. The cells were then washed three times with cold 5% FBS in PBS by centrifugation at 500×g for 3 minutes. Finally, the cells were resuspended in 10 mL of media (RPMI without phenol red, 10% FBS containing penicillin-streptomycin) and an aliquot was removed for cell count. Cells were then used for plating the cytotoxicity assay.

Quantitation of LDH Release

To quantitate LDH release after 24 h incubation, 20 µL of 10× lysis buffer was added to the Adj and MR wells and the content of each well was transferred to a V-bottom 96 well plate and spun down at 500×g for 5 minutes. Subsequently, 170 µL of supernatant was transferred to a separate 96 well plate to use for subsequent assays. In a fresh clear bottom 96 well plate, 50 µL of supernatant was combined with 50 µL of CytoTox 96 Non-Radioactive Cytotoxicity Assay (Promega cat. #G1780) and the plate was incubated in the dark at 25° C. for 30 minutes. Finally, 50 µL of stop solution was added prior to reading the absorbance at 490 nm. The % LDH release was calculated per manufacturer's instructions.

Assessment of T Cell Activation

Up-regulation of CD69 was used to characterize the early activation of the T cells. Quantitation of CD69 was performed using flow cytometry. Briefly, the pelleted cells were fixed by resuspending in 100 µL of 2% PFA in PBS and incubating for 10 min at 25° C. The cells were washed twice with 300 µL of PBS, resuspended in 150 µL of PBS, and were stored at 4° C. in the dark until use. Subsequently, the cells were collected by centrifugation and were resuspended in 100 µL of stain cocktail and incubated for 20 min at 4° C. in the dark. The stain cocktail consisted of Pacific Blue anti-human CD8 clone SK1 (BioLegend cat. #344717) diluted 1:75, PECy7 anti-human CD69 clone FN50 (BioLegend cat. #310911) diluted 1:500, and AlexaFluor647 mouse anti-human ROR1 clone 4A5 diluted 1:500 in PBS. The cells were then washed three times with 300 µL of cold PBS and were resuspended in 150 µL of 2% FBS in PBS. The samples were analyzed on a Mitenyi MACSQuant Analyzer.

Quantitation of Cytokine Release from PBMCs in Redirected T-cell Assay

To measure cytokine release, the MSD® V-PLEX Cytokine Panel 1 Human Kit was used to concurrently measure IFN-γ, IL-2, IL-4, IL-6, IL-10 and TNF-α. The assay was conducted per manufacturer's instructions. Briefly, the V-plex Cytokine Panel 1 plate was washed 3 times with 150 µL/well of Wash Buffer (PBS with 0.05% Tween-20). Next, 50 µL of diluted samples and calibrators were added per well. The plate was sealed with an adhesive plate seal and incubated on a shaker overnight at 4° C., 500 rpm. The following day the plate was washed 3 times with 150 µL/well of Wash Buffer and incubated with 25 µL of detection antibody solution on a shaker for 2 hours at room temperature. The plate was washed 3 more times with Wash Buffer. Lastly, 150 uL of Read Buffer T was added before analysis using the MSD instrument.

Results

Figure 14:
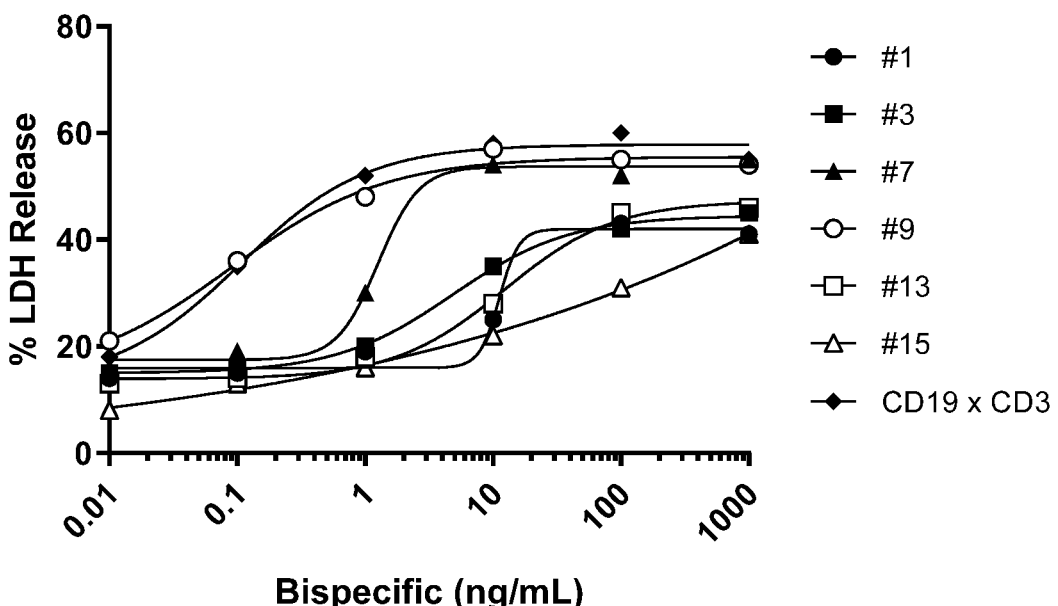
FIG. 14 is a pair of graphs quantitating LDH release from ROR1-transfected MEC cells (Panel A) and cell surface levels of CD69 on CD8$^+$ cells (Panel B), where ROR1-transfected MEC cells are incubated with (1) human PBMCs, and (2) bispecific constructs 1, 3, 7, 9, 13, and 15, and a control anti-CD19/anti-CD3 bispecific binding molecule ("CD19×CD3").
Figure 14:
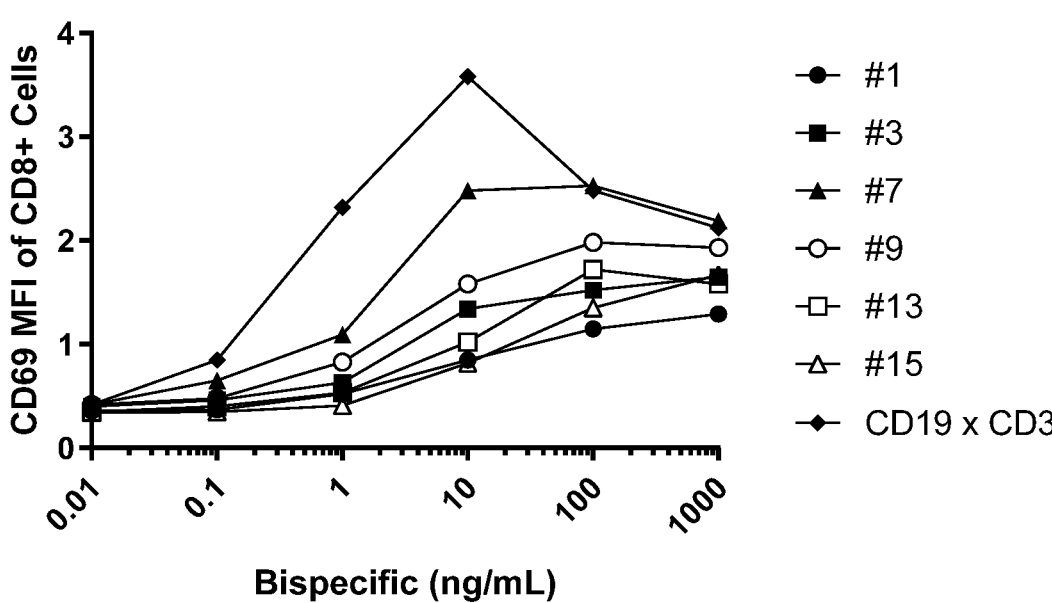

Antigen-dependent killing of ROR1-transfected MEC cells was observed with the majority of bispecific constructs tested, though the relative potencies varied. Representative titration profiles are shown in FIG. 14, Panel A (constructs with configurations A, B and C) and in FIG. 15, Panel A (constructs with configurations A, B, C, D and E). The titration profiles of constructs 2, 8, and 14 (not shown) were similar to the titration profiles of constructs 1, 7, and 13, respectively.

Figure 15:
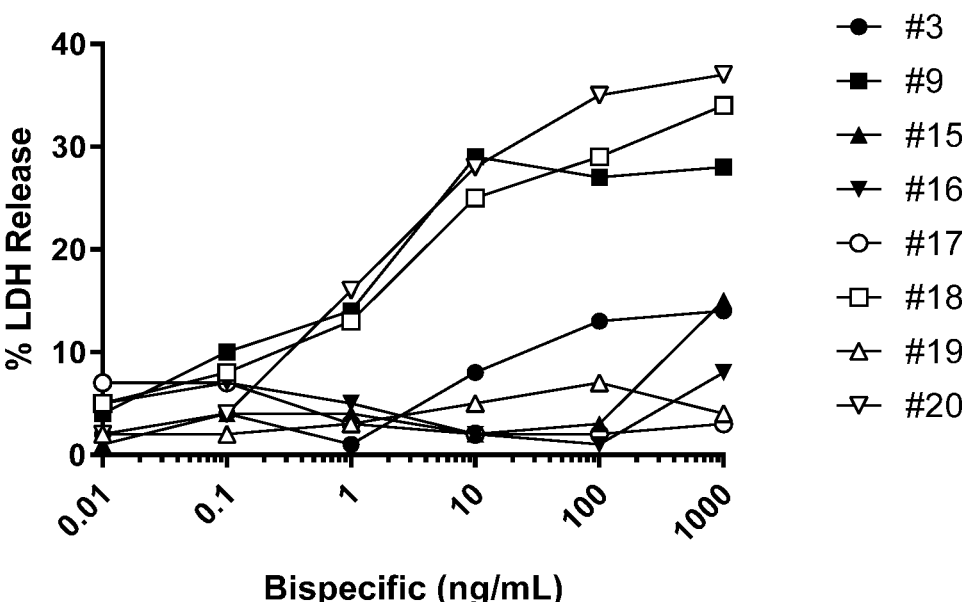
FIG. 15 is a pair of graphs quantitating LDH release from ROR1-transfected MEC cells (Panel A) and cell surface levels of CD69 on CD8$^+$ cells (Panel B), where ROR1-transfected MEC cells are incubated with human PBMCs and bispecific constructs 3, 9, and 15-20.
Figure 15:
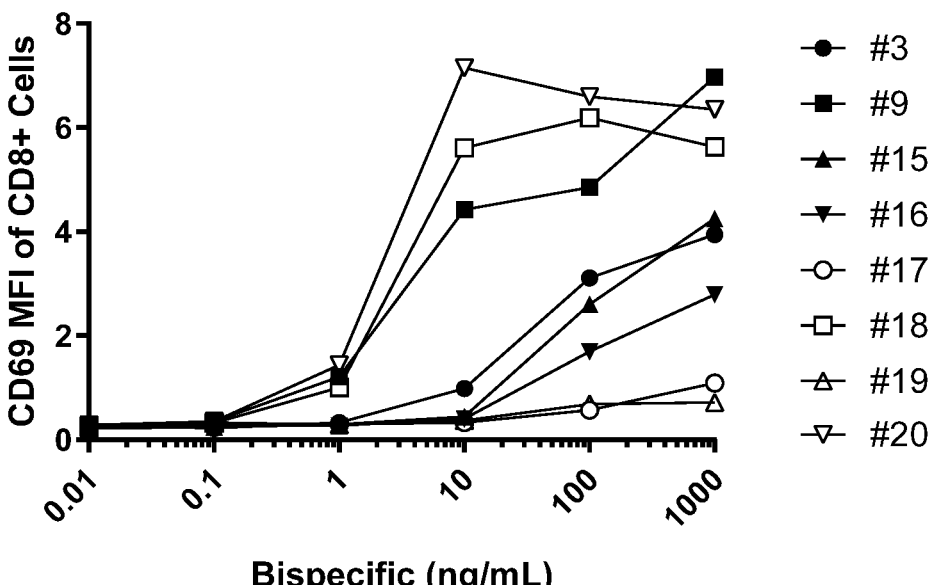

As expected, the absolute potency of the bispecific binding molecules varied to some extent when different PBMC donors were used. Nonetheless, the relative potencies of the different constructs did not fluctuate significantly. For example, bispecific binding molecule construct 9 was consistently one of the most active and with ROR1-transfected MEC target cells displayed an $EC_{50}$ of <0.1 ng/mL with one donor (FIG. 14, Panel A) and 1.1 ng/mL with a second donor (FIG. 15, Panel A).

Figure 16:
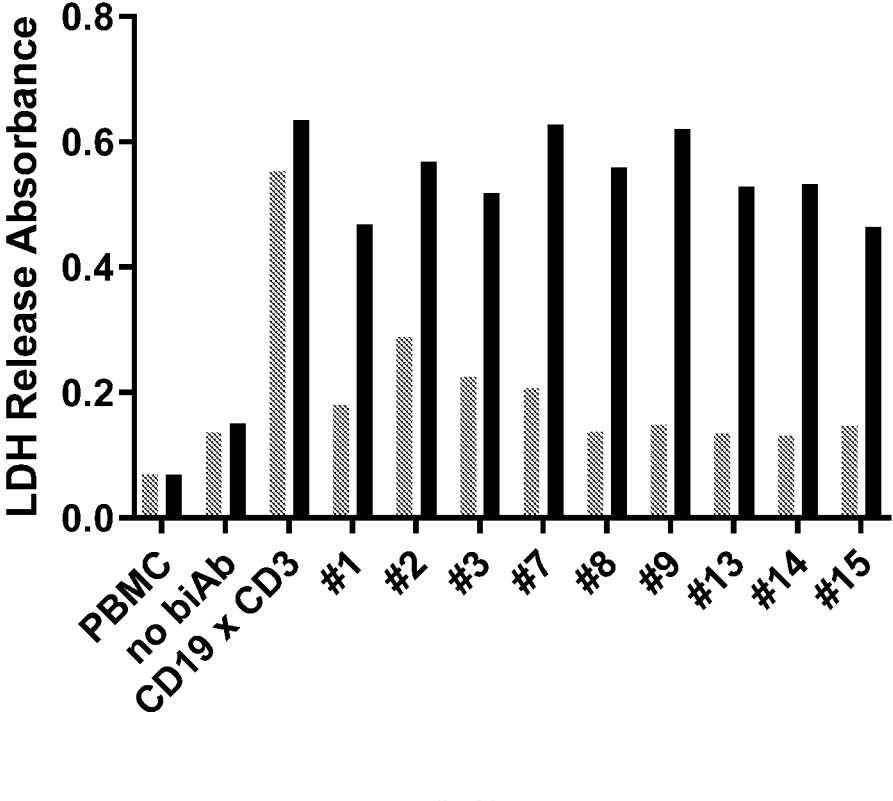
FIG. 16 is a graph comparing LDH release between ROR1-transfected and non-transfected MEC cells incubated with (1) PBMCs, and (2) bispecific constructs 1-3, 7-9, and 13-15 and an anti-CD19/anti-CD3 bispecific binding molecule control. LDH release is also assessed in samples that did not contain target cells ("PBMC") and samples that did not contain a bispecific construct ("no biAb").

Constructs 1-3, 7-9, and 13-15 all demonstrated selective killing at 1 µg/mL (5 nM for constructs 1-3 and 7-9, 8 nM for constructs 13-15 (FIG. 16, black bars). The antigen dependence of the killing was demonstrated by the lack of LDH release in samples that did not contain target cells (FIG. 16, "PBMC") or antibody (FIG. 16, "no biAb") or when non-transfected MEC cells were used as target cells (FIG. 16, gray bars). In contrast, a control anti-CD19/anti-CD3 bispecific binding molecule (Creative Biolabs cat. #BSAB-L002) induced cytotoxicity of both ROR1-transfected and non-transfected MEC cells (FIG. 16, "CD19× CD3"). Bispecific constructs 16-20 were not tested in this experiment.

Activation of T cells in the cultures was assessed by examining the upregulation of CD69, an early marker of T cell activation. Consistent with the cytotoxicity data, activation was observed with all constructs except for #17 and #19, at 1 μg/mL (FIG. 14, Panel B; FIG. 15, Panel B). For the more potent bispecific binding molecules, activation was observed at lower concentrations (FIG. 14, Panel B, compare 7 vs 3; FIG. 15, Panel B, compare 18 vs 3).

Figure 19:
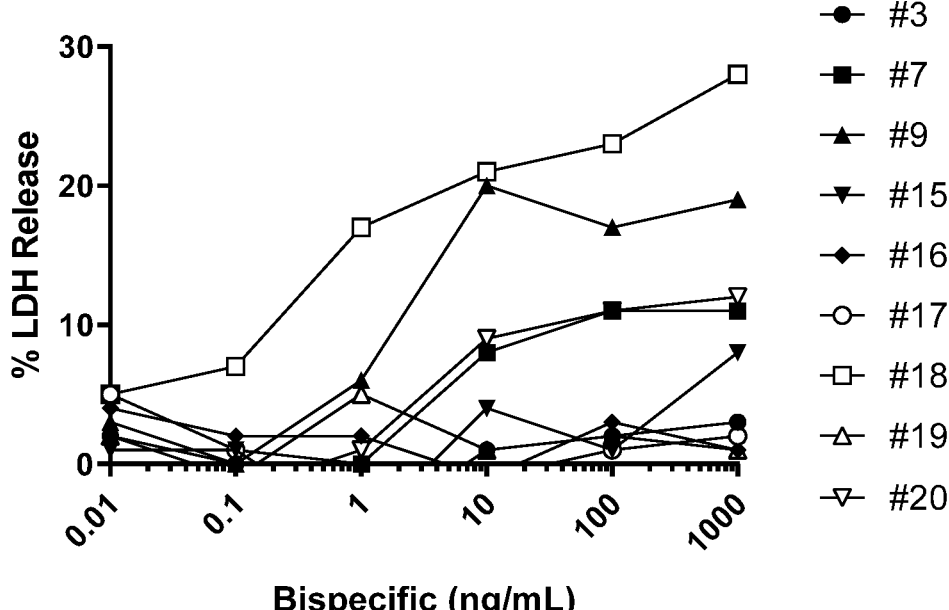
FIG. 19 is a pair of graphs quantitating LDH release from JeKo-1 cells (Panel A) and cell surface levels of CD69 on CD8$^+$ cells (Panel B), where JeKo-1 cells are incubated with human PBMCs and bispecific constructs 3, 7, 9, and 15-20.
Figure 19:
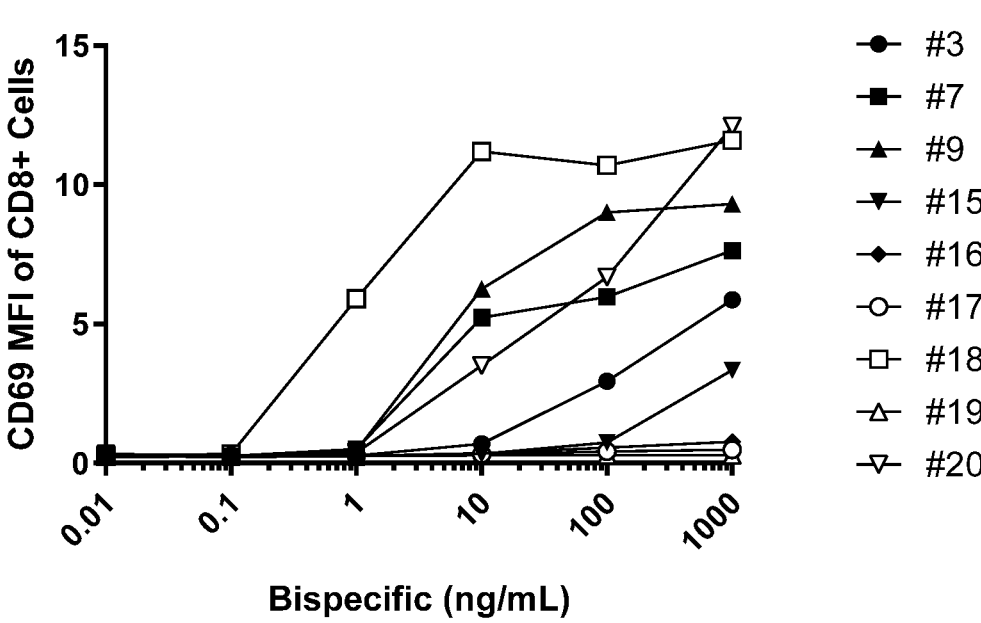
Figure 20:
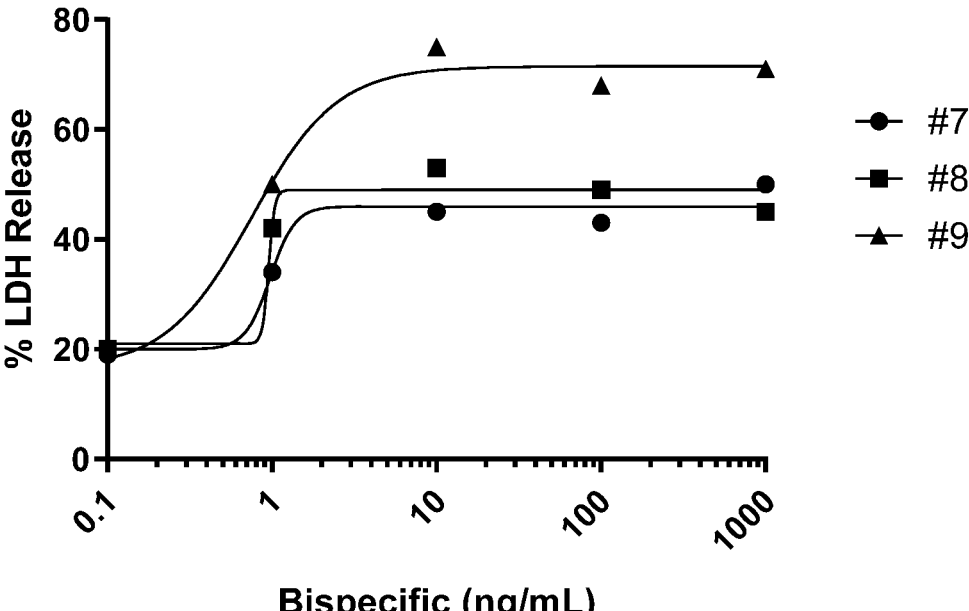
FIG. 20 is a pair of graphs quantitating LDH release from Mino cells (Panel A) and cell surface levels of CD69 on CD8$^+$ cells (Panel B), where Mino cells are incubated with human PBMCs and bispecific constructs 7-9.
Figure 20:
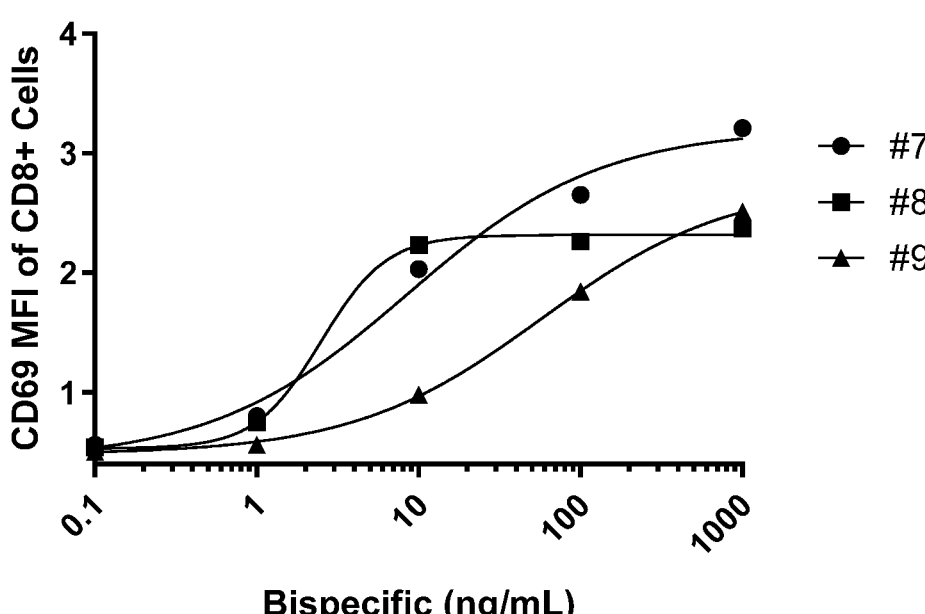

T cell activation, as assessed by increased CD69 expression, generally reflected the cytotoxic activity of the bispecific binding molecules. However, there were examples where CD69 activation was not directly correlated with cytotoxicity (FIG. 19, compare 7 and 9; FIG. 20, compare 7 versus 8 and 9).

Figure 17:
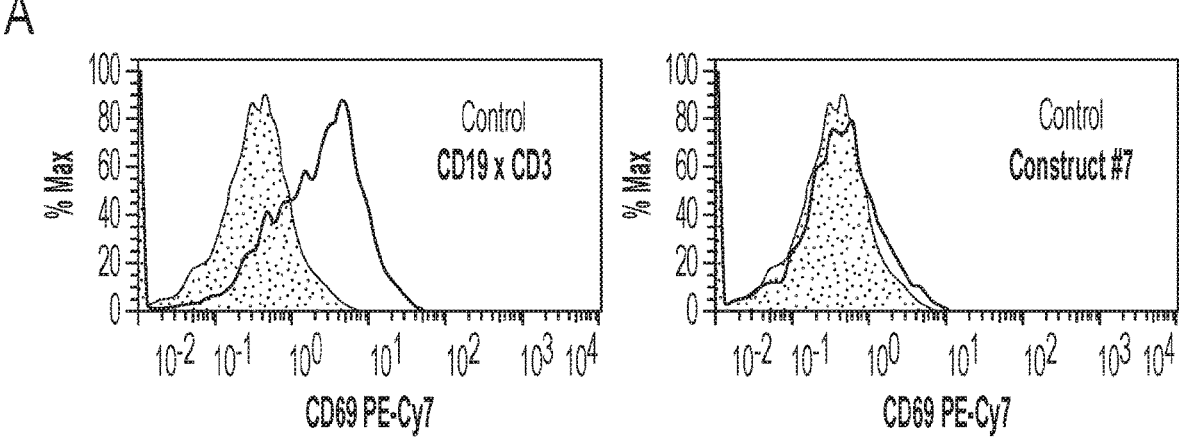
FIG. 17 is a set of graphs assessing CD69 levels on T cells, where ROR1$^-$/CD19$^+$ MEC cells (Panel A) or ROR1$^+$/CD19$^+$ MEC cells (Panel B) are incubated with (1) the T cells, and (2) bispecific construct 7 or a control anti-CD19/anti-CD3 bispecific binding molecule ("CD19×CD3").
Figure 17:
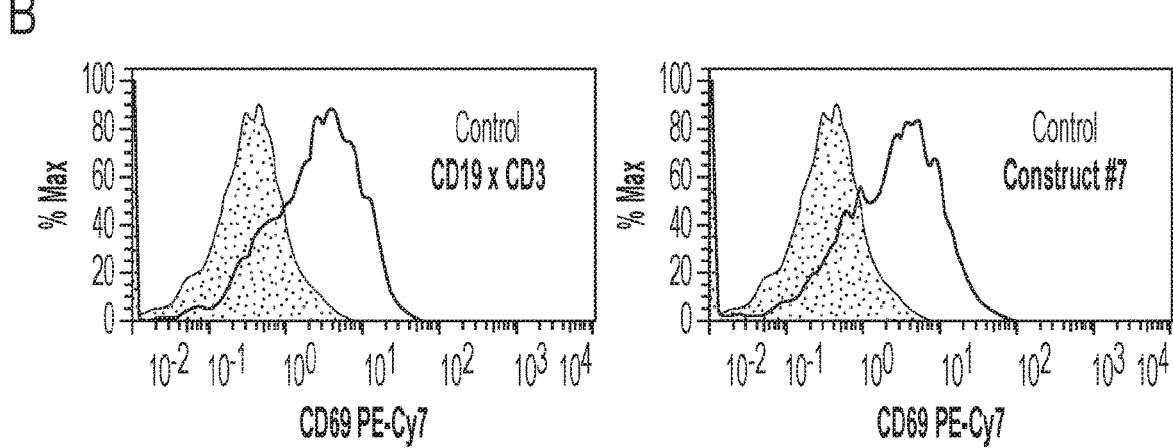

Activation of the T cells was antigen-dependent (FIG. 17). T cells co-cultured with ROR1$^-$/CD19$^+$ MEC cells were activated in the presence of the control CD19×CD3 bispecific binding molecule (FIG. 17, Panel A, left) but not in the presence of the ROR1 bispecific binding molecules (FIG. 17, Panel A, right). However, when T cells were co-cultured with ROR1-transfected MEC cells (ROR1$^+$/CD19$^+$) the T cells were activated in the presence of ROR1 bispecific binding molecules (FIG. 17, Panel B, right). These data demonstrate that ROR1 is required for activation of the T cells by the bispecific constructs characterized in this study.

Figure 18:
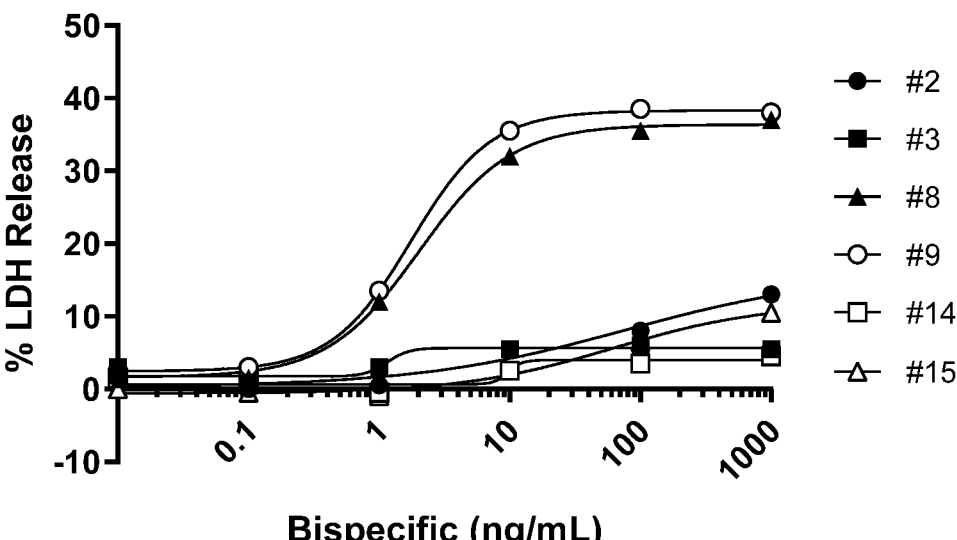
FIG. 18 is a pair of graphs quantitating LDH release from JeKo-1 cells (Panel A) and cell surface levels of CD69 on CD8$^+$ cells (Panel B), where JeKo-1 cells are incubated with human PBMCs and bispecific constructs 2, 3, 8, 9, 14, and 15.
Figure 18:
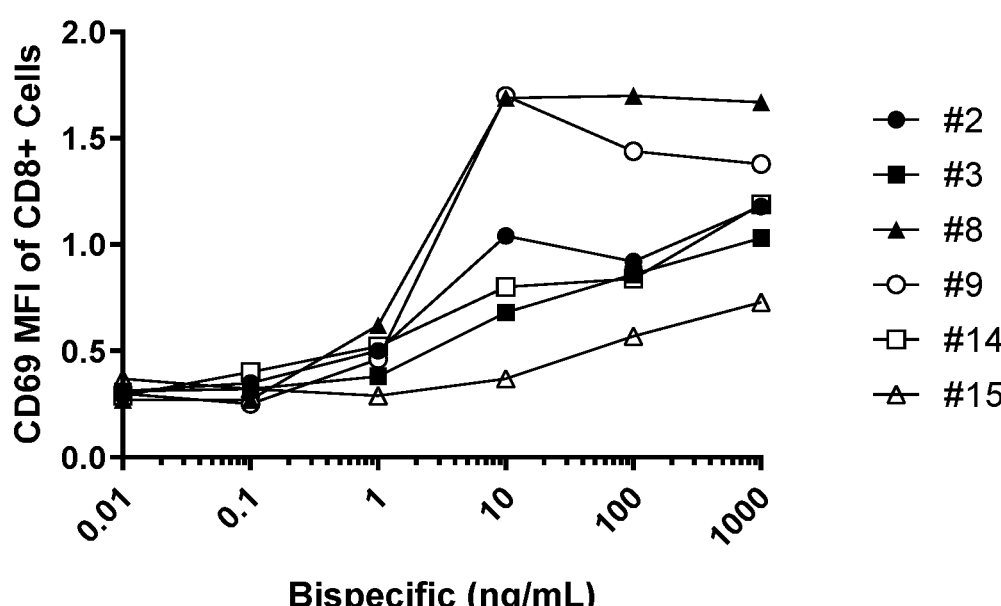

Next, ROR1-dependent killing of different human target cells by the bispecific binding molecules was examined. ROR1-dependent killing of JeKo-1 cells, a mantle cell lymphoma cell line, was observed with all the bispecific binding molecules of configurations A, B, C and E, albeit with varying potencies. Representative titration profiles are shown in FIG. 18, Panel A (constructs 1-15) and FIG. 19, Panel A (constructs 16-20). Consistent with the observations made with ROR1-transfected MEC cells, activation of T cells generally reflected the relative cytotoxicity of the bispecific binding molecules (FIG. 18, Panel B; FIG. 19, Panel B).

A second mantle cell lymphoma cell line, Mino cells, was also tested as a target cell line. All three non-disulfide stabilized constructs with configuration B displayed potent activity towards Mino cells (FIG. 20, Panel A) with the SP34-based CD3 sequence (construct 9) being the most potent. Interestingly, construct 9 activated T cells (as determined by upregulation of CD69) less than the OKT3 based constructs (FIG. 20, Panel B).

Figure 21:
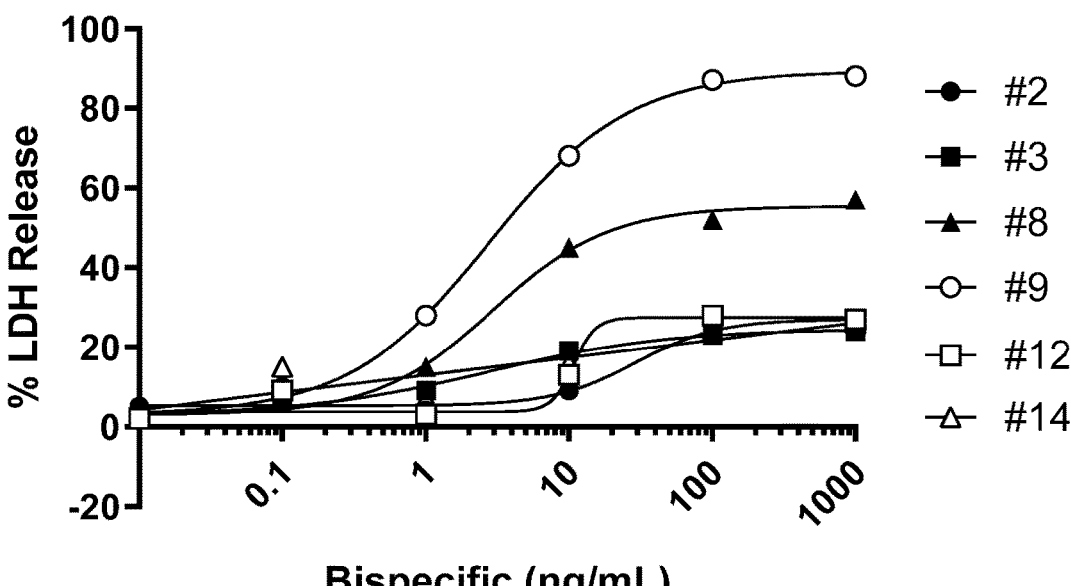
FIG. 21 is a pair of graphs quantitating LDH release from MDA-MB-468 cells (Panel A) and cell surface levels of CD69 on CD8$^+$ cells (Panel B), where MDA-MB-468 cells are incubated with human PBMCs and bispecific constructs 2, 3, 8, 9, 12, and 14.
Figure 21:
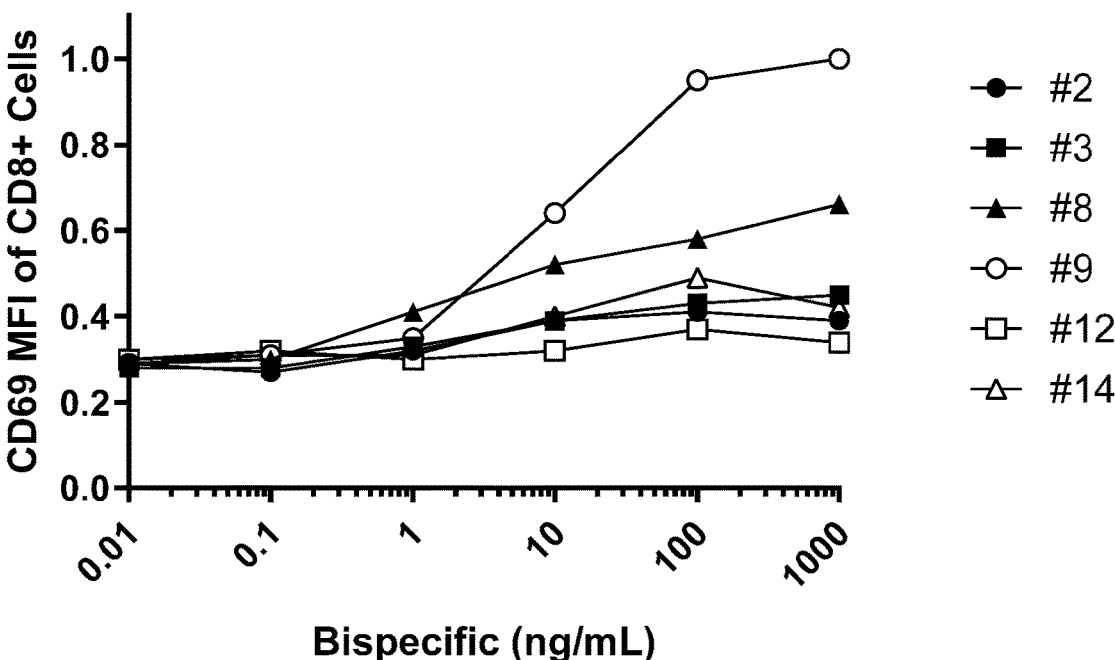
Figure 22:
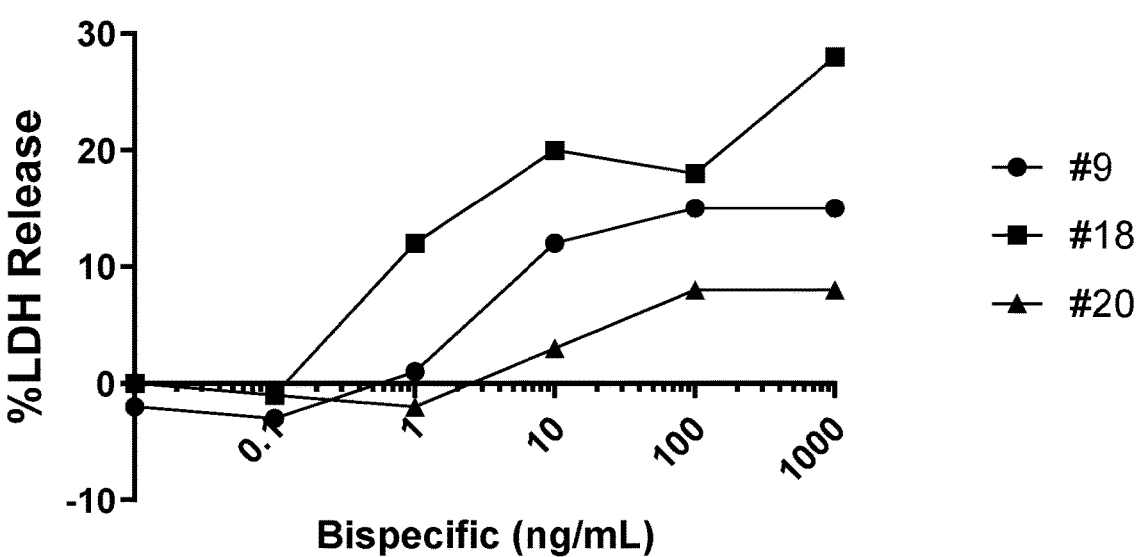
Figure 22:
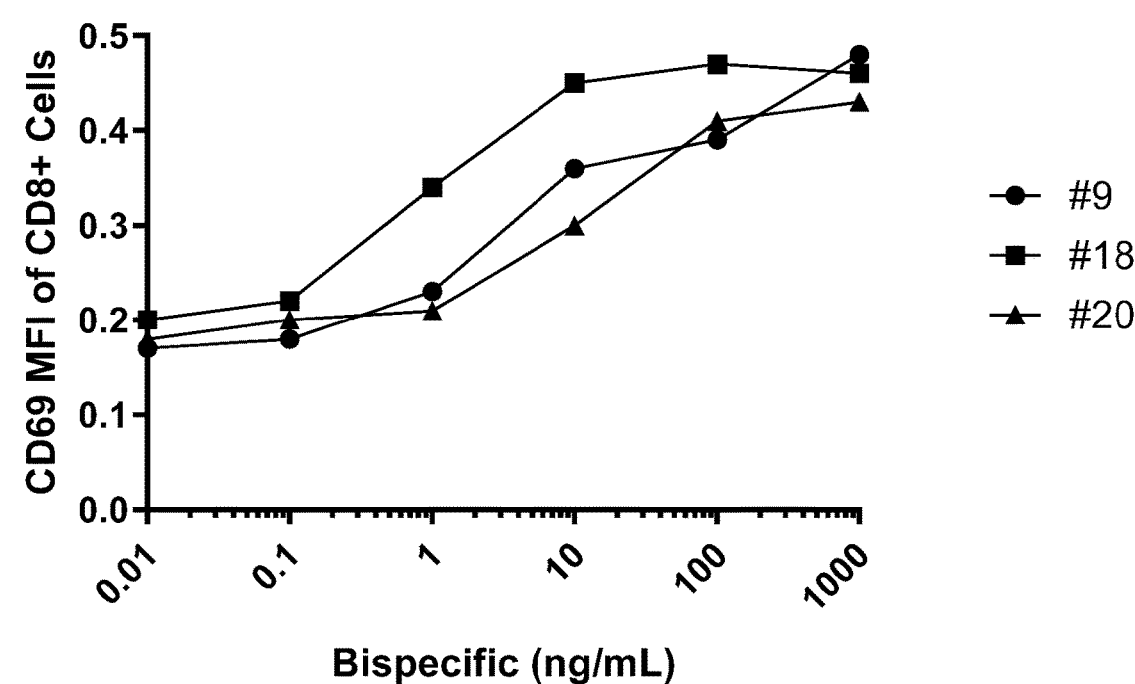

Likewise, ROR1-dependent killing of the breast tumor cell line MDA-MB-468 was observed with varying potencies with bispecific configurations A, B, C and E. Representative titration profiles are shown in FIG. 21, Panel A (constructs 1-15) and FIG. 22, Panel A (constructs 16-20). Consistent with the observations made with ROR1-transfected MEC cells and JeKo-1 cells, activation of T cells generally reflected the relative cytotoxicity of the bispecific binding molecules (FIG. 21, Panel B; FIG. 22, Panel B).

The induction of cytokine release following the activation of T cells in the redirected killing of JeKo-1 cells, ROR1-transfected MEC cells, and mock-transfected (ROR1$^-$) MEC cells was characterized. Representative dose-response graphs are shown for constructs 7, 9, 18, 20 and a control ROR1×CD3 bispecific binding molecule (U.S. Patent Publication 2017/0233472). (FIG. 23 (TNF-α), FIG. 24 (IFN-γ), FIG. 25 (IL-2), FIG. 26 (IL-4), FIG. 27 (IL-6), FIG. 28 (IL-10)). Dose-dependent cytokine production (TNF-α, IFN-γ, IL-2, IL-4, IL-6 and IL-10) was observed with JeKo-1 cells (Panel A) and ROR1-transfected MEC cells (Panel B), but not with mock-transfected (ROR1$^-$) MEC cells (Panel C), for all constructs tested. ROR1-transfected MEC cells express higher levels of ROR1 than JeKo-1 cells (Table 5) and were more sensitive to the bispecific binding molecules tested than the JeKo-1 cells, demonstrating the importance of target expression levels. Secretion of cytokines was dependent on the expression of ROR1. Incubation of 1 μg/mL of the constructs with mock-transfected (ROR1$^-$) MEC cells (Panel C) did not induce secretion of any of the cytokines at levels significantly above background (no bispecific antibody control). By contrast, incubation of the ROR1×CD3 bispecific binding molecule ("control 1") with mock-transfected (ROR1$^-$) MEC cells resulted in some secretion of the inflammatory cytokine IFN-γ (FIG. 24, Panel C). With the exception of IL-6, control 1 induced a higher overall level of cytokine secretion when tested with JeKo-1 cells. By contrast, all of the constructs, including control 1, induced similar levels of cytokine secretion when tested with the higher ROR-expressing transfected MEC cells.

A summary of the activity of some of the bispecific binding molecules versus various target cells is shown in Table 5.

TABLE 5

| | | ROR1 | | EC$_{50}$ | | Max. LDH |
|---|---|---|---|---|---|---|
| Description | Cell Line | Count | Construct | ng/mL | pM | Release (%) |
| Controls | MEC | 0 | | | | |
| | ROR1-transfected MEC | 56,000 | 1 | 11 | 55 | 42 |
| | | | 2 | 5.0 | 25 | 50 |
| | | | 3 | 4.9-10 | 25-50 | 14-45 |
| | | | 7 | 1.3 | 6.5 | 55 |
| | | | 9 | 0.1-1.1 | 0.5-5.5 | 29-57 |
| | | | 13 | 12 | 96 | 46 |
| | | | 14 | 5.0 | 40 | 48 |
| | | | 15 | ND | ND | 15-41 |
| | | | 18 | 3.5 | 17 | 34 |
| | | | 20 | 1.8 | 9.0 | 37 |

Summary of Cell Lines Tested with Bispecific Constructs

TABLE 5-continued

| Summary of Cell Lines Tested with Bispecific Constructs | | | | | | |
|---|---|---|---|---|---|---|
| | | ROR1 | | $EC_{50}$ | | Max. LDH |
| Description | Cell Line | Count | Construct | ng/mL | pM | Release (%) |
| Mantle cell | Mino | 6,689 | 7 | 0.97 | 4.9 | 50 |
| | | | 8 | 0.95 | 4.8 | 53 |
| | | | 9 | 0.75 | 3.8 | 75 |
| | JeKo-1 | 13,000 | 8 | 1.619 | 8.1 | 58 |
| | | | 9 | 1.705 | 8.5 | 60 |
| Breast | MDA-MB-468 | 25,812 | 9 | 5.553 | 27.8 | 30 |
| | HCC1937 | 13,521 | 9 | ND | ND | 12 |
| | MCF7 | 25 | 9 | Inactive | | 0 |
| Lung | NCI-H1975 | 20,291 | 9 | 2.302 | 11.5 | 44 |
| | A549 | 18,133 | 8 | 3.394 | 17.1 | 8 |
| | | | 9 | 9.951 | 49.8 | 13 |
| | NCI-H460 | 1,435 | 9 | ND | ND | 7 |
| Bone osteosarcoma | Saos-2 | 3,281 | 8 | 2.925 | 14.7 | 23 |
| | | | 9 | 14.63 | 73.2 | 35 |
| Ewing sarcoma | A4573 | 4,263 | 8 | 1.204 | 6.1 | 37 |
| | | | 9 | 9.705 | 48.6 | 33 |

Collectively, the redirected T-cell killing of various target cell lines with anti-ROR1/anti-CD3 bispecific binding molecules with a range of properties and configurations identified certain trends.

Based on in vitro cytotoxicity assays using human PBMCs as effector cells and various target cell lines, configurations B, E and C tended to be more potent than configurations A and D. The relative potencies based on configurations may reflect the relative spatial positioning of the CD3 and ROR1 binding arms. The potency may also reflect the impact the various configurations have on trafficking of the bispecific binding molecules. For example, bispecific binding molecules of configurations B and C do not internalize as rapidly or to the same extent as bispecific binding molecules of configuration A.

Although the OKT3-based sequences appeared to have higher affinity for CD3 than the SP34-based sequences, bispecific binding molecules with bivalent SP34-based sequences were frequently more potent. The enhanced activity may reflect affinity, or, additionally or alternatively, the distinct epitope recognized by SP34. Interestingly, when bispecific binding molecules with monovalent CD3 binding were assessed, the trend was different. In some cases, the OKT3-based sequences were more potent than the SP34-based sequences (FIG. 14, compare constructs 13 and 15).

No direct correlation between target cell ROR expression levels and cytotoxicity was observed (Table 5). Nonetheless, the higher affinity variant of the anti-ROR antibody was more potent than the parental WT sequence. This may be of increased importance in situations where the ROR1 expression levels are lower.

The results of these experiments show that although the CD3 and ROR1 binding components can be optimized and characterized separately, the most active bispecific binding molecules can only be identified through empirical testing of different pairings of binding components using different bispecific configurations. The experiments demonstrate that constructs 9 and 18 (configuration B) were consistently among the most potent anti-ROR1/anti-CD3 bispecific binding molecules. This is particularly noteworthy as CD3 binding experiments demonstrated that these constructs were among the weakest binders to Jurkat cells in the absence of ROR1. This is expected to be a useful feature as activation and internalization of CD3 on T cells will be minimal until ROR1 is engaged in the tumor microenvironment.

TABLE 6

| Antigen-Binding Domains | | | | | |
|---|---|---|---|---|---|
| Construct | Schematic (FIG. 1) | CD3 Antibody | Disulfide Stabilized | ROR1 Antibody | Knobs-into-Holes Variant |
| 1 | A | Ab8 | No | Ab1 | No |
| 2 | A | Ab9 | No | Ab1 | No |
| 3 | A | Ab10 | No | Ab1 | No |
| 4 | A | Ab8 | Yes | Ab1 | No |
| 5 | A | Ab9 | Yes | Ab1 | No |
| 6 | A | Ab10 | Yes | Ab1 | No |
| 7 | B | Ab8 | No | Ab1 | No |
| 8 | B | Ab9 | No | Ab1 | No |
| 9 | B | Ab10 | No | Ab1 | No |
| 10 | B | Ab8 | Yes | Ab1 | No |
| 11 | B | Ab9 | Yes | Ab1 | No |
| 12 | B | Ab10 | Yes | Ab1 | No |
| 13 | C | Ab8 | No | Ab1 | Yes |
| 14 | C | Ab9 | No | Ab1 | Yes |
| 15 | C | Ab10 | No | Ab1 | Yes |
| 16 | C | Ab10 | No | Ab2 | Yes |
| 17 | C | Ab10 | Yes | Ab2 | Yes |
| 18 | B | Ab10 | No | Ab2 | No |
| 19 | D | Ab10 | No | Ab2 | Yes |
| 20 | E | Ab10 | No | Ab2 | No |

What is claimed is:

1. A molecule comprising a first antigen-binding domain that specifically binds to an extracellular domain of human receptor tyrosine kinase-like orphan receptor 1 (ROR1), wherein the first antigen-binding domain comprises:
   a) heavy chain (H)-CDR1-3 and light chain (L)-CDR1-3 comprising the amino acid sequences of SEQ ID NOs: 97, 61, 62, 63, 64, and 65, respectively; or
   b) heavy chain (H)-CDR1-3 and light chain (L)-CDR1-3 comprising the amino acid sequences of SEQ ID NOs: 97, 61, 62, 63, 102, and 65, respectively; and
   wherein the molecule comprises a second antigen-binding domain that specifically binds to the extracellular domain of human CD3.

2. The molecule of claim 1, wherein the first antigen binding domain comprises:
   a) a VH comprising the amino acid sequence of SEQ ID NO: 74 and a VL comprising the amino acid sequence of SEQ ID NO: 73; or
   b) a VH comprising the amino acid sequence of SEQ ID NO: 74 and a VL comprising the amino acid sequence of SEQ ID NO: 103.

3. The molecule of claim 1, comprising:
   a) a light chain comprising the amino acid sequence of SEQ ID NO: 16 and a heavy chain comprising the amino acid sequence of SEQ ID NO: 84, SEQ ID NO: 87, or SEQ ID NO: 107; or
   b) a light chain comprising the amino acid sequence of SEQ ID NO: 104 and a heavy chain comprising the amino acid sequence of SEQ ID NO: 84, SEQ ID NO: 87, or SEQ ID NO: 107.

4. An immunoconjugate comprising the molecule of claim 1 conjugated to a cytotoxic agent.

5. A pharmaceutical composition comprising the molecule of claim 1 and a pharmaceutically acceptable excipient.

6. The molecule of claim 1, wherein the second antigen-binding domain comprises:
   a) heavy chain (H)-CDR1-3 and light chain (L)-CDR1-3 comprising the amino acid sequences of SEQ ID NOs: 54, 55, 56, 57, 58, and 59, respectively;
   b) H-CDR1-3 and L-CDR1-3 comprising the amino acid sequences of SEQ ID NOs: 47, 48, 49, 50, 51, and 52, respectively;
   c) H-CDR1-3 and L-CDR1-3 comprising the amino acid sequences of SEQ ID NOs: 47, 53, 49, 50, 51, and 52, respectively;
   d) a VH comprising the amino acid sequence of SEQ ID NO: 70 and a VL comprising the amino acid sequence of SEQ ID NO: 71;
   e) a VHI comprising the amino acid sequence of SEQ ID NO: 66 and a VL comprising the amino acid sequence of SEQ ID NO: 67;
   f) a VH comprising the amino acid sequence of SEQ ID NO: 68 and a VL comprising the amino acid sequence of SEQ ID NO: 69;
   g) a VH comprising the amino acid sequence of SEQ ID NO: 80 and a VL comprising the amino acid sequence of SEQ ID NO: 81;
   h) a VH comprising the amino acid sequence of SEQ ID NO: 76 and a VL comprising the amino acid sequence of SEQ ID NO: 77; or
   i) a VH comprising the amino acid sequence of SEQ ID NO: 78 and a VL comprising the amino acid sequence of SEQ ID NO: 79.

7. An immunoconjugate comprising the molecule of claim 6 conjugated to a cytotoxic agent.

8. A pharmaceutical composition comprising the molecule of claim 6 and a pharmaceutically acceptable excipient.

* * * * *